United States Patent
Heffernan et al.

(10) Patent No.: US 10,533,000 B2
(45) Date of Patent: Jan. 14, 2020

(54) METABOTROPHIC GLUTAMATE RECEPTOR 5 MODULATORS AND METHODS OF USE THEREOF

(75) Inventors: Michele L. R. Heffernan, Worcester, MA (US); Larry Wendell Hardy, Sturbridge, MA (US); Frank Xinhe Wu, Shrewsbury, MA (US); Lakshmi D. Saraswat, Sudbury, MA (US)

(73) Assignee: Sunovion Pharmaceuticals, Inc., Marlborough, MA (US)

(*) Notice: Subject to any disclaimer, the term of this patent is extended or adjusted under 35 U.S.C. 154(b) by 0 days.

(21) Appl. No.: 14/122,519

(22) PCT Filed: May 25, 2012

(86) PCT No.: PCT/US2012/039639
§ 371 (c)(1),
(2), (4) Date: Mar. 10, 2014

(87) PCT Pub. No.: WO2012/162635
PCT Pub. Date: Nov. 29, 2012

(65) Prior Publication Data
US 2014/0221332 A1 Aug. 7, 2014

Related U.S. Application Data

(60) Provisional application No. 61/490,402, filed on May 26, 2011.

(51) Int. Cl.
| | | |
|---|---|---|
| *C07D 413/10* | (2006.01) |
| *C07D 401/10* | (2006.01) |
| *C07D 401/14* | (2006.01) |
| *C07D 413/14* | (2006.01) |
| *C07D 235/18* | (2006.01) |
| *C07D 413/04* | (2006.01) |
| *C07D 413/06* | (2006.01) |
| *C07D 249/08* | (2006.01) |
| *C07D 471/04* | (2006.01) |
| *C07D 487/04* | (2006.01) |
| *C07D 487/08* | (2006.01) |
| *C07D 271/06* | (2006.01) |
| *C07D 271/10* | (2006.01) |

(52) U.S. Cl.
CPC ......... *C07D 413/10* (2013.01); *C07D 235/18* (2013.01); *C07D 249/08* (2013.01); *C07D 271/06* (2013.01); *C07D 271/10* (2013.01); *C07D 401/10* (2013.01); *C07D 401/14* (2013.01); *C07D 413/04* (2013.01); *C07D 413/06* (2013.01); *C07D 413/14* (2013.01); *C07D 471/04* (2013.01); *C07D 487/04* (2013.01); *C07D 487/08* (2013.01)

(58) Field of Classification Search
CPC ........................... C07D 413/10; C07D 401/10
See application file for complete search history.

(56) References Cited

U.S. PATENT DOCUMENTS

| 4,582,836 A | 4/1986 | Carmosin et al. |
| 6,656,469 B1 | 12/2003 | Svensson et al. |
| 2002/0019370 A1 | 2/2002 | Hegde et al. |
| 2009/0048301 A1 | 2/2009 | Chen et al. |

FOREIGN PATENT DOCUMENTS

| EP | 55693 A1 | 7/1982 |
| FR | 1547502 A | 11/1968 |
| JP | 2007045752 A | 2/2007 |
| SU | 1528317 A3 | 12/1989 |
| WO | 1995/030659 A1 | 11/1995 |
| WO | 2010/036613 A1 | 4/2010 |

OTHER PUBLICATIONS

Hedge, et al. Document No. 136:146541 retrieved from CAPLUS; Feb. 14, 2002.*
Zhang, et al. Document No. 149:544847 retrieved from CAPLUS; 2008.*
Fischer, et al. Document No. 153:87797, retrieved from STN; Jun. 24, 2010.*
Bookser, et al. Document No. 152:429707, retrieved from STN; Apr. 1, 2010.*
Peters, et al. Document No. 150: 260233, retrieved from CAPLUS; Feb. 26, 2009.*
Askew, et al. Document No. 151:198447, retrieved from CAPLUS; Jul. 30, 2009.*
Loughborough, et al. Document No. 142:6446, retrieved from STN; (2004).*
Rice, et al. Document No. 135:46140, retreived from STN; 2001.*
Bist, et al. Document No. 154:336119, retreived from STN; Mar. 3, 2011.*
Charton J. et al. "Novel non-carboxylic acid retinoids: 1,2,4-0xadiazol-5-one derivatives", Bioorganic & Medicinal Chemistry Letters, 2009, 19(2), 489-492 [online] Retrieved from STN on the Web, DB CA, AN: 150:229185, compounds with RN 1116016-64-8, 1116016-65-9.
Charton J. et al. "A versatile solid-phase synthesis of 3-aryl-1,2,4-oxadiazolones and analogues", Tetrahedron Letters, 2007, 48(8), 1479-1483 [online] Retrieved from STN on the Web, DB CA, AN: 146:358772, compounds with RN 929907-744, 929907-75-5, 929907-76-6.
International Search Report for PCT/US2012/039639 dated Sep. 27, 2012.
Written Opinion for PCT/US2012/039639, 7 pages (dated Sep. 27, 2012).
Zhang, L. and Zhu, L., Photochemically Stable Fluorescent Heteroditopic Ligands for Zinc Ion, J. Org. Chem., 73:8321-30 (2008).

* cited by examiner

*Primary Examiner* — Shawquia Jackson

(57) ABSTRACT

Compounds that modulate GluR5 activity and methods of using the same are disclosed.

14 Claims, No Drawings

METABOTROPHIC GLUTAMATE RECEPTOR 5 MODULATORS AND METHODS OF USE THEREOF

RELATED APPLICATIONS

This application is a National Stage Application under 35 U.S.C. § 371 from PCT/US2012/039639 filed May 25, 2012 and claims priority to U.S. Provisional Patent Application No. 61/490,402, filed May 26, 2011. The prior applications are incorporated herein by reference in their entirety.

BACKGROUND

The amino acid L-glutamate (which herein is referred to simply as glutamate) is the principal excitatory neurotransmitter in the brain and other elements of the central nervous system of mammals. Glutamate binds to neurons and activates cell surface receptors. Glutamate has significant roles in motor control, cognitive function, sensory perception, and acts as a mediator of persistent changes in the strength of synaptic signaling (synaptic plasticity), thereby modulating long term potentiation (LTP) and long term depression (LTD), which form the basis of learning and memory. Many neurological and neuropsychiatric disorders, including, but not limited to, psychosis spectrum disorders, schizophrenia and other cognitive deficits, are associated with aberrations in the function of (or the regulation by, or the regulation of) glutamate signaling systems.

Glutamate mediates its effect via two distinct types of receptors, the ionotropic receptors and the metabotropic receptors. The family of the metabotropic receptors (mGlu or mGluR) consists of eight different subtypes, which are further classified into three subgroups based on sequence homology, effector coupling and pharmacology. In particular, group I mGlu receptors (mGluR1 and mGluR5) are positively coupled to phospholipase C, while group II mGlu receptors (mGluR2 and mGluR3) and group III receptors (mGluR4, mGluR6, mGluR7, and mGluR8) are negatively coupled to adenylate cyclase (Conn et al. *Annu. Rev. Pharmacol. Toxicol.* 1997; 37:205-37).

mGluR5, which is widely expressed in the central nervous system, has at least two discrete allosteric binding sites, in addition to the orthosteric site, and has been implicated in a range of physiological functions, including phosphoinositide hydrolysis responses, modulation of potassium and voltage dependent calcium channels, modulation of ligand-gated ion channels and acting as a presynaptic autoreceptor at glutamatergic synapses, thereby modulating glutamate release (Conn et al., supra). Accordingly, development of therapeutic agents that modulate mGluR5 via direct agonism or antagonism or by positive or negative allosteric modulation may prove useful for treatment of disorders influenced by the forgoing physiological functions, such as neurological disorders, neuropsychiatric disorders, GERD, drug addiction and alcohol addiction.

SUMMARY

The present invention is based, at least in part, on the discovery that the compounds as disclosed herein are allosteric modulators of mGluR5, for example, negative or positive allosteric modulators.

In various embodiments, a compound of formula (I) or a pharmaceutically acceptable salt thereof is provided:

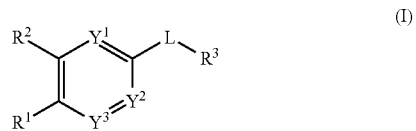

wherein
$Y^1$, $Y^2$, and $Y^3$ are each independently $CR^4$ or N;
$R^1$ is cycloalkyl, heterocycloalkyl, aryl, or heteroaryl;
each $R^2$ and $R^4$ is independently hydrogen, halogen, alkyl, heteroalkyl, cycloalkyl, heterocycloalkyl, aryl, aralkyl, heteroaralkyl, or heteroaryl;
$R^3$ is hydrogen, alkyl, heteroalkyl, cycloalkyl, heterocycloalkyl, aryl, heteroaryl, aralkyl or heteroaralkyl;
L is —C≡C—, —$R^4$C=$CR^4$—, —$C(R^4)_2$—$C(R^4)_2$—, —C(O)—$CR^5R^6$—, —CH(OH)—$CR^5R^6$, —$CR^5R^6$—C(O)—, —$C_{0-6}$alkyl-O—$C_{0-6}$alkyl-, —$NR^6$SO—, —$SONR^6$—, —$NR^6SO_2$—, —$SO_2NR^6$—, —$NR^6$—CO—, —CO—$NR^6$—,

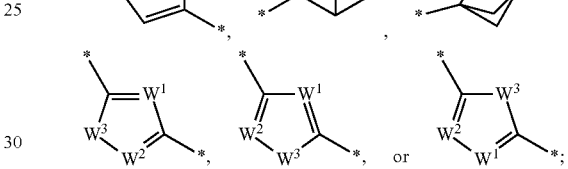

$W^1$ and $W^2$ are each independently N or CH;
$W^3$ is O, S or $NR^5$; and
$R^5$ and $R^6$ are each independently hydrogen or alkyl.

In certain embodiments, the invention provides pharmaceutical compositions comprising a therapeutically effective amount of a compound as disclosed herein and a pharmaceutically acceptable carrier.

In certain embodiments, the invention provides methods for treating a disorder or disease mediated by mGluR5, comprising administering to a subject in need thereof a therapeutically effective amount of a compound as disclosed herein.

In certain embodiments, the invention provides methods for treating neurological disorders, such as neurodegenerative diseases, neuropsychiatric diseases, affective disorders, and loss of cognitive function, and learning and memory disorders, comprising administering to a subject in need thereof a therapeutically effective amount of a compound as disclosed herein.

In certain embodiments, methods are provided for treating psychosis, comprising administering to a subject in need thereof a therapeutically effective amount of a compound as disclosed herein.

In certain embodiments, methods are provided for treating schizophrenia, comprising administering to a subject in need thereof a therapeutically effective amount of a compound as disclosed herein.

In certain embodiments, methods are provided for treating Alzheimer's disease, comprising administering to a subject in need thereof a therapeutically effective amount of a compound as disclosed herein.

In certain embodiments, methods are provided for treating cognitive disorders, comprising administering to a subject in need thereof a therapeutically effective amount of a compound as disclosed herein.

In certain embodiments, methods are provided for treating cognitive impairment associated with schizophrenia.

In certain embodiments, methods are provided for treating tubular sclerosis.

In certain embodiments, the invention provides methods for modulating mGluR5 in a subject by administering to the subject a therapeutically effective amount of a compound as disclosed herein.

In certain embodiments, the invention provides methods for modulating mGluR5 in a cell by contacting the cell with an effective amount of a compound as disclosed herein.

DETAILED DESCRIPTION OF THE INVENTION

Various embodiments of the invention are described herein. It will be recognized that features specified in each embodiment may be combined with other specified features to provide further embodiments.

As used herein, the articles "a" and "an" mean "one or more" or "at least one," unless otherwise indicated. That is, reference to any element of the present invention by the indefinite article "a" or "an" does not exclude the possibility that more than one of the element is present.

The use of any and all examples, or exemplary language (e.g., "such as") provided herein is intended merely to better illuminate the invention and is not intended to limit the scope of the invention.

Compounds

In certain embodiments, a compound of formula (I) is provided:

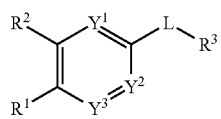

(I)

wherein
$Y^1$, $Y^2$, and $Y^3$ are each independently $CR^4$ or N;
$R^1$ is cycloalkyl, heterocycloalkyl, aryl, or heteroaryl;
each $R^2$ and $R^4$ is independently hydrogen, halogen, alkyl, heteroalkyl, cycloalkyl, heterocycloalkyl, aryl, aralkyl, heteroaralkyl, or heteroaryl;
$R^3$ is alkyl, heteroalkyl, cycloalkyl, heterocycloalkyl, aryl, heteroaryl, aralkyl or heteroaralkyl;
L is —C≡C—, —$R^4$C=$CR^4$—, —C($R^4$)$_2$—C($R^4$)$_2$—, —C(O)—$CR^5R^6$—, —CH(OH)—$CR^5R^6$, —$CR^5R^6$—C(O)—, —C$_{0-6}$alkyl-O—C$_{0-6}$alkyl-, —$NR^6$SO—, —$SONR^6$—, —$NR^6SO_2$—, —$SO_2NR^6$—, —$NR^6$—CO—, —CO—$NR^6$—,

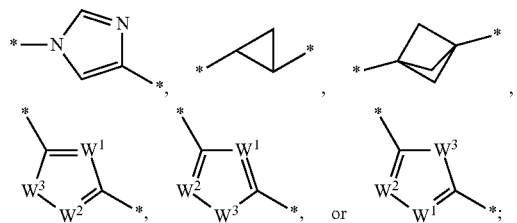

$W^1$ and $W^2$ are each independently N or CH;
$W^3$ is O, S or $NR^5$; and
$R^5$ and $R^6$ are each independently hydrogen or alkyl.

In certain embodiments, one of $Y^1$, $Y^2$, and $Y^3$ is nitrogen and the others are $CR^4$. In certain embodiments, two of $Y^1$, $Y^2$, and $Y^3$ are nitrogen and the other is $CR^4$. In certain embodiments, $Y^1$, $Y^2$, and $Y^3$ are all nitrogen. In certain embodiments, $Y^1$, $Y^2$, and $Y^3$ are all $CR^4$.

In certain embodiments, $R^1$ is cycloalkyl. In certain embodiments, $R^1$ is heterocycloalkyl. In certain embodiments, $R^1$ is aryl. In certain embodiments, $R^1$ is heteroaryl.

In certain embodiments, $R^2$ is hydrogen. In certain embodiments, $R^2$ is halogen. In certain embodiments, $R^2$ is alkyl. In certain embodiments, $R^2$ is heteroalkyl. In certain embodiments, $R^2$ is cycloalkyl. In certain embodiments, $R^2$ is heterocycloalkyl. In certain embodiments, $R^2$ is aryl. In certain embodiments, $R^2$ is aralkyl. In certain embodiments, $R^2$ is heteroaralkyl. In certain embodiments, $R^2$ is heteroaryl.

In certain embodiments, $R^3$ is alkyl. In certain embodiments, $R^3$ is heteroalkyl. In certain embodiments, $R^3$ is cycloalkyl. In certain embodiments, $R^3$ is heterocycloalkyl. In certain embodiments, $R^3$ is cycloalkyl. In certain embodiments, $R^3$ is aryl. In certain embodiments, $R^3$ is heteroaryl. In certain embodiments, $R^3$ is aralkyl. In certain embodiments, $R^3$ is heteroaralkyl.

In certain embodiments, $R^4$ is hydrogen. In certain embodiments, $R^4$ is halogen. In certain embodiments, $R^4$ is alkyl. In certain embodiments, $R^4$ is heteroalkyl. In certain embodiments, $R^4$ is cycloalkyl. In certain embodiments, $R^4$ is heterocycloalkyl. In certain embodiments, $R^4$ is aryl. In certain embodiments, $R^4$ is aralkyl. In certain embodiments, $R^4$ is heteroaralkyl. In certain embodiments, $R^4$ is heteroaryl.

In certain embodiments, L is —C≡C—, —$R^4$C=$CR^4$—, —C($R^4$)$_2$—C($R^4$)$_2$—, —CO—$CH_2$—, —CH(OH)—$CH_2$, —$CH_2$—CO—, —$C_{0-6}$alkyl-O—$C_{0-6}$alkyl-, —$NR^6$SO—, —$SONR^6$—, —$NR^6SO_2$—, —$SO_2NR^6$—, —$NR^6$—CO—, or —CO—$NR^6$—.

In certain embodiments, L is —C≡C—. In certain embodiments, L is —$R^4$C=$CR^4$—. In certain embodiments, L is —C($R^4$)$_2$—C($R^4$)$_2$—. In certain embodiments, L is —CO—$CH_2$—. In certain embodiments, L is —CH(OH)—$CH_2$. In certain embodiments, L is —$CH_2$—CO—. In certain embodiments, L is —$C_{0-6}$alkyl-O—$C_{0-6}$alkyl-. In certain embodiments, L is —$NR^6$SO—. In certain embodiments, L is —$SONR^6$—. In certain embodiments, L is —$NR^6SO_2$—. In certain embodiments, L is —$SO_2NR^6$—. In certain embodiments, L is —$NR^6$—CO—. In certain embodiments, L is —CO—$NR^6$—. In certain embodiments, L is

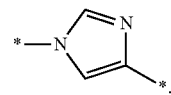

In certain embodiments, L is

In certain embodiments, L is

In certain embodiments, L is

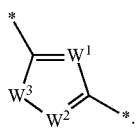

In certain embodiments, L is

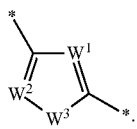

In certain embodiments, L is

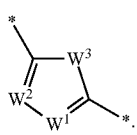

In certain embodiments, L is —C≡C—, —R$^4$C═CR$^4$—, —C(R$^4$)$_2$—C(R$^4$)$_2$—, —C(O)—CR$^5$R$^6$—, —CH(OH)—CR$^5$R$^6$, —CR$^5$R$^6$—C(O)—, —C$_{0-6}$alkyl-O—C$_{0-6}$alkyl-, —NR$^6$SO—, —SONR$^6$—, —NR$^6$SO$_2$—, —SO$_2$NR$^6$—, —NR$^6$—CO—, —CO—NR$^6$—,

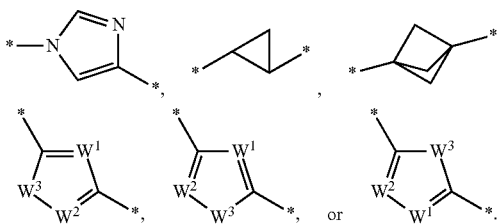

In certain embodiments, a compound of formula (II) or a pharmaceutically acceptable salt thereof is provided:

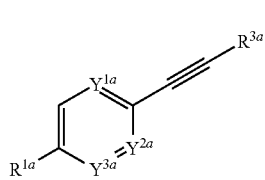

(II)

wherein
Y$^{1a}$, Y$^{2a}$, and Y$^{3a}$ are each independently CR$^{4a}$ or N;
R$^{1a}$ is cycloalkyl, heterocycloalkyl, aryl, or heteroaryl;
R$^{3a}$ is alkyl, heteroalkyl, cycloalkyl, heterocycloalkyl, aryl, heteroaryl, aralkyl or heteroaralkyl; and
R$^{4a}$ is hydrogen, alkyl, heteroalkyl, cycloalkyl, heterocycloalkyl, aryl, aralkyl, heteroaralkyl, or heteroaryl.

In certain embodiments, one of Y$^{1a}$, Y$^{2a}$, and Y$^{3a}$ is nitrogen and the others are CR$^{4a}$. In certain embodiments, two of Y$^{1a}$, Y$^{2a}$, and Y$^{3a}$ are nitrogen and the other is CR$^{4a}$. In certain embodiments, Y$^{1a}$, Y$^{2a}$, and Y$^{3a}$ are all nitrogen. In certain embodiments, Y$^{1a}$, Y$^{2a}$, and Y$^{3a}$ are all CR$^{4a}$.

In certain embodiments, R$^{4a}$ is hydrogen. In certain embodiments, R$^{4a}$ is alkyl. In certain embodiments, R$^{4a}$ is heteroalkyl. In certain embodiments, R$^{4a}$ is cycloalkyl. In certain embodiments, R$^{4a}$ is heterocycloalkyl. In certain embodiments, R$^{4a}$ is aryl. In certain embodiments, R$^{4a}$ is aralkyl. In certain embodiments, R$^{4a}$ is heteroaralkyl. In certain embodiments, R$^{4a}$ is heteroaryl.

In certain embodiments, R$^{1a}$ is cycloalkyl. In certain embodiments, R$^{1a}$ is heterocycloalkyl. In certain embodiments, R$^{1a}$ is aryl. In certain embodiments, R$^{1a}$ is heteroaryl.

In certain embodiments, R$^{3a}$ is alkyl. In certain embodiments, R$^{3a}$ is heteroalkyl. In certain embodiments, R$^{3a}$ is cycloalkyl. In certain embodiments, R$^{3a}$ is heterocycloalkyl. In certain embodiments, R$^{3a}$ is aryl. In certain embodiments, R$^{3a}$ is heteroaryl. In certain embodiments, R$^{3a}$ is aralkyl. In certain embodiments, R$^{3a}$ is heteroaralkyl.

In certain embodiments, R$^{3a}$ is aryl or heteroaryl. In certain embodiments, R$^{3a}$ is

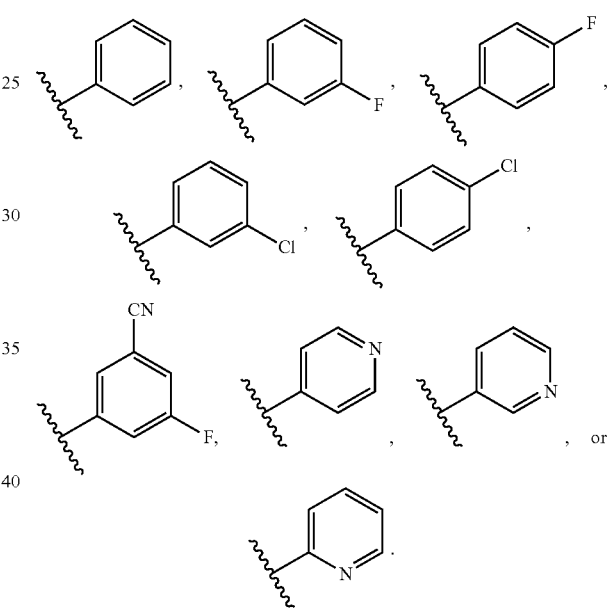

In certain embodiments, R$^{1a}$ is heterocycloalkyl or heteroaryl. In certain embodiments R$^{1a}$ is a 5-membered heteroaryl. In certain embodiments, R$^{1a}$ is

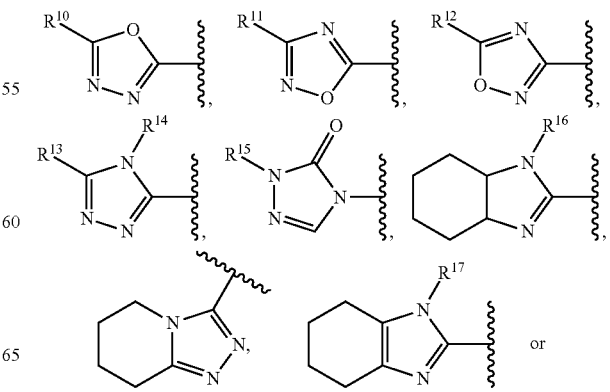

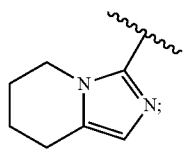

wherein $R^{10}$, $R^{11}$, $R^{12}$, and $R^{13}$ are each independently hydrogen, alkyl, cycloalkyl, heterocyclyl, heteroaryl, heteroalkyl, or aralkyl; and $R^{14}$, $R^{15}$, $R^{16}$ and $R^{17}$ are each independently hydrogen or alkyl; or $R^{13}$ and $R^{14}$ together with the atoms to which they are attached are linked to form a heterocyclyl ring.

In certain embodiments, $R^{1a}$ is heteroaryl, such as a 5-membered heteroaryl ring. In certain embodiments, $R^{1a}$ is

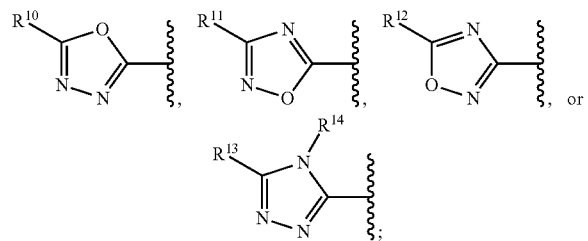

wherein $R^{10}$, $R^{11}$, $R^{12}$, and $R^{13}$ are each independently hydrogen, alkyl, cycloalkyl, heterocyclyl, heteroaryl, heteroalkyl, or aralkyl; and $R^{14}$ is hydrogen or alkyl; or $R^{13}$ and $R^{14}$ together with the atoms to which they are attached are linked to form a heterocyclyl ring.

In certain embodiments, $R^{1a}$ is

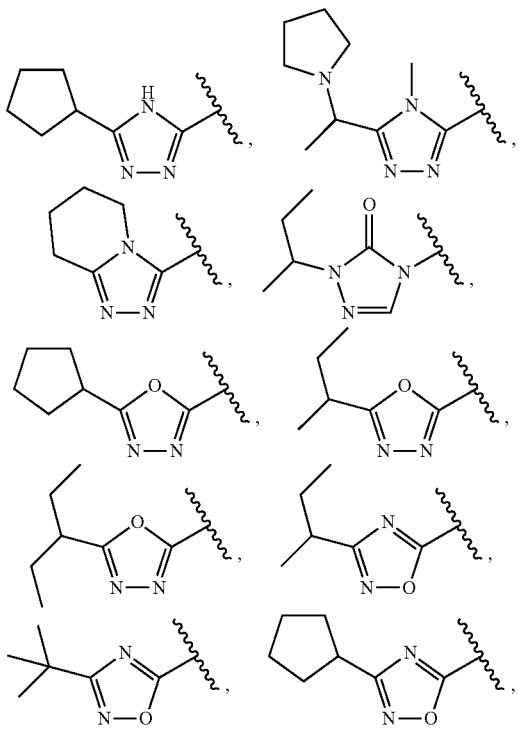

-continued
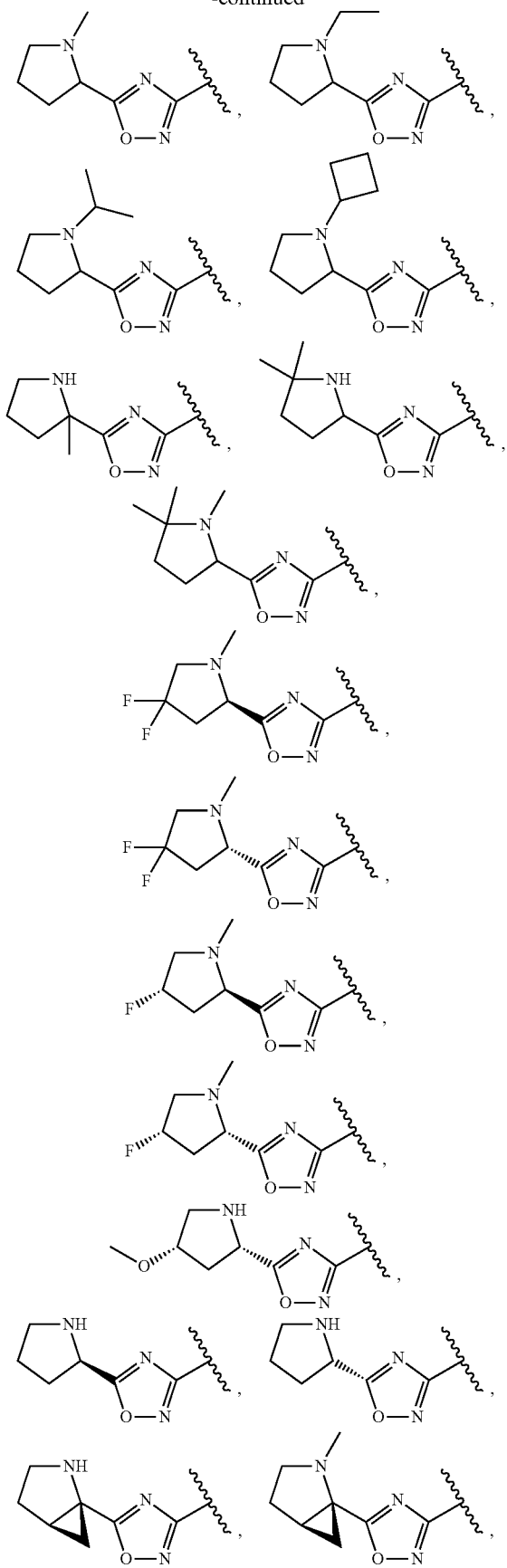
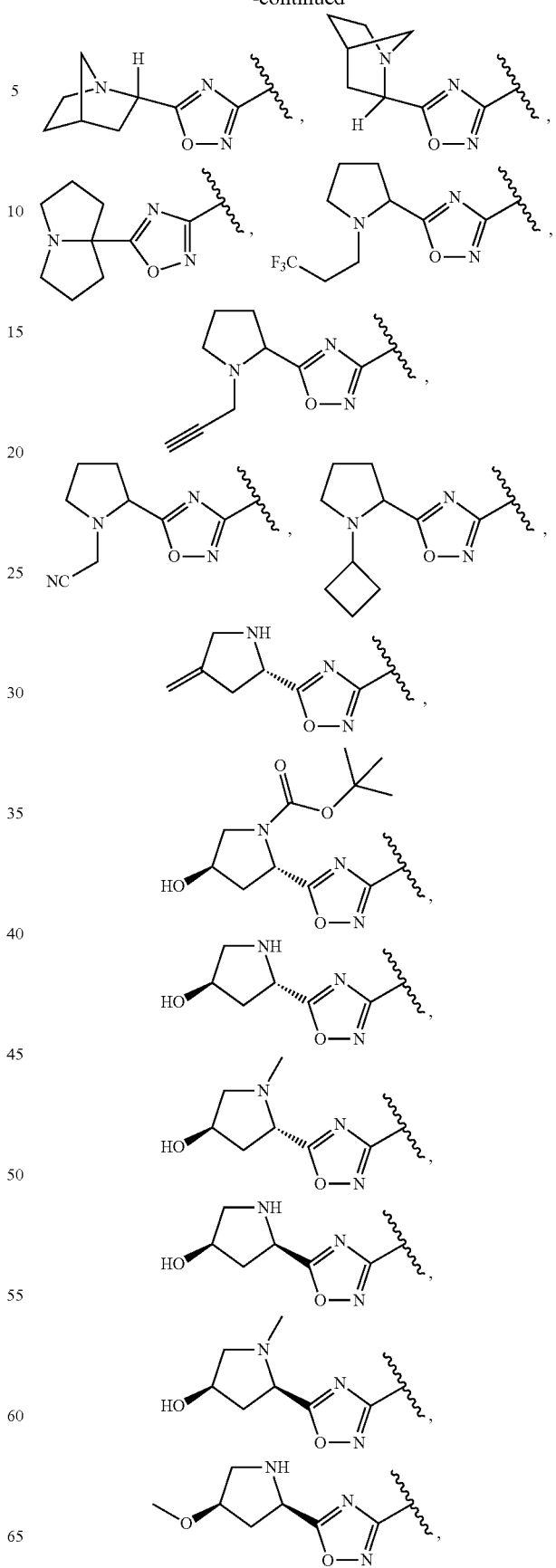

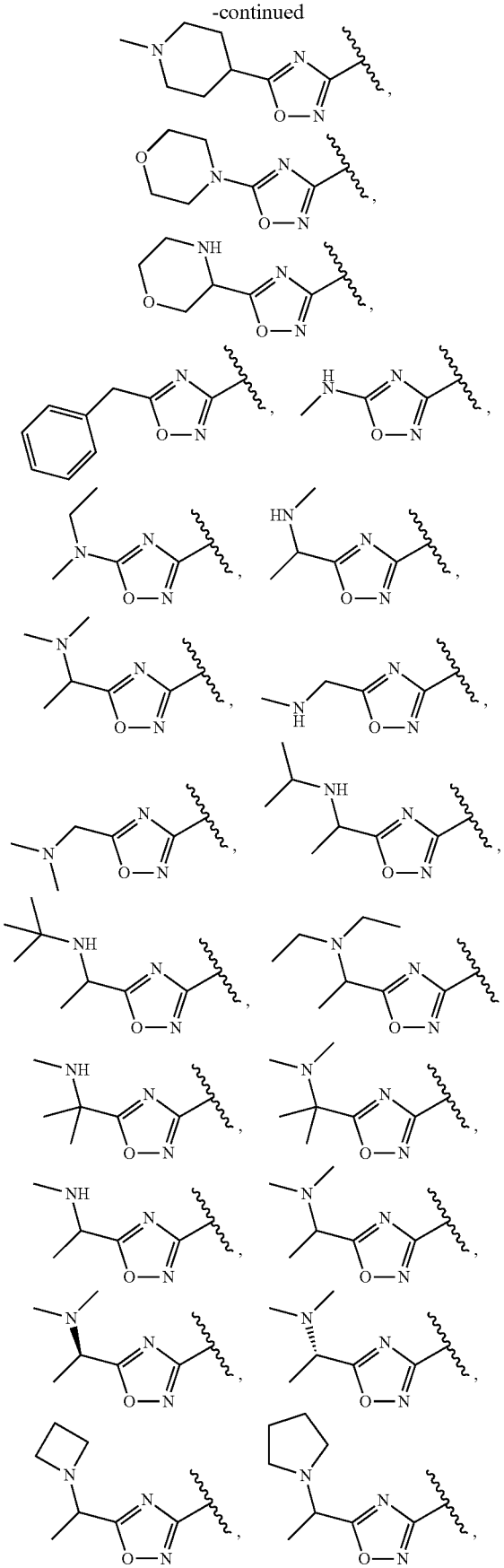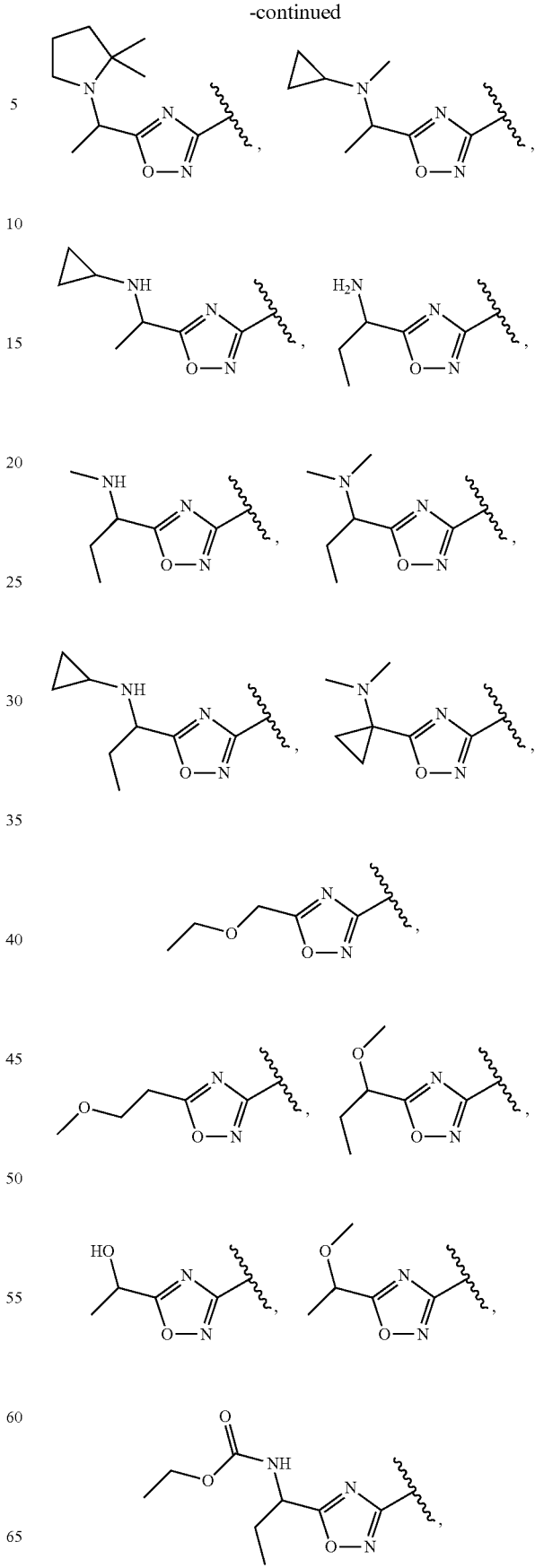

-continued
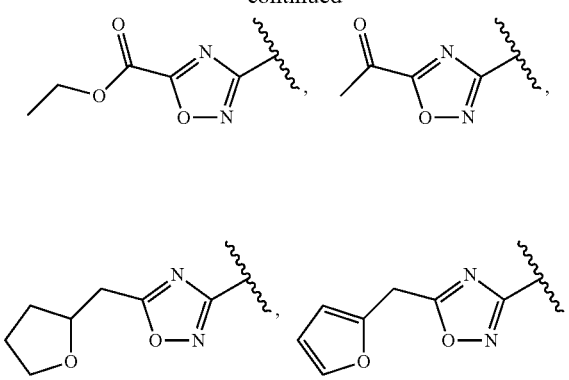
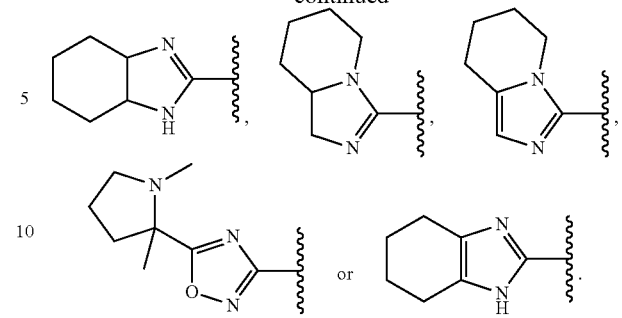
In certain embodiments, a compound of the invention is selected from:
| R$^{1a}$ | R$^{3a}$ | R$^{4a}$ | Y$^{1a}$ | Y$^{2a}$ | Y$^{3a}$ |
|---|---|---|---|---|---|
| 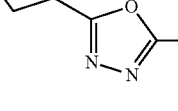 | 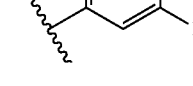 | H | CR$^{4a}$ | CR$^{4a}$ | CR$^{4a}$ |
| 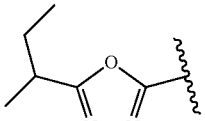 | 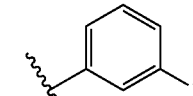 | H | CR$^{4a}$ | CR$^{4a}$ | CR$^{4a}$ |
| 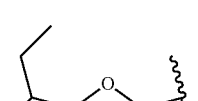 | 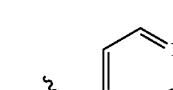 | H | CR$^{4a}$ | CR$^{4a}$ | CR$^{4a}$ |
| 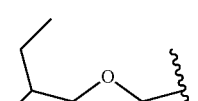 | 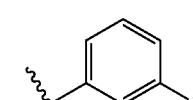 | H | CR$^{4a}$ | CR$^{4a}$ | CR$^{4a}$ |
| 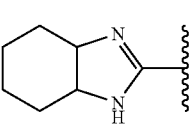 [SMILES: *C1=NC2CCCCC2N1] |  | H | CR$^{4a}$ | CR$^{4a}$ | CR$^{4a}$ |
| 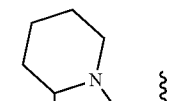 | 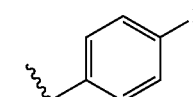 | H | CR$^{4a}$ | CR$^{4a}$ | CR$^{4a}$ |
| 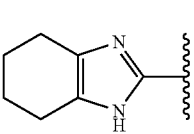 [SMILES: *c1nc2c([nH]1)CCCC2] | 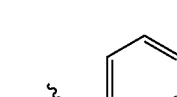 | H | CR$^{4a}$ | CR$^{4a}$ | CR$^{4a}$ |

-continued

| $R^{1a}$ | $R^{3a}$ | $R^{4a}$ | $Y^{1a}$ | $Y^{2a}$ | $Y^{3a}$ |
|---|---|---|---|---|---|
| (bicyclic imidazole structure) | 4-F-phenyl | H | $CR^{4a}$ | $CR^{4a}$ | $CR^{4a}$ |
| cyclopentyl-triazole | 3-F-phenyl | H | $CR^{4a}$ | $CR^{4a}$ | $CR^{4a}$ |
| pyrrolidinyl-methyl-triazole | 2-pyridyl | H | $CR^{4a}$ | $CR^{4a}$ | N |
| (bicyclic triazole structure) | 4-F-phenyl | H | $CR^{4a}$ | $CR^{4a}$ | $CR^{4a}$ |
| sec-butyl-triazolone | 4-pyridyl | H | $CR^{4a}$ | $CR^{4a}$ | $CR^{4a}$ |
| tert-butyl-oxadiazole | 3-F-phenyl | H | $CR^{4a}$ | $CR^{4a}$ | $CR^{4a}$ |
| cyclopentyl-oxadiazole | 3-F-phenyl | H | $CR^{4a}$ | $CR^{4a}$ | $CR^{4a}$ |
| sec-butyl-oxadiazole | 3-F-phenyl | H | $CR^{4a}$ | $CR^{4a}$ | $CR^{4a}$ |
| oxadiazole | 3-F-phenyl | H | $CR^{4a}$ | $CR^{4a}$ | $CR^{4a}$ |
| methyl-oxadiazole | 3-F-phenyl | H | $CR^{4a}$ | $CR^{4a}$ | $CR^{4a}$ |

-continued
| $R^{1a}$ | $R^{3a}$ | $R^{4a}$ | $Y^{1a}$ | $Y^{2a}$ | $Y^{3a}$ |
|---|---|---|---|---|---|
| 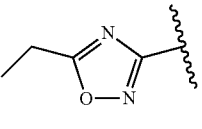 [SMILES: *c1noc(CC)n1] | 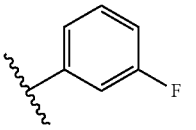 [SMILES: *c1cccc(F)c1] | H | $CR^{4a}$ | $CR^{4a}$ | $CR^{4a}$ |
| 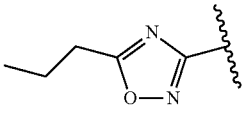 [SMILES: *c1noc(CCC)n1] | 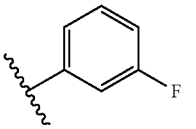 [SMILES: *c1cccc(F)c1] | H | $CR^{4a}$ | $CR^{4a}$ | $CR^{4a}$ |
| 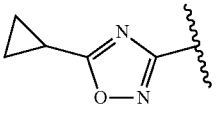 [SMILES: *c1noc(C2CC2)n1] | 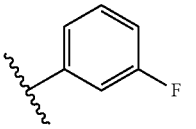 [SMILES: *c1cccc(F)c1] | H | $CR^{4a}$ | $CR^{4a}$ | $CR^{4a}$ |
| 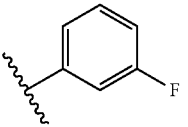 [SMILES: *c1cccc(F)c1] | 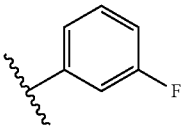 [SMILES: *c1cccc(F)c1] | H | $CR^{4a}$ | $CR^{4a}$ | $CR^{4a}$ |
| 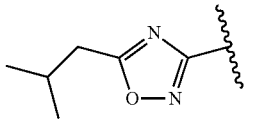 [SMILES: *c1noc(CC(C)C)n1] | 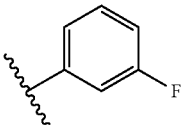 | H | $CR^{4a}$ | $CR^{4a}$ | $CR^{4a}$ |
| 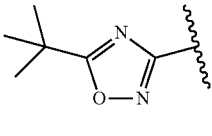 [SMILES: *c1noc(C(C)(C)C)n1] | 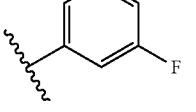 | H | $CR^{4a}$ | $CR^{4a}$ | $CR^{4a}$ |
| 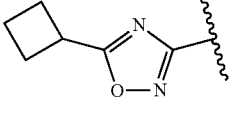 | 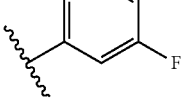 | H | $CR^{4a}$ | $CR^{4a}$ | $CR^{4a}$ |
| 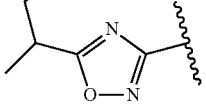 | 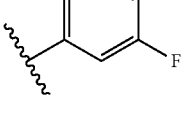 | H | $CR^{4a}$ | $CR^{4a}$ | $CR^{4a}$ |
| 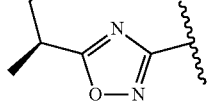 | 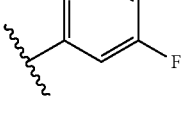 | H | $CR^{4a}$ | $CR^{4a}$ | $CR^{4a}$ |
| 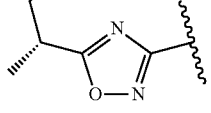 | 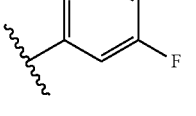 | H | $CR^{4a}$ | $CR^{4a}$ | $CR^{4a}$ |

-continued
| $R^{1a}$ | $R^{3a}$ | $R^{4a}$ | $Y^{1a}$ | $Y^{2a}$ | $Y^{3a}$ |
|---|---|---|---|---|---|
| 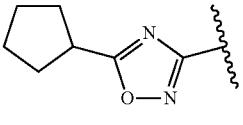 [SMILES: *c1noc(C2CCCC2)n1] | 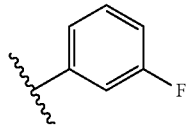 [SMILES: *c1cccc(F)c1] | H | $CR^{4a}$ | $CR^{4a}$ | $CR^{4a}$ |
| 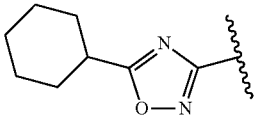 [SMILES: *c1noc(C2CCCCC2)n1] | 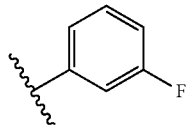 [SMILES: *c1cccc(F)c1] | H | $CR^{4a}$ | $CR^{4a}$ | $CR^{4a}$ |
| 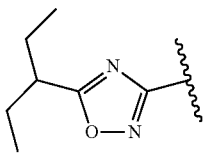 [SMILES: *c1noc(C(CC)CC)n1] | 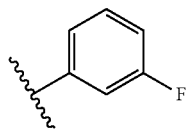 [SMILES: *c1cccc(F)c1] | H | $CR^{4a}$ | $CR^{4a}$ | $CR^{4a}$ |
| 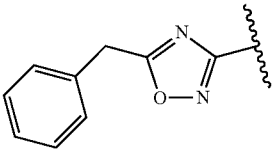 [SMILES: *c1noc(Cc2ccccc2)n1] | 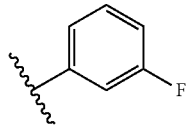 [SMILES: *c1cccc(F)c1] | H | $CR^{4a}$ | $CR^{4a}$ | $CR^{4a}$ |
| 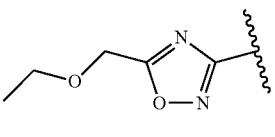 [SMILES: *c1noc(COCC)n1] | 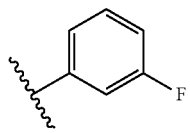 [SMILES: *c1cccc(F)c1] | H | $CR^{4a}$ | $CR^{4a}$ | $CR^{4a}$ |
| 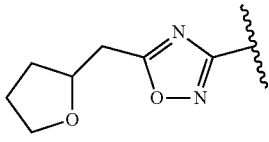 [SMILES: *c1noc(CC2CCCO2)n1] | 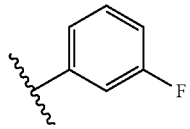 | H | $CR^{4a}$ | $CR^{4a}$ | $CR^{4a}$ |
| 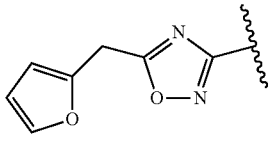 [SMILES: *c1noc(Cc2ccco2)n1] | 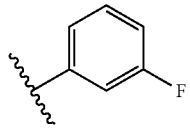 [SMILES: *c1cccc(F)c1] | H | $CR^{4a}$ | $CR^{4a}$ | $CR^{4a}$ |
| 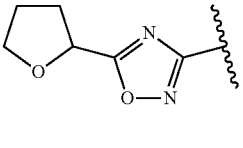 | 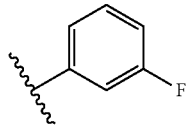 [SMILES: *c1cccc(F)c1] | H | $CR^{4a}$ | $CR^{4a}$ | $CR^{4a}$ |
| 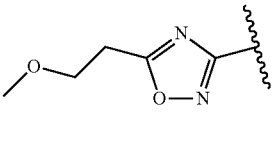 [SMILES: *c1noc(CCOC)n1] | 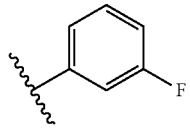 [SMILES: *c1cccc(F)c1] | H | $CR^{4a}$ | $CR^{4a}$ | $CR^{4a}$ |
| 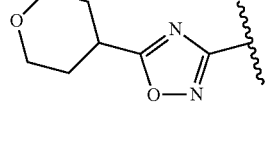 | 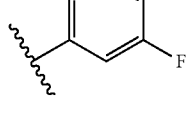 | H | $CR^{4a}$ | $CR^{4a}$ | $CR^{4a}$ |

| R$^{1a}$ | R$^{3a}$ | R$^{4a}$ | Y$^{1a}$ | Y$^{2a}$ | Y$^{3a}$ |
|---|---|---|---|---|---|
| furan-2-yl-1,2,4-oxadiazol-3-yl | 3-fluorophenyl | H | CR$^{4a}$ | CR$^{4a}$ | CR$^{4a}$ |
| (tetrahydrofuran-3-yl)-1,2,4-oxadiazol-3-yl | 3-fluorophenyl | H | CR$^{4a}$ | CR$^{4a}$ | CR$^{4a}$ |
| (1-methoxypropyl)-1,2,4-oxadiazol-3-yl | 3-fluorophenyl | H | CR$^{4a}$ | CR$^{4a}$ | CR$^{4a}$ |
| (1-methylpiperidin-4-yl)-1,2,4-oxadiazol-3-yl | 3-fluorophenyl | H | CR$^{4a}$ | CR$^{4a}$ | CR$^{4a}$ |
| (1-methylpyrrolidin-3-yl)-1,2,4-oxadiazol-3-yl | 3-fluorophenyl | H | CR$^{4a}$ | CR$^{4a}$ | CR$^{4a}$ |
| (1-methylpyrrolidin-2-yl)-1,2,4-oxadiazol-3-yl | 3-fluorophenyl | H | CR$^{4a}$ | CR$^{4a}$ | CR$^{4a}$ |
| (1-ethylpyrrolidin-2-yl)-1,2,4-oxadiazol-3-yl | 3-fluorophenyl | H | CR$^{4a}$ | CR$^{4a}$ | CR$^{4a}$ |
| (1-isopropylpyrrolidin-2-yl)-1,2,4-oxadiazol-3-yl | 3-fluorophenyl | H | CR$^{4a}$ | CR$^{4a}$ | CR$^{4a}$ |
| (1-cyclobutylpyrrolidin-2-yl)-1,2,4-oxadiazol-3-yl | 3-fluorophenyl | H | CR$^{4a}$ | CR$^{4a}$ | CR$^{4a}$ |

-continued

| R$^{1a}$ | R$^{3a}$ | R$^{4a}$ | Y$^{1a}$ | Y$^{2a}$ | Y$^{3a}$ |
|---|---|---|---|---|---|
| 2-methyl-2-(1-methylpyrrolidin-2-yl)-1,3,4-oxadiazole group | 3-fluorophenyl | H | CR$^{4a}$ | CR$^{4a}$ | CR$^{4a}$ |
| 5-(1-(azetidin-1-yl)ethyl)-1,2,4-oxadiazole group | 3-fluorophenyl | H | CR$^{4a}$ | CR$^{4a}$ | CR$^{4a}$ |
| 5-(1-(pyrrolidin-1-yl)ethyl)-1,2,4-oxadiazole group | 3-fluorophenyl | H | CR$^{4a}$ | CR$^{4a}$ | CR$^{4a}$ |
| 5-(1-(cyclopropyl(methyl)amino)ethyl)-1,2,4-oxadiazole group | 3-fluorophenyl | H | CR$^{4a}$ | CR$^{4a}$ | CR$^{4a}$ |
| ethyl 1,2,4-oxadiazole-5-carboxylate group | 3-fluorophenyl | H | CR$^{4a}$ | CR$^{4a}$ | CR$^{4a}$ |
| 5-acetyl-1,2,4-oxadiazole group | 3-fluorophenyl | H | CR$^{4a}$ | CR$^{4a}$ | CR$^{4a}$ |
| 5-(1-hydroxyethyl)-1,2,4-oxadiazole group | 3-fluorophenyl | H | CR$^{4a}$ | CR$^{4a}$ | CR$^{4a}$ |
| 5-(1-methoxyethyl)-1,2,4-oxadiazole group | 3-fluorophenyl | H | CR$^{4a}$ | CR$^{4a}$ | CR$^{4a}$ |
| 5-(pyrrolidin-1-yl)-1,2,4-oxadiazole group | 3-fluorophenyl | H | CR$^{4a}$ | CR$^{4a}$ | CR$^{4a}$ |
| 5-morpholino-1,2,4-oxadiazole group | 3-fluorophenyl | H | CR$^{4a}$ | CR$^{4a}$ | CR$^{4a}$ |

-continued

| $R^{1a}$ | $R^{3a}$ | $R^{4a}$ | $Y^{1a}$ | $Y^{2a}$ | $Y^{3a}$ |
|---|---|---|---|---|---|
| ethyl(methyl)amino-oxadiazolyl | 3-fluorophenyl | H | $CR^{4a}$ | $CR^{4a}$ | $CR^{4a}$ |
| methylamino-oxadiazolyl | 3-fluorophenyl | H | $CR^{4a}$ | $CR^{4a}$ | $CR^{4a}$ |
| isopropyl-oxadiazolyl | 4-fluorophenyl | H | $CR^{4a}$ | $CR^{4a}$ | $CR^{4a}$ |
| sec-butyl-oxadiazolyl | 4-fluorophenyl | H | $CR^{4a}$ | $CR^{4a}$ | $CR^{4a}$ |
| cyclopentyl-oxadiazolyl | 4-fluorophenyl | H | $CR^{4a}$ | $CR^{4a}$ | $CR^{4a}$ |
| tert-butyl-oxadiazolyl | 4-fluorophenyl | H | $CR^{4a}$ | $CR^{4a}$ | $CR^{4a}$ |
| sec-butyl-oxadiazolyl | 2-pyridyl | H | $CR^{4a}$ | $CR^{4a}$ | $CR^{4a}$ |
| (1-methoxyethyl)-oxadiazolyl | 2-pyridyl | H | $CR^{4a}$ | $CR^{4a}$ | $CR^{4a}$ |
| (1-methoxypropyl)-oxadiazolyl | 2-pyridyl | H | $CR^{4a}$ | $CR^{4a}$ | $CR^{4a}$ |
| (1-methylpyrrolidin-2-yl)-oxadiazolyl | 2-pyridyl | H | $CR^{4a}$ | $CR^{4a}$ | $CR^{4a}$ |

-continued

| R¹ᵃ | R³ᵃ | R⁴ᵃ | Y¹ᵃ | Y²ᵃ | Y³ᵃ |
|---|---|---|---|---|---|
| (sec-butyl-1,2,4-oxadiazole) | (4-pyridyl) | H | CR⁴ᵃ | CR⁴ᵃ | CR⁴ᵃ |
| ((S)-sec-butyl-1,2,4-oxadiazole) | (4-pyridyl) | H | CR⁴ᵃ | CR⁴ᵃ | CR⁴ᵃ |
| ((R)-sec-butyl-1,2,4-oxadiazole) | (4-pyridyl) | H | CR⁴ᵃ | CR⁴ᵃ | CR⁴ᵃ |
| (1-methoxyethyl-1,2,4-oxadiazole) | (4-pyridyl) | H | CR⁴ᵃ | CR⁴ᵃ | CR⁴ᵃ |
| (pentan-3-yl-1,2,4-oxadiazole) | (4-pyridyl) | H | CR⁴ᵃ | CR⁴ᵃ | CR⁴ᵃ |
| (1-methoxypropyl-1,2,4-oxadiazole) | (4-pyridyl) | H | CR⁴ᵃ | CR⁴ᵃ | CR⁴ᵃ |
| (pyrrolidin-2-yl-1,2,4-oxadiazole) | (4-pyridyl) | H | CR⁴ᵃ | CR⁴ᵃ | CR⁴ᵃ |
| (N-methylpyrrolidin-2-yl-1,2,4-oxadiazole) | (4-pyridyl) | H | CR⁴ᵃ | CR⁴ᵃ | CR⁴ᵃ |
| (1-(methylamino)ethyl-1,2,4-oxadiazole) | (4-pyridyl) | H | CR⁴ᵃ | CR⁴ᵃ | CR⁴ᵃ |
| (1-(dimethylamino)ethyl-1,2,4-oxadiazole) | (4-pyridyl) | H | CR⁴ᵃ | CR⁴ᵃ | CR⁴ᵃ |

-continued
| R$^{1a}$ | R$^{3a}$ | R$^{4a}$ | Y$^{1a}$ | Y$^{2a}$ | Y$^{3a}$ |
|---|---|---|---|---|---|
| 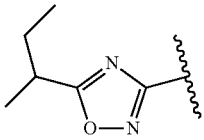 | 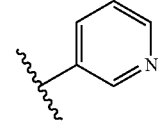 [SMILES: *c1cccnc1] | H | CR$^{4a}$ | CR$^{4a}$ | CR$^{4a}$ |
| 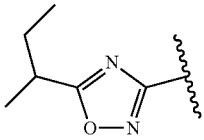 [SMILES: *c1noc(C(C)CC)n1] | 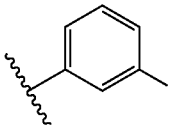 | H | CR$^{4a}$ | N | CR$^{4a}$ |
| 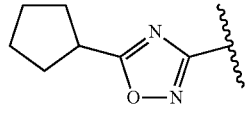 [SMILES: *c1noc(C2CCCC2)n1] | 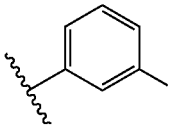 | H | CR$^{4a}$ | N | CR$^{4a}$ |
| 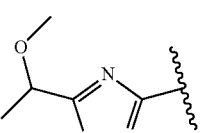 | 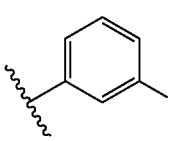 | H | CR$^{4a}$ | N | CR$^{4a}$ |
| 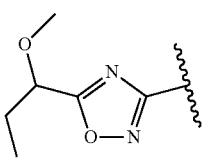 [SMILES: *c1noc(C(CC)OC)n1] | 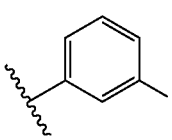 | H | CR$^{4a}$ | N | CR$^{4a}$ |
| 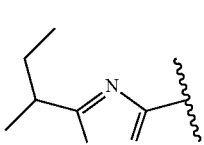 | 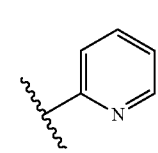 | H | CR$^{4a}$ | N | CR$^{4a}$ |
| 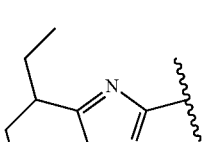 | 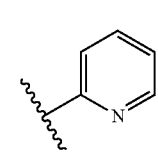 | H | CR$^{4a}$ | N | CR$^{4a}$ |
| 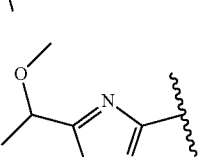 | 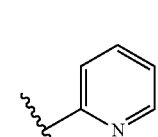 | H | CR$^{4a}$ | N | CR$^{4a}$ |
| 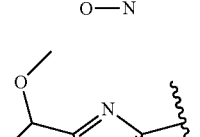 | 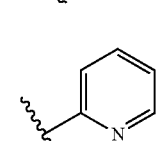 | H | CR$^{4a}$ | N | CR$^{4a}$ |
| 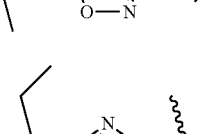 | 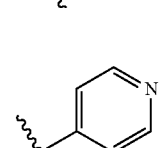 | H | CR$^{4a}$ | N | CR$^{4a}$ |

-continued
| R1a | R3a | R4a | Y1a | Y2a | Y3a |
|---|---|---|---|---|---|
| 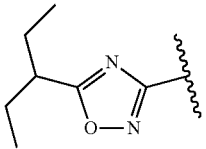 [SMILES: *c1noc(C(CC)CC)n1] | 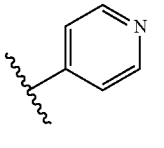 [SMILES: *c1ccncc1] | H | CR4a | N | CR4a |
| 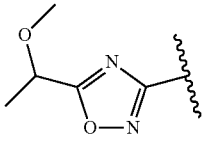 [SMILES: *c1noc(C(C)OC)n1] | 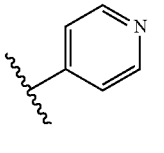 [SMILES: *c1ccncc1] | H | CR4a | N | CR4a |
| 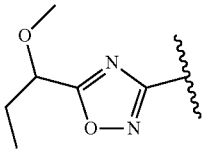 | 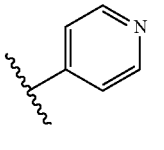 [SMILES: *c1ccncc1] | H | CR4a | N | CR4a |
| 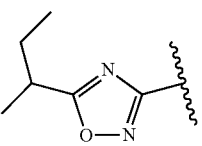 | 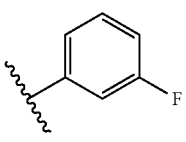 [SMILES: *c1cccc(F)c1] | H | CR4a | CR4a | N |
| 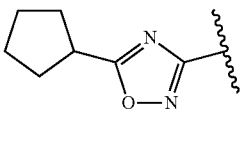 [SMILES: *c1noc(C2CCCC2)n1] | 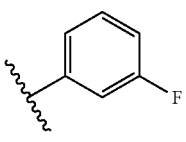 [SMILES: *c1cccc(F)c1] | H | CR4a | CR4a | N |
| 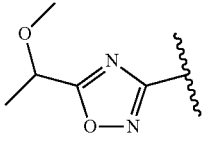 [SMILES: *c1noc(C(C)OC)n1] | 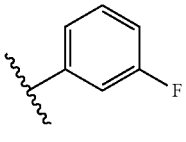 [SMILES: *c1cccc(F)c1] | H | CR4a | CR4a | N |
| 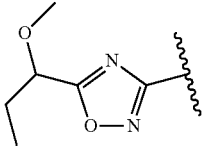 | 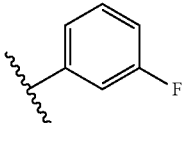 [SMILES: *c1cccc(F)c1] | H | CR4a | CR4a | N |
| 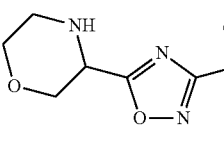 | 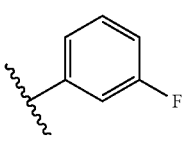 [SMILES: *c1cccc(F)c1] | H | CR4a | CR4a | N |
| 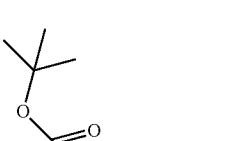 | 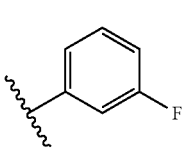 [SMILES: *c1cccc(F)c1] | H | CR4a | CR4a | N |
| 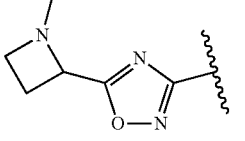 |  | | | | |

-continued
| R$^{1a}$ | R$^{3a}$ | R$^{4a}$ | Y$^{1a}$ | Y$^{2a}$ | Y$^{3a}$ |
|---|---|---|---|---|---|
| 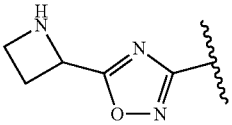 [SMILES: *c1noc(C2CCN2)n1] | 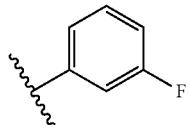 [SMILES: *c1cccc(F)c1] | H | CR$^{4a}$ | CR$^{4a}$ | N |
| 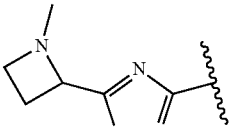 | 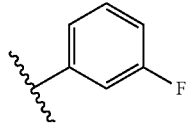 [SMILES: *c1cccc(F)c1] | H | CR$^{4a}$ | CR$^{4a}$ | N |
| 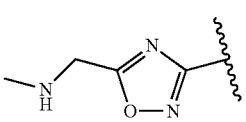 | 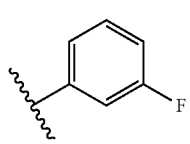 [SMILES: *c1cccc(F)c1] | H | CR$^{4a}$ | CR$^{4a}$ | N |
| 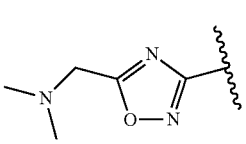 [SMILES: *c1noc(CN(C)C)n1] | 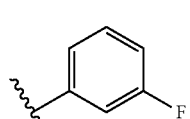 | H | CR$^{4a}$ | CR$^{4a}$ | N |
| 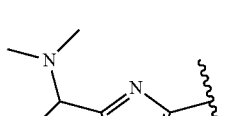 | 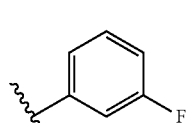 | H | CR$^{4a}$ | CR$^{4a}$ | N |
| 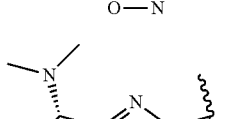 | 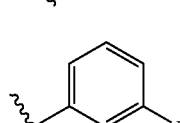 | H | CR$^{4a}$ | CR$^{4a}$ | N |
| 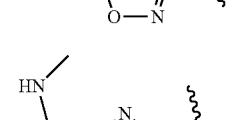 |  | H | CR$^{4a}$ | CR$^{4a}$ | N |
| 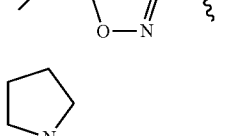 |  | H | CR$^{4a}$ | CR$^{4a}$ | N |
| 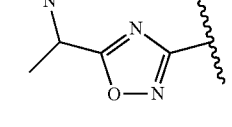 |  | H | CR$^{4a}$ | CR$^{4a}$ | N |
| 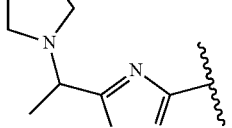 | 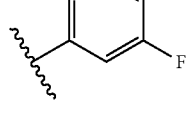 | H | CR$^{4a}$ | CR$^{4a}$ | N |
| 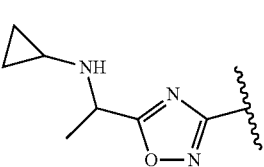 [SMILES: *c1noc(C(C)NC2CC2)n1] | 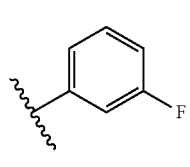 [SMILES: *c1cccc(F)c1] | H | CR$^{4a}$ | CR$^{4a}$ | N |

-continued
| R$^{1a}$ | R$^{3a}$ | R$^{4a}$ | Y$^{1a}$ | Y$^{2a}$ | Y$^{3a}$ |
|---|---|---|---|---|---|
| 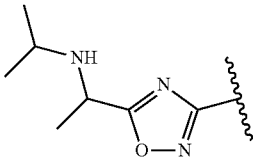 [SMILES: *c1noc(C(C)NC(C)C)n1] | 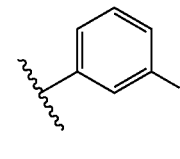 | H | CR$^{4a}$ | CR$^{4a}$ | N |
| 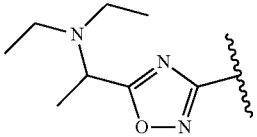 [SMILES: *c1noc(C(C)N(CC)CC)n1] | 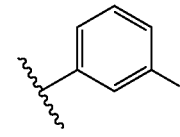 | H | CR$^{4a}$ | CR$^{4a}$ | N |
| 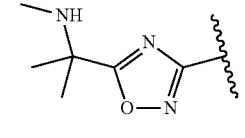 [SMILES: *c1noc(C(C)(C)NC)n1] | 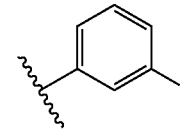 | H | CR$^{4a}$ | CR$^{4a}$ | N |
| 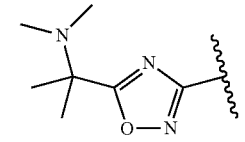 [SMILES: *c1noc(C(C)(C)N(C)C)n1] | 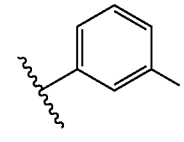 | H | CR$^{4a}$ | CR$^{4a}$ | N |
| 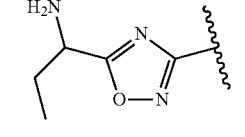 | 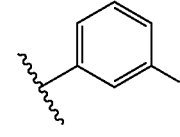 | H | CR$^{4a}$ | CR$^{4a}$ | N |
| 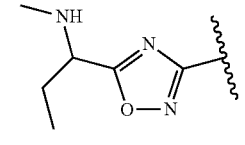 [SMILES: *c1noc(C(CC)NC)n1] | 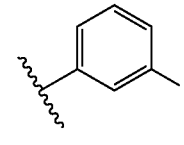 | H | CR$^{4a}$ | CR$^{4a}$ | N |
| 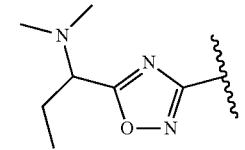 [SMILES: *c1noc(C(CC)N(C)C)n1] | 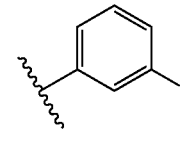 | H | CR$^{4a}$ | CR$^{4a}$ | N |
| 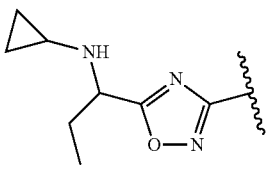 [SMILES: *c1noc(C(CC)NC2CC2)n1] | 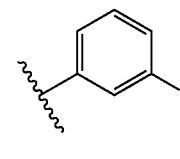 | H | CR$^{4a}$ | CR$^{4a}$ | N |
| 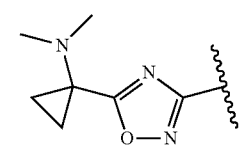 [SMILES: *c1noc(C2(N(C)C)CC2)n1] | 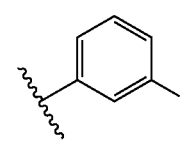 | H | CR$^{4a}$ | CR$^{4a}$ | N |
| 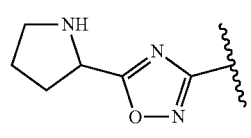 | 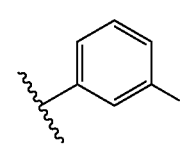 | H | CR$^{4a}$ | CR$^{4a}$ | N |

-continued
| R$^{1a}$ | R$^{3a}$ | R$^{4a}$ | Y$^{1a}$ | Y$^{2a}$ | Y$^{3a}$ |
|---|---|---|---|---|---|
| 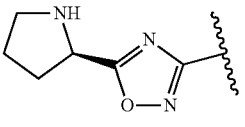 [SMILES: *c1noc([C@H]2CCCN2)n1] | 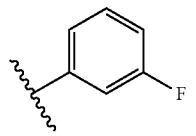 [SMILES: *c1cccc(F)c1] | H | CR$^{4a}$ | CR$^{4a}$ | N |
| 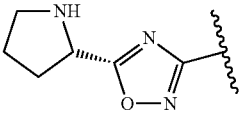 | 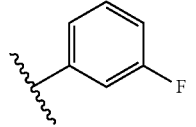 [SMILES: *c1cccc(F)c1] | H | CR$^{4a}$ | CR$^{4a}$ | N |
| 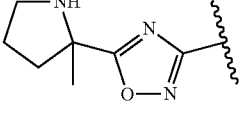 | 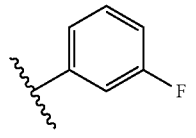 [SMILES: *c1cccc(F)c1] | H | CR$^{4a}$ | CR$^{4a}$ | N |
| 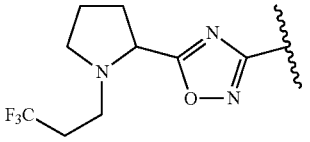 [SMILES: *c1noc(C2CCCN2CCC(F)(F)F)n1] | 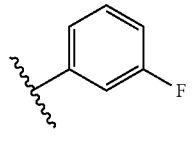 [SMILES: *c1cccc(F)c1] | H | CR$^{4a}$ | CR$^{4a}$ | N |
| 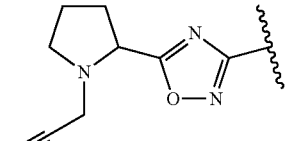 | 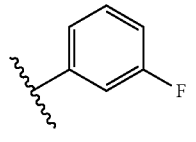 [SMILES: *c1cccc(F)c1] | H | CR$^{4a}$ | CR$^{4a}$ | N |
| 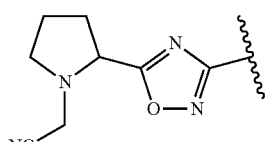 | 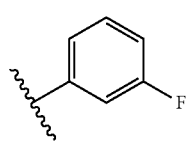 [SMILES: *c1cccc(F)c1] | H | CR$^{4a}$ | CR$^{4a}$ | N |
| 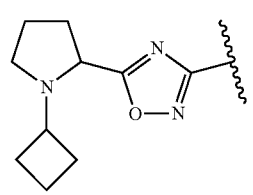 [SMILES: *c1noc(C2CCCN2C2CCC2)n1] | 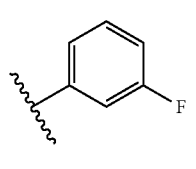 [SMILES: *c1cccc(F)c1] | H | CR$^{4a}$ | CR$^{4a}$ | N |
| 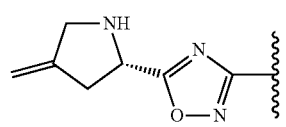 [SMILES: *c1noc([C@@H]2CC(=C)CN2)n1] | 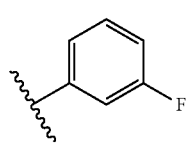 [SMILES: *c1cccc(F)c1] | H | CR$^{4a}$ | CR$^{4a}$ | N |
| 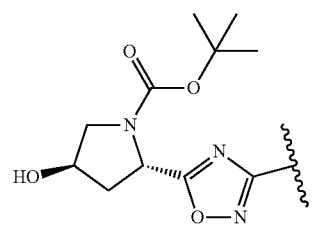 [SMILES: *c1noc([C@@H]2C[C@@H](O)CN2C(=O)OC(C)(C)C)n1] | 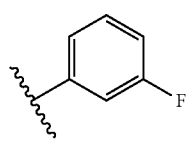 [SMILES: *c1cccc(F)c1] | H | CR$^{4a}$ | CR$^{4a}$ | N |

-continued

| R¹ᵃ | R³ᵃ | R⁴ᵃ | Y¹ᵃ | Y²ᵃ | Y³ᵃ |
|---|---|---|---|---|---|
| (3-F-phenyl pyrrolidinol-oxadiazole) | 3-fluorophenyl | H | CR⁴ᵃ | CR⁴ᵃ | N |
| (N-methyl pyrrolidinol-oxadiazole) | 3-fluorophenyl | H | CR⁴ᵃ | CR⁴ᵃ | N |
| (pyrrolidinol-oxadiazole isomer) | 3-fluorophenyl | H | CR⁴ᵃ | CR⁴ᵃ | N |
| (N-methyl pyrrolidinol-oxadiazole isomer) | 3-fluorophenyl | H | CR⁴ᵃ | CR⁴ᵃ | N |
| (methoxy pyrrolidine-oxadiazole) | 3-fluorophenyl | H | CR⁴ᵃ | CR⁴ᵃ | N |
| (sec-butyl oxadiazole) | 2-pyridyl | H | CR⁴ᵃ | CR⁴ᵃ | N |
| (methoxyethyl oxadiazole) | 2-pyridyl | H | CR⁴ᵃ | CR⁴ᵃ | N |
| (3-pentyl oxadiazole) | 2-pyridyl | H | CR⁴ᵃ | CR⁴ᵃ | N |
| (cyclopentyl oxadiazole) | 2-pyridyl | H | CR⁴ᵃ | CR⁴ᵃ | N |
| (1-methoxypropyl oxadiazole) | 2-pyridyl | H | CR⁴ᵃ | CR⁴ᵃ | N |

| $R^{1a}$ | $R^{3a}$ | $R^{4a}$ | $Y^{1a}$ | $Y^{2a}$ | $Y^{3a}$ |
|---|---|---|---|---|---|
| (2,2-dimethylpyrrolidin-1-yl)ethyl-1,2,4-oxadiazole | pyridin-2-yl | H | $CR^{4a}$ | $CR^{4a}$ | N |
| isopropylamino-ethyl-1,2,4-oxadiazole | pyridin-2-yl | H | $CR^{4a}$ | $CR^{4a}$ | N |
| tert-butylamino-ethyl-1,2,4-oxadiazole | pyridin-2-yl | H | $CR^{4a}$ | $CR^{4a}$ | N |
| pyrrolidin-1-yl-ethyl-1,2,4-oxadiazole | pyridin-2-yl | H | $CR^{4a}$ | $CR^{4a}$ | N |
| dimethylamino-ethyl-1,2,4-oxadiazole | pyridin-2-yl | H | $CR^{4a}$ | $CR^{4a}$ | N |
| methylamino-dimethyl-1,2,4-oxadiazole | pyridin-2-yl | H | $CR^{4a}$ | $CR^{4a}$ | N |
| dimethylamino-dimethyl-1,2,4-oxadiazole | pyridin-2-yl | H | $CR^{4a}$ | $CR^{4a}$ | N |
| methoxyacetamido-propyl-1,2,4-oxadiazole | pyridin-2-yl | H | $CR^{4a}$ | $CR^{4a}$ | N |
| methylamino-propyl-1,2,4-oxadiazole | pyridin-2-yl | H | $CR^{4a}$ | $CR^{4a}$ | N |

-continued
| R$^{1a}$ | R$^{3a}$ | R$^{4a}$ | Y$^{1a}$ | Y$^{2a}$ | Y$^{3a}$ |
|---|---|---|---|---|---|
| 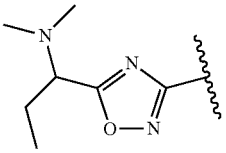 [SMILES: *c1noc(C(CC)N(C)C)n1] | 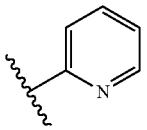 [SMILES: *c1ccccn1] | H | CR$^{4a}$ | CR$^{4a}$ | N |
| 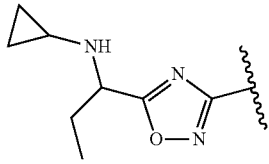 [SMILES: *c1noc(C(CC)NC2CC2)n1] | 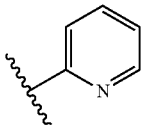 | H | CR$^{4a}$ | CR$^{4a}$ | N |
| 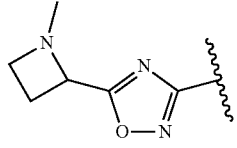 [SMILES: *c1noc(C2CCN2C)n1] | 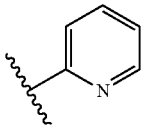 [SMILES: *c1ccccn1] | H | CR$^{4a}$ | CR$^{4a}$ | N |
| 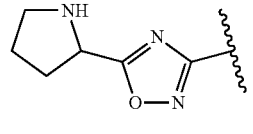 [SMILES: *c1noc(C2CCCN2)n1] | 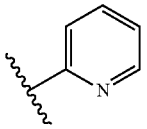 [SMILES: *c1ccccn1] | H | CR$^{4a}$ | CR$^{4a}$ | N |
| 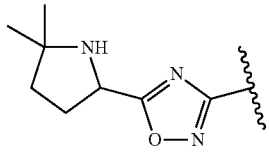 [SMILES: *c1noc(C2CCC(C)(C)N2)n1] | 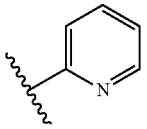 [SMILES: *c1ccccn1] | H | CR$^{4a}$ | CR$^{4a}$ | N |
| 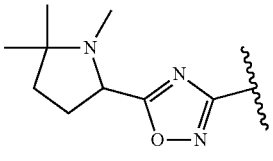 [SMILES: *c1noc(C2CCC(C)(C)N2C)n1] | 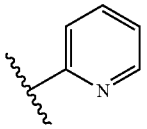 [SMILES: *c1ccccn1] | H | CR$^{4a}$ | CR$^{4a}$ | N |
| 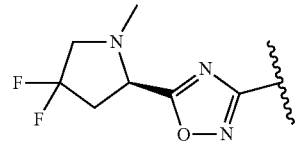 [SMILES: *c1noc([C@H]2CC(F)(F)CN2C)n1] | 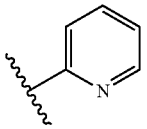 | H | CR$^{4a}$ | CR$^{4a}$ | N |
| 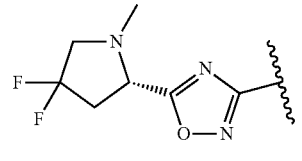 [SMILES: *c1noc([C@@H]2CC(F)(F)CN2C)n1] | 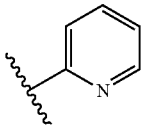 [SMILES: *c1ccccn1] | H | CR$^{4a}$ | CR$^{4a}$ | N |
| 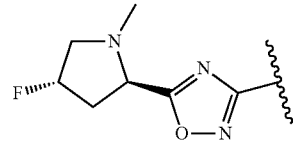 [SMILES: *c1noc([C@H]2C[C@H](F)CN2C)n1] | 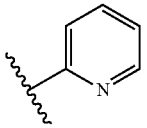 [SMILES: *c1ccccn1] | H | CR$^{4a}$ | CR$^{4a}$ | N |
| 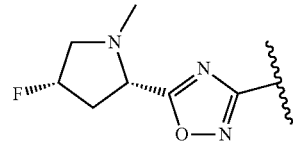 [SMILES: *c1noc([C@@H]2C[C@H](F)CN2C)n1] | 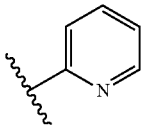 [SMILES: *c1ccccn1] | H | CR$^{4a}$ | CR$^{4a}$ | N |

-continued

| R^{1a} | R^{3a} | R^{4a} | Y^{1a} | Y^{2a} | Y^{3a} |
|---|---|---|---|---|---|
| (4-methoxy-pyrrolidinyl)-1,2,4-oxadiazole | 2-pyridyl | H | CR^{4a} | CR^{4a} | N |
| (pyrrolidinyl-cyclopropyl)-1,2,4-oxadiazole | 2-pyridyl | H | CR^{4a} | CR^{4a} | N |
| (N-methyl-pyrrolidinyl-cyclopropyl)-1,2,4-oxadiazole | 2-pyridyl | H | CR^{4a} | CR^{4a} | N |
| azabicyclic-1,2,4-oxadiazole | 2-pyridyl | H | CR^{4a} | CR^{4a} | N |
| azabicyclic-1,2,4-oxadiazole | 2-pyridyl | H | CR^{4a} | CR^{4a} | N |
| pyrrolizidinyl-1,2,4-oxadiazole | 2-pyridyl | H | CR^{4a} | CR^{4a} | N |
| sec-butyl-1,2,4-oxadiazole | 4-pyridyl | H | CR^{4a} | CR^{4a} | N |
| (1-methoxyethyl)-1,2,4-oxadiazole | 3-pyridyl | H | CR^{4a} | CR^{4a} | N |
| (1-ethylpropyl)-1,2,4-oxadiazole | 4-pyridyl | H | CR^{4a} | CR^{4a} | N |
| (1-methoxypropyl)-1,2,4-oxadiazole | 4-pyridyl | H | CR^{4a} | CR^{4a} | N |

-continued

| $R^{1a}$ | $R^{3a}$ | $R^{4a}$ | $Y^{1a}$ | $Y^{2a}$ | $Y^{3a}$ |
|---|---|---|---|---|---|
| pyrrolidin-2-yl-1,2,4-oxadiazole | 4-pyridyl | H | $CR^{4a}$ | $CR^{4a}$ | N |
| 1-(methylamino)ethyl-1,2,4-oxadiazole | 4-pyridyl | H | $CR^{4a}$ | $CR^{4a}$ | N |
| pyrrolidin-2-yl-1,2,4-oxadiazole | 3-pyridyl | H | $CR^{4a}$ | $CR^{4a}$ | N |
| pyrrolidin-2-yl-1,2,4-oxadiazole | phenyl | H | $CR^{4a}$ | $CR^{4a}$ | N |
| pyrrolidin-2-yl-1,2,4-oxadiazole | 3-chlorophenyl | H | $CR^{4a}$ | $CR^{4a}$ | N |
| pyrrolidin-2-yl-1,2,4-oxadiazole | 4-chlorophenyl | H | $CR^{4a}$ | $CR^{4a}$ | N |
| pyrrolidin-2-yl-1,2,4-oxadiazole | 3-cyano-5-fluorophenyl | H | $CR^{4a}$ | $CR^{4a}$ | N |
| 1-(pyrrolidin-1-yl)ethyl-4-methyl-1,2,4-triazole | 2-pyridyl | H | $CR^{4a}$ | $CR^{4a}$ | N |
| 1,5,5-trimethylpyrrolidin-2-yl-4-methyl-1,2,4-triazole | 2-pyridyl | H | $CR^{4a}$ | $CR^{4a}$ | N |

| $R^{1a}$ | $R^{3a}$ | $R^{4a}$ | $Y^{1a}$ | $Y^{2a}$ | $Y^{3a}$ |
|---|---|---|---|---|---|
| 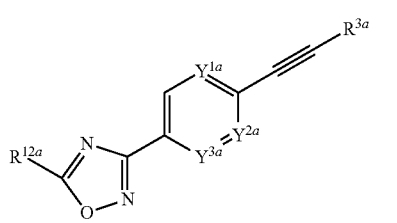 | 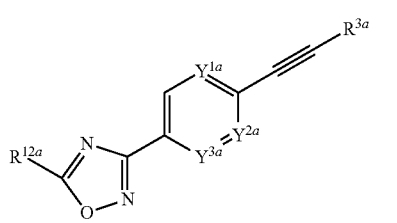 | H | $CR^{4a}$ | $CR^{4a}$ | N |

In certain embodiments, the invention provides compounds of formula IIa or pharmaceutically acceptable salts thereof:

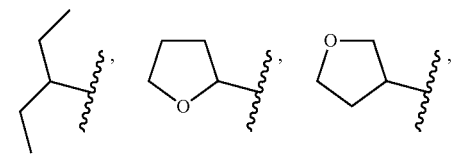

(IIa)

wherein $Y^{1a}$, $Y^{2a}$, and $Y^{3a}$ are each independently $CR^{4a}$ or N;

$R^{3a}$ is alkyl, heteroalkyl, cycloalkyl, heterocycloalkyl, aryl, heteroaryl, aralkyl or heteroaralkyl;

$R^{4a}$ is hydrogen, alkyl, heteroalkyl, cycloalkyl, heterocycloalkyl, aryl, aralkyl, heteroaralkyl, or heteroaryl; and $R^{12a}$ is hydrogen, alkyl, cycloalkyl, heterocyclyl, heteroaryl, heteroalkyl, or aralkyl.

In certain embodiments, $R^{12a}$ is hydrogen, methyl, ethyl, n-propyl, isopropyl, t-butyl, isobutyl, sec-butyl, cyclopropyl, cyclobutyl, cyclopentyl, cyclohexyl, benzyl, methylamine, ethylmethylamine, methylaminomethyl, dimethylaminomethyl, ethoxymethyl, methoxyethyl, acyl, ethoxycarbonyl

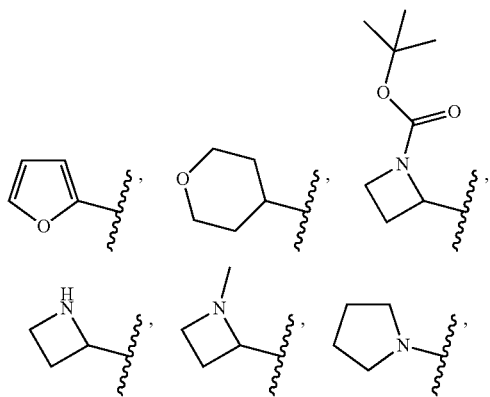

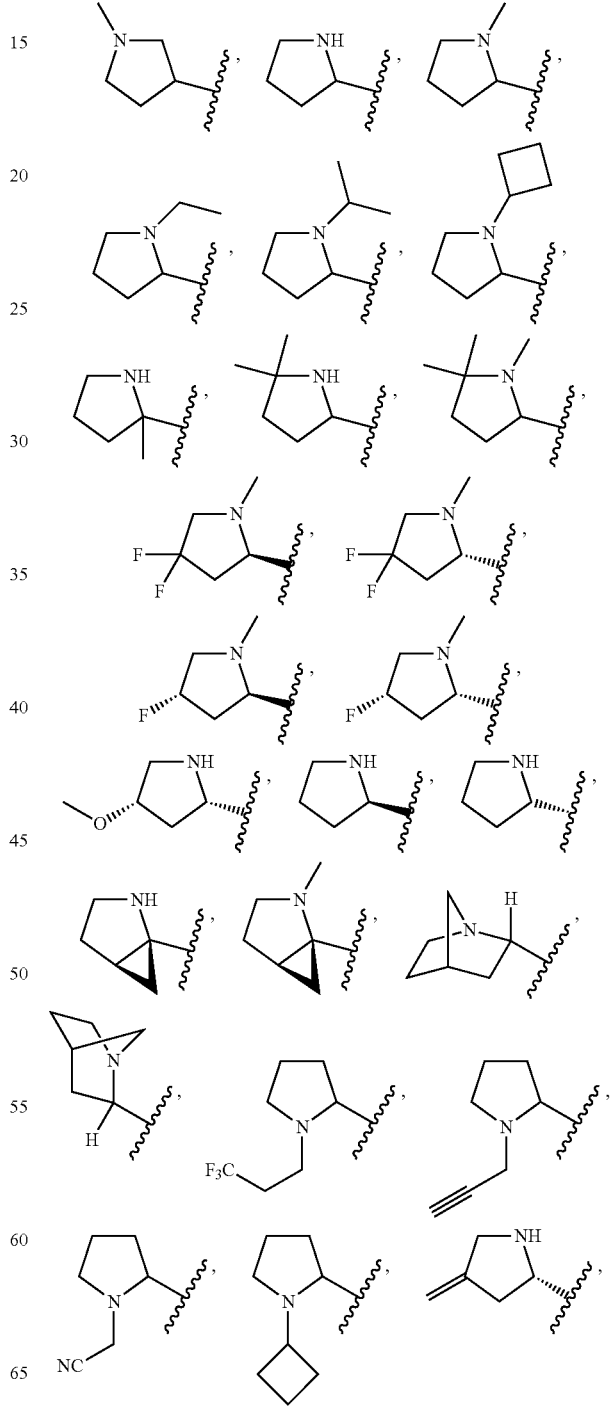

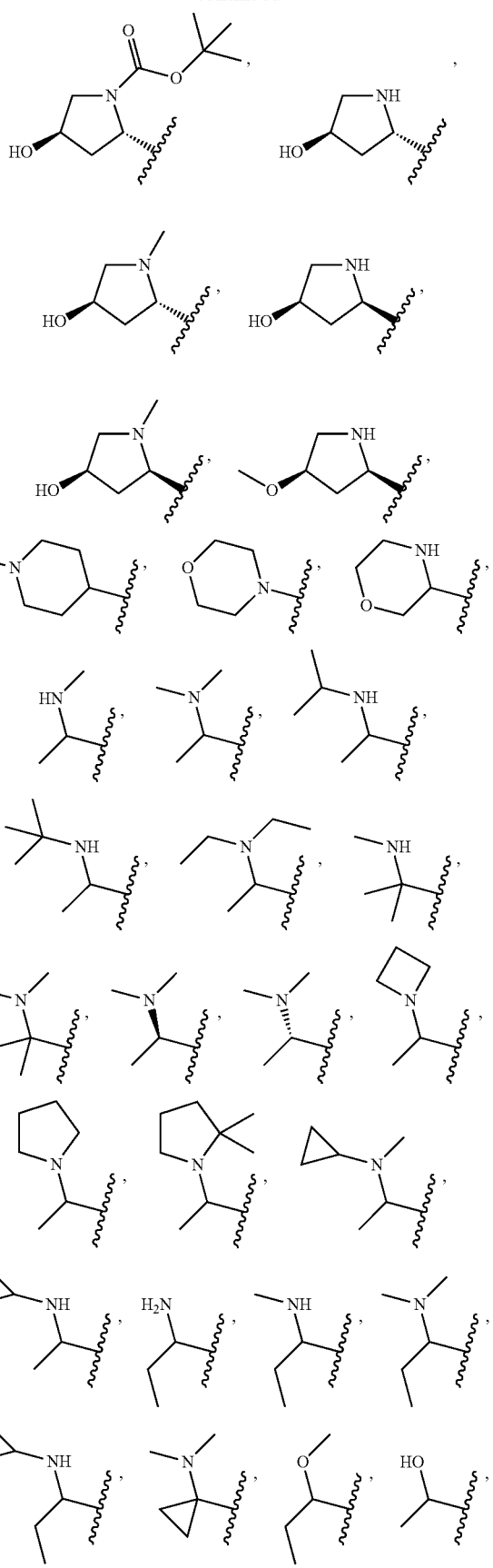

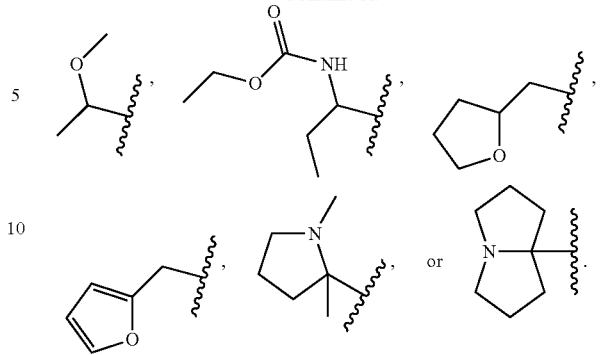

It should be noted that if there is a discrepancy between a depicted structure and a chemical name given that structure, the depicted structure is to be accorded more weight.

As used herein, the term "alkyl" includes linear saturated monovalent hydrocarbon radicals that have 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radicals having 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred to as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo ("haloalkyl").

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkoxy" refers to a straight or branched chain, containing the stated number of carbon atoms and an oxygen atom at the terminal position through which the alkoxy group is attached to the molecule. Examples of alkoxy include, but are not limited to, —O—$CH_3$, —O—$CF_3$, —O—$CH_2$—

CH$_3$, —O—CH$_2$—CH$_2$—CH$_3$, —O—CH—(CH$_3$)$_2$, and —O—CH$_2$—CH$_2$—O—CH$_3$. In one embodiment, the alkoxy is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 (C$_{2-20}$), 2 to 15 (C$_{2-15}$), 2 to 12 (C$_{2-12}$), 2 to 10 (C$_{2-10}$), or 2 to 6 (C$_{2-6}$) carbon atoms, or a branched monovalent hydrocarbon radical of 3 to 20 (C$_{3-20}$), 3 to 15 (C$_{3-15}$), 3 to 12 (C$_{3-12}$), 3 to 10 (C$_{3-10}$), or 3 to 6 (C$_{3-6}$) carbon atoms. Examples of alkynyl groups include, but are not limited to, ethynyl (—C≡CH) and propargyl (—CH$_2$C≡CH). For example, C$_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "aralkyl" refers to a monovalent alkyl group substituted with aryl. Aralkyl includes, but is not limited to, phenylmethyl (benzyl). In certain embodiments, both the alkyl and aryl portions may be optionally substituted with one or more substituents as described herein elsewhere.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl may be bicyclic, tricyclic, or tetracyclic, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

The terms "bicyclic" and "multicyclic" as used herein include fused, spirocylic, and bridged bicyclic and multicyclic compounds.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 (C$_{3-20}$), from 3 to 15 (C$_{3-15}$), from 3 to 12 (C$_{3-12}$), from 3 to 10 (C$_{3-10}$), or from 3 to 7 (C$_{3-7}$) carbon atoms. In certain embodiments, cycloalkyl may be a bicyclic, tricyclic, or tetracyclic ring system, where at least one of the rings is a cycloalkyl ring. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere.

The term "haloalkyl" refers to an alkyl as defined above that is substituted by one or more halo groups. In some embodiments, the haloalkyl is monohaloalkyl, dihaloalkyl or polyhaloalkyl, including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. In some embodiments, the polyhaloalkyl contains up to 12 or 10 or 8 or 6 or 4 or 3 or 2 halo groups. Representative examples of haloalkyl moieties include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl includes alkyl groups having all hydrogen atoms replaced with halo atoms.

The term "halogen" or "halo" includes fluorine, bromine, chlorine, and iodine.

As used herein, and unless otherwise specified, the term "heteroalkyl" refers to a stable straight or branched chain (saturated or unsaturated), or cyclic hydrocarbon radical, or combinations thereof, consisting of the stated number of carbon atoms and at least one, such as one to three, heteroatoms selected from O, N, Si, and S, and wherein the nitrogen and sulfur atoms are optionally oxidized and the nitrogen heteroatom can optionally be quaternized. In certain embodiments, the heteroatom(s) may be placed at any interior position of the heteroalkyl group. In certain embodiments, the heteroatom(s) may be placed at a terminal position, such as the position at which the alkyl group is attached to the remainder of the molecule. In certain embodiments where an oxygen atom is at the terminal position where the alkyl group is attached to the remainder of the molecule, it is referred to as an "alkoxy" group. Examples of heteroalkyl include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms can be consecutive, such as, for example, —CH$_2$—NH—O—CH$_3$ and —CH$_2$—O—Si(CH$_3$)$_3$. In certain embodiments, the heteroalkyl is optionally substituted as described herein elsewhere.

The term "heteroaralkyl" as used herein refers to a monovalent alkyl group substituted with heteroaryl. Heteroaralkyl includes, but is not limited to, pyridylmethyl. In certain embodiments, both the alkyl and heteroaryl portions may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In certain embodiments, each ring of a heteroaryl group can contain one or two O atoms, one or two S atoms, and/or one to four N atoms, provided that the total number of heteroatoms in each ring is four or less and each ring contains at least one carbon atom. In certain embodiments, each ring of a heteroaryl group can contain one O atom, one S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic ring systems, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

The term "heteroatom" includes atoms of any element other than carbon or hydrogen, including, but not limited to, nitrogen, oxygen and sulfur.

As used herein, and unless otherwise specified, the term "heterocycloalkyl" or "heterocyclyl" refers to an optionally substituted monocyclic or multicyclic radical or ring system which contains at least one non-aromatic (saturated or partially saturated) ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, and the other(s) of the rings may be saturated, partially unsaturated, or aromatic and may be carbocyclic or contain one or more heteroatoms independently selected from O, S, and N. In certain embodiments, nitrogen or sulfur atoms may be optionally oxidized and the nitrogen atoms may be optionally quaternized. The heterocycloalkyl or heterocyclyl may be attached to the remainder of the molecule at a heteroatom or a carbon atom. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl or heterocycloalkyl is optionally substituted with one or more substituents as described herein elsewhere.

As used herein, and unless otherwise specified, the terms "optionally substituted" and "substituted" are intended to mean that a group, including, but not limited to, alkyl, alkenyl, alkynyl, cycloalkyl, heteroalkyl, alkoxy, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (=O), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$) NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

It will be noted that the structure of some of the compounds of this invention include asymmetric carbon atoms. It is to be understood accordingly that the stereoisomers arising from such asymmetry (e.g., all enantiomers and diastereomers) are included within the scope of this invention, unless indicated otherwise. Furthermore, the structures and other compounds and moieties discussed in this application also include any tautomers or geometric isomers (e.g., cis/trans or E/Z) thereof. Accordingly, a compound of the present invention may be in the form of one of the possible isomers, rotamers, atropisomers, tautomers or mixtures thereof, for example, as substantially pure geometric (e.g., cis or trans) isomers, diastereomers, optical isomers (e.g., antipodes), racemates or mixtures thereof.

As used herein, and unless otherwise specified, the term "solvate" refers to a compound provided herein or a salt thereof, which further includes a stoichiometric or nonstoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two or more chiral centers is substantially free of other diastereomers. A typical stereomerically pure compound comprises greater than about 80% by weight of one stereoisomer, greater than about 90% by weight of one stereoisomer, greater than about 95% by weight of one stereoisomer, greater than about 97% by weight of one stereoisomer, greater than about 99% by weight, greater than 99.5%, or even greater than 99.9% of one stereoisomer.

In describing an optically active compound, the prefixes R and S are used to denote the absolute configuration of the molecule about its chiral center(s). The (+) and (−) notations are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent(s), after the onset of symptoms of the particular disease (e.g., adjuctive or combination therapy).

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

Any formula given herein is also intended to include unlabeled forms as well as isotopically labeled forms of the compounds. For example, any hydrogen represented by "H" in the formulae herein is intended to represent all isotopic forms of hydrogen (e.g., $^1$H, $^2$H or D, or $^3$H or T) unless otherwise specified; any carbon represented in any of the formulae disclosed herein are intended to represent all isotopic forms of carbon (e.g., $^{11}$C, $^{13}$C, $^{14}$C) unless otherwise specified; similarly, any nitrogen represented by "N" is intended to represent all isotopic forms of nitrogen (e.g., $^{14}$N, $^{18}$N) unless otherwise specified. Enrichment with heavier isotopes, particularly deuterium (i.e., $^2$H or D) may afford certain therapeutic advantages including, but not limited to, greater metabolic stability, for example, increased in vivo half-life or reduced dosage requirements or an improvement in therapeutic index. Other examples of isotopes include, but are not limited to, oxygen, sulfur, phosphorous, fluorine, iodine and chlorine, such as $^{18}$F, $^{15}$O, $^{31}$P, $^{32}$P, $^{35}$S, $^{36}$Cl and $^{125}$I. The invention includes various isotopically labeled compounds as defined herein, for example those into which radioactive isotopes, such as $^3$H, $^{13}$C and $^{14}$C are present. In some embodiments, the atoms in the formulae herein occur in their natural abundance. In some embodiments, one or more hydrogen atom may be enriched in $^2$H; or/and one or more carbon atom may be enriched in $^{11}$C, $^{13}$C or $^{14}$C; or/and one or more nitrogen may be enriched in $^{14}$N.

Isotopically labeled compounds of this invention can generally be prepared by carrying out the procedures disclosed in the schemes or in the examples and preparations described below by substituting a readily available isotopically labeled reagent for a non-isotopically labeled reagent.

Neurological Diseases and Disorders

As used herein, and unless otherwise specified, the term "neurological disorder" includes diseases, disorders or conditions of the central or peripheral nervous system of a mammal. The term "neurological disorder" includes, but is not limited to, neurodegenerative diseases, neuropsychiatric diseases, affective disorders, and loss of cognitive function, learning and memory disorders. The term "neurological disorder" also includes conditions associated with the disorder. For instance, a method of treating a neurodegenerative disorder includes methods of treating loss of memory and/or loss of cognition associated with a neurodegenerative disorder. The term "neurological disorder" also includes diseases or conditions that are implicated, at least in part, in monoamine (e.g., norepinephrine) signaling pathways (e.g., cardiovascular disease).

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Neuropsychiatric Diseases and Disorders

The term "neuropsychiatric disease" includes those neuropsychiatric diseases and disorders set forth in *The Diagnostic and Statistical Manual of Mental Disorders*, Revised, Fourth Ed., (DSM-IV-R), published by the American Psychiatric Association, which is incorporated herein by reference. Such disorders include, but are not limited to, aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, and psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability.

The terms "attention deficit disorder" (ADD), "attention deficit disorder with hyperactivity (ADDH)," and "attention deficit/hyperactivity disorder" (AD/HD), are used herein in accordance with the accepted meanings as found in the *Diagnostic and Statistical Manual of Mental Disorders*, 4th Ed., American Psychiatric Association (DSM-IV™-R). ADD and ADHD include disorders that are most prevalent in children and are associated with increased motor activity and a decreased attention span that may result in inappropriate actions in learning and social situations.

The term "psychosis" includes mental states in which a subject suffering from psychosis undergoes a loss of contact with reality. Symptoms of pyschosis include hallucinations, delusions and impaired sight. In some embodiments, the psychosis may be associated with another neuropsychiatric disorder, for example, schizophrenia, schizophreniform disorder, schizoaffective disorder, brief psychotic disorder, bipolar disorder, clinical depression, psychosocial disorder. In some embodiments, the psychosis is related to general medical conditions, for example, brain tumors, brain damage, an epileptic disorder, dementia, multiple sclerosis, Lyme disease, Alzheimer's disease, Parkinson's disease, electrolyte disorders, hypoglycemia and AIDS. In some embodiments, the psychosis is substance-induced psychosis.

The term "schizophrenia" includes a mental disorders characterized by the disintegration of the process of thinking and emotional responsiveness, and includes symptoms such as auditory hallucinations, paranoid delusions, disorganized speech, disorganized thinking, and extensive withdrawal of the patient's interests from other people. The term "schizophrenia" also includes schizophreniform disorder and schizoaffective disorder. So-called negative symptoms of schizophrenia include affect blunting, anergia, alogia and social withdrawal. Positive symptoms of schizophrenia include delusion and hallucination. Cognitive symptoms of schizophrenia include impairment in obtaining, organizing, and using intellectual knowledge.

Affective Disorders

As used herein, and unless otherwise specified, the term "affective disorder" includes agoraphobia; anxiety and anxiety disorders (including but not limited to acute stress disorder, anxiety due to a general medical condition, dental phobia, generalized anxiety disorder, panic disorder, separation anxiety disorder, social anxiety disorder, social phobia, specific phobia, and substance-induced anxiety disorder); bipolar disorders; depression (including but not limited to dysthymia, major depressive disorder, seasonal affective disorder, seasonal depression, unipolar depression, and postpartum depression); fatigue associated with depression including but limited to chronic fatigue syndrome; mood disorders (including disorders due to a general medical condition and substance-induced mood-disorders); obsessive-compulsive disorder; panic attack; perimenopause, menopause, and male menopause; post-traumatic stress disorder; premenstrual syndrome (PMS) and premenstrual dysphoric disorder (PDD); and sleep disorders including insomnia and narcolepsy.

Cognitive Function, Learning, and Memory Disorders

As used herein, and unless otherwise specified, the terms "cognitive dysfunction," "cognitive function disorder," "learning disorder", and "memory disorder" apply to disorders that may be treated by improving mammalian brain function. The terms include disorders in which subjects exhibit symptoms of memory or learning loss, have impaired ability to learn new information or to recall previously learned information or past efforts. In some embodiments, these disorders cause marked impairment in social or occupational functioning and represent a significant decline from a previous level of functions. In some embodiments, the cognitive dysfunction may be associated with, for example, adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval, semantic memory; sensory integration of environmental cues including temperature, odor, sounds, touch, and taste; social cognition; and speech disorders.

Substance Abuse and Eating Disorders

The term "substance abuse" includes a pattern of behavior in which a subject uses a substance in a abusive manner and is used herein in a manner consistent with its accepted meaning in the art. (See, e.g., DSM-IV™.) Examples of substance abuse include abuse of or addiction to canabbis, cocaine, morphine, opioids, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives.

The term "eating disorder," as used herein, refers to abnormal compulsions to avoid eating or uncontrollable impulses to consume abnormally large amounts of food.

Eating disorders include, but are not limited to, anorexia nervosa, binge eating, bulimia nervosa, cachexia, compulsive eating disorder, emesis, and obesity.

Pain

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, carpal tunnel syndrome, AIDS pain, arthropathy, migraine, trigeminal neuralgia, cardiac ischaemia, neuropathy arising from chronic alcohol use, and diabetic peripheral neuropathic pain (see, e.g., Harrison's *Principles of Internal Medicine*, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, the term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including PGE2 induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

Pharmaceutical Compositions

In certain embodiments, the present invention provides a pharmaceutical composition comprising a compound as disclosed herein and a pharmaceutically acceptable carrier.

The term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329). Except insofar as any conventional carrier is incompatible with the active ingredient, its use in the therapeutic or pharmaceutical compositions is contemplated by the invention.

The pharmaceutical composition may be formulated for particular routes of administration such as oral, intravenous, intraperitoneal, parenteral, enteral, sublingual, vaginal, subcutaneous, transdermal, transmucosal, sublabial, buccal, intracerebral, intracerebroventricular, intramuscular, intranasal, intrathecal, inhalation, topical, or rectal administration, etc. In addition, the pharmaceutical compositions of the present invention may be in a solid form including capsules, tablets, pills, granules, powders, thin film, or suppositories, or in a liquid form including solutions, suspensions, gels, creams, or emulsions. The pharmaceutical compositions may be subjected to conventional pharmaceutical operations such as sterilization and/or can contain conventional inert diluents, lubricating agents or buffering agents, as well as adjuvants, such as preservatives, stabilizers, wetting agents, emulsifiers and buffers.

In some embodiments, the pharmaceutical compositions are tablets or gelatin capsules comprising the active ingredient together with a) diluents, (e.g., lactose, dextrose, sucrose, mannitol, sorbitol, cellulose and/or glycine); b) lubricants, (e.g., silica, talcum, stearic acid, its magnesium or calcium salt and/or polyethyleneglycol); c) binders, (e.g., magnesium aluminum silicate, starch paste, gelatin, tragacanth, methylcellulose, sodium carboxymethylcellulose and/or polyvinylpyrrolidone); d) disintegrants, (e.g., starches, agar, alginic acid or its sodium salt, or effervescent mixtures); or e) absorbents, colorants, flavors and sweeteners; or any combination thereof.

Tablets may be either film coated or enteric coated according to methods known in the art.

Suitable compositions for oral administration include an effective amount of a compound as disclosed herein in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions may contain one or more agents selected from sweetening agents, flavoring agents, coloring agents and preservatives. Tablets generally contain the active ingredient(s) in admixture with nontoxic pharmaceutically acceptable excipients that are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Formulations for oral use may be presented as hard gelatin capsules in which the active ingredient(s) are mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories may be prepared from fatty emulsions or suspensions. Such compositions may be sterilized and/or contain adjuvants, such as preserving, stabilizing, wetting or emulsifying agents, solution promoters, salts for regulating the osmotic pressure and/or buffers. In addition, they may also contain other therapeutic agents. Such compositions may be prepared according to conventional mixing, granulating or coating methods, respectively, and contain about 0.1-75%, or contain about 1-50%, of the active ingredient.

Suitable compositions for transdermal application include an effective amount of a compound as disclosed herein with a carrier. Carriers include absorbable pharmacologically acceptable solvents to assist passage through the skin of the subject. For example, transdermal devices may be in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, (e.g., to the skin and eyes), include aqueous solutions, suspensions, ointments, creams, gels or sprayable formulations, (e.g., for delivery by aerosol and the like). Such topical compositions may contain solubilizers, stabilizers, tonicity enhancing agents, buffers and preservatives.

Topical application may also pertain to an inhalation or to an intranasal application. Such compositions may be delivered in the form of a dry powder (either alone, as a mixture, for example, a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising a compound as disclosed herein as active ingredient(s), since water may facilitate the degradation of certain compounds. Anhydrous pharmaceutical compositions and dosage forms of the invention may be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include hermetically sealed foils, plastics, unit dose containers (e.g., vials), blister packs, and strip packs.

The invention further provides pharmaceutical compositions and dosage forms that comprise one or more agents that reduce the rate by which a compound as disclosed herein will decompose. Such agents, referred to herein as "stabilizers," include antioxidants such as ascorbic acid, pH buffers, or salt buffers, etc.

The pharmaceutical composition or combination of the present invention may be present in a unit dosage in an amount of about 0.001 mg-10 g, 0.01-500 mg or about 0.01-250 mg or about 0.01-150 mg or about 0.01-100 mg, or about 0.01-50 mg of active ingredient for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

A therapeutically effective amount in vivo may range depending on the route of administration, between about 0.0001-500 mg/kg, or between about 0.0001-100 mg/kg, or between about 0.0003-10 mg/kg.

Methods of Treatment, Prevention, and/or Management

Binding to mGluR5 Receptor

In various embodiments, a method of binding a compound as disclosed herein to a metabotropic glutamate receptor, such as mGluR5 is provided. The method comprises contacting mGluR5 with an amount of compound as disclosed herein effective to bind a metabotropic glutamate receptor.

In one embodiment, a method of modulating the activity of mGluR5 via the binding of an mGluR5 ligand to mGluR5 is provided. The method comprises contacting mGluR5 with an amount of a compound as disclosed herein effective to modulate the activity of mGluR5. In one embodiment, the ligand is L-glutamate. In another embodiment, the ligand is a drug molecule or another small molecule known to have binding affinity to mGluR5. In another embodiment, the mGluR5 ligand is a radioactively labeled compound, known to bind to mGluR5. In other embodiments, binding to metabotropic glutamate receptor may be assessed using PET imaging as is known in the art, e.g. utilizing appropriate PET ligands. In some embodiments, the ligand is an allosteric modulator (e.g., a positive or negative allosteric modulator), antagonist, or inverse agonist of mGluR5.

Modulation of mGluR5 Receptor Activity

In various embodiments, a method of modulating (e.g., inhibiting or augmenting) the activity of a metabotropic glutamate receptor, such as mGluR5 is provided. The method comprises contacting the receptor, such as mGluR5, with an amount of a compound as disclosed herein, or a pharmaceutically acceptable salt thereof effective to modulate the activity of a metabotropic glutamate receptor, in vitro or in vivo. In certain embodiments, mGluR5 is contacted with a compound as disclosed herein by administering to a subject a therapeutically effective amount of a compound as disclosed herein, or a pharmaceutically acceptable salt or solvate thereof. In certain embodiments, the subject may be a mammal, such as a human, dog, monkey, baboon, rat, or mouse, preferably a human.

In certain embodiments, a compound as disclosed herein increases or augments the activity of metabotropic glutamate receptor, such as mGluR5. In some embodiments, the activity of mGluR5 is increased or augmented in the presence or absence of an mGluR5 ligand (e.g., glutamate) by about 1%, about 5%, about 10%, about 20%, about 30%, about 40%, about 50%, about 60%, about 70%, about 80%, about 90%, about 95%, about 99% or more, as compared with the activity obtained in the absence of a compound as disclosed herein. In certain such embodiments a compound as disclosed herein will not increase or augment the activity of mGluR5 in the absence of glutamate. In certain embodiments, the increase or augmentation of receptor activity is dose-dependent. Increase of mGluR5 activity may be measured using assays known in the art, for example, by in vitro functional assays as described herein elsewhere. In certain embodiments, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g., utilizing appropriate membrane preparations. In certain embodiments, the assay involves treatment of a test subject (e.g., a mouse or a rat) with a compound as disclosed herein as well as a reference compound, followed by isolation of brain tissue and ex vivo analysis of receptor occupancy. In certain embodiments, the mGluR5 modulator is a positive allosteric modulator.

In certain embodiments, methods of increasing or augmenting the activity of a metabotropic glutamate receptor, such as mGluR5 in the presence or absence of glutamate, in a subject (e.g., human) comprising administering to the subject an effective amount of compound as disclosed herein are provided. In some embodiments, the activity of mGluR5 is increased or augmented by about 1%, about 5%, about 10%, about 20%, about 30%, about 40%, about 50%, about 60%, about 70%, about 80%, about 90%, about 95%, about 99% or more, when measured using an assay known in the art compared to the activity obtained in the absence of administration of a compound as disclosed herein.

In certain embodiments, a method of increasing or augmenting the activity of a metabotropic glutamate receptor, such as mGluR5, by a metabotropic glutamate receptor ligand is provided. In one embodiment, the method comprises contacting mGluR5 receptor with a potentiator, an allosteric agonist, or a positive allosteric modulator of the mGluR5 receptor in an amount effective to increase or augment the activity. In another embodiment, a potentiator, an allosteric agonist, or a positive allosteric modulator of the mGluR5 receptor is a compound as disclosed herein.

In certain embodiments, a compound as disclosed herein inhibits or reduces the activity of metabotropic glutamate receptor, such as mGluR5. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, as compared with the activity obtained without contacting with the compounds as disclosed herein. In certain embodiments, the inhibition or reduction of receptor activity is dose-dependent Inhibition of mGluR5 activity may be measured using assays known in the art, for example, the in vitro functional assays as described herein elsewhere. In one embodiment, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g. utilizing appropriate membrane preparations. In one embodiment, the assay involves treatment of a test subject (e.g., a mice or a rat) with a compound set forth herein as well as a reference compound, followed by isolation of brain tissue and ex vivo analysis of receptor occupancy. In one embodiment, the mGluR5 modulator is a negative allosteric modulator.

In certain embodiments, methods of inhibiting or reducing the activity of a metabotropic glutamate receptor, such as mGluR5, in a subject (e.g., human) comprising administering to the subject an effective amount of a compound as disclosed herein are provided. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, when measured using an assay known in the art and compared to the activity obtained in the absence of administration of a compound as disclosed herein.

In one embodiment, a method of inhibiting or reducing the activity of a metabotropic glutamate receptor, such as mGluR5, by a metabotropic glutamate receptor ligand is provided. In one embodiment, the method comprises contacting mGluR5 receptor with an amount of an antagonist, an inverse agonist, or an allosteric modulator of the mGluR5 receptor effective to inhibit or reduce the activity of the metabotropic glutamate receptor. In another embodiment, an antagonist, an inverse agonist, or an allosteric modulator of the mGluR5 receptor is a compound as disclosed herein.

Treatment, Prevention, and/or Management of mGluR5 Related Disorders and Conditions In certain embodiments, a method of treating, preventing, and/or managing a neurological disorder, such as a neurodegenerative disorder, neuropsychiatric disorder, affective disorder, or a cognitive function, learning or memory disorder, comprising administering to a subject in need thereof an effective amount of a compound as disclosed herein is provided.

In certain embodiments, a method of treating psychosis, schizophrenia, cognitive impairment associated with schizophrenia, or a cognitive disorder (such as Alzheimer's disease), comprising administering to a subject in need thereof an effective amount of a compound as disclosed herein is provided.

In certain embodiments, the compounds as disclosed herein inhibit the activity of mGluR5. In certain embodiments, the compounds as disclosed herein are positive allosteric modulators of mGluR5. In other embodiments, the compounds as disclosed herein are antagonists of mGluR5. In certain embodiments, the compounds as disclosed herein are selective for mGluR5 over other CNS-related targets. In certain embodiments, the compounds as disclosed herein are highly brain penetrable in mammals, such as rodents, and human. In some embodiments, inhibition or potentiation of mGluR5 activity may be assessed by functional assays as described herein elsewhere. In certain embodiments, the efficacious concentration of the compounds set forth herein is less than 10 nM, less than 100 nM, less than 1 µM, less than 10 µM, less than 100 µM, less than 1 µM, or less than 1 mM. In other embodiments, compound's activity may be assessed in various art-recognized animal models.

In some embodiments, a method of treating, preventing, and/or managing a neurodegenerative disease [including but not limited to Alzheimer's disease (including the accompanying symptoms of mild, moderate, or severe cognitive impairment); amyotropic lateral sclerosis (ALS); anoxic and ischemic injuries; ataxia and convulsion (including for the treatment and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g. spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor), and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (including but not limited to neurodegeneration caused by caused by acquired immunodeficiency syndrome (AIDS) and encephalopathies)], comprising administering to a subject in need thereof an effective amount of a compound as disclosed herein is provided. For example, without being limited by a particular theory, mGluR5 modulators may be effective in treating Parkinson's disease, and efficacious in a variety of animal models for Parkinson's disease. See, e.g., Jaeschke, G., et al., *Expert Opin. Ther. Pat.* 2008, 18, 123; Glatthar R., et al., WO 2006/89700 A1.

In some embodiments, a method of treating, preventing, and/or managing a neuropsychiatric disorder (including but limited to: aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability), comprising administering to a subject in need thereof an effective amount of a compound as disclosed herein is provided.

In some embodiments, a method of treating, preventing and/or managing disorders of cognition, learning or memory or of improving cognitive function, memory and learning abilities (including but not limited to: adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval, semantic memory; sensory integration of environmental cues including temperature, odor, sounds, touch, and taste; social cognition; and speech disorders), comprising administering to a subject in need thereof an effective amount of a compound as disclosed herein is provided.

In some embodiments, a method of treating, preventing, and/or managing gastrointestinal disorders (including but not limited to acid reflux; dyspepsia; gastroesophageal reflux disorder (GERD); and irritable bowel syndrome), comprising administering to a subject in need thereof an effective amount of a as disclosed herein is provided. For example, without being limited by a particular theory, mGluR5 modulators may be effective in treating gastrointestinal disorders in human. See, e.g., Jaeschke, G., et al., *Expert Opin. Ther. Pat.* 2008, 18, 123; Bolea C., et al., WO 2004/78728 A1.

In some embodiments, a method of treating, preventing, and/or managing all categories of pain (including but not limited to: pain described in terms of stimulus or nerve response; somatic pain (normal nerve response to a noxious stimulus); neuropathic pain (abnormal response of a injured or altered sensory pathway often without clear noxious input, and including chemotherapy-induced neuropathy, diabetic peripheral neuropathic pain, HIV/AIDS peripheral neuropathy, neuropathic cancer pain, and post-herpetic neuralgia); abdominal pain; acute thermal hyperalgesia; allodynia; burns; causalgia; central pain; complex regional pain syndrome (CRPS); dental pain; dual mechanism pain; dysesthesia; ear ache; episiotomy pain; eye pain; fibromyalgia; gynecological pain including dysmeorrhoea; headache (including acute and chronic tension headache and cluster headache); heart pain; hyperalgesia; hyperesthesia; hyperpathia; itching conditions including contact dermatitis, pruritis, and itch due to atopic dermatitis and hemodialysis; labor pain; low back pain; mechanical allodynia; mixed etiology pain; musculo-skeletal pain including that following physical trauma; neck pain; orofacial pain; pain associated with cystitis; pain cause by convulsion; pain resulting from dysfunction of the nervous system (i.e., organic pain states that share clinical features of neuropathic pain and possibly common pathophysiology mechanism, but are not initiated by an identifiable lesion in any part of the nervous system); pain that is a symptom or a result of a disease state or syndrome (such as AIDS pain, ankylosing spondylitis; arthritis pain, cancer pain, cardiac ischaemia, carpal tunnel syndrome, diabetic peripheral neuropathic pain, episcleritis, gout, inflammation, irritable bowel syndrome, migraine, neuropathy arising from chronic alcohol use, repetitive motion injury, pain from autoimmune diseases, pain from respiratory diseases, scar pain, sciatica; scleritis; and trigeminal neuralgia); pain that is categorized in terms of its severity (mild, moderate, or severe pain); pain that is categorized temporally (chronic pain and acute pain); phantom limb pain; post-surgical pain; reflex sympathetic dystrophy; sinus pain; and visceral pain) comprising administering to a subject in need thereof an effective amount of a compound as disclosed herein is provided. See e.g., Jaeschke, G., et al., *Expert Opin. Ther. Pat.* 2008, 18, 123; Cosford, N. D. P., et al., WO 2003/51315 A2.

In some embodiments, a method of treating, preventing, and/or managing migraine, comprising administering to a subject in need thereof an effective amount of a compound as disclosed herein is provided. For example, without being limited by a particular theory, mGluR5 modulators may be effective in the treatment and prevention of migraine in human, and may have comparable efficacy to triptans in treating migraine. See, e.g., Jaeschke, G., et al., *Expert Opin. Ther. Pat.* 2008, 18, 123.

In some embodiments, a method of treating, preventing, and/or managing substance abuse disorder or eating disorder (including but not limited to the abuse of or addiction to canabbis, cocaine, morphine, opioid, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives; anorexia nervosa; binge eating; bulimia nervosa; cachexia; compulsive eating disorder; emesis; and obesity) comprising administering to a subject in need thereof an effective amount of a compound as disclosed herein is provided. See e.g., Jaeschke, G., et al., *Expert Opin. Ther. Pat.* 2008, 18, 123.

In other embodiments, a method of treating, preventing, and/or managing a disorder of the genitourinary tract or a sexual disorder (including but limited to: lower urinary tract disorder; overactive bladder; urinary incontinence including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psychosexual dysfunction, including without limitation, inhibited sexual desire, inhibited sexual excitement, inhibited female orgasm, inhibited male orgasm, functional dyspareunia, functional vaginismus, and atypical psychosexual dysfunction), comprising administering to a subject in need thereof an effective amount of a compound as disclosed herein is provided.

In other embodiments, a method of treating, preventing, and/or managing cancer, including but not limited to, oral cancer and glioneuronal cancer, comprising administering to a subject in need thereof an effective amount of a compound as disclosed herein is provided.

In some embodiments, a compound as disclosed herein is active in at least one model, which can be used to measure the activity of the compounds and estimate their efficacy in treating a disorder related to mGluR5. For example, when the model is for depression (e.g., mean immobility), the compounds are active when they inhibit mean immobility of a test subject by about 5%, about 10%, about 20%, about 30%, about 40%, about 50%, about 60%, about 70%, about 80%, about 90%, about 95%, about 99%, or more, when compared to vehicle. In some embodiments, the compound as disclosed herein produce a similar disparity in measured endpoint between treated animals and animals administered vehicle.

Other exemplary diseases and conditions that may be treated, prevented, and/or managed using the methods, compounds as disclosed herein and compositions thereof, include, but are not limited to: metabolic diseases including diabetes and pulmonary/respiratory diseases including asthma, chronic obstructive pulmonary disease (COPD), chronic bronchitis, cystic fibrosis, and emphysema.

In certain embodiments, the compounds as described herein treat, prevent, and/or manage a neurological disorder, without causing addiction to said compounds. Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound set forth herein will be that amount of the compound which is the lowest dose effective to produce a therapeutic or prophylactic effect. Such an effective dose will generally depend upon the factors described above. Generally, oral, intravenous, intracerebroventricular, and subcutaneous doses of the compounds set forth herein for a patient will range from about 0.005 to about 100 mg per kilogram or about 0.05 mg per kilogram to about 5 mg per kilogram of body weight per day. In one embodiment, the oral dose of a compound set forth herein will range from about 1 mg to about 1 g per day or 10 mg to about 300 mg per day. In another embodiment, the oral dose of a compound set forth herein will range from about 20 mg to about 250 mg per day. In another embodiment, the oral dose of a compound set forth herein will range from about 100 mg to about 300 mg per day. In another embodiment, the oral dose of a compound set forth herein will range from about 10 mg to about 100 mg per day. In another embodiment, the oral dose of a compound set forth herein will range from about 25 mg to about 50 mg per day. In another embodiment, the oral dose of a compound set forth herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein. In certain embodiments, the second compound is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is lurasidone, olanzapine, risperidone, aripiprazole, amisulpride, asenapine, blonanserin, clozapine, clotiapine, illoperidone, mosapramine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, or L-DOPA.

EXAMPLES

Certain embodiments are illustrated by the following non-limiting examples.

Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., J. Org. Chem., 43: 2923 (1978)) was performed using silica gel 60 (Merck Art 9385) or various MPLC systems.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 400 MHz field strength. Chemical shifts are reported in the form of delta ($\delta$) values given in parts per million (ppm) relative to an internal standard, such as tetramethylsilane (TMS). Alternatively, $^1$H NMR spectra were referenced to signals from residual protons in deuterated solvents as follows: $CDCl_3$=7.25 ppm; DMSO-$d_6$=2.49 ppm;

$C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

As used herein, and unless otherwise specified, "4 Å MS" means 4 angstrom molecular sieves, "Ac" means acetyl, "aq" means aqueous, "BINAP" means 2,2'-bis(diphenylphosphino)-1,1'-binaphthyl, "cat." means catalytic, "DCE" means 1,2-dichloroethane, "DCM" means dichloromethane, "Dess-Martin reagent" means 1,1,1-tris(acetyloxy)-1,1-dihydro-1,2-benziodoxol-3-(1H)-one, "DIEA" means diisopropylethylamine, "DME" means 1,2-dimethoxyethane, "DMF" means dimethylformamide, "DMF-DMA" means N,N-dimethylformamide dimethylacetal, "EDCI" means N-(3-dimethylaminopropyl)-N'-ethylcarbodiimide hydrochloride, "equiv" means equivalent(s), "Et" means ethyl, "EtOAc" means ethyl acetate, "EtOH" means ethanol, "h" or "hr" means hour(s), "HOBt" means hydroxybenzotriazole, Lawesson's reagent means 2,4-bis(4-methoxyphenyl)-1,3,2,4-dithiadiphosphetane-2,4-disulfide, "m-CPBA" means 3-chloro-perbenzoic acid, "Me" means methyl, "MeCN" means acetonitrile, "MeOH" means methanol, "min" means minute(s), "Ms" means mesyl ($CH_3SO_2$—), "PE" means petroleum ether, "PPA" means polyphosphoric acid, "RT" or "rt" means room temperature, "TBD" means 2,3,4,6,7,8-hexahydro-1H-pyrimido[1,2-a]pyrimidine, "TBDMSCl" means tert-butyldimethylsilyl chloride, "t-BuOH" means tert-butanol, "t-BuONa" means sodium tert-butoxide, "TBDMSCl" means tert-butyldimethylsilyl chloride, "TBTU" means 2-(1H-benzotriazole-1-yl)-1,1,3,3-tetramethyluronium tetrafluoroborate, "TEA" means triethylamine, "TFA" means trifluoroacetic acid, "THF" means tetrahydrofuran, "TMSI" means iodotrimethylsilane, "o-Tol" means o-tolyl (2-$CH_3C_6H_4$), "p-Tol" means p-tolyl (4-$CH_3C_6H_4$), "Ts" means tosyl (p-$CH_3C_6H_4SO_2$), and "Xantphos" means 4,5-bis(diphenylphosphino)-9,9-dimethylxanthene.

For those compounds containing basic nitrogen center(s), the HCl salt was prepared by treating the free base with excess HCl etherate solution.

mGluR5 PAM $EC_{50}$ values: ++++ is ≤30 nM; +++ is between 30 and 100 nM; ++ is between 100 and 300 nM; + is between 300 and 1,000 nM. Fold shift at 10 μM: +++ is ≥3; ++ is between 2.0 and 2.9; + is between 1.5 and 1.9.

Example 1.1

Synthesis of Compound 1: 2-cyclopentyl-5-(4-((3-fluorophenyl)ethynyl)phenyl)-1,3,4-oxadiazole

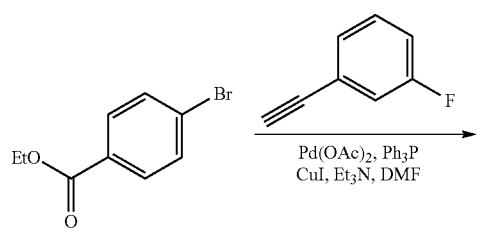

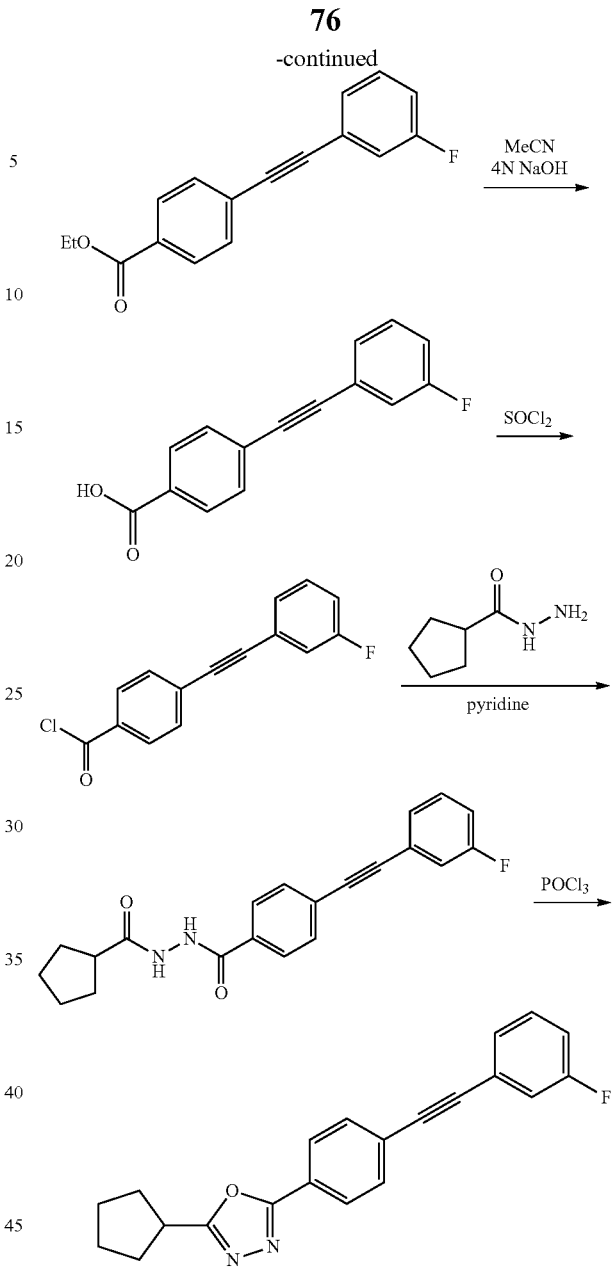

Example 1.1a

Synthesis of ethyl 4-((3-fluorophenyl)ethynyl)benzoate

A solution of ethyl 4-bromobenzoate (3 g, 13.2 mmol, 1 equiv), 1-ethynyl-3-fluorobenzene (3.17 g, 26.4 mmol, 2 equiv), CuI (500 mg, 2.64 mmol, 0.2 equiv), Pd(AcO)$_2$ (600 mg, 2.64 mmol, 0.2 equiv), PPh$_3$ (3.11 g, 11.88 mmol, 0.9 equiv) and Et$_3$N (6.67 g, 66 mmol) in DMF (80 mL) was stirred under N$_2$ at 70° C. for 3.5 h. After cooling to room temperature, the reaction mixture was diluted with water and extracted with ethyl acetate (3×100 mL). The combined organic layers were washed with brine, dried over anhydrous sodium sulfate and concentrated under reduced pressure. After purification by column chromatography, 3.2 g of the desired product was obtained. MS (ESI): 269 (MH$^+$).

Example 1.1b

Synthesis of 4-((3-fluorophenyl)ethynyl)benzoic acid

To a solution of ethyl 4-((3-fluorophenyl)ethynyl)benzoate (3.2 g, 11.9 mmol) in MeCN (100 mL) was added 4 N aqueous sodium hydroxide (1.9 g, 39.6 mmol). The mixture was stirred at 60° C. for 5 h. After the solvent was removed, the aqueous layer was adjusted pH to 3 with 10% HCl, then filtered and dried to give the desired product, which was directly used for the next step without further purification. MS (ESI): 241 (MH$^+$).

Example 1.1c

Synthesis of 4-((3-fluorophenyl)ethynyl)benzoyl chloride

A solution of 4-((3-fluorophenyl)ethynyl)benzoic acid (67 mg, 0.28 mmol) in SOCl$_2$ (3 mL) was stirred at reflux for 0.5 h. Then excess SOCl$_2$ was removed under reduced pressure to give the desired product, which was directly used for the next step.

Example 1.1d

Synthesis of N'-(cyclopentanecarbonyl)-4-((3-fluorophenyl)ethynyl)benzohydrazide To a solution of cyclopentanecarbohydrazide (42 mg, 0.33 mmol) in pyridine (2 mL) was added ((3-fluorophenyl)ethynyl)benzoyl chloride (72 mg, 0.28 mmol) in toluene (5 mL) dropwise. The reaction mixture was stirred at 80° C. for 2 h, then concentrated and purified by column chromatography to give 70 mg of the desired product. MS (ESI): 351 (MH$^+$).

Example 1.1e

Synthesis of 2-cyclopentyl-5-(4-((3-fluorophenyl)ethynyl)phenyl)-1,3,4-oxadiazole A solution of N'-(cyclopentanecarbonyl)-4-((3-fluorophenyl)ethynyl)benzohydrazide (70 mg, 0.2 mmol) in phosphorus oxychloride (8 mL) was stirred at 100° C. for 1 h. Then excess phosphorus oxychloride was removed, the residue was diluted with water and adjusted pH to 8 with aqueous Na$_2$CO$_3$. The aqueous mixture was extracted with ethyl acetate (3×50 mL) and washed with brine. The combined organic layers were dried over Na$_2$SO$_4$, filtered and concentrated and purified by column chromatography to give 42 mg of the desired product. MS (ESI): 333 (MH$^+$); $^1$H NMR (300 MHz, CDCl$_3$) δ 8.05 (d, J=8.5 Hz, 2H), 7.66 (d, J=8.6 Hz, 2H), 7.38-7.34 (m, 2H), 7.25-7.24 (m, 1H), 7.12-7.08 (m, 1H), 3.44-3.39 (m, 1H), 2.22-2.13 (m, 2H), 2.07-1.98 (m, 2H), 1.94-1.88 (m, 2H), 1.82-1.17 (m, 2H). mGluR5 PAM EC$_{50}$: +. Fold shift at 10 μM: +++.

Example 1.2

Synthesis of Compound 2: 2-(sec-butyl)-5-(4-((3-fluorophenyl)ethynyl)phenyl)-1,3,4-oxadiazole

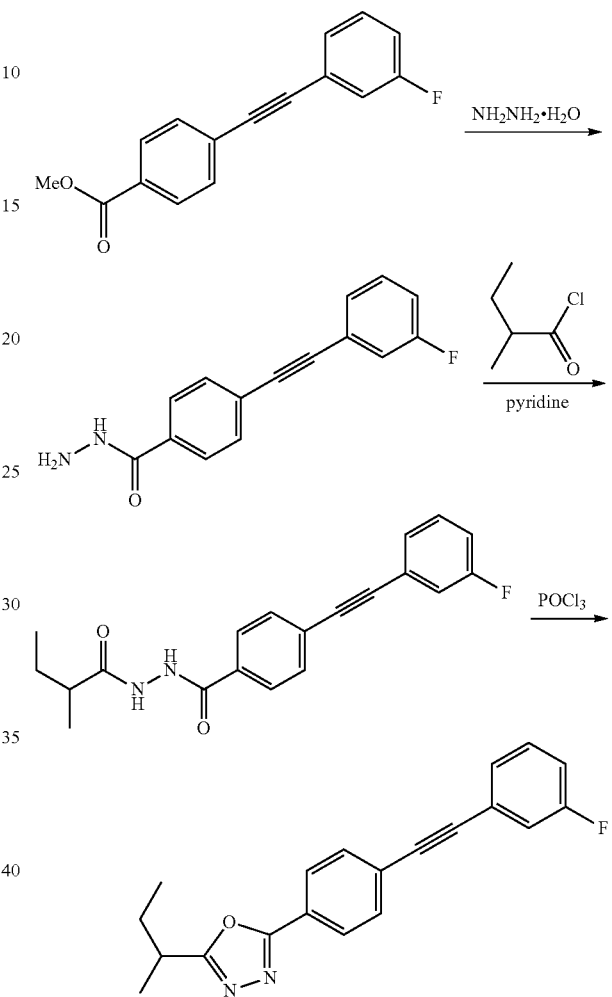

Example 1.2a

Synthesis of 4-((3-fluorophenyl)ethynyl)benzohydrazide

To a solution of methyl 4-((3-fluorophenyl)ethynyl)benzoate (0.9 g, 3.5 mmol) in MeOH (20 mL) was added 80% hydrazine hydrate (10 mL). The reaction mixture was stirred at reflux for 2 h, then concentrated to give the desired product, which was directly used for the next step without further purification. MS (ESI): 255 (MH$^+$).

Example 1.2b

Synthesis of 4-((3-fluorophenyl)ethynyl)-N'-(2-methylbutanoyl)benzohydrazide The title compound was prepared according to the experimental procedure described in Example 1.1d. MS (ESI): 339 (MH$^+$).

Example 1.2c

Synthesis of 2-(sec-butyl)-5-(4-((3-fluorophenyl)ethynyl)phenyl)-1,3,4-oxadiazole The title compound was prepared according to the experimental procedure described in Example 1.1e. MS (ESI): 321 (MH$^+$); $^1$H NMR (300 MHz, CDCl$_3$) δ 8.06 (d, J=8.6 Hz, 2H), 7.68 (d, J=8.6 Hz, 2H), 7.37-7.34 (m, 2H), 7.28-7.24 (m, 1H), 7.12-7.09 (m, 1H), 3.16-3.09 (m, 1H), 1.99-1.91 (m, 1H), 1.83-1.73 (m, 1H), 1.46 (d, J=7.0 Hz, 3H), 1.04-0.99 (t, J=7.4 Hz, 3H). mGluR5 PAM EC$_{50}$: ++. Fold shift at 10 µM: ++.

Example 1.3

Synthesis of Compound 3: 2-(pentan-3-yl)-5-(4-(pyridin-4-ylethynyl)phenyl)-1,3,4-oxadiazole

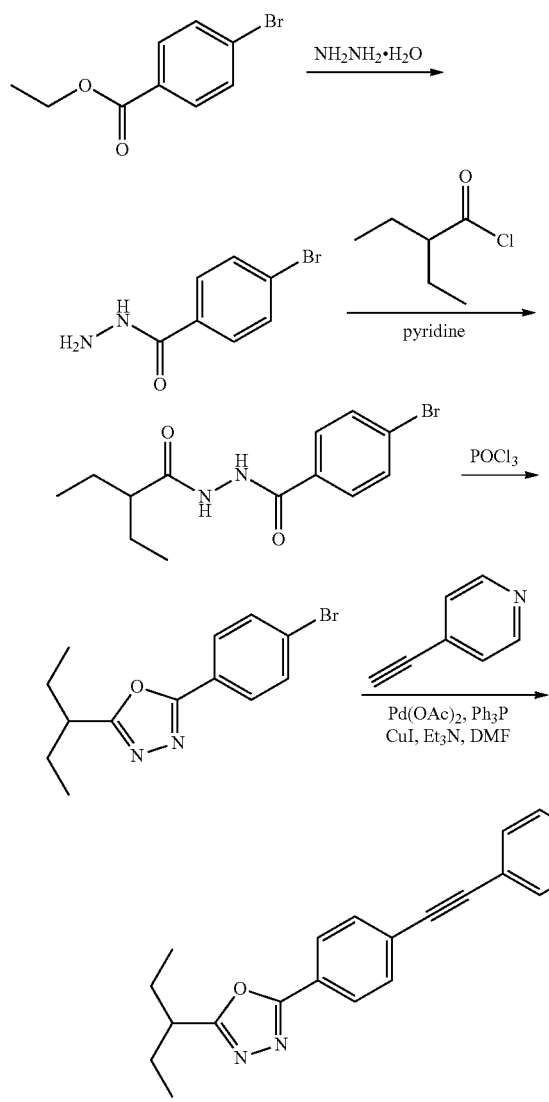

Example 1.3a

Synthesis of 4-bromo-N'-(2-ethylbutanoyl)benzohydrazide

The title compound was prepared according to the experimental procedure described in Example 1.1d. MS (ESI): 313, 315 (MH$^+$).

Example 1.3b

Synthesis of 2-(4-bromophenyl)-5-(pentan-3-yl)-1,3,4-oxadiazole

The title compound was prepared according to the experimental procedure described in Example 1.1e. MS (ESI): 295, 297 (MH$^+$).

Example 1.3c

Synthesis of 2-(pentan-3-yl)-5-(4-(pyridin-4-ylethynyl)phenyl)-1,3,4-oxadiazole

The title compound was prepared according to the experimental procedure described in Example 2.1c. MS (ESI): 318 (MH$^+$); $^1$H NMR (300 MHz, CD$_3$OD) δ 8.90 (br s, 2H), 8.23-8.15 (m, 4H), 7.91 (d, J=7.7 Hz, 2H), 3.03-2.98 (m, 1H), 1.93-1.83 (m, 4H), 1.01-0.96 (t, J=7.3 Hz, 6H). mGluR5 PAM EC$_{50}$: +++. Fold shift at 10 µM: +++.

Example 1.4

Synthesis of Compound 4: 2-(4-((3-fluorophenyl)ethynyl)phenyl)-5-(pentan-3-yl)-1,3,4-oxadiazole

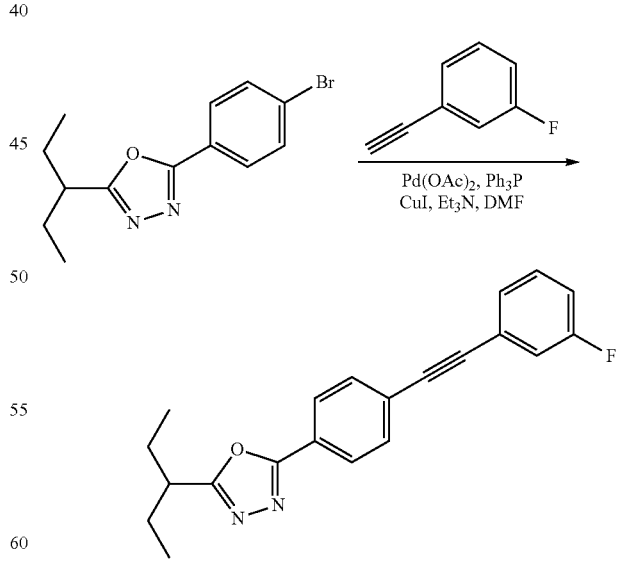

The title compound was prepared according to the experimental procedure described in Example 2.1c. MS (ESI): 335 (MH$^+$); $^1$H NMR (300 MHz, CDCl$_3$) δ 8.06 (d, J=8.4 Hz, 2H), 7.67 (d, J=8.4 Hz, 2H), 7.37-7.34 (m, 2H), 7.26-7.25 (m, 1H), 7.13-7.06 (m, 1H), 2.99-2.94 (m, 1H), 1.91-1.74

(m, 4H), 0.99-0.94 (t, J=7.4 Hz, 6H). mGluR5 PAM EC$_{50}$: +++. Fold shift at 10 μM: +++.

Example 2.1

Synthesis of Compound 5: 2-(4-(phenylethynyl) phenyl)-3a,4,5,6,7,7a-hexahydro-1H-benzo[d]imidazole

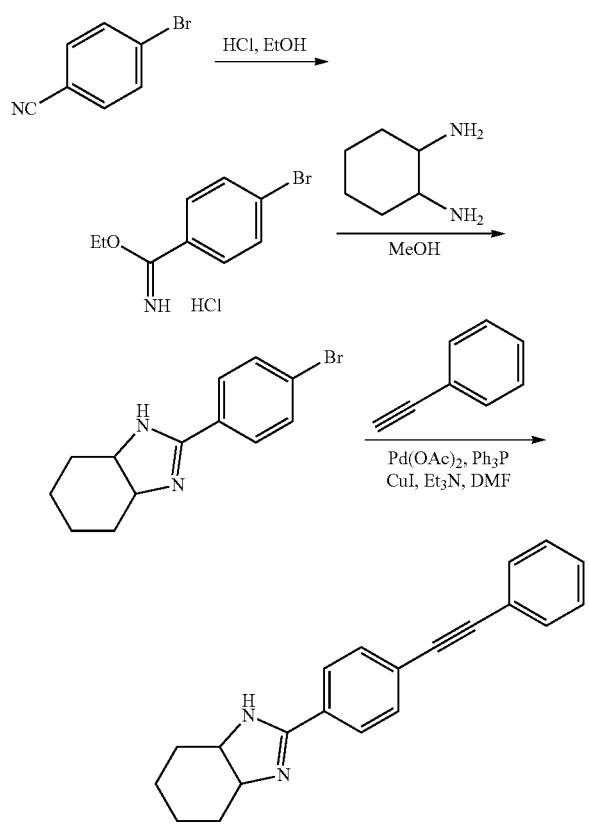

Example 2.1a

Synthesis of ethyl 4-bromobenzimidate hydrochloride

To a solution of 4-bromobenzonitrile (2 g, 11.0 mmol) in anhydrous ethanol (70 mL) was bubbled HCl gas for 10 minutes. After stirring at room temperature overnight, the mixture was concentrated to give the desired product, which was used for the next step without further purification. MS (ESI): 228, 230 (MH$^+$).

Example 2.1b

Synthesis of 2-(4-bromophenyl)-3a,4,5,6,7,7a-hexahydro-1H-benzo[d]imidazole

A solution of cyclohexane-1,2-diamine (324 mg, 1.22 mmol) and ethyl 4-bromobenzimidate hydrochloride (750 mg, 1.22 mmol) in methanol (30 mL) was stirred overnight. After diluting with water, the reaction mixture was adjusted to pH 8 with aq Na$_2$CO$_3$ and extracted with EtOAc (3×50 mL). The combined organic layers were washed with brine and dried over Na$_2$SO$_4$. Then the solvent was removed to give 510 mg of the desired product, which was purified by column chromatography. MS (ESI): 279, 281 (MH$^+$).

Example 2.1c Synthesis of 2-(4-(phenylethynyl) phenyl)-3a,4,5,6,7,7a-hexahydro-1H-benzo[d]imidazole A solution of 2-(4-bromophenyl)-3a,4,5,6,7,7a-hexahydro-1H-benzo[d]imidazole (237 mg, 0.85 mmol), 1-ethynylbenzene (216 mg, 2.12 mmol), Pd(OAc)$_2$ (38.2 mg, 0.17 mmol), PPh$_3$ (200 mg, 0.76 mmol), CuI (16.2 mg, 0.085 mmol) and Et$_3$N (0.7 mL) in DMF (8 mL) was stirred in a sealed tube at 70° C. for 3.5 hours. After cooling to room temperature, the reaction mixture was diluted with H$_2$O and extracted with EtOAc (2×50 mL). The combined organic layers were washed with brine and dried over anhydrous sodium sulfate, then concentrated under reduced pressure to provide 175 mg of the desired compound. MS (ESI): 301 (MH$^+$); $^1$H NMR (300 MHz, CDCl$_3$) δ 7.79 (d, J=8.5 Hz, 2H), 7.62-7.52 (m, 4H), 7.41-7.35 (m, 3H), 5.06 (br s, 1H), 3.16 (m, 2H), 2.52-2.17 (m, 2H), 1.87 (d, J=7.9 Hz, 2H), 1.71-1.32 (m, 4H).

Example 2.2

Synthesis of Compound 6: 3-(4-((4-fluorophenyl) ethynyl)phenyl)-1,5,6,7,8,8a-hexahydroimidazo[1,5-a]pyridine

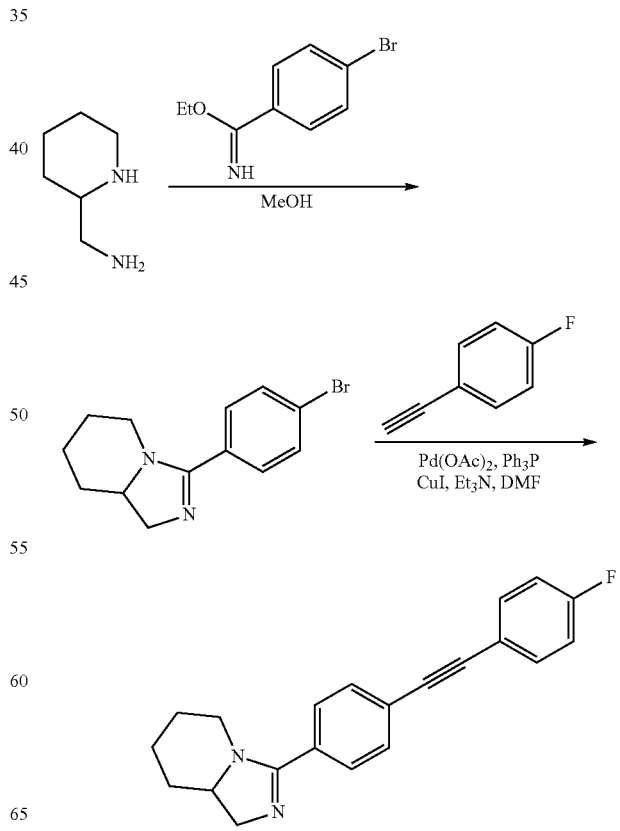

Example 2.2a

Synthesis of 3-(4-bromophenyl)-1,5,6,7,8,8a-hexahydroimidazo[1,5-a]pyridine

The title compound was prepared according to the experimental procedure described in Example 2.1b. MS (ESI): 279,281 (MH+).

Example 2.2b

Synthesis of 3-(4-((4-fluorophenyl)ethynyl)phenyl)-1,5,6,7,8,8a-hexahydroimidazo[1,5-a]pyridine The title compound was prepared according to the experimental procedure described in Example 2.1c. MS (ESI): 319 (MH+); $^1$H NMR (300 MHz, CDCl$_3$) δ 7.57-7.46 (m, 6H), 7.09-7.03 (t, J=8.7 Hz, 2H), 4.00-3.92 (m, 1H), 3.69-3.58 (m, 2H), 3.55-3.42 (m, 1H), 2.99-2.89 (m, 1H), 2.09-2.05 (m, 1H), 1.97-1.88 (m, 1H), 1.77-1.73 (m, 1H), 1.58-1.26 (m, 3H).

Example 3.1

Synthesis of Compound 7: 2-(4-(phenylethynyl)phenyl)-3a,4,5,6,7,7a-hexahydro-1H-benzo[d]imidazole DMSO (0.11 mL, 1.58 mmol) in dichloromethane (3 mL) dropwise over 5 min. After 10 min, 2-(4-bromophenyl)-3a,4,5,6,7,7a-hexahydro-1H-benzo[d]imidazole (0.2 g, 0.72 mmol) in dichloromethane (20 mL) was added over 10 min, followed by addition of triethylamine (0.5 mL) dropwise over 10 min. The mixture was gradually warmed to room temperature over 6 h, and then quenched with water. The organic phase was washed with brine, dried over Na$_2$SO$_4$, concentrated, and purified by column chromatography to give 152 mg of the desired product. MS (ESI): 277, 279 (MH+).

Example 3.1b

Synthesis of 2-(4-(phenylethynyl)phenyl)-4,5,6,7-tetrahydro-1H-benzo[d]imidazole The title compound was prepared according to the experimental procedure described in Example 2.1c. MS (ESI): 299 (MH+); $^1$H NMR (300 MHz, CDCl$_3$) δ 7.78 (d, J=8.4 Hz, 2H), 7.58-7.52 (m, 4H), 7.38-7.35 (m, 3H), 2.67 (br s, 4H), 1.87 (br s, 4H).

Example 3.2

Synthesis of Compound 8: 3-(4-((4-fluorophenyl)ethynyl)phenyl)-5,6,7,8-tetrahydroimidazo[1,5-a]pyridine

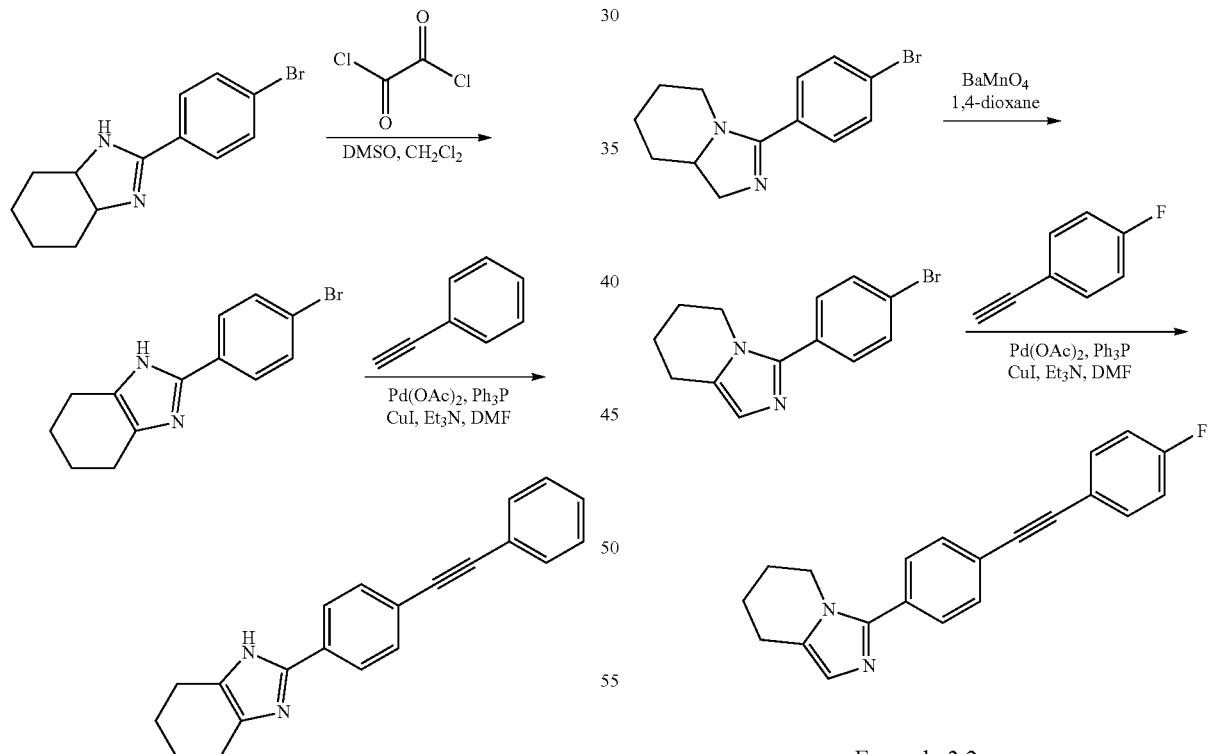

Example 3.1a

Synthesis of 2-(4-bromophenyl)-4,5,6,7-tetrahydro-1H-benzo[d]imidazole

To a stirred solution of oxalyl chloride (0.1 g, 0.79 mmol) in dichloromethane (2 mL) under N$_2$ at −78° C. was added

Example 3.2a

Synthesis of 3-(4-bromophenyl)-5,6,7,8-tetrahydroimidazo[1,5-a]pyridine

A solution of 3-(4-bromophenyl)-1,5,6,7,8,8a-hexahydroimidazo[1,5-a]pyridine (0.5 g, 1.8 mmol) and barium manganate (2 g, 7.8 mmol) in 1,4-dioxane (30 mL) was stirred at reflux for 2 days. Then the mixture was diluted with water (100 mL) and extracted with ethyl acetate (3×100 mL). After washing with brine and drying over Na₂SO₄, the combined organic layers were concentrated and purified by column chromatography to give 75 mg of the desired product. MS (ESI): 277, 279 (MH⁺).

Example 3.2b

Synthesis of 3-(4-((4-fluorophenyl)ethynyl)phenyl)-5,6,7,8-tetrahydroimidazo[1,5-a]pyridine The title compound was prepared according to the experimental procedure described in Example 2.1c. MS (ESI): 317 (MH⁺); ¹H NMR (300 MHz, CDCl₃) δ 7.70-7.68 (m, 2H), 7.60-7.51 (m, 4H), 7.09-7.04 (t, J=8.7 Hz, 2H), 6.92 (s, 1H), 4.12-4.08 (t, J=5.7 Hz, 2H), 2.92-2.88 (t, J=6.6 Hz, 2H), 1.99-1.84 (m, 4H).

Example 4.1

Synthesis of Compound 9: 3-cyclopentyl-5-(4-((3-fluorophenyl)ethynyl)phenyl)-4H-1,2,4-triazole Example 4.1b Synthesis of 3-cyclopentyl-5-(4-((3-fluorophenyl)ethynyl)phenyl)-4H-1,2,4-triazole The title compound was prepared according to the experimental procedure described in Example 2.1c. MS (ESI): 332 (MH⁺); ¹H NMR (300 MHz, CDCl₃) δ 10.46 (br s, 1H), 8.08 (d, J=8.4 Hz, 2H), 7.62 (d, J=8.4 Hz, 2H), 7.35-7.32 (m, 2H), 7.24 (d, J=1.9 Hz, 1H), 7.10-7.03 (m, 1H), 3.31-3.26 (m, 1H), 2.24-2.16 (m, 2H), 1.97-1.86 (m, 4H), 1.79-1.73 (m, 2H).

Example 4.2

Synthesis of Compound 10: 2-(4-methyl-5-(1-(pyrrolidin-1-yl)ethyl)-4H-1,2,4-triazol-3-yl)-5-(pyridin-2-ylethynyl)pyridine

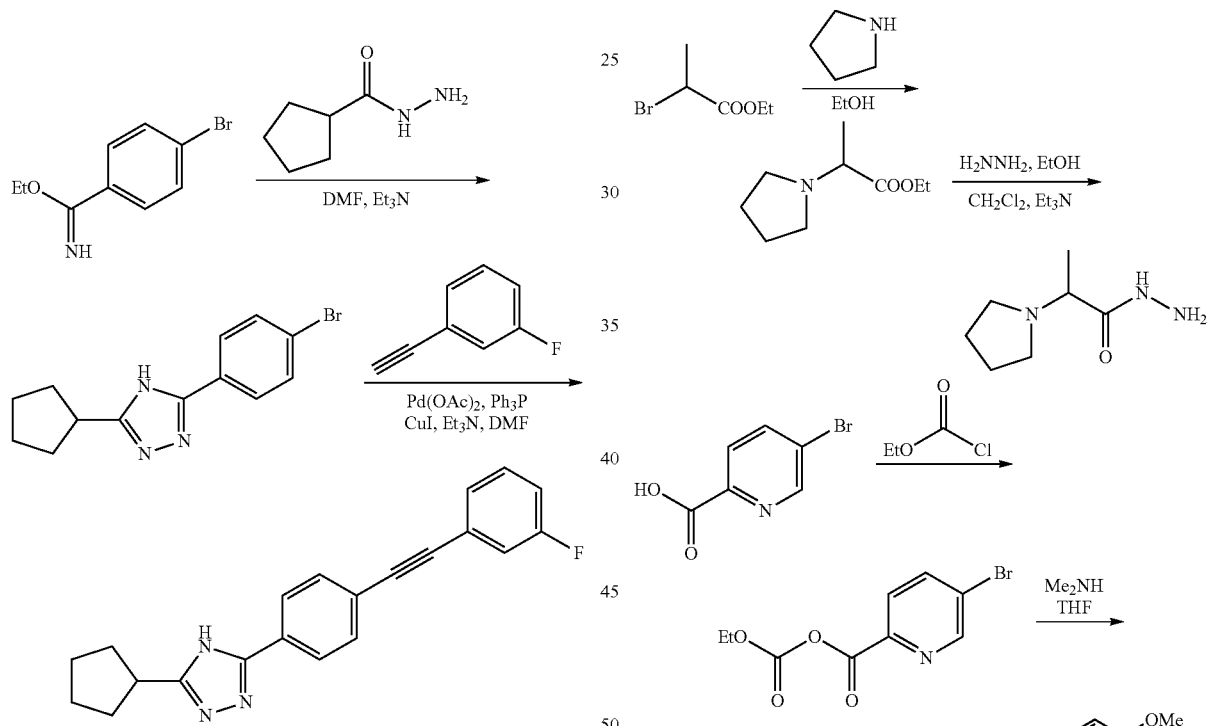

Example 4.1a

Synthesis of 3-(4-bromophenyl)-5-cyclopentyl-4H-1,2,4-triazole

To a solution of cyclopentanecarbohydrazide (204 mg, 1.6 mmol) and ethyl 4-bromobenzimidate (383 mg, 1.7 mmol) in DMF (8 mL) was added Et₃N (1 mL) and the reaction mixture was stirred at 90° C. overnight. After cooling to room temperature, the mixture was diluted with water (50 mL) and extracted with ethyl acetate (3×50 mL). The combined organic layers were washed with brine and dried over Na₂SO₄. After filtration, the solution was concentrated and purified by column chromatography to give 108 mg of the desired product. MS (ESI): 292, 294 (MH⁺).

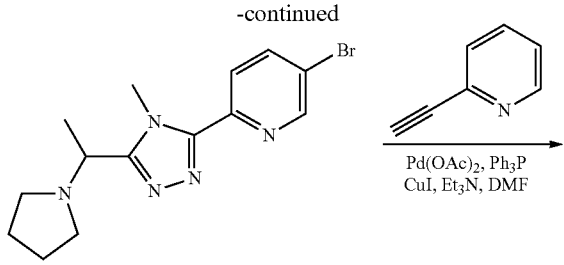

Example 4.2a

Synthesis of ethyl 2-(pyrrolidin-1-yl)propanoate

A solution of ethyl 2-bromopropanoate (1.0 g, 5.5 mmol) and pyrrolidine (1.2 g, 16.5 mmol) in ethanol (20 mL) was stirred at room temperature overnight. After removing the ethanol, the mixture was diluted with water (20 mL) and extracted with EtOAc (3×30 mL). The combined organic layers were washed with brine, dried over $Na_2SO_4$, and concentrated to give the desired product, which was directly used for the next step without further purification. MS (ESI): 172 (MH$^+$).

Example 4.2b

Synthesis of 2-(pyrrolidin-1-yl)propanehydrazide

A solution of ethyl 2-(pyrrolidin-1-yl)propanoate (855 mg, 5 mmol) and 80% hydrazine hydrate (5 mL) in ethanol (50 mL) was heated at reflux overnight. After cooling to room temperature, the reaction mixture was concentrated to give the desired product, which was directly used for the next step without further purification. MS (ESI): 158 (MH$^+$).

Example 4.2c

Synthesis of 5-bromopicolinic (ethyl carbonic) anhydride

To a solution of 5-bromopicolinic acid (1.0 g, 4.95 mmol) and ethyl carbonochloridate (588 mg, 5.4 mmol) in dichloromethane (50 mL) was added $Et_3N$ (2 mL). After stirring at room temperature for 3 h, the reaction mixture was concentrated to give the desired product. MS (ESI): 274, 276 (MH$^+$).

Example 4.2d

Synthesis of 5-bromo-N-methylpicolinamide

To a solution of 5-bromopicolinic(ethyl carbonic) anhydride (1.2 g, 4.5 mmol) in THF (20 mL) was added 33% dimethylamine solution (3 mL), then the reaction mixture was stirred at 50° C. for 5 h. After cooling to room temperature, the mixture was diluted with water (80 mL) and extracted with EtOAc (3×100 mL). The combined organic layers were washed with brine, dried over $Na_2SO_4$, and concentrated to give the desired product. MS (ESI): 215, 217 (MH$^+$).

Example 4.2e

Synthesis of 5-bromo-N-methylpyridine-2-carbothioamide

To a solution of 5-bromo-N-methylpicolinamide (1 equiv) in THF (0.11 M) was added Lawesson's reagent (0.42 equiv). The reaction was stirred at room temperature until the reaction was complete (approximately 6 hours), then the mixture was diluted with $H_2O$ and extracted with EtOAc. The combined organic layers was washed with brine and dried over $Na_2SO_4$. Then the solution was concentrated and purified by flash chromatography. MS (ESI): 231, 233 (MH$^+$).

Example 4.2f

Synthesis of 3-ethyl-8-bromo-5,6-dihydro-[1,2,4]triazolo[3,4-a]isoquinoline

A solution of 5-bromo-N-methylpyridine-2-carbothioamide (80 mg, 0.35 mmol), 2-(pyrrolidin-1-yl)propanehydrazide (66 mg, 0.42 mmol), silver benzoate (160 mg, 0.7 mmol) and acetic acid (63 mg, 1.05 mmol) in dichloromethane (10 mL) was stirred at room temperature for 6 h. Then the mixture was adjusted pH to 8 with aqueous $Na_2CO_3$ solution and extracted with dichloromethane (3×50 mL). The combined organic layers were washed with brine, dried over $Na_2SO_4$, concentrated, and purified by column chromatography to give 60 mg of the desired product. MS (ESI): 336, 338 (MH$^+$).

Example 4.2g

Synthesis of the HCl salt of 3-ethyl-8-((3-fluorophenyl)ethynyl)-5,6-dihydro[1,2,4]triazolo[3,4-a]isoquinoline

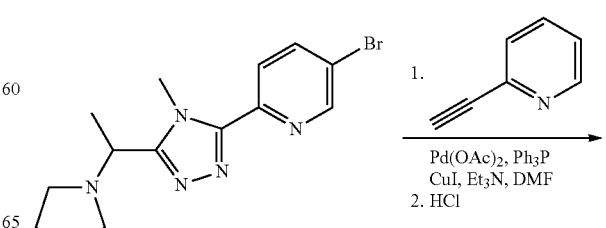

89

-continued

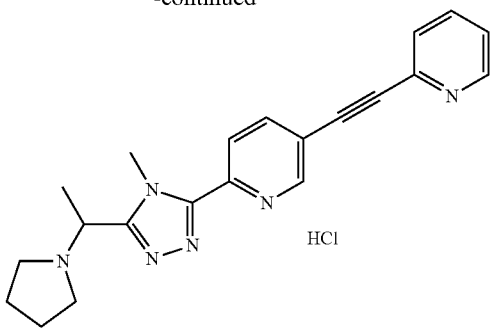

The title compound was prepared according to the experimental procedure described in Example 2.1c. MS (ESI): 359 (MH+); ¹H NMR (300 MHz, CDCl₃) δ 8.85 (d, J=1.4 Hz, 1H), 8.68 (d, J=4.7 Hz, 1H), 8.32 (d, J=8.3 Hz, 1H), 8.02-7.98 (dd, J=8.3, 2.0 Hz, 1H), 7.78-7.72 (m, 1H), 7.61-7.58 (d, J=7.7 Hz, 1H), 7.34-7.30 (m, 1H), 4.11-4.04 (q, J=6.9 Hz, 1H), 2.69-2.67 (m, 2H), 2.49-2.46 (m, 2H), 1.85-1.70 (m, 4H), 1.58 (d, J=6.8 Hz, 3H). mGluR5 PAM EC₅₀: ++.

Example 4.3

Synthesis of Compound 11: 3-(4-((4-fluorophenyl)ethynyl)phenyl)-5,6,7,8-tetrahydro-[1,2,4]triazolo[4,3-a]pyridine

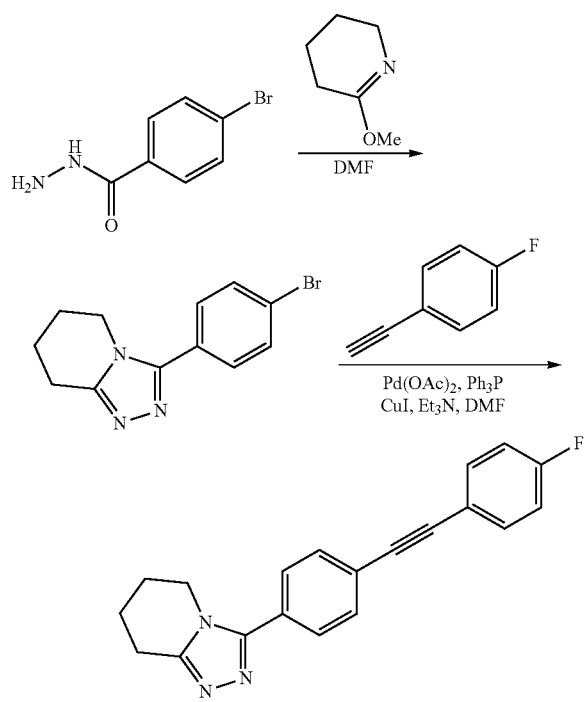

Example 4.3a

Synthesis of 3-(4-bromophenyl)-5,6,7,8-tetrahydro-[1,2,4]triazolo[4,3-a]pyridine A solution of 6-methoxy-2,3,4,5-tetrahydropyridine (102 mg, 0.9 mmol) and 4-bromobenzohydrazide (194 mg, 0.9

90 mmol) in N,N-dimethylformamide (10 mL) was stirred at 90° C. for 4 h. After cooling to room temperature, the mixture was diluted with water (50 mL) and extracted with ethyl acetate (3×50 mL). After washing with brine and drying over Na₂SO₄, the combined organic layers were concentrated and purified by column chromatography to give 130 mg of the desired product. MS (ESI): 278, 280 (MH+).

Example 4.3b

Synthesis of 3-(4-((4-fluorophenyl)ethynyl)phenyl)-5,6,7,8-tetrahydro-[1,2,4]triazolo[4,3-a]pyridine The title compound was prepared according to the experimental procedure described in Example 2.1c. MS (ESI): 318 (MH+); ¹H NMR (300 MHz, CDCl₃) δ 7.73-7.70 (m, 2H), 7.66-7.63 (m, 2H), 7.57-7.52 (m, 2H), 7.11-7.05 (t, J=8.7 Hz, 2H), 4.10-4.06 (t, J=5.4 Hz, 2H), 3.13-3.09 (t, J=5.9 Hz, 2H), 2.06-2.01 (m, 4H).

Example 6.1

Synthesis of Compound 16: 1-(sec-butyl)-4-(4-(pyridin-4-ylethynyl)phenyl)-1H-1,2,4-triazol-5(4H)-one

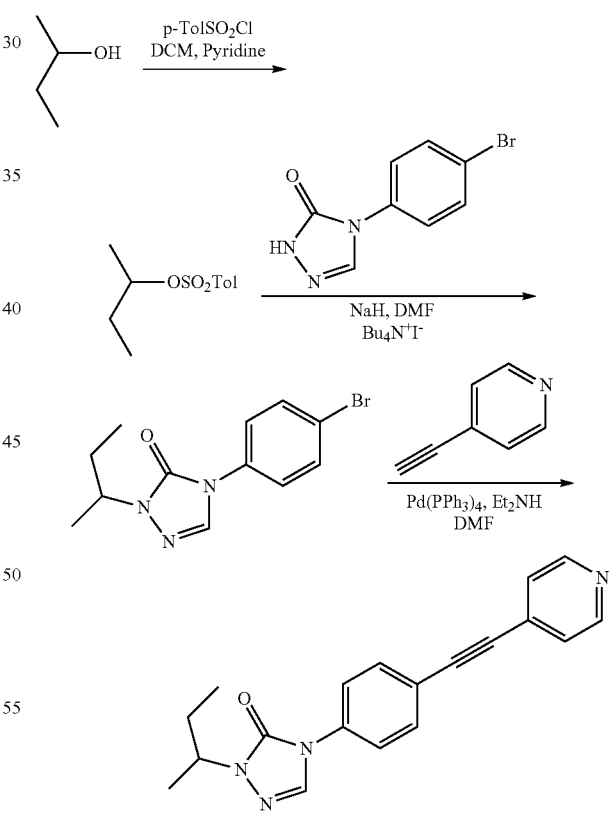

Example 6.1a

Synthesis of sec-butyl 4-methylbenzenesulfonate

To a stirred solution of 2-butanol (5 g) and pyridine (7 mL) in DCM (100 mL) at 0° C. was added solid 4-methylbenzene-1-sulfonyl chloride in several portions. The mixture was stirred and allowed to warm to rt for 1.5 h. The reaction was quenched by careful addition of saturated aqueous NaHCO$_3$ (100 mL). The organic layer was separated and washed with saturated aqueous NaHCO$_3$ (100 mL), water (100 mL), and brine (100 mL), dried over anhydrous Na$_2$SO$_4$, and concentrated under reduced pressure. The crude product was purified by silica gel chromatography.

Example 6.1b

Synthesis of (4-bromophenyl)-1-(sec-butyl)-1H-1,2,4-triazol-5(4H)-one

To a stirred solution of 4-(4-bromophenyl)-1H-1,2,4-triazol-5(4H)-one (1.14 g, 4.75 mmol) in DMF (20 mL) at 0° C. was added NaH (620 mg, 60% in mineral oil. 15.5 mmol) and tetrabutylammonium iodide (84 mg, 0.227 mmol). The mixture was stirred for 30 min. Then, a solution of sec-butyl 4-methylbenzenesulfonate (1.5 g, 6.5 mmol) in DMF (5 mL) was added. The mixture was stirred at room temperature overnight, diluted with ethyl acetate (150 mL), washed with aqueous NaHCO$_3$ (100 mL) and brine (100 mL), dried over Na$_2$SO$_4$. The crude product was purified by silica gel chromatography. MS (ES+): 296, 298 (MH$^+$).

Example 6.1c

Synthesis of 1-(sec-butyl)-4-(4-(pyridin-4-ylethynyl)phenyl)-1H-1,2,4-triazol-5(4H)-one To a solution of 4-(4-bromophenyl)-1-(sec-butyl)-1H-1,2,4-triazol-5(4H)-one (85 mg, 0.29 mmol) in DMF (1 mL) under N$_2$ was added 4-ethynylpyridine (41 mg, 0.39 mmol), Pd(PPh$_3$)$_4$ (30 mg, 0.026 mmol), Et$_2$NH (0.15 mL) and CuI (29 mg, 0.15 mmol). The mixture was sealed under nitrogen and heated in a microwave reactor at 60° C. for 4 h, diluted with brine (10 mL), and extracted with ethyl acetate (2×10 mL). The combined organic layers were dried over Na$_2$SO$_4$ and concentrated under reduced pressure. The crude product was purified by silica gel chromatography. MS (ES+): 319 (MH$^+$); $^1$H-NMR (400 MHz, CDCl$_3$) δ 8.70-8.80 (br s, 2H), 7.746 (s, 1H), 7.70-7.65 (m, 4H), 7.45-7.35 (m, 2H), 4.30 (m, 1H), 1.90 (m, 1H), 1.76 (m, 1H), 1.40 (d, J=6.6 Hz, 3H), 0.90 (t, J=7.3 Hz, 3H).

Example 7.1

Synthesis of Compound 17: 3-(tert-butyl)-5-(4-((3-fluorophenyl)ethynyl)phenyl)-1,2,4-oxadiazole

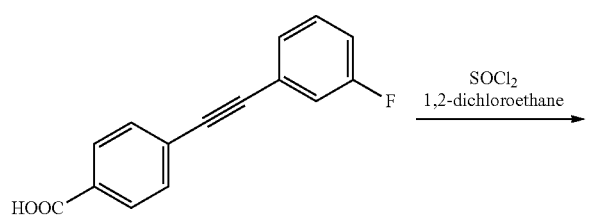

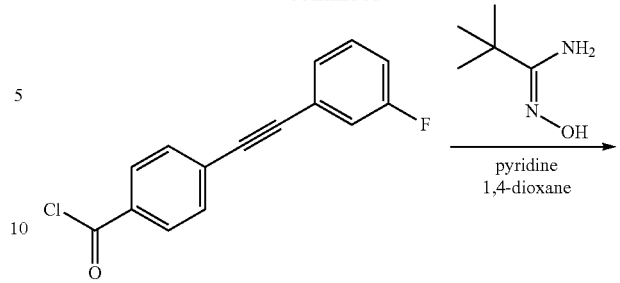

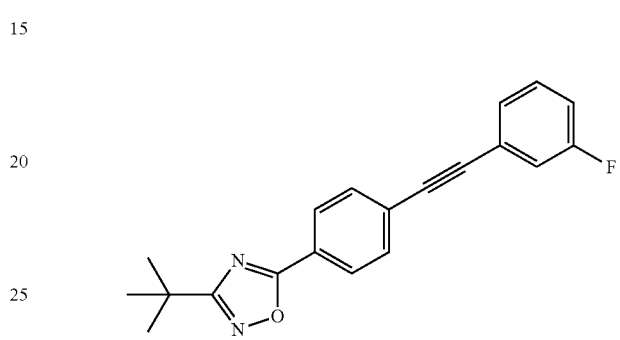

Example 7.1a

Synthesis of 4-((3-fluorophenyl)ethynyl)benzoyl chloride

A solution of 4-((3-fluorophenyl)ethynyl)benzoic acid (300 mg, 1.25 mmol) and excess SOCl$_2$ (0.2 mL) in 1,2-dichloroethane was stirred at reflux for 1.5 h. Then the reaction mixture was concentrated to give the desired product, which was directly used for the next step without further purification.

Example 7.1b

Synthesis of 3-(tert-butyl)-5-(4-((3-fluorophenyl)ethynyl)phenyl)-1,2,4-oxadiazole A solution of 4-((3-fluorophenyl)ethynyl)benzoyl chloride (1.25 mmol), N-hydroxypivalimidamide (145 mg, 1.25 mmol) and pyridine (1.5 mL) in dioxane (30 mL) was stirred at 80° C. for 6 h. After cooling to room temperature, the mixture was diluted with water (50 mL) and extracted with EtOAc (3×100 mL). The combined organic layers were concentrated and purified by column chromatography to give 31 mg of the desired product. MS (ESI): 321 (MH$^+$); $^1$H NMR (300 MHz, CDCl$_3$) δ 8.14 (d, J=8.6 Hz, 2H), 7.68 (d, J=8.6 Hz, 2H), 7.43-7.34 (m, 2H), 7.26-7.25 (m, 1H), 7.17-7.04 (m, 1H), 1.46 (s, 9H). mGluR5 PAM EC$_{50}$: +.

Example 7.2

Synthesis of Compound 18: 3-cyclopentyl-5-(4-((3-fluorophenyl)ethynyl)phenyl)-1,2,4-oxadiazole

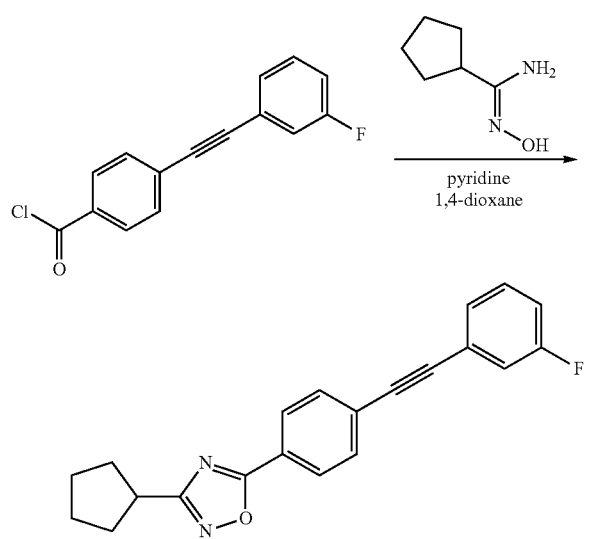

The title compound was prepared according to the experimental procedure described in Example 7.1b. MS (ESI): 333 (MH+); $^1$H NMR (300 MHz, CDCl$_3$) δ 8.13 (d, J=8.5 Hz, 2H), 7.67 (d, J=8.5 Hz, 2H), 7.37-7.33 (m, 2H), 7.25-7.24 (m, 1H), 7.10-7.09 (m, 1H), 3.33-3.28 (m, 1H), 2.18-2.07 (m, 2H), 2.00-1.83 (m, 4H), 1.75-1.67 (m, 2H).

Example 7.3

Synthesis of Compound 19: 3-(sec-butyl)-5-(4-((3-fluorophenyl)ethynyl)phenyl)-1,2,4-oxadiazole

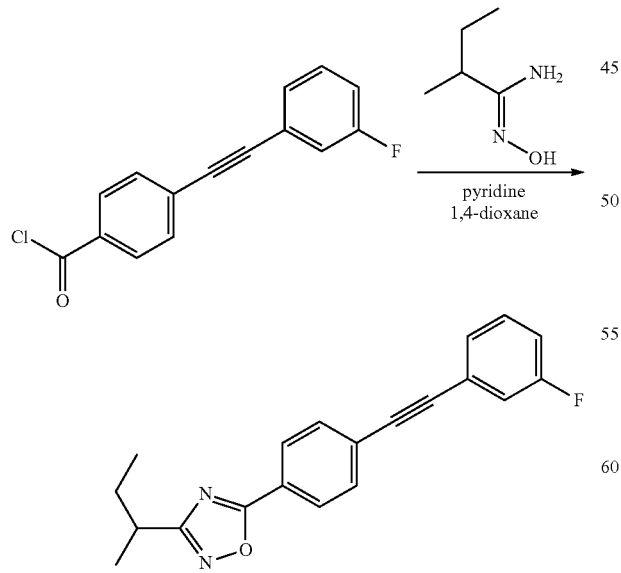

The title compound was prepared according to the experimental procedure described in Example 7.1b. MS (ESI): 321 (MH+); $^1$H NMR (300 MHz, CDCl$_3$) δ 8.16-8.13 (dd, J=6.9, 1.8 Hz, 2H), 7.70-7.67 (dd, J=6.6, 1.8 Hz, 2H), 7.40-7.23 (m, 2H), 7.26-7.25 (m, 1H), 7.14-7.07 (m, 1H), 3.03-2.93 (m, 1H), 1.94-1.66 (m, 2H), 1.40 (d, J=6.9 Hz, 3H), 0.99-0.94 (t, J=7.4 Hz, 3H).

Example 8.1

Synthesis of Compound 20: 3-(4-((3-fluorophenyl)ethynyl)phenyl)-1,2,4-oxadiazole

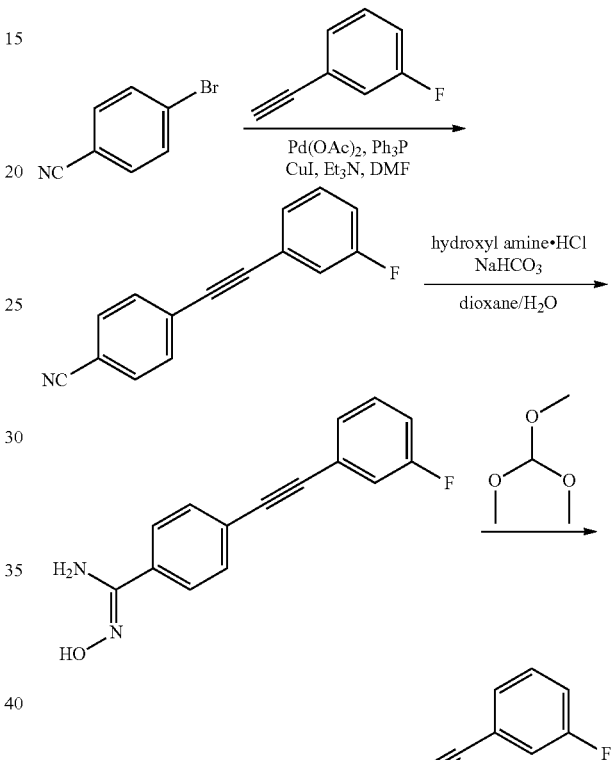

Example 8.1a

Synthesis of 4-((3-fluorophenyl)ethynyl)benzonitrile

A solution of 4-bromobenzonitrile (10 g, 54.6 mmol), 1-ethynyl-3fluorobenzene (13.1 g, 109.2 mmol), Pd(OAc)$_2$ (614 mg, 2.73 mmol), PPh$_3$ (7.15 mg, 27.3 mmol), CuI (520 mg, 27.3 mmol), and Et$_3$N (12 mL) in DMF (200 mL) was stirred in a sealed tube at 70° C. for 3.5 hours. After cooling to room temperature, the reaction mixture was diluted with H$_2$O and extracted with EtOAc (2×50 mL). The combined organic layers were washed with brine and dried over anhydrous sodium sulfate. After filtration and concentration, the crude product was purified by silica gel chromatography to produce 10.3 g of the desired product. MS (ESI): 222 (MH+).

Example 8.1b

Synthesis of 4((3-fluorophenyl)ethynyl)-N'-hydroxybenzimidamide

A solution of 4-((3-fluorophenyl)ethynyl)benzonitrile (10.3 g, 46.4 mmol), hydroxylamine hydrochloride (32.2 g, 464 mmol), NaHCO$_3$ (39.0 g, 464 mmol) in dioxane/water (300/200 mL) was stirred at room temperature overnight. Then the suspension was extracted with EtOAc (3×300 mL). The combined organic layers were washed with brine and dried over anhydrous sodium sulfate. After filtration and concentration, the crude product was purified by silica gel chromatography to produce 11.8 g of the desired product. MS (ESI): 255 (MH$^+$).

Example 8.1c

Synthesis of Compound 20: 3-(4-((3-fluorophenyl)ethynyl)phenyl)-1,2,4-oxadiazole A solution of 4-((3-fluorophenyl)ethynyl)-N'-hydroxybenzimidamide (300 mg, 1.18 mmol) in trimethoxymethane (1250 mg, 11.8 mmol) was stirred at 110° C. overnight. After cooling to rt, the reaction mixture was diluted with water (50 mL) and extracted with EtOAc (3×100 mL). The combined organic layers were concentrated and purified by column chromatography to give 220 mg of the desired product. MS (ESI): 265 (MH$^+$); $^1$H NMR (300 MHz, CDCl$_3$) δ 8.79 (s, 1H), 8.15 (d, J=8.4 Hz, 2H), 7.68 (d, J=8.4 Hz, 2H), 7.37-7.31 (m, 2H), 7.26-7.25 (m, 1H), 7.12-7.05 (m, 1H).

Example 8.2

Synthesis of Compound 21: 3-(4-((3-fluorophenyl)ethynyl)phenyl)-1,2,4-oxadiazole

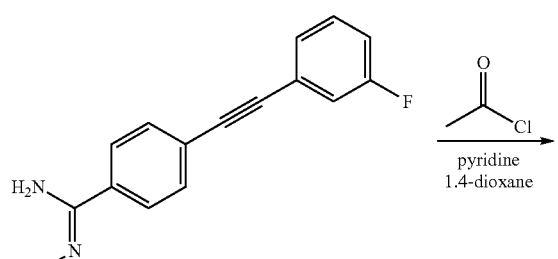

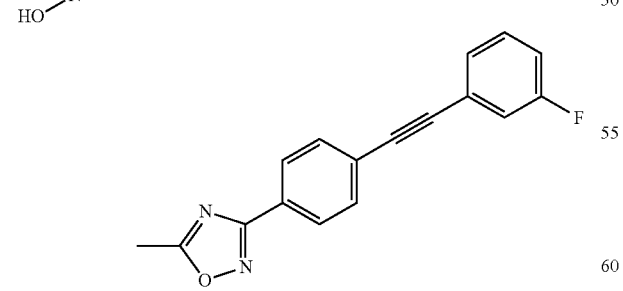

The title compound was prepared according to the experimental procedure described in Example 7.1b. MS (ESI): 279 (MH$^+$); $^1$H NMR (300 MHz, CDCl$_3$) δ 8.08 (d, J=8.3 Hz, 2H), 7.64 (d, J=8.3 Hz, 2H), 7.39-7.33 (m, 2H), 7.25-7.24 (m, 1H), 7.12-7.05 (m, 1H), 2.68 (s, 3H).

Example 8.3

Synthesis of Compound 22: 5-ethyl-3-(4-((3-fluorophenyl)ethynyl)phenyl)-1,2,4-oxadiazole

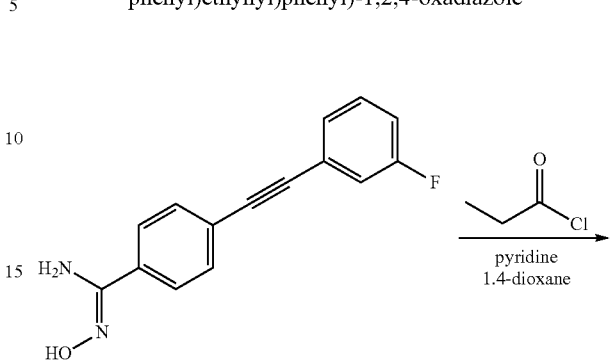

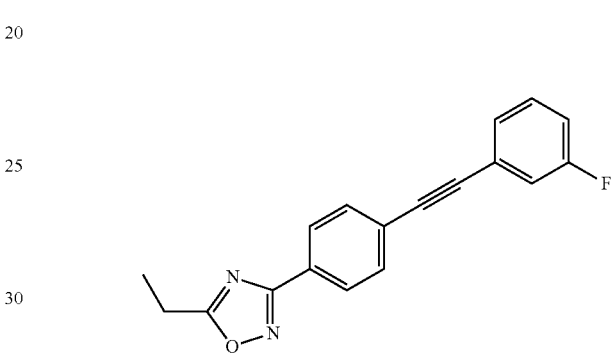

The title compound was prepared according to the experimental procedure described in Example 7.1b. MS (ESI): 293 (MH$^+$); $^1$H NMR (300 MHz, CDCl$_3$) δ 8.09 (d, J=8.6 Hz, 2H), 7.65 (d, J=8.6 Hz, 2H), 7.36-7.33 (m, 2H), 7.28-7.24 (m, 1H), 7.12-7.05 (m, 1H), 3.05-2.97 (q, 2H), 1.50-1.45 (t, J=7.6 Hz, 3H).

Example 8.4

Synthesis of Compound 23: 3-(4-((3-fluorophenyl)ethynyl)phenyl)-5-propyl-1,2,4-oxadiazole

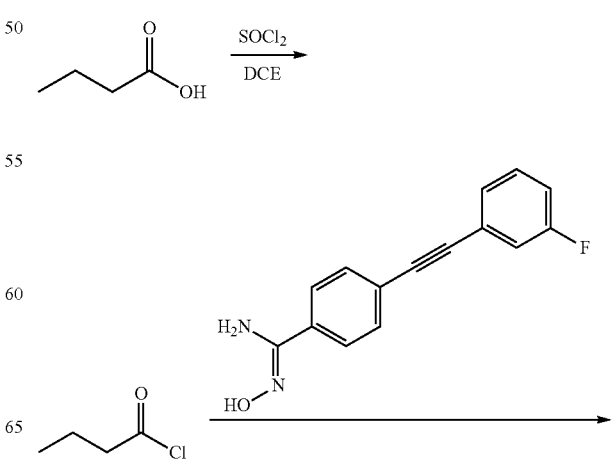

-continued

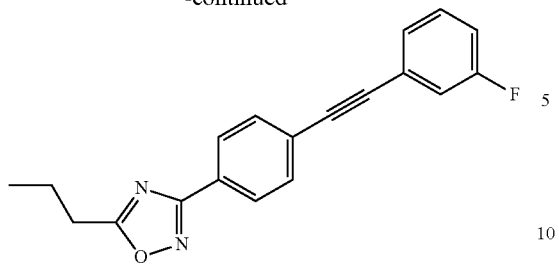

Example 8.4a

Synthesis of Butyryl Chloride

A solution of butyric acid (352 mg, 4 mmol) and excess SOCl$_2$ (0.5 mL) in 1,2-dichloroethane was stirred at reflux for 1.5 h. Then the suspension was concentrated to give the desired product, which was used for the next step without further purification.

Example 8.4b

Synthesis of 3-(4-((3-fluorophenyl)ethynyl)phenyl)-5-propyl-1,2,4-oxadiazole

The title compound was prepared according to the experimental procedure described in Example 7.1b. MS (ESI): 307 (MH$^+$); $^1$H NMR (300 MHz, CDCl$_3$) δ 8.09 (d, J=7.9 Hz, 2H), 7.65 (d, J=8.0 Hz, 2H), 7.34 (s, 2H), 7.24 (s, 1H), 7.19-7.08 (m, 1H), 2.97-2.92 (t, J=7.5 Hz, 2H), 1.99-1.87 (m, 2H), 1.10-1.05 (t, J=7.3 Hz, 3H).

Example 8.5

Synthesis of Compound 24: 3-(4-((3-fluorophenyl)ethynyl)phenyl)-5-isopropyl-1,2,4-oxadiazole

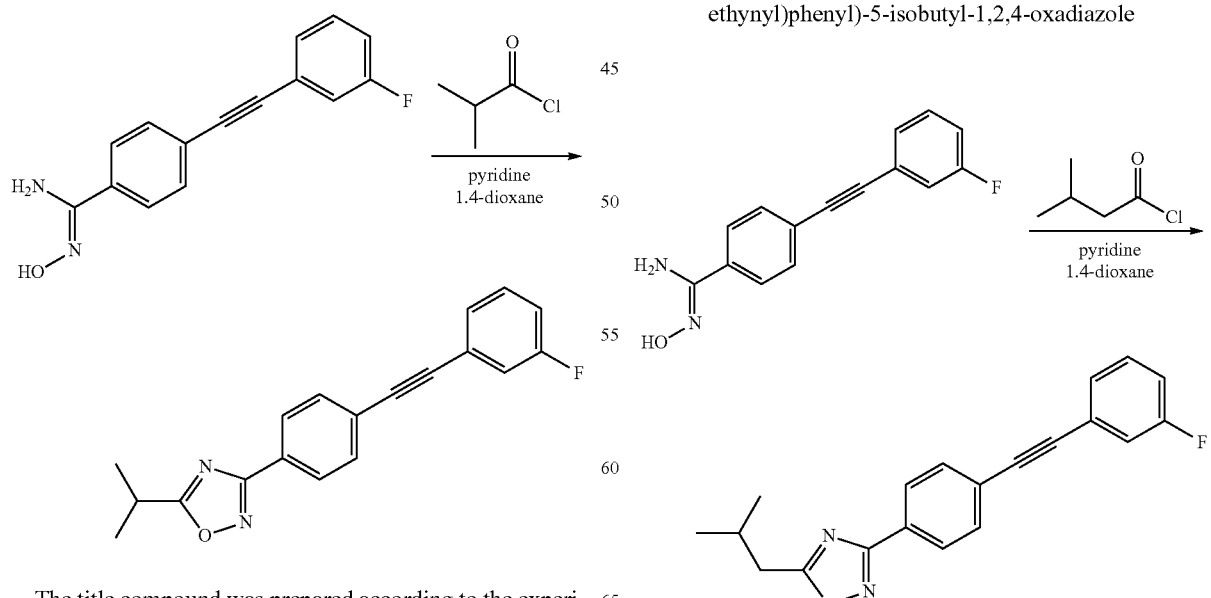

The title compound was prepared according to the experimental procedure described in Example 7.1b. MS (ESI): 307 (MH$^+$); $^1$H NMR (300 MHz, CDCl$_3$) δ 8.08 (d, J=8.5 Hz, 2H), 7.64 (d, J=8.5 Hz, 2H), 7.39-7.33 (m, 2H), 7.24 (d, J=2.2 Hz, 1H), 7.11-7.05 (m, 1H), 3.36-3.26 (m, 1H), 1.48 (d, J=7.0 Hz, 6H). mGluR5 PAM EC$_{50}$: +. Fold shift at 10 μM: ++.

Example 8.6

Synthesis of Compound 25: 5-cyclopropyl-3-(4-((3-fluorophenyl)ethynyl)phenyl)-1,2,4-oxadiazole

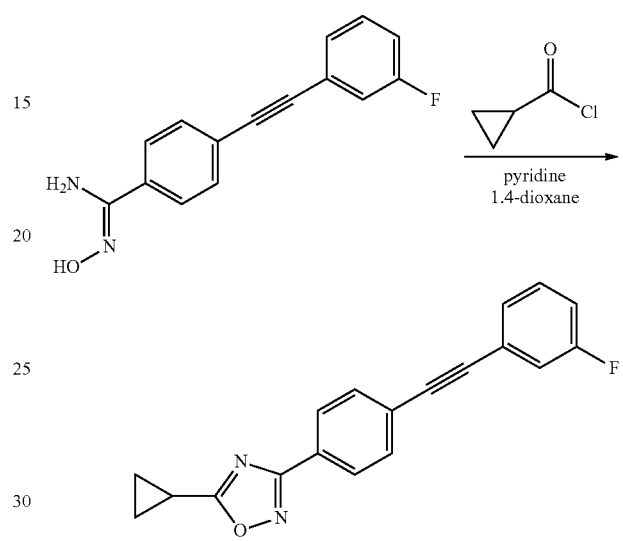

The title compound was prepared according to the experimental procedure described in Example 7.1b. MS (ESI): 307 (MH$^+$); $^1$H NMR (300 MHz, CDCl$_3$) δ 8.06 (d, J=8.5 Hz, 2H), 7.64 (d, J=8.5 Hz, 2H), 7.36-7.33 (m, 2H), 7.24 (d, J=2.4 Hz, 1H), 7.12-7.05 (m, 1H), 2.33-2.24 (m, 1H), 1.37-1.24 (m, 4H).

Example 8.7

Synthesis of Compound 26: 3-(4-((3-fluorophenyl)ethynyl)phenyl)-5-isobutyl-1,2,4-oxadiazole The title compound was prepared according to the experimental procedure described in Example 7.1b. MS (ESI): 321 (MH⁺); ¹H NMR (300 MHz, CDCl₃) δ 8.09 (d, J=8.5 Hz, 2H), 7.64 (d, J=8.5 Hz, 2H), 7.36-7.33 (m, 2H), 7.25-7.24 (m, 1H), 7.12-7.05 (m, 1H), 2.85 (d, J=7.1 Hz, 2H), 2.35-2.24 (m, 1H), 1.03 (d, J=6.7 Hz, 6H). mGluR5 PAM EC$_{50}$: +.

Example 8.8

Synthesis of Compound 27: 5-(tert-butyl)-3-(4-((3-fluorophenyl)ethynyl)phenyl)-1,2,4-oxadiazole

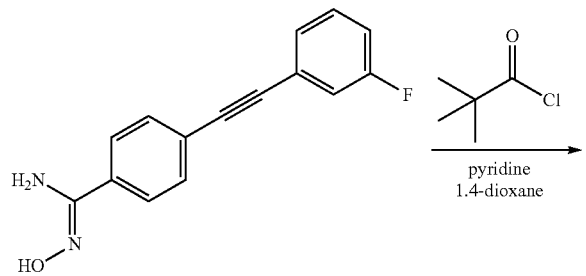

The title compound was prepared according to the experimental procedure described in Example 7.1b. MS (ESI): 321 (MH⁺); ¹H NMR (300 MHz, CDCl₃) δ 8.10 (d, J=8.5 Hz, 2H), 7.64 (d, J=8.5 Hz, 2H), 7.39-7.34 (m, 2H), 7.25-7.24 (m, 1H), 7.12-7.05 (m, 1H), 1.28 (s, 9H). mGluR5 PAM EC$_{50}$: ++. Fold shift at 10 µM: +.

Example 8.9

Synthesis of Compound 28: 5-cyclobutyl-3-(4-((3-fluorophenyl)ethynyl)phenyl)-1,2,4-oxadiazole

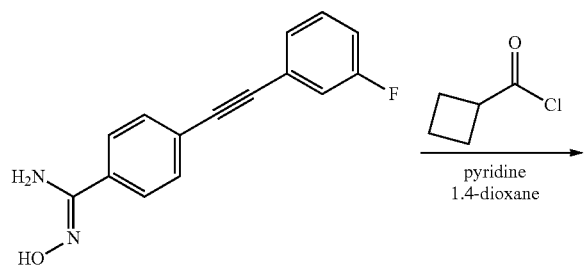

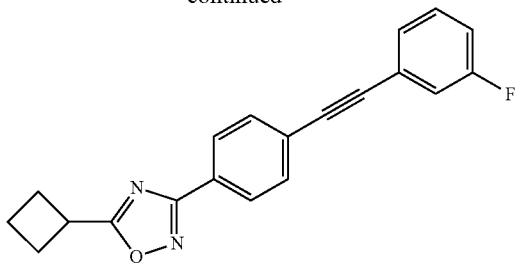

The title compound was prepared according to the experimental procedure described in Example 7.1b. MS (ESI): 321 (MH⁺); ¹H NMR (300 MHz, CDCl₃) δ 8.10 (d, J=8.5 Hz, 2H), 7.64 (d, J=8.5 Hz, 2H), 7.36-7.33 (m, 2H), 7.24 (d, J=0.9 Hz, 1H), 7.11-7.07 (m, 1H), 3.87-3.81 (m, 1H), 2.60-2.48 (m, 4H), 2.20-2.11 (m, 2H).

Example 8.10

Synthesis of Compound 29: 5-5-(sec-butyl)-3-(4-((3-fluorophenyl)ethynyl)phenyl)-1,2,4-oxadiazole

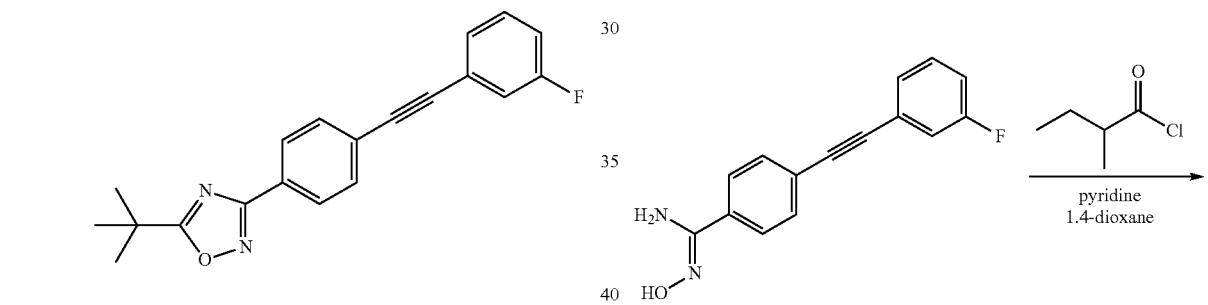

The title compound was prepared according to the experimental procedure described in Example 7.1b. MS (ESI): 321(MH⁺); ¹H NMR (300 MHz, CDCl₃) δ 8.10 (d, J=8.4 Hz, 2H), 7.64 (d, J=8.4 Hz, 2H), 7.39-7.30 (m, 2H), 7.25-7.24 (m, 1H), 7.11-7.04 (m, 1H), 3.17-3.10 (m, 1H), 1.99-1.74 (m, 2H), 1.45 (d, J=6.9 Hz, 3H), 1.14-1.02 (t, J=6.6 Hz, 3H). mGluR5 PAM EC$_{50}$: ++. Fold shift at 10 µM: +++.

Example 8.11 and Example 8.12

Synthesis of Compound 30: (S)-5-(sec-butyl)-3-(4-((3-fluorophenyl)ethynyl)phenyl)-1,2,4-oxadiazole and Compound 31: (R)-5-(sec-butyl)-3-(4-((3-fluorophenyl)ethynyl)phenyl)-1,2,4-oxadiazole

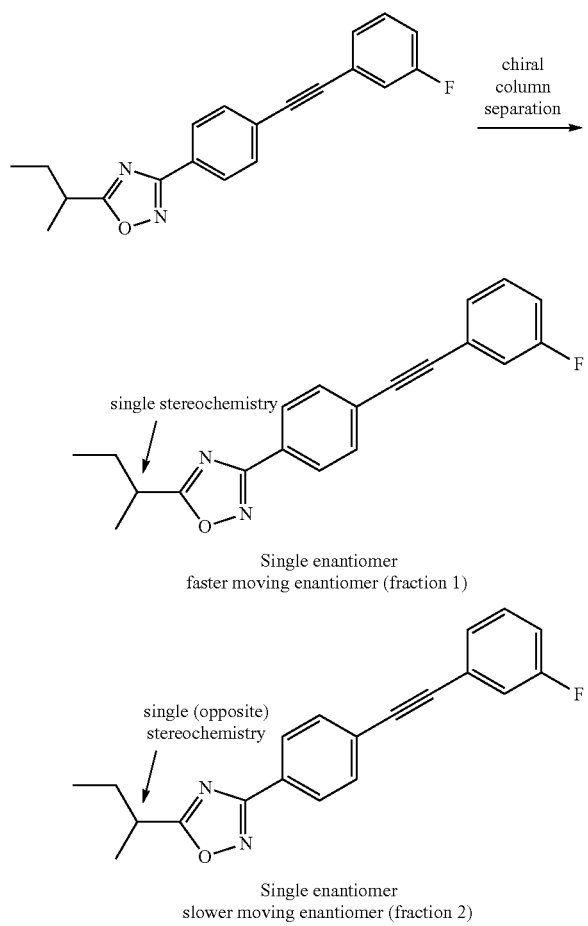

Racemic 5-(sec-butyl)-3-(4-((3-fluorophenyl)ethynyl)phenyl)-1,2,4-oxadiazole was separated into the corresponding two single enantiomer compounds (S)-5-(sec-butyl)-3-(4-((3-fluorophenyl)ethynyl)phenyl)-1,2,4-oxadiazole and (R)-5-(sec-butyl)-3-(4-((3-fluorophenyl)ethynyl)phenyl)-1,2,4-oxadiazole using chiral chromatography with an isocratic SFC method. The column used was a 3.0×25.0 cm ChiralPak AD-H from Chiral Technologies (West Chester, Pa.). The $CO_2$ co-solvent was methanol with 0.1% isopropylamine. Isocratic Method: 11% Co-solvent at 80 mL/min System pressure: 150 bar. Column temperature 25° C.

Compound 30: Faster moving enantiomer (fraction 1) of 5-(sec-butyl)-3-(4-((3-fluorophenyl)ethynyl)phenyl)-1,2,4-oxadiazole: Retention time=2.1 min. 99.8% ee. mGluR5 PAM $EC_{50}$: +. Fold shift at 10 μM: ++.

Compound 31: Slower moving enantiomer (fraction 2) of 5-(sec-butyl)-3-(4-((3-fluorophenyl)ethynyl)phenyl)-1,2,4-oxadiazole: Retention time=2.5 min. 99.4% ee. mGluR5 PAM $EC_{50}$: +. Fold shift at 10 μM: ++.

Example 8.13

Synthesis of Compound 32: 5-cyclopentyl-3-(4-((3-fluorophenyl)ethynyl)phenyl)-1,2,4-oxadiazole

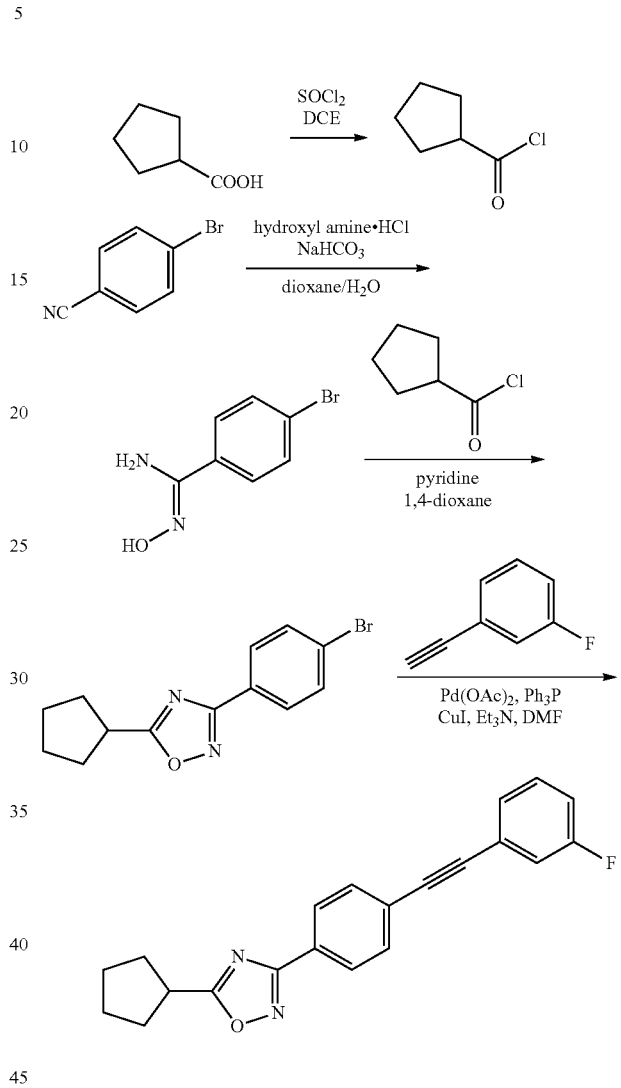

Example 8.13a

Synthesis of Cyclopentanecarbonyl Chloride

The title compound was prepared according to the experimental procedure described in Example 7.1a.

Example 8.13b

Synthesis of 4-bromo-N'-hydroxybenzimidamide

The title compound was prepared according to the experimental procedure described in Example 8.1b. MS (ESI): 214, 216 (MH+).

Example 8.13c

Synthesis of 3-(4-bromophenyl)-5-cyclopentyl-1,2,4-oxadiazole

The title compound is prepared according to the experimental procedure described in Example 7.1b. MS (ESI): 293, 295 (MH+).

Example 8.13d

Synthesis of 5-cyclopentyl-3-(4-((3-fluorophenyl)ethynyl)phenyl)-1,2,4-oxadiazole The title compound was prepared according to the experimental procedure described in Example 8.1a. MS (ESI): 333 (MH$^+$); $^1$H NMR (300 MHz, CDCl$_3$) δ 8.10 (d, J=8.4 Hz, 2H), 7.64 (d, J=8.4 Hz, 2H), 7.36-7.24 (m, 3H), 7.12-7.05 (m, 1H), 3.48-3.37 (m, 1H), 2.26-1.98 (m, 8H). mGluR5 PAM EC$_{50}$: ++. Fold shift at 10 μM: +++.

Example 8.14

Synthesis of Compound 33: 5-cyclohexyl-3-(4-((3-fluorophenyl)ethynyl)phenyl)-1,2,4-oxadiazole

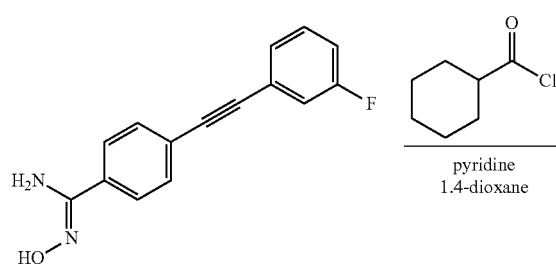

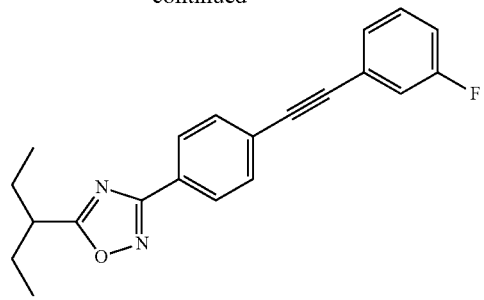

The title compound was prepared according to the experimental procedure described in Example 7.1b. MS (ESI): 347 (MH$^+$); $^1$H NMR (300 MHz, CDCl$_3$) δ 8.09 (d, J=8.5 Hz, 2H), 7.64 (d, J=8.5 Hz, 2H), 7.36-7.33 (m, 2H), 7.24 (d, J=2.1 Hz, 1H), 7.11-7.05 (m, 1H), 3.07-3.00 (m, 1H), 2.19-2.13 (m, 2H), 1.92-1.87 (m, 2H), 1.79-1.66 (m, 3H), 1.51-1.33 (m, 3H).

Example 8.15

Synthesis of Compound 34: 3-(4-((3-fluorophenyl)ethynyl)phenyl)-5-(pentan-3-yl)-1,2,4-oxadiazole

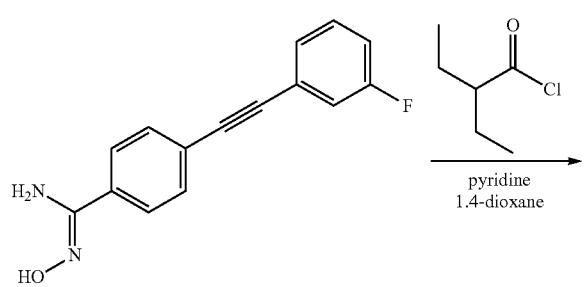

The title compound was prepared according to the experimental procedure described in Example 7.1b. MS (ESI): 335 (MH$^+$); $^1$H NMR (300 MHz, CDCl$_3$) δ 8.11 (d, J=8.4 Hz, 2H), 7.65 (d, J=8.4 Hz, 2H), 7.36-7.33 (m, 2H), 7.25 (d, J=1.9 Hz, 1H), 7.12-7.07 (m, 1H), 3.00-2.94 (m, 1H), 1.93-1.81 (m, 4H), 0.98-0.92 (t, J=7.4 Hz, 6H). mGluR5 PAM EC$_{50}$: ++. Fold shift at 10 μM: +++.

Example 8.16

Synthesis of Compound 35: 5-benzyl-3-(4-((3-fluorophenyl)ethynyl)phenyl)-1,2,4-oxadiazole

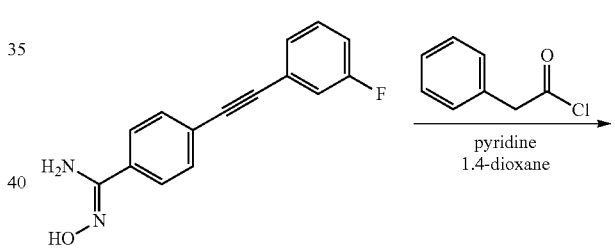

The title compound was prepared according to the experimental procedure described in Example 7.1b. MS (ESI): 355 (MH$^+$); $^1$H NMR (300 MHz, CDCl$_3$) δ 8.09 (d, J=8.4 Hz, 2H), 7.64 (d, J=8.5 Hz, 2H), 7.40-7.24 (m, 8H), 7.11-7.05 (m, 1H), 4.31 (s, 2H).

Example 8.17

Synthesis of Compound 36: 5-benzyl-3-(4-((3-fluorophenyl)ethynyl)phenyl)-1,2,4-oxadiazole

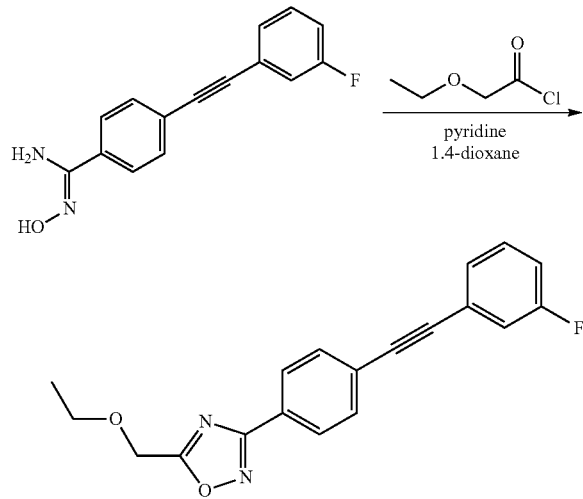

The title compound was prepared according to the experimental procedure described in Example 7.1b. MS (ESI): 323 (MH+); 1H NMR (300 MHz, CDCl3) δ 8.11 (d, J=8.5 Hz, 2H), 7.65 (d, J=8.5 Hz, 2H), 7.39-7.33 (m, 2H), 7.24 (d, J=2.2 Hz, 1H), 7.12-7.05 (m, 1H), 4.81 (s, 2H), 3.78-3.71 (q, J=6.9 Hz, 2H), 1.25-1.35 (t, J=6.9 Hz, 3H).

Example 8.18

Synthesis of Compound 37: 3-(4-((3-fluorophenyl)ethynyl)phenyl)-5-((tetrahydrofuran-2-yl)methyl)-1,2,4-oxadiazole

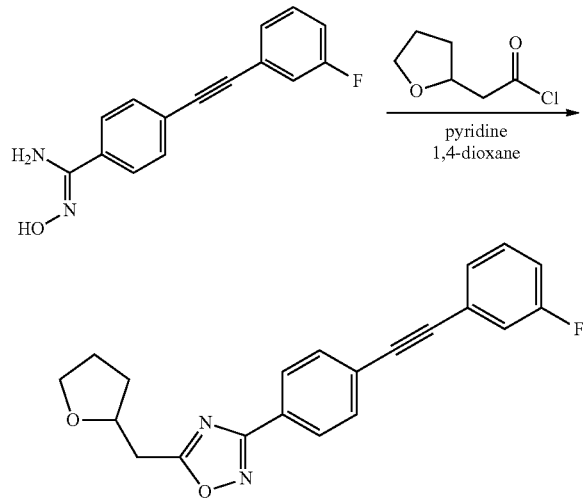

The title compound was prepared according to the experimental procedure described in Example 7.1b. MS (ESI): 349 (MH+); 1H NMR (300 MHz, CDCl3) δ 8.10 (d, J=8.3 Hz, 2H), 7.64 (d, J=8.3 Hz, 2H), 7.36-7.33 (m, 2H), 7.25-7.24 (m, 1H), 7.11-7.07 (m, 1H), 4.47-4.43 (m, 1H), 3.99-3.92 (m, 1H), 3.86-3.78 (m, 1H), 3.28-3.10 (m, 2H), 2.23-2.17 (m, 1H), 2.03-1.96 (m, 2H), 1.78-1.58 (m, 1H).

Example 8.19

Synthesis of Compound 38: 3-(4-((3-fluorophenyl)ethynyl)phenyl)-5-(furan-2-ylmethyl)-1,2,4-oxadiazole

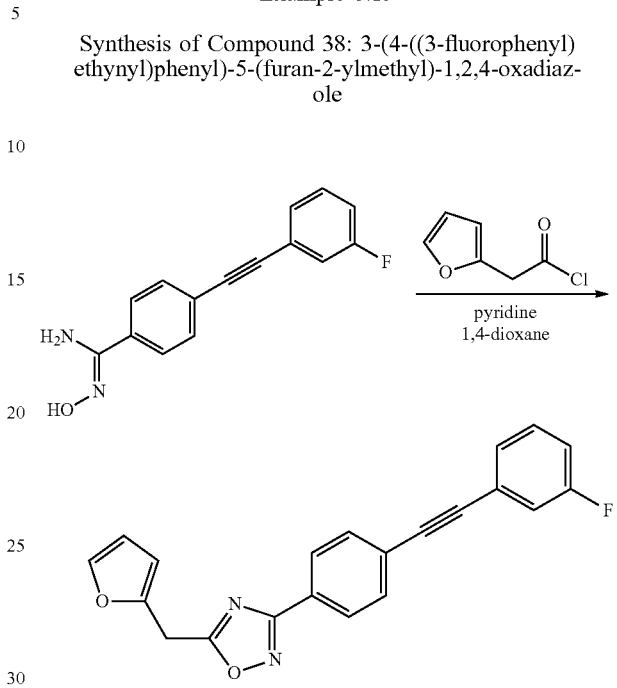

The title compound was prepared according to the experimental procedure described in Example 7.1b. MS (ESI): 345 (MH+); 1H NMR (300 MHz, CDCl3) δ 8.09 (d, J=8.6 Hz, 2H), 7.62 (d, J=8.6 Hz, 2H), 7.43-7.42 (dd, J=1.8, 0.8 Hz, 1H), 7.36-7.33 (m, 2H), 7.25-7.24 (m, 1H), 7.12-7.05 (m, 1H), 6.41-6.36 (m, 2H), 4.38 (s, 2H).

Example 8.20

Synthesis of Compound 39: 3-(4-((3-fluorophenyl)ethynyl)phenyl)-5-(tetrahydrofuran-2-yl)-1,2,4-oxadiazole

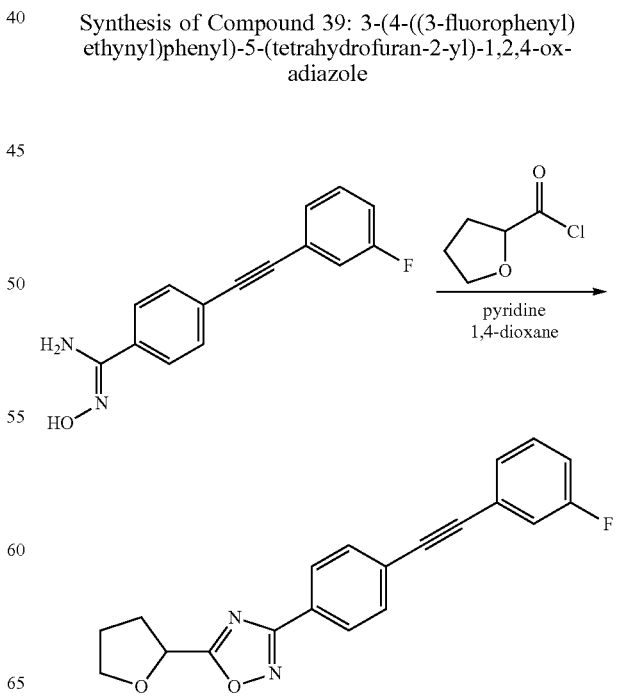

The title compound was prepared according to the experimental procedure described in Example 7.1b. MS (ESI): 335 (MH+); ¹H NMR (300 MHz, CDCl₃) δ 8.11 (d, J=8.4 Hz, 2H), 7.64 (d, J=8.4 Hz, 2H), 7.36-7.33 (m, 2H), 7.27-7.24 (m, 1H), 7.12-7.05 (m, 1H), 5.30-5.26 (m, 1H), 4.21-4.01 (m, 2H), 2.53-2.29 (m, 2H), 2.22-2.05 (m, 2H). mGluR5 PAM EC$_{50}$: +. Fold shift at 10 μM: ++.

Example 8.21

Synthesis of Compound 40: 3-(4-((3-fluorophenyl)ethynyl)phenyl)-5-(2-methoxyethyl)-1,2,4-oxadiazole

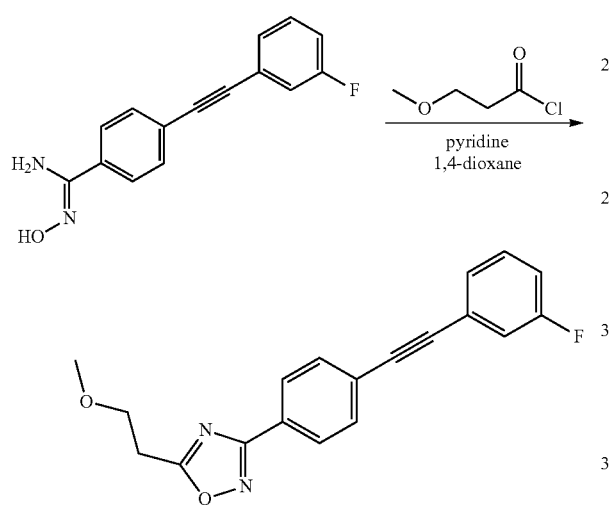

The title compound was prepared according to the experimental procedure described in Example 7.1b. MS (ESI): 323 (MH+); ¹H NMR (300 MHz, CDCl₃) δ 8.10 (d, J=8.4 Hz, 2H), 7.64 (d, J=8.4 Hz, 2H), 7.36-7.33 (m, 2H), 7.25-7.24 (m, 1H), 7.12-7.06 (m, 1H), 3.92-3.88 (t, J=6.4 Hz, 2H), 3.42 (s, 3H), 3.27-3.22 (t, J=6.4 Hz, 2H). mGluR5 PAM EC$_{50}$: +.

Example 8.22

Synthesis of Compound 41: 3-(4-((3-fluorophenyl)ethynyl)phenyl)-5-(tetrahydro-2H-pyran-4-yl)-1,2,4-oxadiazole

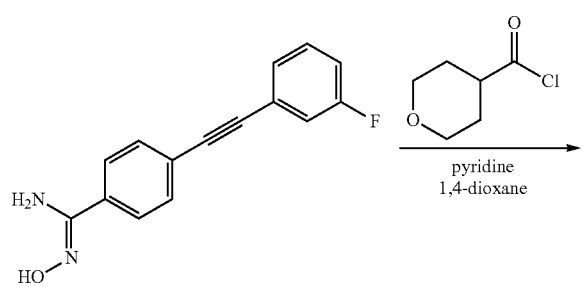

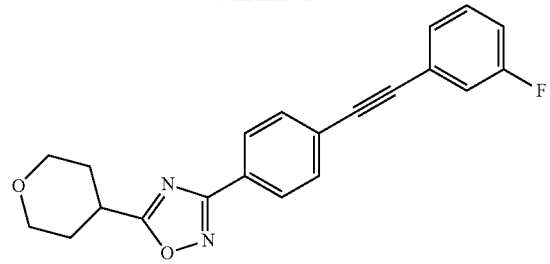

The title compound was prepared according to the experimental procedure described in Example 7.1b. MS (ESI): 349 (MH+); ¹H NMR (300 MHz, CDCl₃) δ 8.09 (d, J=8.3 Hz, 2H), 7.65 (d, J=8.3 Hz, 2H), 7.36-7.33 (m, 2H), 7.25-7.24 (m, 1H), 7.12-7.06 (m, 1H), 4.12-4.06 (m, 2H), 3.64-3.56 (m, 2H), 3.32-3.25 (m, 1H), 2.13-2.04 (m, 4H).

Example 8.23

Synthesis of Compound 42: 3-(4-((3-fluorophenyl)ethynyl)phenyl)-5-(furan-2-yl)-1,2,4-oxadiazole

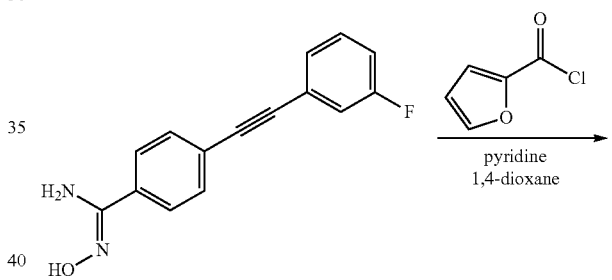

The title compound was prepared according to the experimental procedure described in Example 7.1b. MS (ESI): 331 (MH+); ¹H NMR (300 MHz, CDCl₃) δ 8.20 (d, J=8.5 Hz, 2H), 7.77-7.73 (m, 1H), 7.70 (d, J=8.5 Hz, 2H), 7.42-7.20 (m, 4H), 7.14-7.02 (m, 1H), 6.66-6.63 (m, 1H).

Example 8.24

Synthesis of Compound 43: 3-(4-((3-fluorophenyl)ethynyl)phenyl)-5-(tetrahydrofuran-3-yl)-1,2,4-oxadiazole

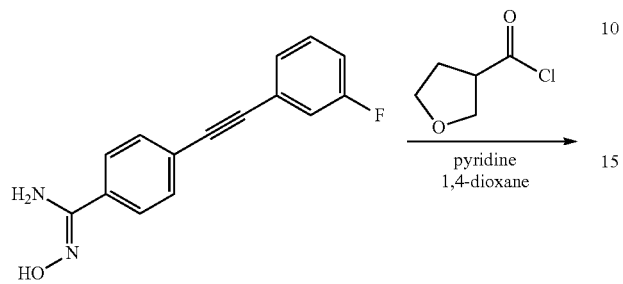

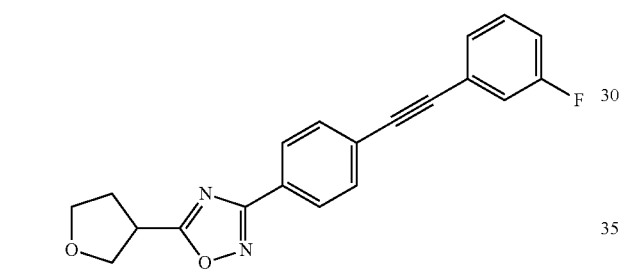

The title compound was prepared according to the experimental procedure described in Example 7.1b. MS (ESI): 335 (MH⁺); ¹H NMR (300 MHz, CDCl₃) δ 8.09 (d, J=8.4 Hz, 2H), 7.65 (d, J=8.4 Hz, 2H), 7.37-7.33 (m, 2H), 7.24 (d, J=2.3 Hz, 1H), 7.10-7.08 (m, 1H), 4.29-4.21 (m, 1H), 4.18-4.08 (m, 2H), 4.06-3.96 (m, 1H), 3.89-3.74 (m, 1H), 2.50-2.43 (m, 2H).

Example 8.25

Synthesis of Compound 44: 3-(4-((3-fluorophenyl)ethynyl)phenyl)-5-(1-methoxypropyl)-1,2,4-oxadiazole

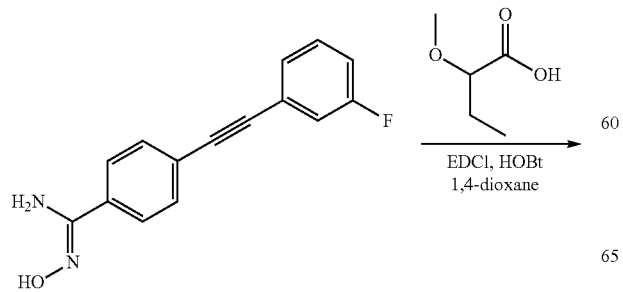

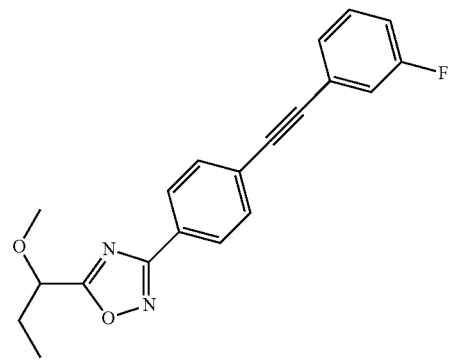

A solution of 4((3-fluorophenyl)ethynyl)-N'-hydroxybenzimidamide (0.3 g, 1.18 mmol, 1 equiv), 2-methoxybutanoic acid (0.21 g, 1.77 mmol, 1.5 equiv), EDCI (0.34 g, 1.77 mmol, 1.5 equiv) and HOBt (0.24 g, 1.77 mmol, 1.5 equiv) in 1,4-dioxane (40 mL) was stirred at 70° C. overnight. After cooling to rt, the reaction mixture was diluted with water and extracted with ethyl acetate (3×20 mL). The combined organic layers were dried over Na₂SO₄. After filtration and concentration, the residue was purified by silica gel chromatography to give 45 mg of the desired product. MS (ESI): 337 (MH⁺); ¹H NMR (300 MHz, CDCl₃) δ 8.14 (d, J=8.4 Hz, 2H), 7.67 (d, J=8.4 Hz, 2H), 7.36-7.33 (m, 2H), 7.25-7.24 (m, 1H), 7.12-7.07 (m, 1H), 4.57-4.53 (t, J=6.5 Hz, 1H), 3.49 (s, 3H), 2.11-2.00 (m, 2H), 1.07-1.02 (t, J=7.4 Hz, 3H). mGluR5 PAM EC₅₀: ++.

Example 8.26

Synthesis of Compound 45: 3-(4-((3-fluorophenyl)ethynyl)phenyl)-5-(1-methylpiperidin-4-yl)-1,2,4-oxadiazole

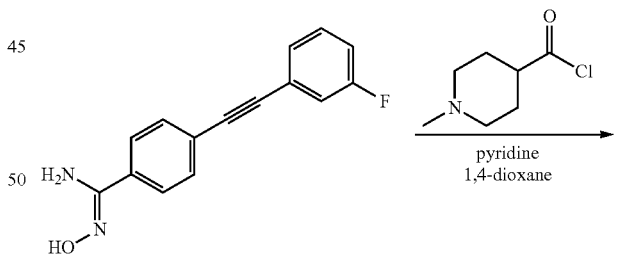

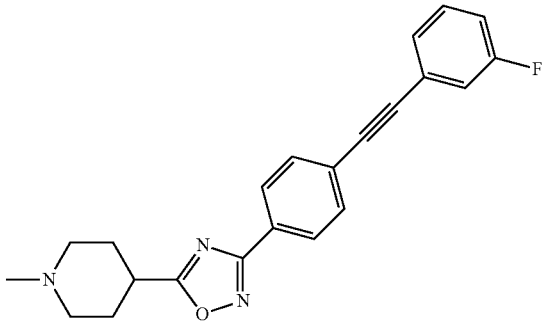

The title compound was prepared according to the experimental procedure described in Example 7.1b. MS (ESI): 362 (MH$^+$); $^1$H NMR (300 MHz, CDCl$_3$) δ 8.08 (d, J=8.2 Hz, 2H), 7.67 (d, J=7.9 Hz, 2H), 7.37-7.35 (m, 2H), 7.25 (m, 1H), 7.10 (m, 1H), 3.73-3.48 (m, 3H), 3.18-3.06 (m, 2H), 2.99-2.77 (m, 5H), 2.52-2.42 (m, 2H).

Example 8.27

Synthesis of Compound 46: 3-(4-((3-fluorophenyl)ethynyl)phenyl)-5-(1-methylpyrrolidin-3-yl)-1,2,4-oxadiazole

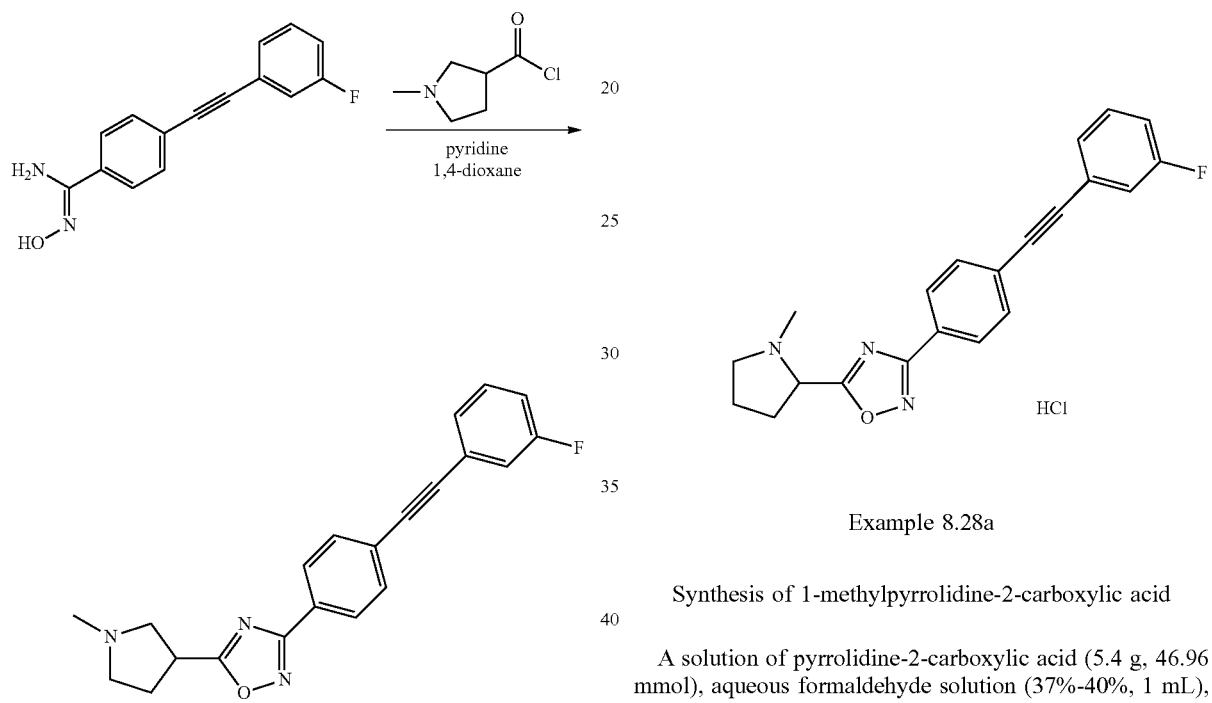

The title compound was prepared according to the experimental procedure described in Example 7.1b. MS (ESI): 348 (MH$^+$); $^1$H NMR (300 MHz, CDCl$_3$) δ 8.09 (d, J=8.6 Hz, 2H), 7.65 (d, J=8.6 Hz, 2H), 7.36-7.33 (m, 2H), 7.24 (d, J=2.2 Hz, 1H), 7.11-7.08 (m, 1H), 3.76-3.70 (m, 1H), 3.11-3.05 (m, 1H), 2.95-2.89 (m, 1H), 2.77-2.72 (m, 2H), 2.45-2.34 (m, 5H).

Example 8.28

Synthesis of the HCl salt of Compound 47: 3-(4-((3-fluorophenyl)ethynyl)phenyl)-5-(1-methylpyrrolidin-2-yl)-1,2,4-oxadiazole

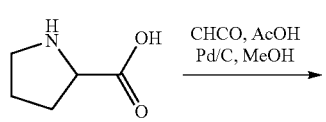

Example 8.28a

Synthesis of 1-methylpyrrolidine-2-carboxylic acid

A solution of pyrrolidine-2-carboxylic acid (5.4 g, 46.96 mmol), aqueous formaldehyde solution (37%-40%, 1 mL), catalytic CH$_3$COOH and Pd/C (1 g, 10% weight) in MeOH (100 mL) was stirred under H$_2$ (1 atm) for 2 h. The completion of reaction was monitored by LC-MS. The catalyst was removed by filtration, and the filtrate was concentrated to give 5.8 g of the desired product, which was directly used for the next step without further purification. MS (ESI): 130 (MH$^+$).

Example 8.28b

Synthesis of the HCl salt of 3-(4-((3-fluorophenyl)ethynyl)phenyl)-5-(1-methylpyrrolidin-2-yl)-1,2,4-oxadiazole The free base was then converted to the corresponding HCl salt. MS (ESI): 348 (MH$^+$); $^1$H NMR (300 MHz, CDCl$_3$) δ 8.14 (d, J=8.6 Hz, 2H), 7.65 (d, J=8.6 Hz, 2H), 7.37-7.33 (m, 2H), 7.24 (d, J=2.3 Hz, 1H), 7.12-7.07 (m, 1H), 3.80-3.74 (dd, J=8.5, 6.7 Hz, 1H), 3.31-3.25 (m, 1H), 2.58-2.50 (m, 1H), 2.48 (s, 3H), 2.44-2.32 (m, 1H), 2.28-2.08 (m, 2H), 1.98-1.96 (m, 1H). mGluR5 PAM EC$_{50}$: ++. Fold shift at 10 μM: +.

Example 8.29
Synthesis of the HCl salt of Compound 48: 5-(1-ethylpyrrolidin-2-yl)-3-(4-((3-fluorophenyl)ethynyl)phenyl)-1,2,4-oxadiazole
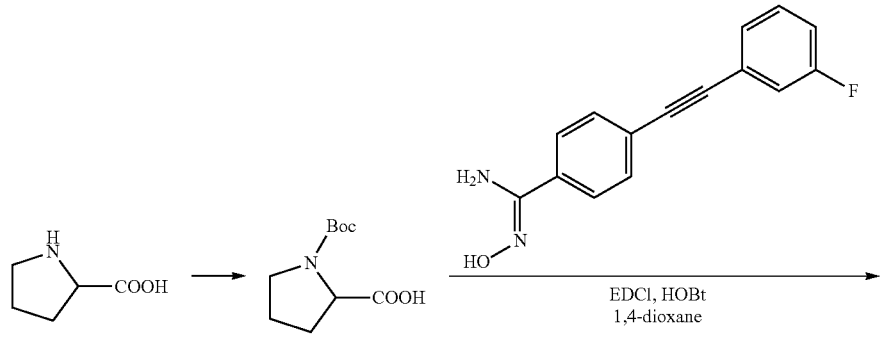
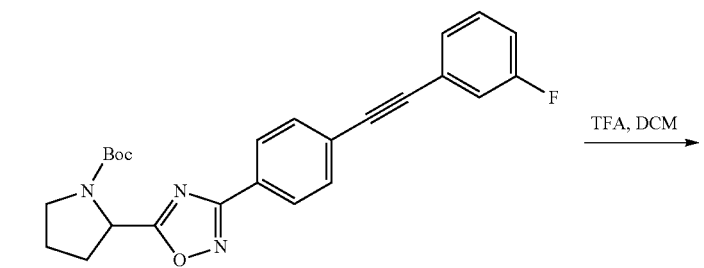
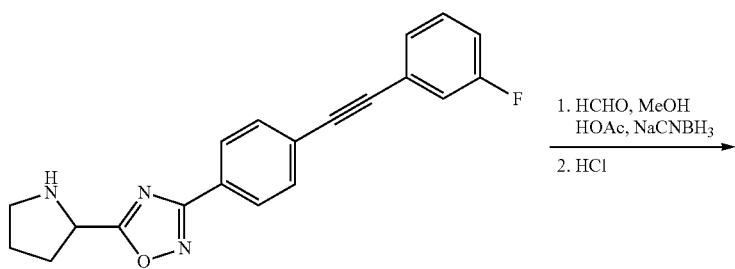
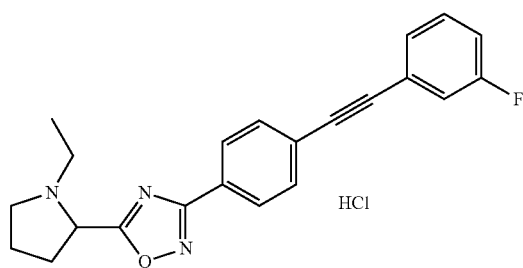

Example 8.29a

Synthesis of tert-butyl 2-(3-(4-((3-fluorophenyl)ethynyl)phenyl)-1,2,4-oxadiazol-5-yl)pyrrolidine-1-carboxylate The title compound was prepared according to the experimental procedure described in Example 8.25. MS (ESI): 434 (MH$^+$).

Example 8.29b

Synthesis of 3-(4-((3-fluorophenyl)ethynyl)phenyl)-5-(pyrrolidin-2-yl)-1,2,4-oxadiazole A solution of tert-butyl 2-(3-(4-((3-fluorophenyl)ethynyl)phenyl)-1,2,4-oxadiazol-5-yl)pyrrolidine-1-carboxylate (1.5 g, 3.46 mmol) and CF$_3$COOH (3 mL) in DCM was stirred at room temperature for 4 h. After dilution with water (50 mL), the reaction mixture was adjusted with aq Na$_2$CO$_3$ and extracted with DCM (3×100 mL). The combined organic layers were concentrated and purified by column chromatography to give 0.8 g of the desired product. MS (ESI): 334 (MH$^+$).

Example 8.29c

Synthesis of the HCl salt of 5-(1-ethylpyrrolidin-2-yl)-3-(4-((3-fluorophenyl)ethynyl)phenyl)-1,2,4-oxadiazole A solution of 3-(4-((3-fluorophenyl)ethynyl)phenyl)-5-(pyrrolidin-2-yl)-1,2,4-oxadiazole (100 mg, 0.3 mmol), aqueous acetaldehyde (0.1 mL) and 2 drops CH$_3$COOH in MeOH was stirred at room temperature for 5 min. Then NaCNBH$_3$ (0.2 g) was added into the mixture. Upon completion of the reaction, the suspension was diluted with water (30 mL) and extracted with EtOAc (3×50 mL). After filtration and concentration, 80 mg of the desired product was obtained by column chromatography purification. MS (ESI): 362 (MH$^+$). The free base was converted to the corresponding HCl salt. $^1$H NMR (300 MHz, CD$_3$OD) δ 8.16 (d, J=8.7 Hz, 2H), 7.74 (d, J=8.7 Hz, 2H), 7.46-7.15 (m, 4H), 5.30-5.10 (m, 1H), 4.01-3.30 (m, 4H), 2.90-2.21 (m, 4H), 1.48-1.43 (t, J=7.2 Hz, 3H). mGluR5 PAM EC$_{50}$: ++.

Example 8.30

Synthesis of the HCl salt of Compound 49: 3-(4-((3-fluorophenyl)ethynyl)phenyl)-5-(1-isopropylpyrrolidin-2-yl)-1,2,4-oxadiazole

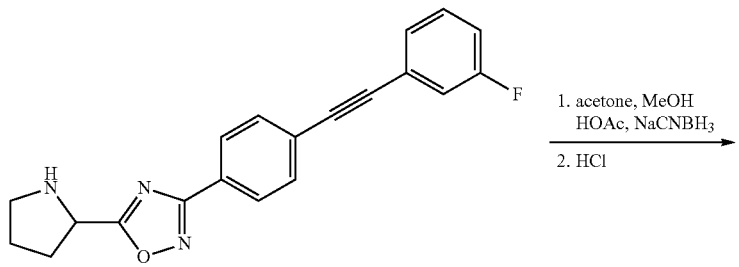

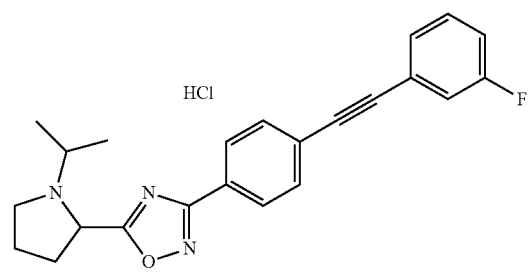

The title compound was prepared according to the experimental procedure described in Example 8.29c. MS (ESI): 376 (MH+); ¹H NMR (300 MHz, CD₃OD) δ 8.16 (d, J=8.6 Hz, 2H), 7.74 (d, J=8.6 Hz, 2H), 7.45-7.37 (m, 2H), 7.34-7.30 (m, 1H), 7.22-7.15 (m, 1H), 5.36 (br s, 1H), 4.04 (br s, 1H), 3.80-3.72 (m, 1H), 3.62-3.55 (m, 1H), 2.81-2.72 (m, 1H), 2.62-2.51 (m, 1H), 2.34-2.27 (m, 2H), 1.50-1.45 (t, J=6.9 Hz, 6H). mGluR5 PAM EC₅₀: +.

Example 8.31

Synthesis of the HCl salt of Compound 50: 5-(1-cyclobutylpyrrolidin-2-yl)-3-(4-((3-fluorophenyl)ethynyl)phenyl)-1,2,4-oxadiazole

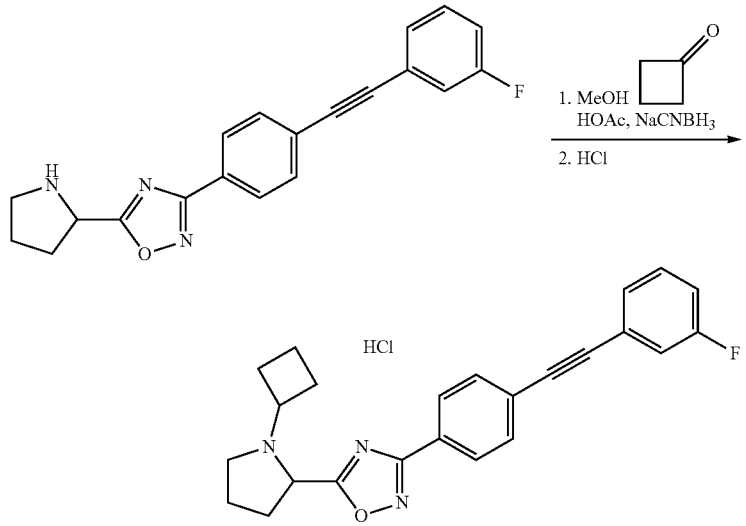

The title compound was prepared according to the experimental procedure described in Example 8.29c. MS (ESI): 388 (MH+); ¹H NMR (300 MHz, CD₃OD) δ 8.15 (d, J=8.4 Hz, 2H), 7.73 (d, J=8.4 Hz, 2H), 7.45-7.17 (m, 4H), 5.25-5.08 (m, 1H), 4.19-4.00 (m, 1H), 3.85-3.70 (m, 1H), 3.40-3.30 (m, 1H), 2.85-2.55 (m, 2H), 2.38-2.34 (m, 6H), 1.94-1.84 (m, 2H). mGluR5 PAM EC₅₀: +.

Example 8.32

Synthesis of the HCl salt of Compound 51: 5-(1,2-dimethylpyrrolidin-2-yl)-3-(5-((3-fluorophenyl)ethynyl)pyridin-2-yl)-1,2,4-oxadiazole

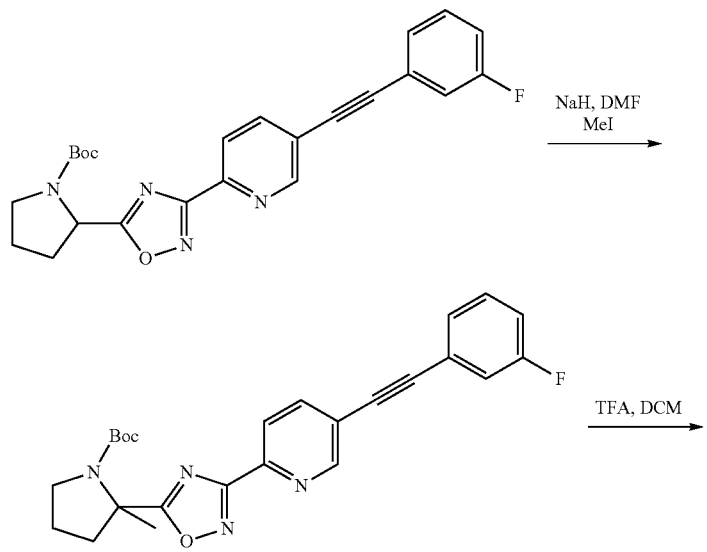

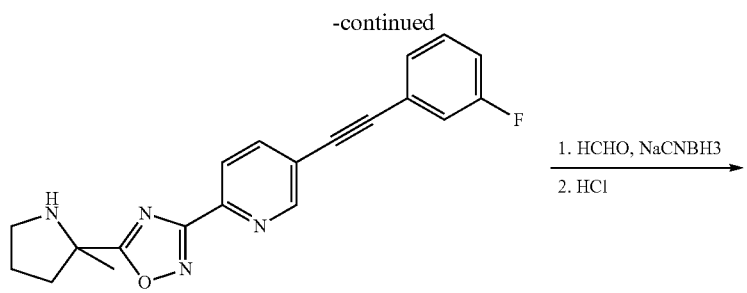

Example 8.32a

Synthesis of tert-butyl 2-(3-(5-((3-fluorophenyl)ethynyl)pyridin-2-yl)-1,2,4-oxadiazol-5-yl)-2-methylpyrrolidine-1-carboxylate A solution of tert-butyl 2-(3-(5-((3-fluorophenyl)ethynyl)pyridin-2-yl)-1,2,4-oxadiazol-5-yl)pyrrolidine-1-carboxylate (200 mg, 0.6 mmol) and excess NaH in DMF was stirred at room temperature for 20 min. Then CH$_3$I (1 mL) was added dropwise. The suspension was diluted with water and extracted with EtOAc (3×100 mL). After filtration and concentration, 50 mg of the desired product was obtained by column chromatography purification. MS (ESI): 448 (MH$^+$).

Example 8.32b

Synthesis of 3-(5-((3-fluorophenyl)ethynyl)pyridin-2-yl)-5-(2-methylpyrrolidin-2-yl)-1,2,4-oxadiazole The title compound was prepared according to the experimental procedure described in Example 8.29b. MS (ESI): 348 (MH$^+$).

Example 8.32c

Synthesis of the HCl salt of 5-(1,2-dimethylpyrrolidin-2-yl)-3-(5-((3-fluorophenyl)ethynyl)pyridin-2-yl)-1,2,4-oxadiazole The title compound was prepared according to the experimental procedure described in Example 8.29c. MS (ESI): 362 (MH$^+$); $^1$H NMR (300 MHz, CD$_3$OD) δ 8.92 (s, 1H), 8.31-8.20 (m, 2H), 7.50-7.34 (m, 3H), 7.25-7.18 (m, 1H), 3.80 (br s, 2H), 3.09-3.02 (m, 3H), 2.79 (s, 1H), 2.56 (s, 1H), 2.38 (s, 2H), 2.01-1.99 (m, 3H). mGluR5 PAM EC$_{50}$: ++++. Fold shift at 10 μM: +.

Example 8.33

Synthesis of the HCl salt of Compound 52: 5-(1-(azetidin-1-yl)ethyl)-3-(4-((3-fluorophenyl)ethynyl)phenyl)-1,2,4-oxadiazole

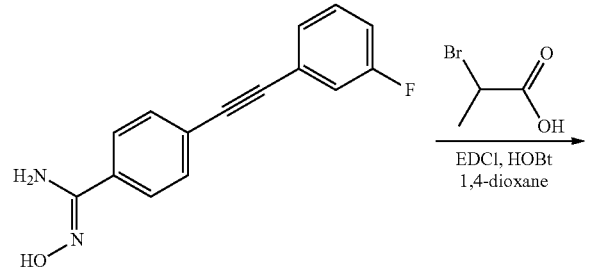

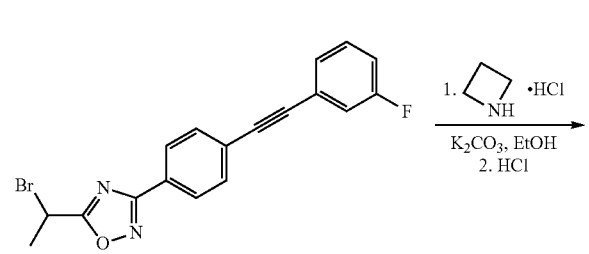

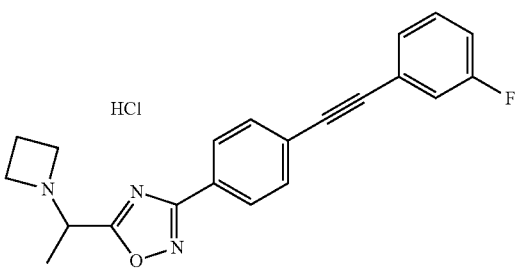

Example 8.33a

Synthesis of 5-(1-bromoethyl)-3-(4-((3-fluorophenyl)ethynyl)phenyl)-1,2,4-oxadiazole The title compound was prepared according to the experimental procedure described in Example 8.25. MS (ESI): 371, 373 (MH$^+$).

Example 8.33b

Synthesis of the HCl salt of 5-(1-(azetidin-1-yl)ethyl)-3-(4-((3-fluorophenyl)ethynyl)phenyl)-1,2,4-oxadiazole A solution of 5-(1-bromoethyl)-3-(4-((3-fluorophenyl)ethynyl)phenyl)-1,2,4-oxadiazole (250 mg, 0.67 mmol), azetidine hydrochloride (1 g, 10.7 mmol), and K$_2$CO$_3$ (0.5 g, 3.6 mmol) in ethanol (20 mL) was stirred at 60° C. for 3 h. Then silica gel was added to the mixture. After concentration, 140 mg of the desired product was obtained by column chromatography purification. MS (ESI): 348 (MH$^+$); $^1$H NMR (300 MHz, CD$_3$OD) δ 8.14 (d, J=8.4 Hz, 2H), 7.72 (d, J=8.4 Hz, 2H), 7.48-7.37 (m, 2H), 7.33-7.29 (m, 1H), 7.21-7.14 (m, 1H), 5.27-5.20 (m, 1H), 4.86-4.46 (m, 4H), 2.71-2.50 (m, 2H), 1.76 (d, J=6.9 Hz, 3H). mGluR5 PAM EC$_{50}$: +.

Example 8.34

Synthesis of the HCl salt of Compound 53: 3-(4-((3-fluorophenyl)ethynyl)phenyl)-5-(1-(pyrrolidin-1-yl)ethyl)-1,2,4-oxadiazole

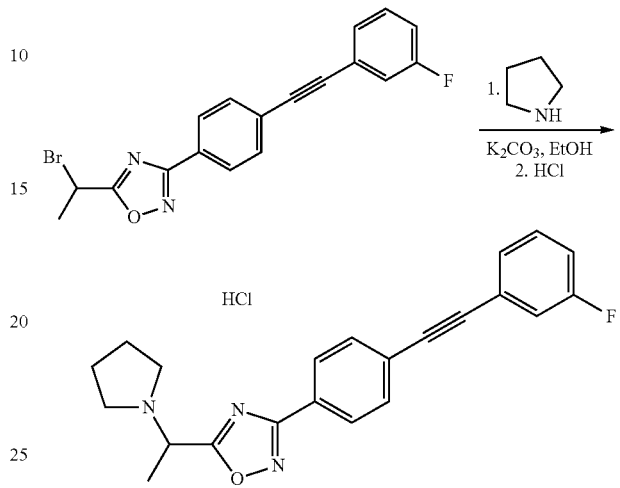

The title compound was prepared according to the experimental procedure described in Example 8.33b. MS (ESI): 362 (MH$^+$); $^1$H NMR (300 MHz, CD$_3$OD) δ 8.04 (d, J=8.4 Hz, 2H), 7.62 (d, J=8.7 Hz, 2H), 7.36-7.29 (m, 2H), 7.27-7.26 (m, 1H), 7.22-7.03 (m, 1H), 5.13-5.06 (m, 1H), 3.49 (br s, 4H), 2.05 (br s, 4H), 1.79 (d, J=6.9 Hz, 3H). mGluR5 PAM EC$_{50}$: +.

Example 8.35

Synthesis of the HCl salt of Compound 54: N-(1-(3-(4-((3-fluorophenyl)ethynyl)phenyl)-1,2,4-oxadiazol-5-yl)ethyl)-N-methylcyclopropanamine

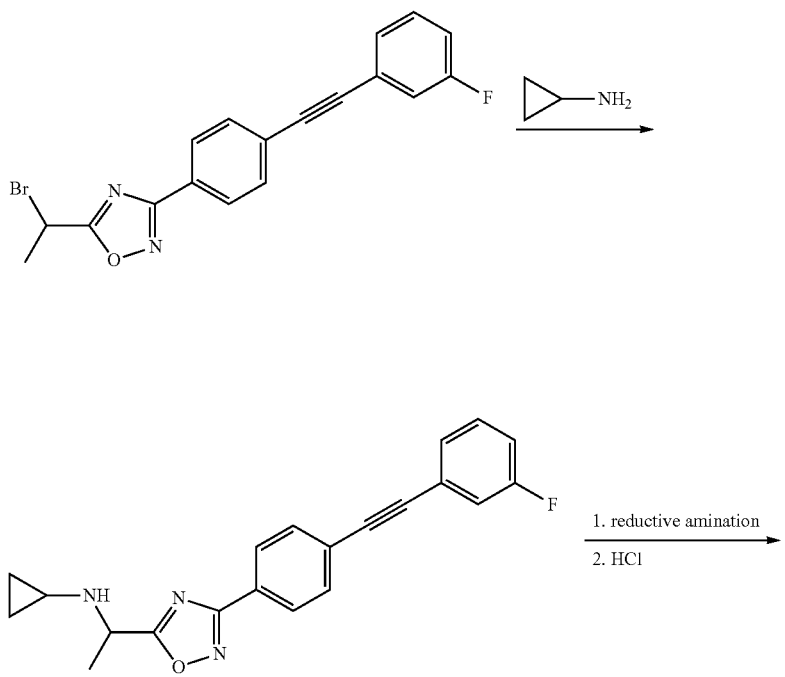

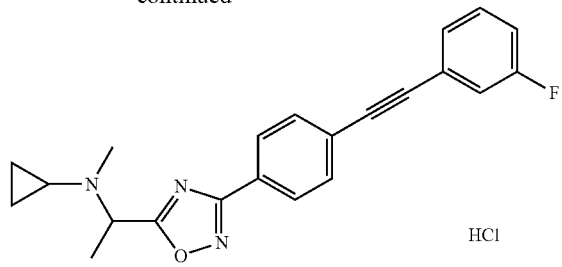

HCl

Example 8.35a

Synthesis of N-(1-(3-(4-((3-fluorophenyl)ethynyl)phenyl)-1,2,4-oxadiazol-5-yl)ethyl)cyclopropanamine The title compound was prepared according to the experimental procedure described in Example 8.33b. MS (ESI): 348 (MH$^+$).

Example 8.35b

Synthesis of the HCl salt of N-(1-(3-(4-((3-fluorophenyl)ethynyl)phenyl)-1,2,4-oxadiazol-5-yl)ethyl)-N-methylcyclopropanamine The title compound was prepared according to the experimental procedure described for Example 8.29c. MS (ESI): 362 (MH$^+$); $^1$H NMR (300 MHz, CD$_3$OD) δ 8.17 (d, J=8.5 Hz, 2H), 7.73 (d, J=8.5 Hz, 2H), 7.48-7.38 (m, 2H), 7.33-7.29 (m, 1H), 7.21-7.15 (m, 1H), 5.38-5.31 (q, 1H), 3.16-3.10 (m, 4H), 1.97 (d, J=7.0 Hz, 3H), 1.09-0.98 (m, 4H). mGluR5 PAM EC$_{50}$: +.

Example 8.36

Synthesis of Compound 55: ethyl 3-(4-((3-fluorophenyl)ethynyl)phenyl)-1,2,4-oxadiazole-5-carboxylate

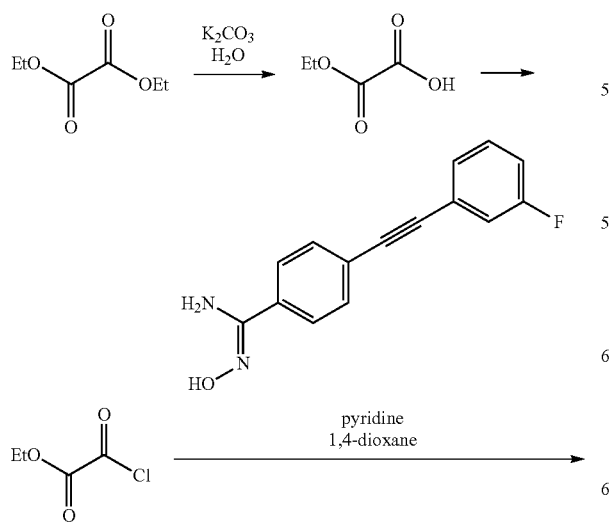

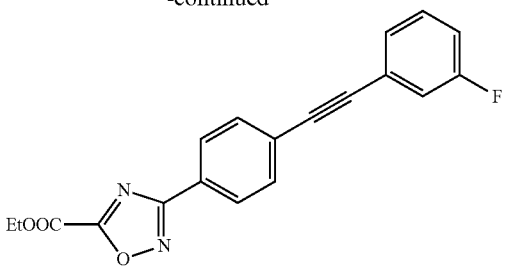

Example 8.36a

Synthesis of 2-ethoxy-2-oxoacetic acid

A solution of diethyl oxalate (20 g, 0.137 mmol) and K$_2$CO$_3$ (10 g, 0.072 mmol) in water was stirred at 50° C. for 6 h. After cooling to room temperature, the suspension was filtered, acidified to pH 3~4 with 4 N HCl, and extracted with EtOAc (5×100 mL). The combined organic layers were washed with brine and dried over anhydrous sodium sulfate. After filtration, the solution was concentrated to give 7 g of the desired product, which was directly used for the next step without further purification.

Example 8.36b

Synthesis of ethyl 3-(4-((3-fluorophenyl)ethynyl)phenyl)-1,2,4-oxadiazole-5-carboxylate The title compound was prepared according to the experimental procedure as described in Example 7.1b. MS (ESI): 337 (MH$^+$); $^1$H NMR (300 MHz, CDCl$_3$) δ 8.17 (d, J=8.4 Hz, 2H), 7.68 (d, J=8.4 Hz, 2H), 7.40-7.34 (m, 2H), 7.25 (d, J=2.4 Hz, 1H), 7.13-7.06 (m, 1H), 4.64-4.56 (q, 2H), 1.54-1.49 (t, J=7.1 Hz, 3H).

Example 8.37

Synthesis of Compound 56: 1-(3-(4-((3-fluorophenyl)ethynyl)phenyl)-1,2,4-oxadiazol-5-yl)ethanone

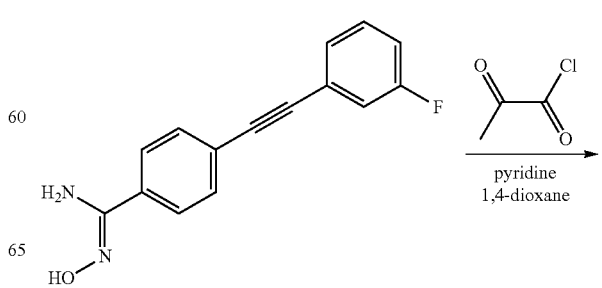

-continued

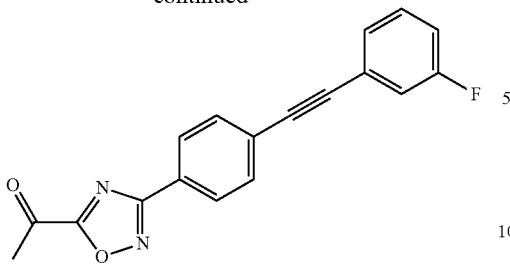

The title compound was prepared according to the experimental procedure described in Example 7.1b. MS (ESI): 307 (MH$^+$); $^1$H NMR (300 MHz, CDCl$_3$) δ 8.17 (d, J=8.3 Hz, 2H), 7.74 (d, J=8.3 Hz, 2H), 7.37-7.34 (m, 2H), 7.26 (d, J=2.3 Hz, 1H), 7.10-7.09 (m, 1H), 2.85 (s, 3H).

Example 8.38

Synthesis of Compound 57: 1-(3-(4-((3-fluorophenyl)ethynyl)phenyl)-1,2,4-oxadiazol-5-yl)ethanol

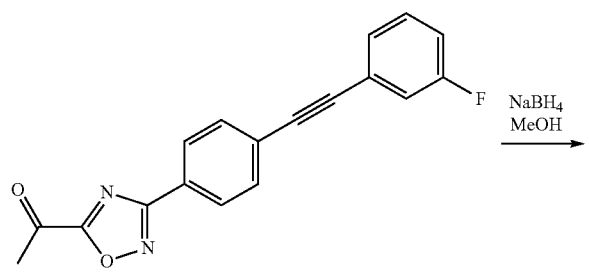

A solution of 1-(3-(4-(3-fluorophenyl)ethynyl)phenyl)-1,2,4-oxadiazol-5-yl)ethanone (50 mg, 0.16 mmol) and NaBH$_4$ (0.2 g, 26 mmol) in methanol was stirred at room temperature. After completion of the reaction, the suspension was diluted with water (30 mL) and extracted with EtOAc (3×50 mL). The combined organic layers were concentrated and 30 mg of the desired product was obtained by flash column chromatography. MS (ESI): 309 (MH$^+$); $^1$H NMR (300 MHz, CDCl$_3$) δ 8.11 (d, J=8.4 Hz, 2H), 7.66 (d, J=8.4 Hz, 2H), 7.39-7.31 (m, 2H), 7.25 (d, J=1.8 Hz, 1H), 7.12-7.05 (m, 1H), 5.23-5.14 (m, 1H), 2.67 (d, J=5.8 Hz, 1H), 1.75 (d, J=6.7 Hz, 3H).

Example 8.39

Synthesis of Compound 58: 3-(4-((3-fluorophenyl)ethynyl)phenyl)-5-(1-methoxyethyl)-1,2,4-oxadiazole

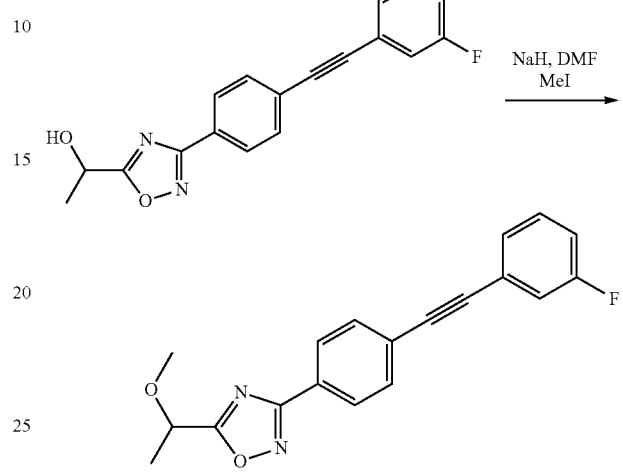

A solution of 1-(3-(4-((3-fluorophenyl)ethynyl)phenyl)-1,2,4-oxadiazol-5-yl)ethanol (30 mg, 0.096 mmol) and NaH (0.1 g, 4 mmol) in DMF was stirred at room temperature for 30 mins. Then CH$_3$I (0.5 g, 3.5 mmol) was added dropwise to the reaction mixture. After dilution with water (30 mL) and extraction with EtOAc (3×50 mL), the solution was concentrated and purified by column chromatography to give 7.1 mg of the desired product. MS (ESI): 323 (MH$^+$); $^1$H NMR (300 MHz, CDCl$_3$) δ 8.13 (d, J=8.5 Hz, 2H), 7.66 (d, J=8.5 Hz, 2H), 7.37-7.33 (m, 2H), 7.25 (d, J=2.0 Hz, 1H), 7.13-7.05 (m, 1H), 4.77-4.70 (m, 1H), 3.50 (s, 3H), 1.69 (d, J=6.7 Hz, 3H). mGluR5 PAM EC$_{50}$: ++. Fold shift at 10 μM: ++.

Example 8.40

Synthesis of the HCl salt of Compound 59: 3-(4-((3-fluorophenyl)ethynyl)phenyl)-5-(pyrrolidin-1-yl)-1,2,4-oxadiazole

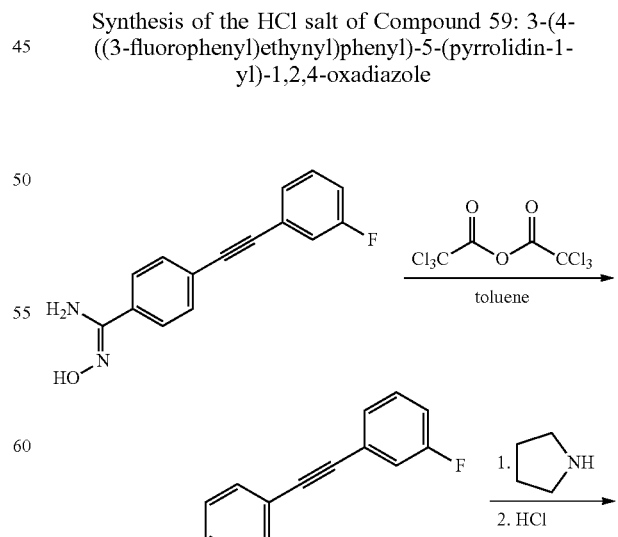

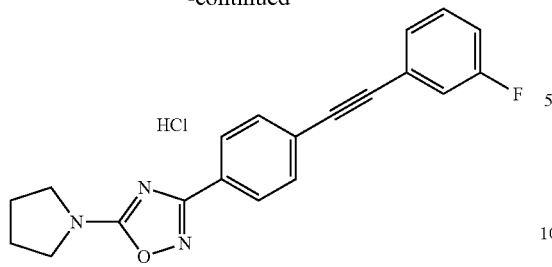

Example 8.40a

Synthesis of 3-(4-((3-fluorophenyl)ethynyl)phenyl)-5-(trichloromethyl)-1,2,4-oxadiazole 4-((3-Fluorophenyl)ethynyl)-N'-hydroxybenzimidamide (300 mg, 1.2 mmol) and 2,2,2-trichloroacetic anhydride (364 mg, 1.2 mmol) in toluene were stirred at 120° C. After completion of the reaction, the suspension was diluted with water (40 mL) and extracted with EtOAc (3×100 mL), and the combined organic layers was concentrated and purified by column chromatography to give 320 mg of the desired product. MS (ESI): 381, 383 (MH⁺).

Example 8.40b

Synthesis of the HCl salt of 3-(4-((3-fluorophenyl)ethynyl)phenyl)-5-(pyrrolidin-1-yl)-1,2,4-oxadiazole A solution of 3-(4-((3-fluorophenyl)ethynyl)phenyl)-5-(trichloromethyl)-1,2,4-oxadiazole (100 mg, 0.26 mmol) and pyrrolidine (38 mg, 0.54 mmol) in 1-methylpyrrolidin-2-one (2 mL) was stirred at 130° C. After completion of the reaction, the mixture was diluted with water (40 mL) and extracted with EtOAc (3×50 mL), the combined organic layers were concentrated and purified by column chromatography to give 50 mg of the desired product. MS (ESI): 334 (MH⁺); ¹H NMR (300 MHz, CDCl₃) δ 8.04-8.01 (d, J=8.5 Hz, 2H), 7.63-7.59 (d, J=8.5 Hz, 2H), 7.36-7.32 (m, 2H), 7.25-7.23 (m, 1H), 7.11-7.05 (m, 1H), 3.69-3.64 (t, J=6.9 Hz, 4H), 2.10-2.05 (m, 4H).

Example 8.41

Synthesis of the HCl salt of Compound 60: 4-(3-(4-((3-fluorophenyl)ethynyl)phenyl)-1,2,4-oxadiazol-5-yl)morpholine

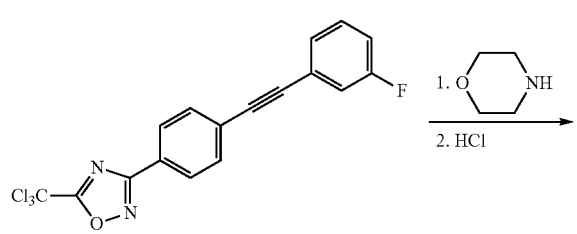

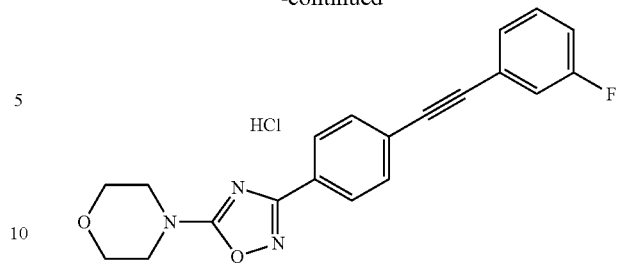

The title compound was prepared according to the experimental procedure described in Example 8.40b. MS (ESI): 350 (MH⁺); ¹H NMR (300 MHz, CDCl₃) δ 8.14-8.11 (d, J=8.4 Hz, 2H), 7.69-7.66 (d, J=8.4 Hz, 2H), 7.40-7.32 (m, 2H), 7.28-7.25 (m, 1H), 7.13-7.06 (m, 1H), 3.96-3.92 (m, 2H), 3.90-3.79 (m, 6H).

Example 8.42

Synthesis of the HCl salt of Compound 61: N-ethyl-3-(4-((3-fluorophenyl)ethynyl)phenyl)-N-methyl-1,2,4-oxadiazol-5-amine

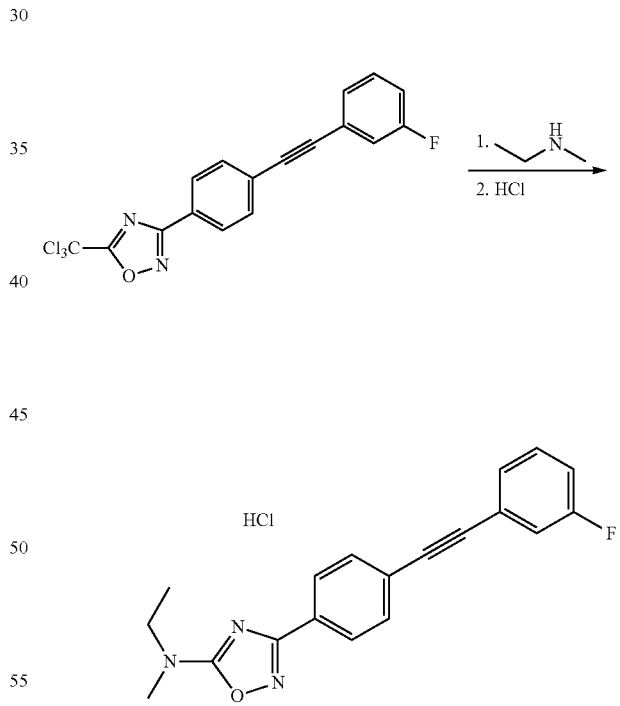

The title compound was prepared according to the experimental procedure described in Example 8.40b. MS (ESI): 322 (MH⁺); ¹H NMR (300 MHz, CDCl₃) δ 8.04-8.01 (d, J=8.4 Hz, 2H), 7.63-7.60 (d, J=8.4 Hz, 2H), 7.36-7.32 (m, 2H), 7.27-7.23 (m, 1H), 7.11-7.04 (m, 1H), 3.65-3.57 (q, 2H), 3.20 (s, 3H), 1.32-1.27 (t, J=7.2 Hz, 3H). mGluR5 PAM EC₅₀: +.

Example 8.43

Synthesis of the HCl salt of Compound 62: 3-(4-((3-fluorophenyl)ethynyl)phenyl)-N-methyl-1,2,4-oxadiazol-5-amine

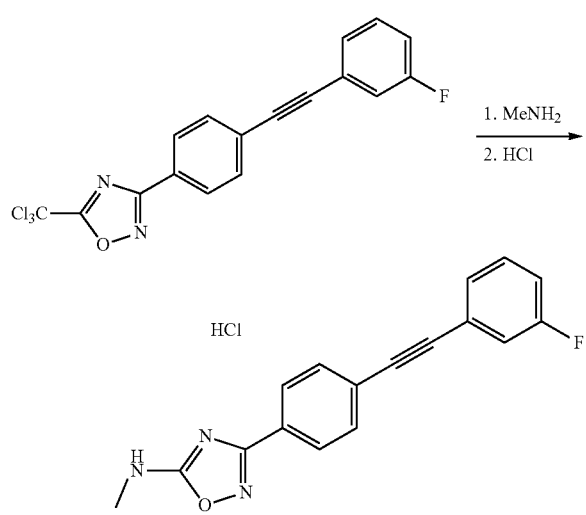

The title compound was prepared according to the experimental as described in Example 8.40b. MS (ESI): 294 (MH+); 1H NMR (300 MHz, CDCl3) δ 8.02 (d, J=8.1 Hz, 2H), 7.65 (d, J=7.5 Hz, 2H), 7.38-7.32 (m, 2H), 7.24-7.23 (m, 1H), 7.11-7.04 (m, 1H), 5.16 (m, 1H), 3.17 (d, J=6.0 Hz, 3H).

Example 9.1

Synthesis of Compound 63: 3-(4-((4-fluorophenyl)ethynyl)phenyl)-5-isopropyl-1,2,4-oxadiazole

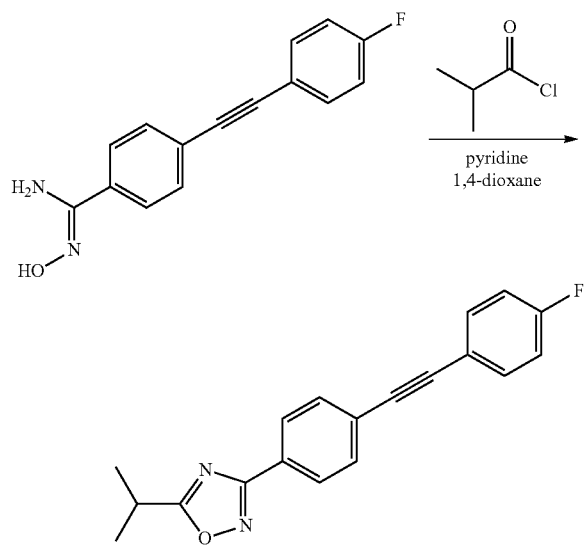

The title compound was prepared according to the experimental procedure described in Example 7.1b. MS (ESI): 307 (MH+); 1H NMR (300 MHz, CDCl3) δ 8.09 (d, J=8.4 Hz, 2H), 7.63 (d, J=8.4 Hz, 2H), 7.58-7.51 (m, 2H), 7.11-7.05 (t, J=8.4 Hz, 2H), 3.36-3.27 (m, 1H), 1.48 (d, J=7.0 Hz, 6H).

Example 9.2

Synthesis of Compound 64: 5-(sec-butyl)-3-(4-((4-fluorophenyl)ethynyl)phenyl)-1,2,4-oxadiazole

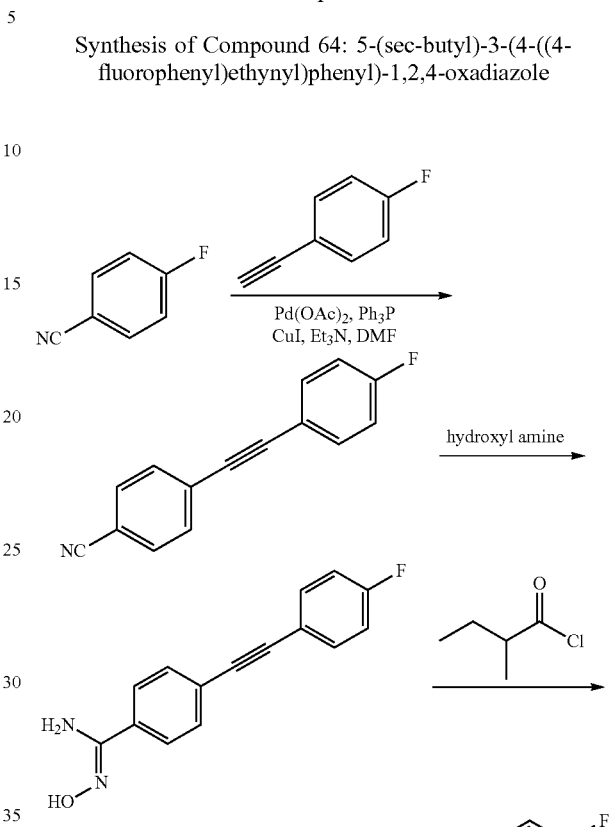

Example 9.2a

Synthesis of 4-((4-fluorophenyl)ethynyl)-N'-hydroxybenzimidamide

The title compound was prepared according to the experimental procedure described in Example 8.1a and 8.1b. MS (ESI): 255 (MH+).

Example 9.2b

Synthesis of 5-(sec-butyl)-3-(4-((4-fluorophenyl)ethynyl)phenyl)-1,2,4-oxadiazole The title compound was prepared according to the experimental procedure described in Example 7.1b. MS (ESI): 321 (MH+); 1H NMR (300 MHz, CDCl3) δ 8.09 (d, J=8.0 Hz, 2H), 7.63 (d, J=8.0 Hz, 2H), 7.56-7.52 (m, 2H), 7.11-7.05 (m, 2H), 3.17-3.10 (m, 1H), 2.00-1.74 (m, 2H), 1.45 (d, J=6.9 Hz, 3H), 1.08-1.02 (t, J=7.3 Hz, 3H).

Example 9.3

Synthesis of Compound 65: 5-cyclopentyl-3-(4-((4-fluorophenyl)ethynyl)phenyl)-1,2,4-oxadiazole

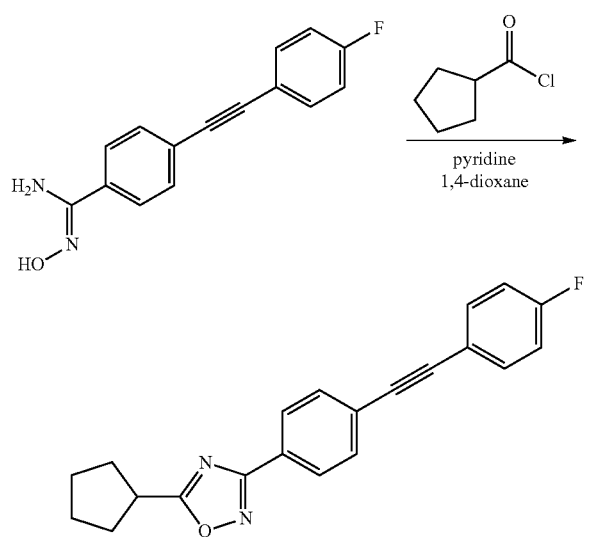

The title compound was prepared according to the experimental procedure described in Example 7.1b. MS (ESI): 333 (MH+); ¹H NMR (300 MHz, CDCl₃) δ 8.08 (d, J=8.3 Hz, 2H), 7.63 (d, J=8.3 Hz, 2H), 7.57-7.52 (m, 2H), 7.08 (d, J=8.3 Hz, 2H), 3.45-3.39 (m, 1H), 2.23-2.15 (m, 2H), 2.09-2.02 (m, 2H), 2.00-1.89 (m, 2H), 1.84-1.74 (m, 2H).

Example 9.4

Synthesis of Compound 66: 5-(tert-butyl)-3-(4-((4-fluorophenyl)ethynyl)phenyl)-1,2,4-oxadiazole

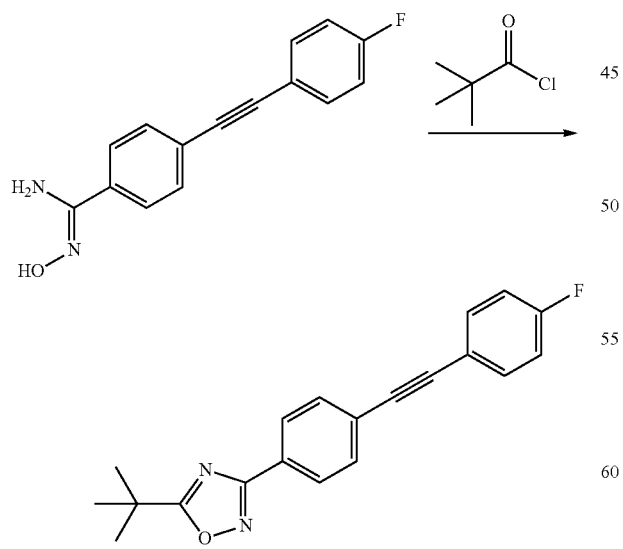

The title compound is prepared according to the experimental procedure described in Example 7.1b. MS (ESI): 321 (MH+); ¹H NMR (300 MHz, CDCl₃) δ 8.09 (d, J=8.1 Hz, 2H), 7.63 (d, J=8.4 Hz, 2H), 7.57-7.52 (m, 2H), 7.10-7.05 (t, J=8.7 Hz, 2H), 1.52 (s, 9H). mGluR5 PAM EC$_{50}$: ++. Fold shift at 10 μM: +.

Example 10.1

Synthesis of the HCl salt of Compound 67: 5-(tert-butyl)-3-(4-((4-fluorophenyl)ethynyl)phenyl)-1,2,4-oxadiazole

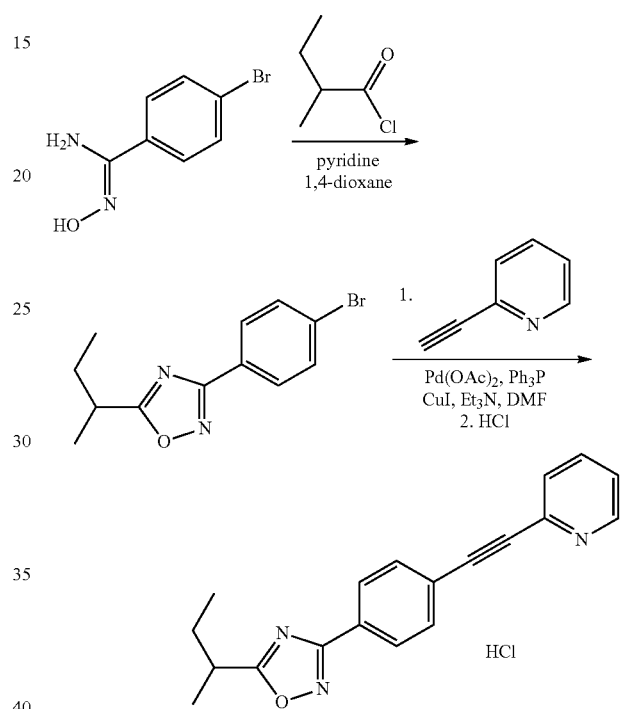

Example 10.1a

Synthesis of 3-(4-bromophenyl)-5-sec-butyl-1,2,4 oxadiazole

The title compound was prepared according to the experimental procedure described in Example 7.1b. MS (ESI): 281, 283 (MH+).

Example 10.1b

Synthesis of the HCl salt of 5-(tert-butyl)-3-(4-((4-fluorophenyl)ethynyl)phenyl)-1,2,4-oxadiazole The title compound was prepared according to the experimental procedure described in Example 8.1a. MS (ESI): 304 (MH+); ¹H NMR (300 MHz, CDCl₃) δ 8.67-8.64 (m, 1H), 8.11 (d, J=8.6 Hz, 2H), 7.75-7.69 (m, 3H), 7.58-7.55 (m, 1H), 7.31-7.26 (m, 1H), 3.17-3.09 (m, 1H), 1.97-1.89 (m, 1H), 1.84-1.76 (m, 1H), 1.45 (d, J=7.1 Hz, 3H), 1.02-0.96 (t, J=7.4 Hz, 3H). mGluR5 PAM EC$_{50}$: ++++. Fold shift at 10 μM: +.

Example 10.2

Synthesis of the HCl salt of Compound 68: 5-(1-methoxyethyl)-3-(4-(pyridin-2-ylethynyl)phenyl)-1,2,4-oxadiazole

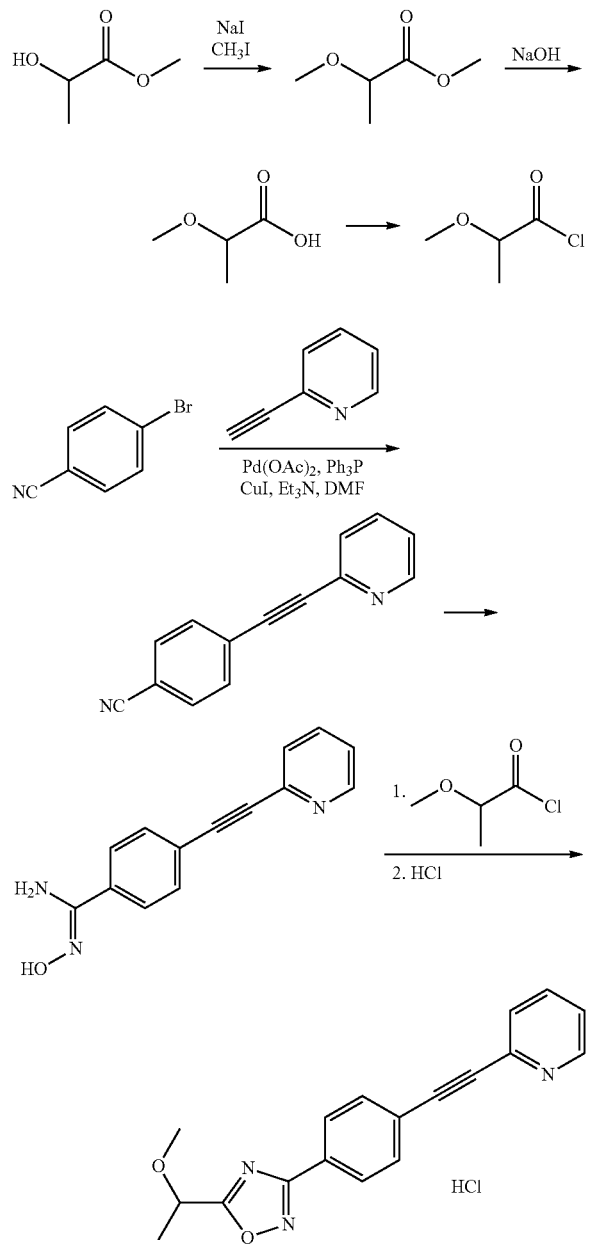

Example 10.2a

Synthesis of 4-(pyridin-2-ylethynyl)benzonitrile

The title compound was prepared according to the experimental procedure described in Example 8.1a. MS (ESI): 205 (MH$^+$).

Example 10.2b

Synthesis of N'-hydroxy-4-(pyridin-2-ylethynyl)benzimidamide

The title compound was prepared according to the experimental procedure describe din Example 8.1b. MS (ESI): 238 (MH$^+$).

Example 10.2c

Synthesis of the HCl salt of 5-(1-methoxyethyl)-3-(4-(pyridin-2-ylethynyl)phenyl)-1,2,4-oxadiazole The title compound was prepared according to the experimental procedure described in Example 8.25. MS (ESI): 306 (MH$^+$); $^1$H NMR (300 MHz, CD$_3$OD) δ 8.86 (d, J=5.8 Hz, 1H), 8.62-8.55 (td, J=7.9, 1.5 Hz, 1H), 8.26-8.22 (m, 3H), 8.04-7.99 (m, 1H), 7.90 (d, J=8.5 Hz, 2H), 4.86-4.79 (q, 1H), 3.48 (s, 3H), 1.65 (d, J=6.7 Hz, 3H).

Example 10.3

Synthesis of the HCl salt of Compound 69: 5-(1-methoxypropyl)-3-(4-(pyridin-2-ylethynyl)phenyl)-1,2,4-oxadiazole

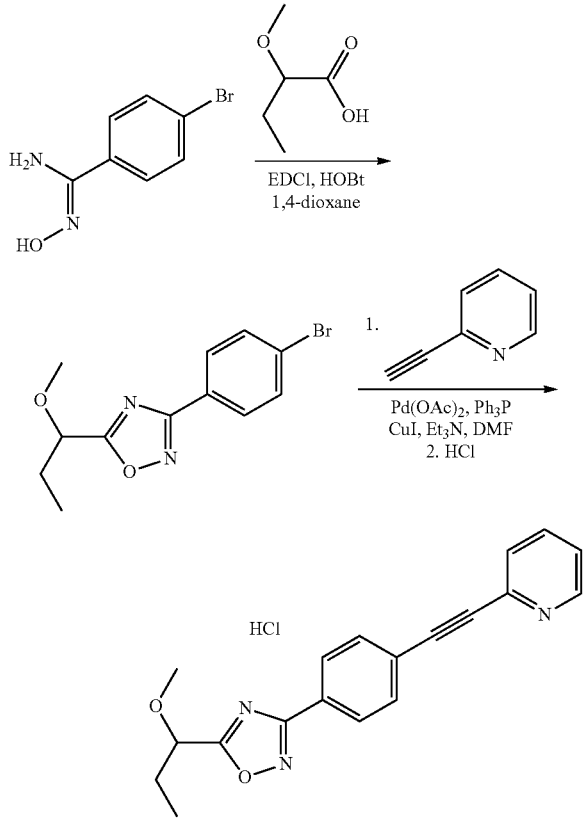

Example 10.3a

Synthesis of 3-(4-bromophenyl)-5-(1-methoxypropyl) 1,2,4-oxadiazole

The title compound was prepared according to the experimental procedure described in Example 8.25. MS (ESI): 297, 299 (MH⁺).

Example 10.3b

Synthesis of the HCl salt of 5-(1-methoxypropyl)-3-(4-(pyridin-2-ylethynyl)phenyl)-1,2,4-oxadiazole The title compound was prepared according to the experimental procedure describe din Example 8.1a. MS (ESI): 320 (MH⁺); ¹H NMR (300 MHz, CD₃OD) δ 8.72 (d, J=5.1 Hz, 1H), 8.27-8.18 (m, 3H), 7.96 (d, J=7.7 Hz, 1H), 7.83 (d, J=8.3 Hz, 2H), 7.75-7.71 (t, J=6.1 Hz, 1H), 4.64-4.60 (t, J=6.5 Hz, 1H), 3.46 (s, 3H), 2.04-1.97 (m, 2H), 1.05-0.99 (t, J=7.4 Hz, 3H).

Example 10.4

Synthesis of the HCl salt of Compound 70: 5-(1-methylpyrrolidin-2-yl)-3-(4-(pyridin-2-ylethynyl)phenyl)-1,2,4-oxadiazole

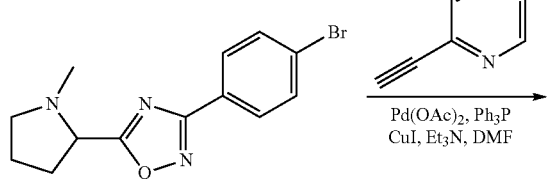

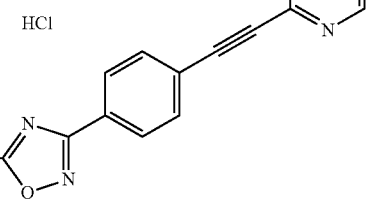

The title compound was prepared according to the experimental procedure described in Example 8.1a. MS (ESI): 331 (MH⁺); ¹H NMR (300 MHz, CD₃OD) δ 8.89 (d, J=5.1 Hz, 1H), 8.66-8.61 (td, J=7.9, 1.3 Hz, 1H), 8.28 (d, J=8.3 Hz, 3H), 8.09-8.05 (m, 1H), 7.94 (d, J=8.3 Hz, 2H), 5.17 (m, 1H), 3.95 (m, 1H), 3.55-3.49 (m, 1H), 3.24 (s, 3H), 2.90-2.83 (m, 1H), 2.59-2.22 (m, 3H). mGluR5 PAM EC₅₀: ++++.

Example 11.1

Synthesis of the HCl salt of Compound 71: 5-(sec-butyl)-3-(4-(pyridin-4-ylethynyl)phenyl)-1,2,4-oxadiazole

Example 11.1a

Synthesis of 3-(4-bromophenyl)-5-sec-butyl-1,2,4-oxadiazole

The title compound was prepared according to the experimental procedure described in Example 8.25. MS (ESI): 281, 283 (MH⁺).

Example 11.1b

Synthesis of the HCl salt of 5-(sec-butyl)-3-(4-(pyridin-4-ylethynyl)phenyl)-1,2,4-oxadiazole The title compound was prepared according to the experimental procedure described in Example 8.1a. MS (ESI): 304 (MH⁺); ¹H NMR (300 MHz, CDCl₃) δ 8.65 (br s, 2H), 8.14-8.10 (m, 2H), 7.68-7.65 (m, 2H), 7.41 (d, J=4.5 Hz, 2H), 3.19-3.09 (m, 1H), 2.01-1.85 (m, 1H), 1.83-1.71 (m, 1H), 1.44 (d, J=7.0 Hz, 3H), 1.29-1.26 (t, J=7.4 Hz, 3H). mGluR5 PAM EC₅₀: ++. Fold shift at 10 μM: +.

Example 11.2

Synthesis of the HCl salt of Compound 72: (S)-5-(sec-butyl)-3-(4-(pyridin-4-ylethynyl)phenyl)-1,2,4-oxadiazole

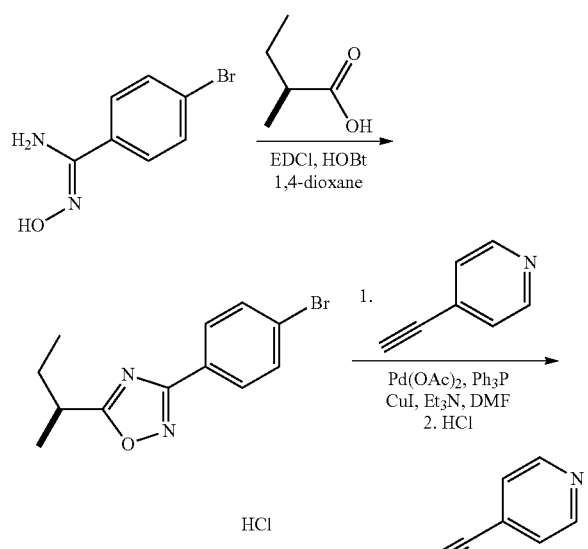

Example 11.2a

Synthesis of (S)-3-(4-bromophenyl)-5-sec-butyl-1,2,4-oxadiazole

The title compound was prepared according to the experimental procedure described in Example 8.25. MS (ESI): 281, 283 (MH$^+$).

Example 11.2b

Synthesis of the HCl salt of (S)-5-(sec-butyl)-3-(4-(pyridin-4-ylethynyl)phenyl)-1,2,4-oxadiazole The title compound was prepared according to the experimental procedure described in Example 8.1a. MS (ESI): 304 (MH$^+$); $^1$H NMR (300 MHz, DMSO-d$_6$) δ 8.87 (d, J=6.2 Hz, 2H), 8.13 (d, J=8.2 Hz, 2H), 8.01 (d, J=6.0 Hz, 2H), 7.86 (d, J=8.3 Hz, 2H), 3.25-3.18 (m, 1H), 1.88-1.69 (m, 2H), 1.37 (d, J=6.9 Hz, 3H), 0.93-0.88 (t, J=7.4 Hz, 3H). mGluR5 PAM EC$_{50}$: ++. Fold shift at 10 μM: +.

Example 11.3

Separation of Compound 71: (S)-5-(sec-butyl)-3-(4-(pyridin-4-ylethynyl)phenyl)-1,2,4-oxadiazole and Compound 72: (R)-5-(sec-butyl)-3-(4-(pyridin-4-ylethynyl)phenyl)-1,2,4-oxadiazole

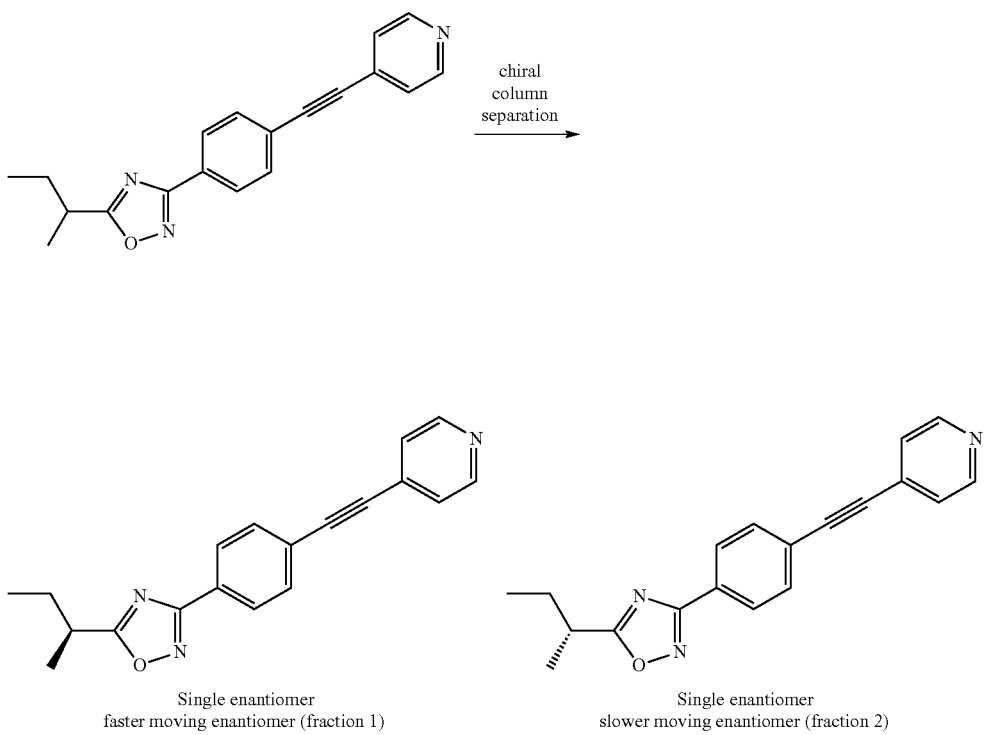

Racemic 5-(sec-butyl)-3-(4-(pyridin-4-ylethynyl)phenyl)-1,2,4-oxadiazole was separated into the corresponding two single enantiomer compounds (S)-5-(sec-butyl)-3-(4-(pyridin-4-ylethynyl)phenyl)-1,2,4-oxadiazole and (R)-5-(sec-butyl)-3-(4-(pyridin-4-ylethynyl)phenyl)-1,2,4-oxadiazole using chiral chromatography with an isocratic SFC method. The column used was a 3.0×25.0 cm ChiralPak AD-H from Chiral Technologies (West Chester, Pa.). The $CO_2$ co-solvent was methanol. Isocratic Method: 10% Co-solvent at 80 mL/min System pressure: 125 bar. Column temperature 25° C.

Compound 72: Faster moving enantiomer (fraction 1): (S)-5-(sec-butyl)-3-(4-(pyridin-4-ylethynyl)phenyl)-1,2,4-oxadiazole Retention time=3.7 min. 100% ee. mGluR5 PAM $EC_{50}$: ++. Fold shift at 10 μM: +.

Compound 73: Slower moving enantiomer (fraction 2): (R)-5-(sec-butyl)-3-(4-(pyridin-4-ylethynyl)phenyl)-1,2,4-oxadiazole Retention time=4.2 min. 99.0% ee. mGluR5 PAM $EC_{50}$: +++. Fold shift at 10 μM: +++.

Example 11.4

Synthesis of the HCl salt of Compound 74: 5-(1-methoxyethyl)-3-(4-(pyridin-4-ylethynyl)phenyl)-1,2,4-oxadiazole Example 11.4a Synthesis of 4-(pyridin-4-ylethynyl)benzonitrile The title compound was prepared according to the experimental procedure described in Example 8.1a. MS (ESI): 205 ($MH^+$).

Example 11.4b

Synthesis of N'-hydroxy-4-(pyridin-4-ylethynyl)benzimidamide

The title compound was prepared according to the experimental procedure described in Example 8.1b. MS (ESI): 238 ($MH^+$).

Example 11.4c

Synthesis of the HCl salt of 5-(1-methoxyethyl)-3-(4-(pyridin-4-ylethynyl)phenyl)-1,2,4-oxadiazole The title compound was prepared according to the experimental procedure described in Example 8.25. MS (ESI): 306 ($MH^+$); $^1H$ NMR (300 MHz, DMSO-$d_6$) δ 8.87 (d, J=6.5 Hz, 2H), 8.14 (d, J=8.5 Hz, 2H), 8.00 (d, J=6.5 Hz, 2H), 7.88 (d, J=8.5 Hz, 2H), 4.92-4.84 (m, 1H), 3.38 (s, 3H), 1.56 (d, J=6.7 Hz, 3H). PAM $EC_{50}$: ++++. Fold shift at 10 μM: ++.

Example 11.5

Synthesis of the HCl salt of Compound 75: 5-(pentan-3-yl)-3-(4-(pyridin-4-ylethynyl)phenyl)-1,2,4-oxadiazole

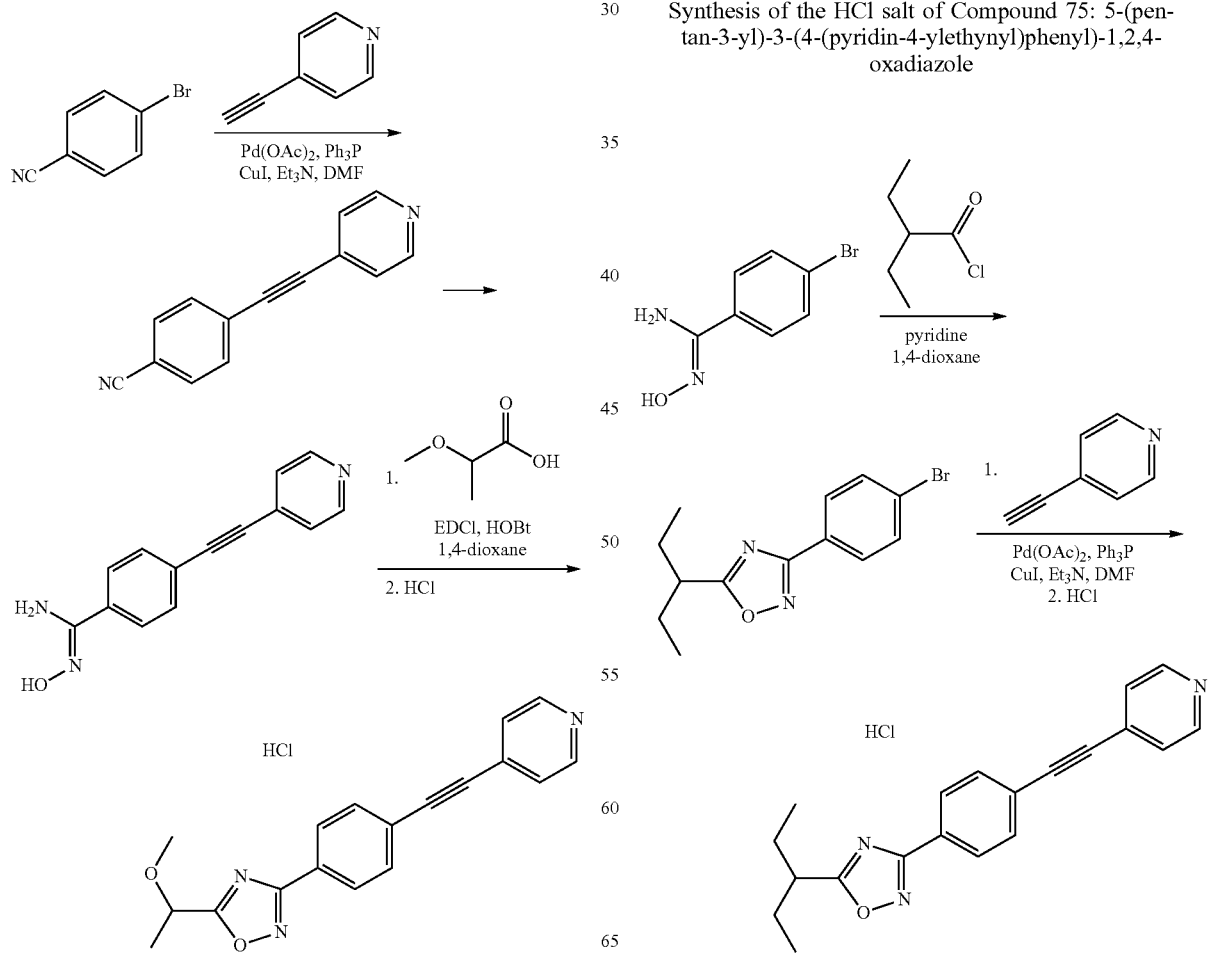

Example 11.5a

Synthesis of 3-(4-bromophenyl)-5-(pentan-3-yl)-1,2,4-oxadiazole

The title compound was prepared according to the experimental procedure described in Example 7.1b. MS (ESI): 295, 297 (MH$^+$).

Example 11.5b

Synthesis of the HCl salt of 5-(pentan-3-yl)-3-(4-(pyridin-4-ylethynyl)phenyl)-1,2,4-oxadiazole The title compound was prepared according to the experimental procedure described in Example 8.1a. MS (ESI): 318 (MH$^+$); $^1$H NMR (300 MHz, CD$_3$OD) δ 8.60-8.58 (dd, J=4.8, 1.5 Hz, 2H), 8.13 (d, J=8.4 Hz, 2H), 7.74 (d, J=8.4, Hz, 2H), 7.59-7.56 (dd, J=4.5, 1.5 Hz, 2H), 3.05-2.97 (m, 1H), 1.93-1.82 (m, 4H), 0.97-0.92 (t, J=7.4 Hz, 6H). PAM EC$_{50}$: +++. Fold shift at 10 μM: ++.

Example 11.6

Synthesis of the HCl salt of Compound 76: 5-(1-methoxypropyl)-3-(4-(pyridin-4-ylethynyl)phenyl)-1,2,4-oxadiazole

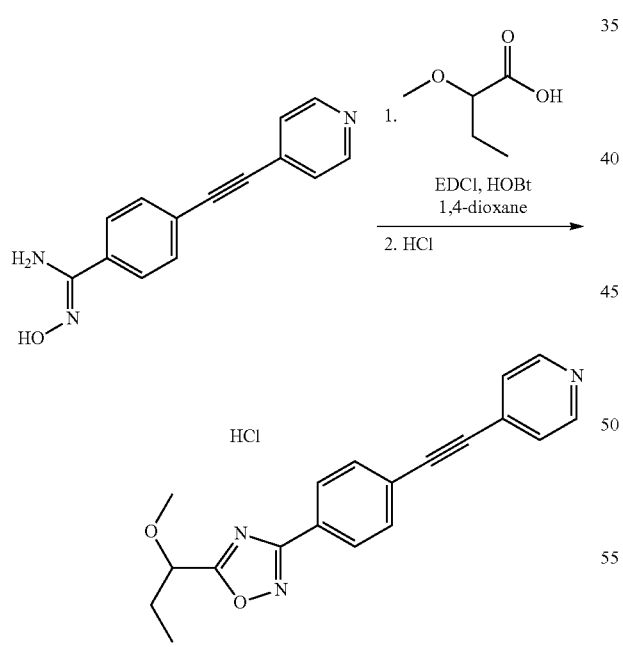

The title compound was prepared according to the experimental procedure described in Example 8.25. MS (ESI): 320 (MH$^+$); $^1$H NMR (300 MHz, DMSO-d$_6$) δ 8.88 (d, J=6.5 Hz, 2H), 8.14 (d, J=8.5 Hz, 2H), 8.02 (d, J=6.5 Hz, 2H), 7.88 (d, J=8.5 Hz, 2H), 4.73-4.68 (t, J=6.5 Hz, 1H), 3.37 (s, 3H), 1.98-1.88 (m, 2H), 0.95-0.90 (t, J=7.4 Hz, 3H). PAM EC$_{50}$: +++.

Example 11.7

Synthesis of the 2HCl salt of Compound 77: 3-(4-(pyridin-4-ylethynyl)phenyl)-5-(pyrrolidin-2-yl)-1,2,4-oxadiazole

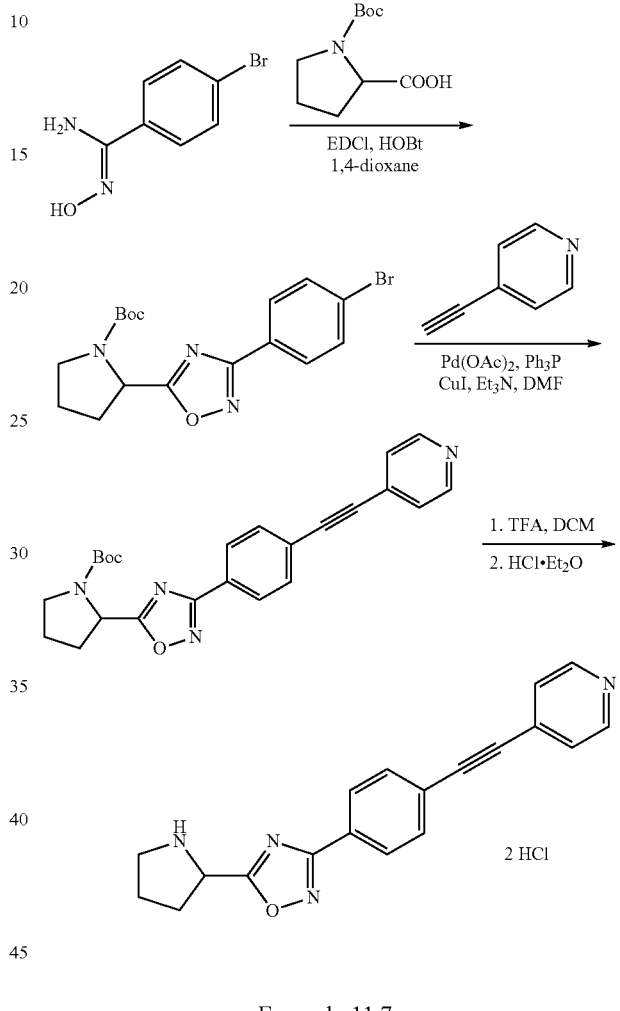

Example 11.7a

Synthesis of tert-butyl 2-(3-(4-bromophenyl)-1,2,4-oxadiazol-5-yl)pyrrolidine-1-carboxylate The title compound was prepared according to the experimental procedure described in Example 8.25. MS (ESI): 394, 396 (MH$^+$).

Example 11.7b

Synthesis of tert-butyl 2-(3-(4-(pyridin-4-ylethynyl)phenyl)-1,2,4-oxadiazol-5-yl)pyrrolidine-1-carboxylate The title compound was prepared according to the experimental procedure described in Example 8.1a. MS (ESI): 417 (MH$^+$).

Example 11.7c

Synthesis of the 2HCl salt of tert-butyl 2-(3-(4-(pyridin-4-ylethynyl)phenyl)-1,2,4-oxadiazol-5-yl)pyrrolidine-1-carboxylate The title compound was prepared according to the experimental procedure described in Example 8.29b. MS (ESI): 317 (MH$^+$); $^1$H NMR (300 MHz, CD$_3$OD) δ 8.92-8.90 (dd, J=6.9, 0.9 Hz, 2H), 8.27-8.23 (m, 4H), 7.92 (d, J=8.7 Hz, 2H), 5.28-5.23 (t, J=7.7 Hz, 1H), 3.64-3.46 (m, 2H), 2.73-2.68 (m, 1H), 2.50-2.43 (m, 1H), 2.33-2.27 (m, 2H). PAM EC$_{50}$: ++. Fold shift at 10 µM: +++.

Example 11.8

Synthesis of the HCl salt of Compound 78: 5-(1-methylpyrrolidin-2-yl)-3-(4-(pyridin-4-ylethynyl)phenyl)-1,2,4-oxadiazole

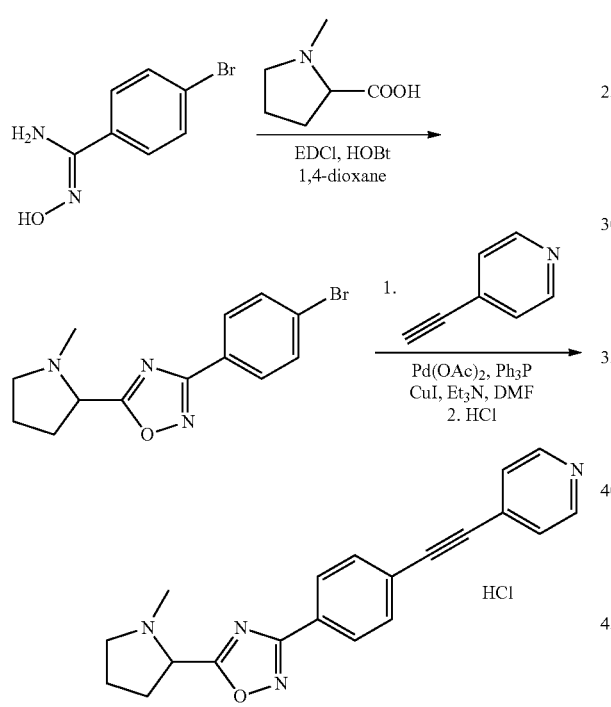

Example 11.8a

Synthesis of 3-(4-bromophenyl)-5-(1-methylpyrrolidin-2-yl)-1,2,4-oxadiazole

The title compound was prepared according to the experimental procedure described in Example 8.25. MS (ESI): 308, 310 (MH$^+$).

Example 11.8b

Synthesis of the HCl salt of 5-(1-methylpyrrolidin-2-yl)-3-(4-(pyridin-4-ylethynyl)phenyl)-1,2,4-oxadiazole The title compound was prepared according to the experimental procedure described in Example 8.1a. MS (ESI): 331 (MH$^+$); $^1$H NMR (300 MHz, DMSO-d$_6$+D$_2$O) δ 8.80 (d, J=6.5 Hz, 2H), 8.16 (d, J=8.3 Hz, 2H), 8.04 (d, J=6.1 Hz, 2H), 7.89 (d, J=8.3 Hz, 2H), 5.12-5.06 (t, J=8.5 Hz, 1H), 3.79-3.71 (m, 1H), 3.39-3.30 (m, 1H), 3.06 (s, 3H), 2.72-2.63 (m, 1H), 2.46-2.33 (m, 1H), 2.26-2.11 (m, 2H). PAM EC$_{50}$: ++++. Fold shift at 10 µM: +++.

Example 11.9

Synthesis of the HCl salt of Compound 79: N-methyl-1-(3-(4-(pyridin-4-ylethynyl)phenyl)-1,2,4-oxadiazol-5-yl)ethanamine

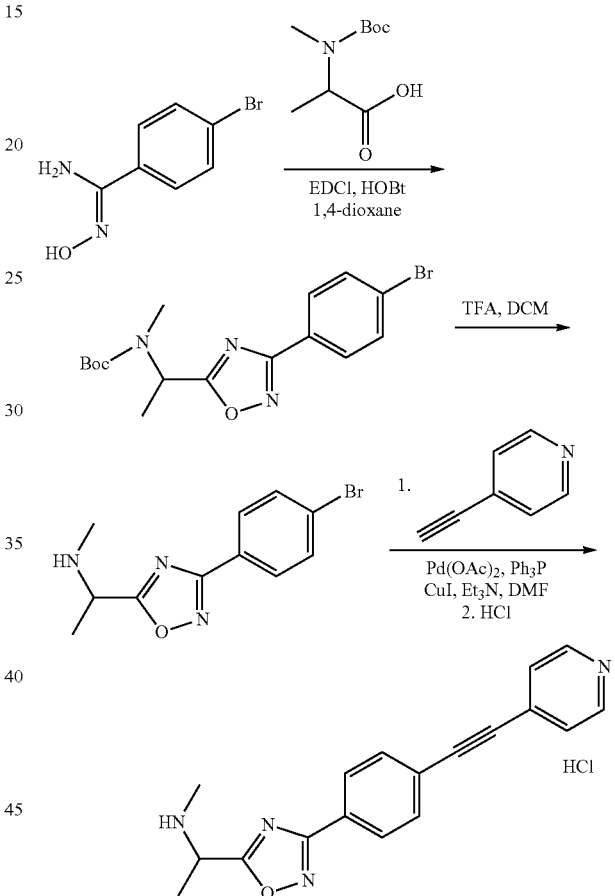

Example 11.9a

Synthesis of tert-butyl 1-(3-(4-bromophenyl)-1,2,4-oxadiazol-5-yl)ethyl(methyl)carbamate The title compound was prepared according to the experimental procedure described in Example 8.25. MS (ESI): 382, 384 (MH$^+$).

Example 11.9b

Synthesis of 1-(3-(4-bromophenyl)-1,2,4-oxadiazol-5-yl)-N-methylethanamine

The title compound was prepared according to the experimental procedure described in Example 8.29b. MS (ESI): 282, 284 (MH$^+$).

Example 11.9c

Synthesis of the HCl salt of N-methyl-1-(3-(4-(pyridin-4-ylethynyl)phenyl)-1,2,4-oxadiazol-5-yl)ethanamine The title compound was prepared according to the experimental procedure described in Example 8.1a. MS (ESI): 305 (MH+); $^1$H NMR (300 MHz, CD$_3$OD) δ 8.90 (d, J=6.7 Hz, 2H), 8.28-8.21 (m, 4H), 7.92 (d, J=8.5 Hz, 2H), 5.05-5.03 (q, 1H), 2.93 (s, 3H), 1.86 (d, J=7.0 Hz, 3H). PAM EC$_{50}$: ++. Fold shift at 10 µM: +++.

Example 11.10

Synthesis of the HCl salt of Compound 80: N,N-dimethyl-1-(3-(4-(pyridin-4-ylethynyl)phenyl)-1,2,4-oxadiazol-5-yl)ethanamine

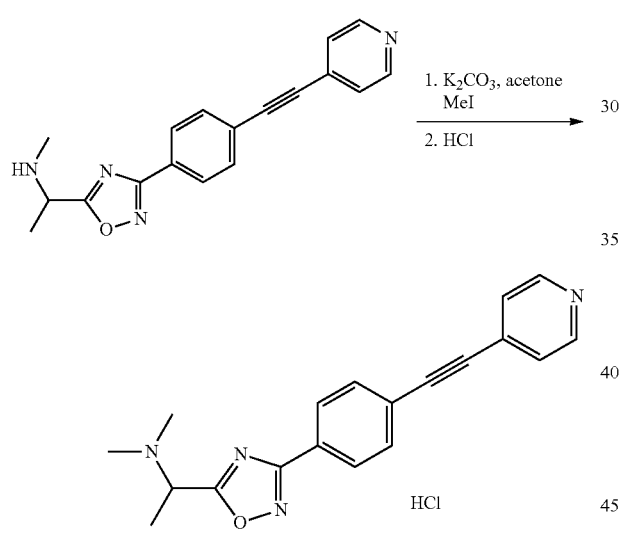

To a solution of N-methyl-1-(3-(4-(pyridin-4-ylethynyl)phenyl)-1,2,4-oxadiazol-5-yl) ethanamine (0.1 g, 0.33 mmol, 1 equiv) and excess K$_2$CO$_3$ in acetone (5.0 mL) was added iodomethane (9.37 mg, 0.66 mmol, 2 equiv) dropwise at room temperature over one hour. The reaction mixture was quenched with water (20 mL) and extracted with ethyl acetate (3×20 mL). The combined organic layers were dried over Na$_2$SO$_4$ and concentrated under reduced pressure to give 95 mg of the desired product, which was purified by silica gel chromatography. MS (ESI): 319 (MH+); $^1$H NMR (300 MHz, CD$_3$OD) δ 8.90 (d, J=6.4 Hz, 2H), 8.28-8.20 (m, 4H), 7.92 (d, J=8.6 Hz, 2H), 5.27-5.24 (q, 1H), 3.09 (s, 6H), 1.92 (d, J=7.1 Hz, 3H). PAM EC$_{50}$: ++++. Fold shift at 10 µM: +++.

Example 12.1

Synthesis of the HCl salt of Compound 81: 5-(sec-butyl)-3-(4-(pyridin-3-ylethynyl)phenyl)-1,2,4-oxadiazole

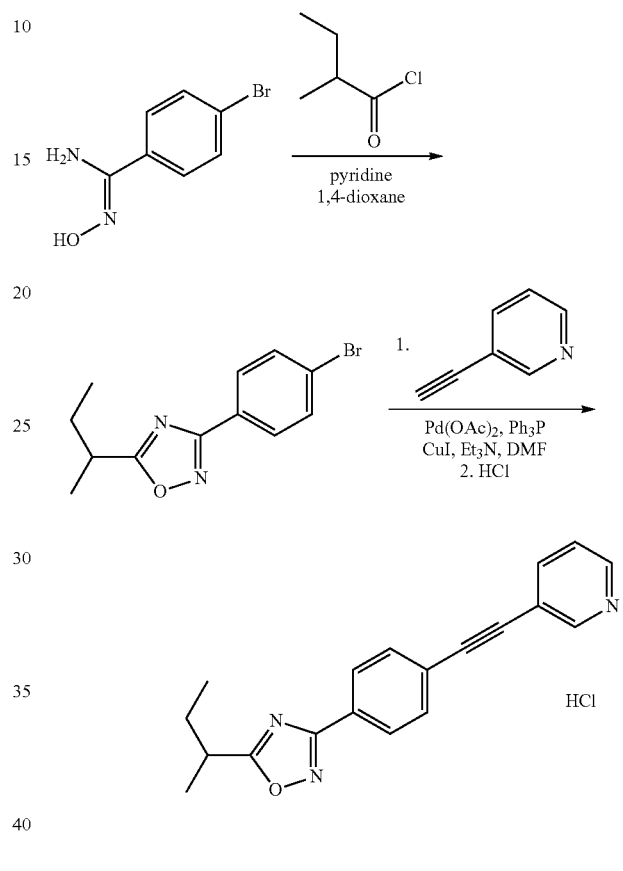

Example 12.1a

Synthesis of 3-(4-bromophenyl)-5-sec-butyl-1,2,4-oxadiazole

The title compound was prepared according to the experimental procedure described in Example 7.1b. MS (ESI): 281, 283 (MH+).

Example 12.1b

Synthesis of the HCl salt of 5-sec-butyl-3-(4-(pyridin-3-ylethynyl)phenyl)-1,2,4-oxadiazole The title compound was prepared according to the experimental procedure described in Example 8.1a. MS (ESI): 304 (MH+); $^1$H NMR (300 MHz, CDCl$_3$) δ 8.81 (d, J=1.4 Hz, 1H), 8.60-8.58 (dd, J=4.9, 1.7 Hz, 1H), 8.12 (d, J=8.6 Hz, 2H), 7.87-7.83 (m, 1H) 7.67 (d, J=8.6 Hz, 2H), 7.35-7.30 (m, 1H), 3.18-3.11 (m, 1H), 2.00-1.90 (m, 1H), 1.84-1.77 (m, 1H), 1.46 (d, J=7.0 Hz, 3H), 1.02-0.97 (t, J=7.4 Hz, 3H). PAM EC$_{50}$: +.

Example 13.1

Synthesis of Compound 82: 5-(sec-butyl)-3-(6-((3-fluorophenyl)ethynyl)pyridin-3-yl)-1,2,4-oxadiazole

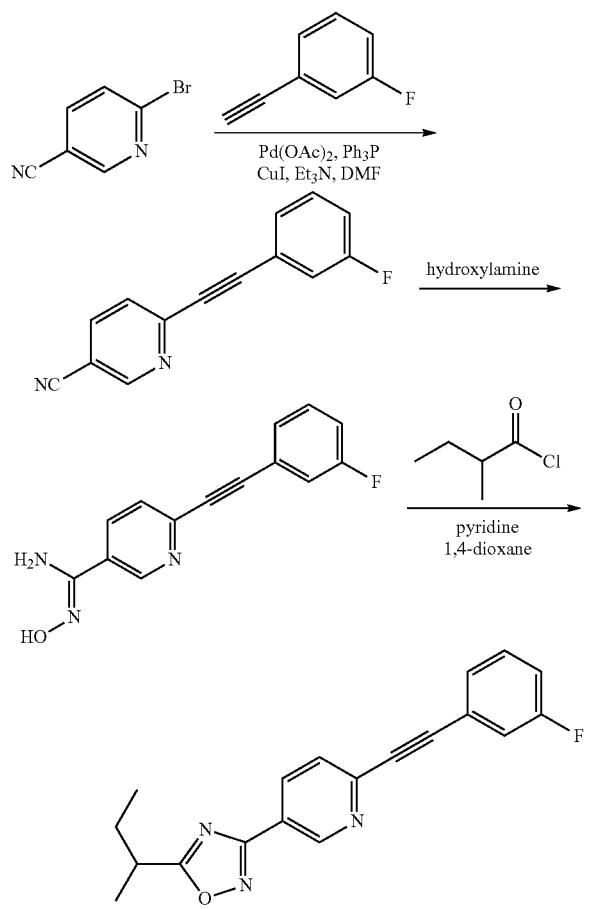

Example 13.1a

Synthesis of 6-((3-fluorophenyl)ethynyl)nicotinonitrile

The title compound was prepared according to the experimental procedure described in Example 8.1a. MS (ESI): 223 (MH+).

Example 13.1b

Synthesis of 6-((3-fluorophenyl)ethynyl)-N'-hydroxynicotinimidamide

The title compound was prepared according to the experimental procedure described in Example 8.1b. MS (ESI): 256 (MH+).

Example 13.1c

Synthesis of 5-(sec-butyl)-3-(6-((3-fluorophenyl)ethynyl)pyridin-3-yl)-1,2,4-oxadiazole The title compound was prepared according to the experimental procedure described in Example 7.1b. MS (ESI): 322 (MH+); $^1$H NMR (300 MHz, CDCl$_3$) δ 9.34-9.32 (dd, J=2.1, 0.8 Hz, 1H), 8.40-8.36 (dd, J=8.1, 2.1 Hz, 1H), 7.68-7.65 (dd, J=8.1, 0.8 Hz, 1H), 7.44-7.31 (m, 3H), 7.14-7.12 (m, 1H), 3.17-3.12 (m, 1H), 1.98-1.90 (m, 1H), 1.85-1.80 (m, 1H), 1.46 (d, J=7.0 Hz, 3H), 1.03-0.97 (t, J=7.4 Hz, 3H). PAM EC$_{50}$: +++. Fold shift at 10 μM: ++.

Example 13.2

Synthesis of Compound 83: 5-cyclopentyl-3-(6-((3-fluorophenyl)ethynyl)pyridin-3-yl)-1,2,4-oxadiazole

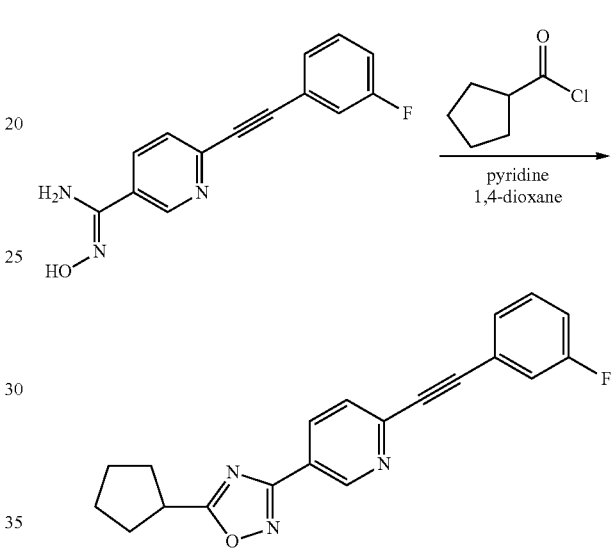

The title compound was prepared according to the experimental procedure described in Example 7.1b. MS (ESI): 334 (MH+); $^1$H NMR (300 MHz, CDCl$_3$) δ 9.33-9.31 (dd, J=2.1, 0.7 Hz, 1H), 8.40-8.36 (dd, J=8.1, 2.1 Hz, 1H), 7.68-7.64 (dd, J=8.2, 0.7 Hz, 1H), 7.44-7.31 (m, 3H), 7.14-7.12 (m, 1H), 3.47-3.41 (m, 1H), 2.23-2.18 (m, 2H), 2.07-1.99 (m, 2H), 1.92-1.87 (m, 2H), 1.79-1.75 (m, 2H). PAM EC$_{50}$: ++. Fold shift at 10 μM: ++.

Example 13.3

Synthesis of Compound 84: 3-(6-((3-fluorophenyl)ethynyl)pyridin-3-yl)-5-(1-methoxyethyl)-1,2,4-oxadiazole

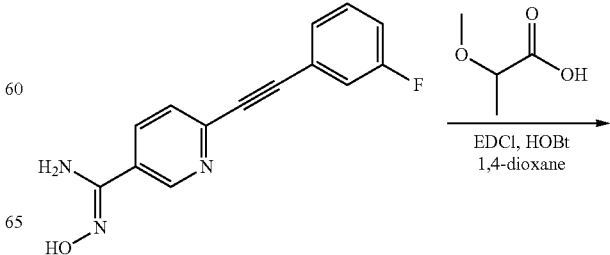

-continued

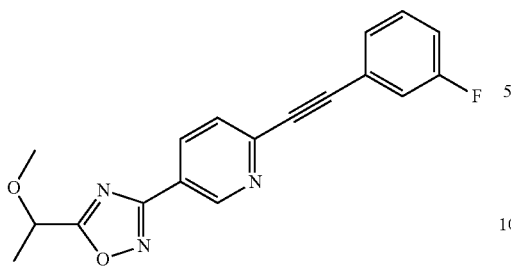

The title compound was prepared according to the experimental procedure described in Example 8.25. MS (ESI): 324 (MH+); 1H NMR (300 MHz, CDCl3) δ 9.36 (d, J=1.3 Hz, 1H), 8.43-8.39 (dd, J=8.2, 2.2 Hz, 1H), 7.69-7.66 (dd, J=8.2, 0.8 Hz, 1H), 7.44-7.31 (m, 3H), 7.16-7.13 (m, 1H), 4.79-4.72 (q, 1H), 3.51 (s, 3H), 1.65 (d, J=6.7 Hz, 3H). PAM EC$_{50}$: +++. Fold shift at 10 µM: +++.

Example 13.4

Synthesis of Compound 85: 3-(6-((3-fluorophenyl)ethynyl)pyridin-3-yl)-5-(1-methoxypropyl)-1,2,4-oxadiazole

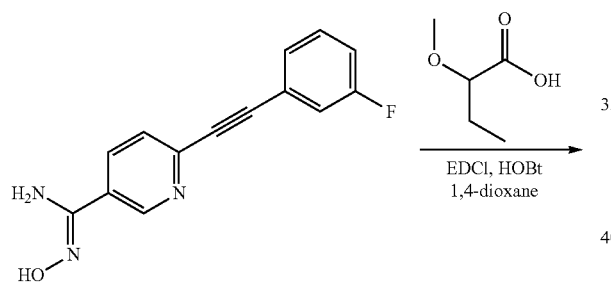

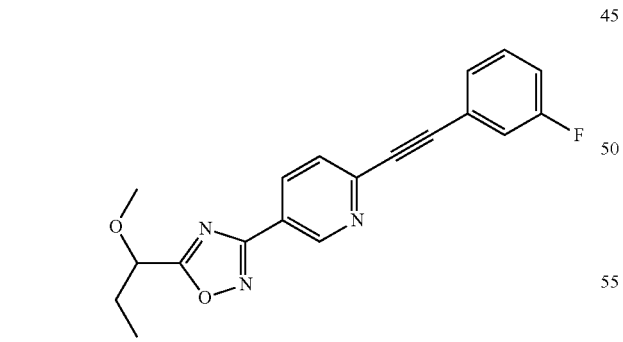

The title compound was prepared according to the experimental procedure described in Example 8.25. MS (ESI): 338 (MH+); 1H NMR (300 MHz, CDCl3) δ 9.37-9.36 (dd, J=2.1, 0.8 Hz, 1H), 8.43-8.40 (dd, J=8.2, 2.2 Hz, 1H), 7.69-7.66 (dd, J=8.2, 0.8 Hz, 1H), 7.44-7.31 (m, 3H), 7.16-7.10 (m, 1H), 4.57-4.52 (t, J=6.6 Hz, 1H), 3.49 (s, 3H), 2.08-2.03 (m, 2H), 1.07-1.02 (t, J=7.4 Hz, 3H). PAM EC$_{50}$: ++++. Fold shift at 10 µM: +++.

Example 14.1

Synthesis of Compound 86: 5-(sec-butyl)-3-(6-(pyridin-2-ylethynyl)pyridin-3-yl)-1,2,4-oxadiazole

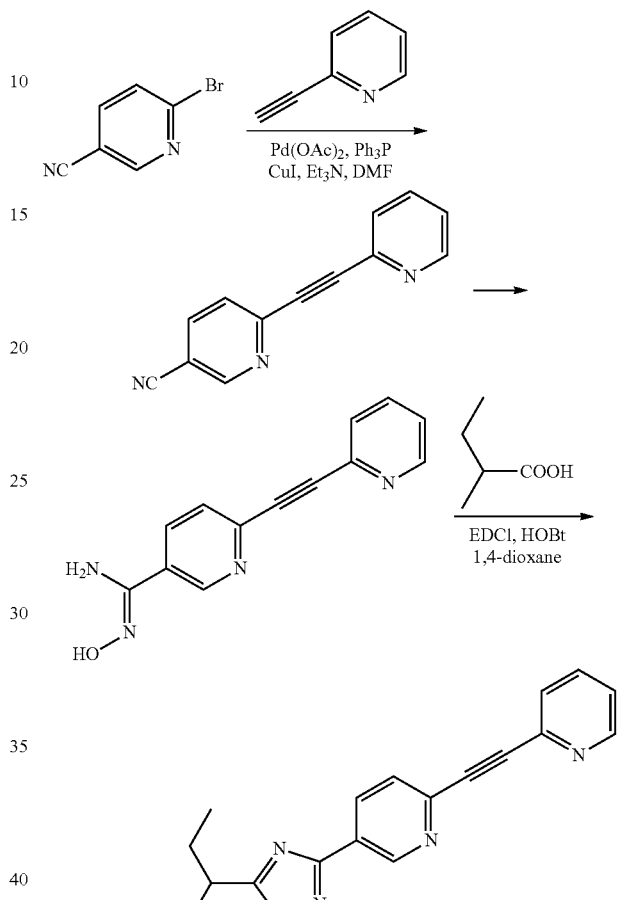

Example 14.1a

Synthesis of 6-(pyridin-2-ylethynyl)nicotinonitrile

The title compound was prepared according to the experimental procedure described in Example 8.1a. MS (ESI): 206 (MH+).

Example 14.1b

Synthesis of N'-hydroxy-6-(pyridin-2-ylethynyl)nicotinimidamide

The title compound was prepared according to the experimental procedure described in Example 8.1b. MS (ESI): 239 (MH+).

Example 14.1c

Synthesis of 5-(sec-butyl)-3-(6-(pyridin-2-ylethynyl)pyridin-3-yl)-1,2,4-oxadiazole The title compound was prepared according to the experimental procedure described in Example 8.25. MS (ESI): 305

(MH⁺); ¹H NMR (300 MHz, CDCl₃) δ 9.35-9.34 (m, 1H), 8.68 (d, J=4.7 Hz, 1H), 8.41-8.38 (dd, J=8.1, 2.1 Hz, 1H), 7.77-7.66 (m, 3H), 7.35-7.30 (m, 1H), 3.19-3.12 (m, 1H), 1.99-1.90 (m, 1H), 1.84-1.75 (m, 1H), 1.46 (d, J=7.2 Hz, 3H), 1.02-0.97 (t, J=7.5 Hz, 3H). PAM EC₅₀: +++. Fold shift at 10 µM: ++.

Example 14.2

Synthesis of Compound 87: 5-(pentan-3-yl)-3-(6-(pyridin-2-ylethynyl)pyridin-3-yl)-1,2,4-oxadiazole

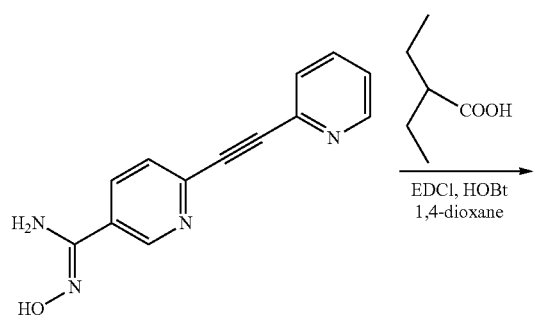

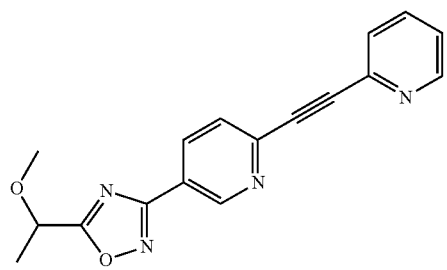

The title compound was prepared according to the experimental procedure described in Example 8.25. MS (ESI): 307 (MH⁺); ¹H NMR (300 MHz, CDCl₃) δ 9.37 (d, J=1.4 Hz, 1H), 8.68 (d, J=4.8 Hz, 1H), 8.42 (d, J=8.1 Hz, 1H), 7.78-7.66 (m, 3H), 7.36-7.31 (m, 1H), 4.79-4.72 (m, 1H), 3.50 (s, 3H), 1.70 (d, J=6.6 Hz, 3H).

Example 14.4

Synthesis of Compound 89: 5-(1-methoxypropyl)-3-(6-(pyridin-2-ylethynyl)pyridin-3-yl)-1,2,4-oxadiazole

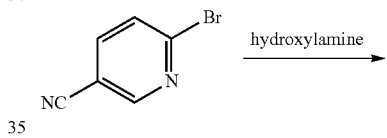

The title compound was prepared according to the experimental procedure described in Example 8.25. MS (ESI): 319 (MH⁺); ¹H NMR (300 MHz, CDCl₃) δ 9.35-9.34 (dd, J=2.0, 1.7 Hz, 1H), 8.69-8.67 (m, 1H), 8.42-8.39 (dd, J=8.1, 2.1 Hz, 1H), 7.77-7.72 (m, 2H), 7.68-7.66 (m, 1H), 7.35-7.30 (m, 1H), 3.02-2.97 (m, 1H), 1.92-1.83 (m, 4H), 0.98-0.93 (t, J=7.4 Hz, 6H). PAM EC₅₀: ++++. Fold shift at 10 µM: +++.

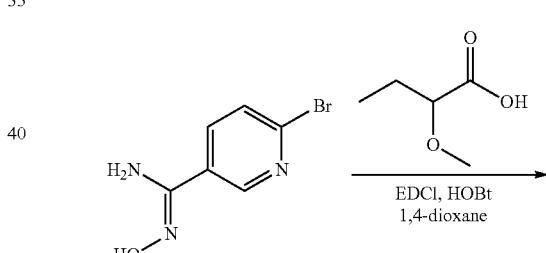

Example 14.3

Synthesis of Compound 88: 5-(1-methoxyethyl)-3-(6-(pyridin-2-ylethynyl)pyridin-3-yl)-1,2,4-oxadiazole

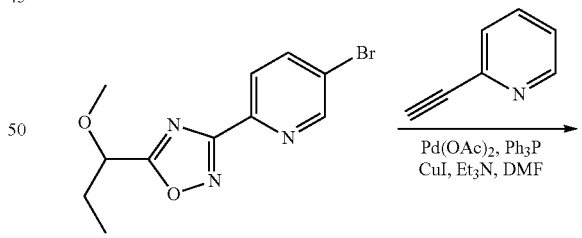

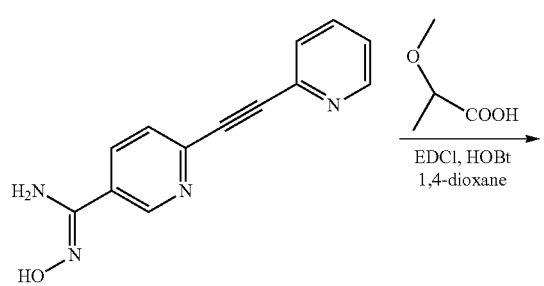

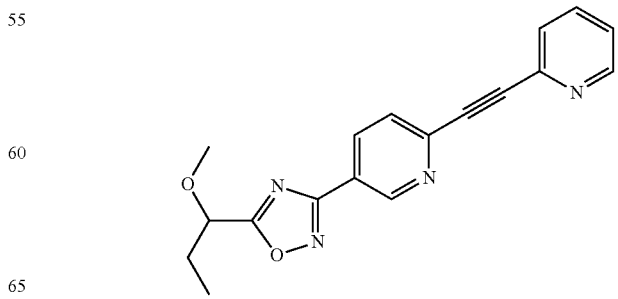

Example 14.4a

Synthesis of 6-bromo-N'-hydroxynicotinimidamide

The title compound was prepared according to the experimental procedure described in Example 8.1b. MS (ESI): 215, 217 (MH+).

Example 14.4b

Synthesis of 3-(6-bromopyridin-3-yl)-5-(1-methoxypropyl)-1,2,4-oxadiazole

The title compound was prepared according to the experimental procedure described in Example 8.25. MS (ESI): 298, 300 (MH+).

Example 14.4c

Synthesis of 5-(1-methoxypropyl)-3-(6-(pyridin-2-ylethynyl)pyridin-3-yl)-1,2,4-oxadiazole The title compound was prepared according to the experimental procedure described in Example 8.1a. MS (ESI): 321 (MH+); $^1$H NMR (300 MHz, CDCl$_3$) δ 9.37 (s, 1H), 8.68 (d, J=4.2 Hz, 1H), 8.43 (d, J=7.8 Hz, 1H), 7.78-7.66 (m, 3H), 7.35-7.31 (m, 1H), 4.56-4.52 (t, J=6.5 Hz, 1H), 3.49 (s, 3H), 2.07-1.98 (m, 2H), 1.07-1.02 (t, J=7.3 Hz, 3H). PAM EC$_{50}$: +.

Example 15.1

Synthesis of Compound 90: 5-(sec-butyl)-3-(6-(pyridin-4-ylethynyl)pyridin-3-yl)-1,2,4-oxadiazole

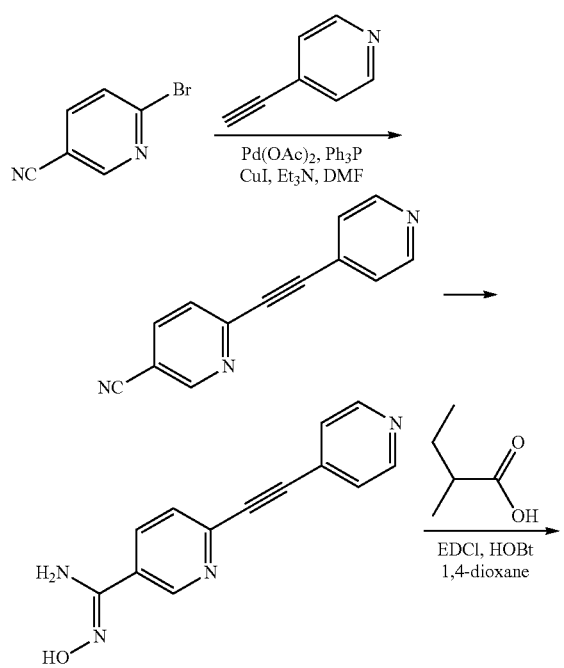

-continued

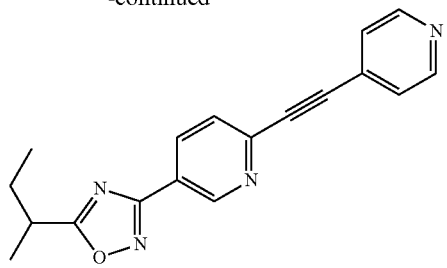

Example 15.1a

Synthesis of 6-(pyridin-4-ylethynyl)nicotinonitrile

The title compound was prepared according to the experimental procedure described in Example 8.1a. MS (ESI): 206 (MH+).

Example 15.1b

Synthesis of N-hydroxy-6-(pyridin-4-ylethynyl)nicotinimidamide

The title compound was prepared according to the experimental procedure described in Example 8.1b. MS (ESI): 239 (MH+).

Example 15.1c

Synthesis of 5-(sec-butyl)-3-(6-(pyridin-4-ylethynyl)pyridin-3-yl)-1,2,4-oxadiazole The title compound was prepared according to the experimental procedure described in Example 8.25. MS (ESI): 305 (MH+); $^1$H NMR (300 MHz, CD$_3$OD) δ 9.27-9.26 (dd, J=2.1, 0.8 Hz, 1H), 8.65-8.63 (m, 2H), 8.54-8.51 (dd, J=8.2, 2.2 Hz, 1H), 7.89-7.86 (dd, J=8.2, 0.8 Hz, 1H), 7.66-7.64 (m, 2H), 3.25-3.18 (m, 1H), 1.97-1.90 (m, 1H), 1.87-1.78 (m, 1H), 1.46 (d, J=7.0 Hz, 3H), 1.03-0.98 (t, J=7.4 Hz, 3H). PAM EC$_{50}$: ++++. Fold shift at 10 μM: +++.

Example 15.2

Synthesis of Compound 91: 5-(pentan-3-yl)-3-(6-(pyridin-4-ylethynyl)pyridin-3-yl)-1,2,4-oxadiazole

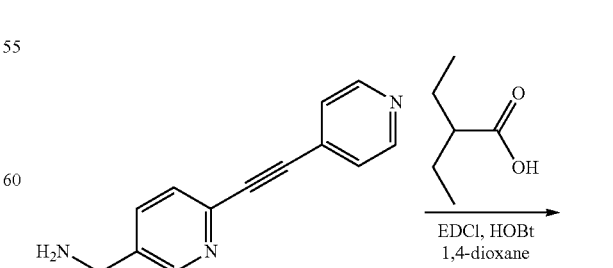

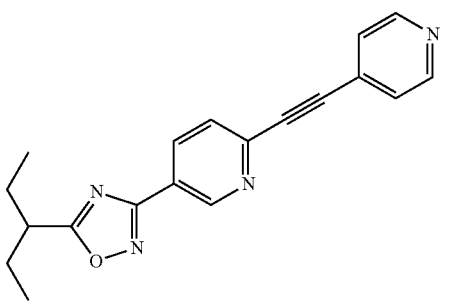

The title compound was prepared according to the experimental procedure described in Example 8.25. MS (ESI): 319 (MH+); 1H NMR (300 MHz, CDCl3) δ 9.36 (d, J=1.4 Hz, 1H), 8.68 (d, J=3.2 Hz, 2H), 8.44-8.40 (dd, J=8.2, 2.1 Hz, 1H), 7.70 (d, J=8.1 Hz, 1H), 7.49 (d, J=5.8 Hz, 2H), 3.05-2.95 (m, 1H), 1.94-1.83 (m, 4H), 0.98-0.93 (t, J=7.4 Hz, 6H). PAM EC$_{50}$: ++++. Fold shift at 10 µM: ++.

Example 15.3

Synthesis of Compound 92: 5-(1-methoxyethyl)-3-(6-(pyridin-4-ylethynyl)pyridin-3-yl)-1,2,4-oxadiazole

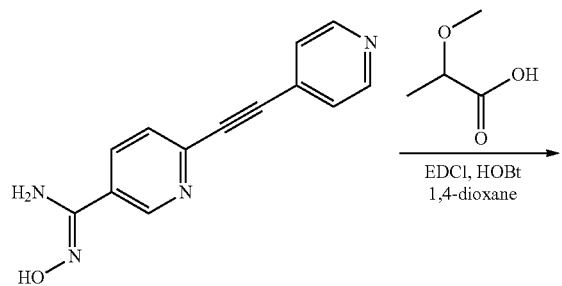

The title compound was prepared according to the experimental procedure described in Example 8.25. MS (ESI): 307 (MH+); 1H NMR (300 MHz, CDCl3) δ 9.38-9.37 (dd, J=2.2, 0.8 Hz, 1H), 8.68 (d, J=6.1 Hz, 2H), 8.46-8.42 (dd, J=8.1, 2.2 Hz, 1H), 7.73-7.69 (dd, J=8.2, 0.8 Hz, 1H), 7.49 (d, J=6.1 Hz, 2H), 4.79-4.72 (m, 1H), 3.51 (s, 3H), 1.70 (d, J=6.7 Hz, 3H). PAM EC$_{50}$: ++. Fold shift at 10 µM: ++.

Example 15.4

Synthesis of Compound 93: 5-(pentan-3-yl)-3-(6-(pyridin-4-ylethynyl)pyridin-3-yl)-1,2,4-oxadiazole

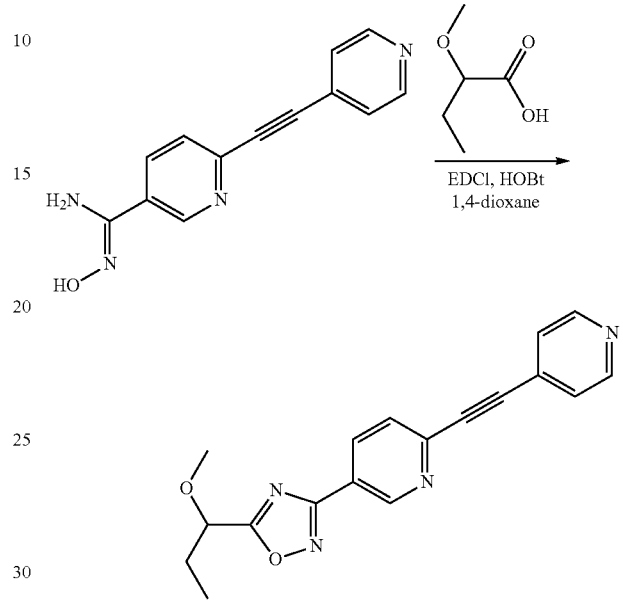

The title compound was prepared according to the experimental procedure described in Example 8.25. MS (ESI): 321 (MH+); 1H NMR (300 MHz, CDCl3) δ 9.38 (d, J=0.9 Hz, 1H), 8.70-8.67 (dd, J=4.2, 1.5 Hz, 2H), 8.47-8.43 (dd, J=8.1, 2.1 Hz, 1H), 7.73-7.69 (dd, J=8.1 0.9 Hz, 1H), 7.50-7.48 (dd, J=4.5, 1.8 Hz, 2H), 4.57-4.52 (t, J=6.3 Hz, 1H), 3.5 (s, 3H), 2.11-2.01 (m, 2H), 1.07-1.02 (t, J=7.5 Hz, 3H). PAM EC$_{50}$: +++. Fold shift at 10 µM: +++.

Example 16.1

Synthesis of the HCl salt of Compound 94: 5-(sec-butyl)-3-(5-((3-fluorophenyl)ethynyl)pyridin-2-yl)-1,2,4-oxadiazole

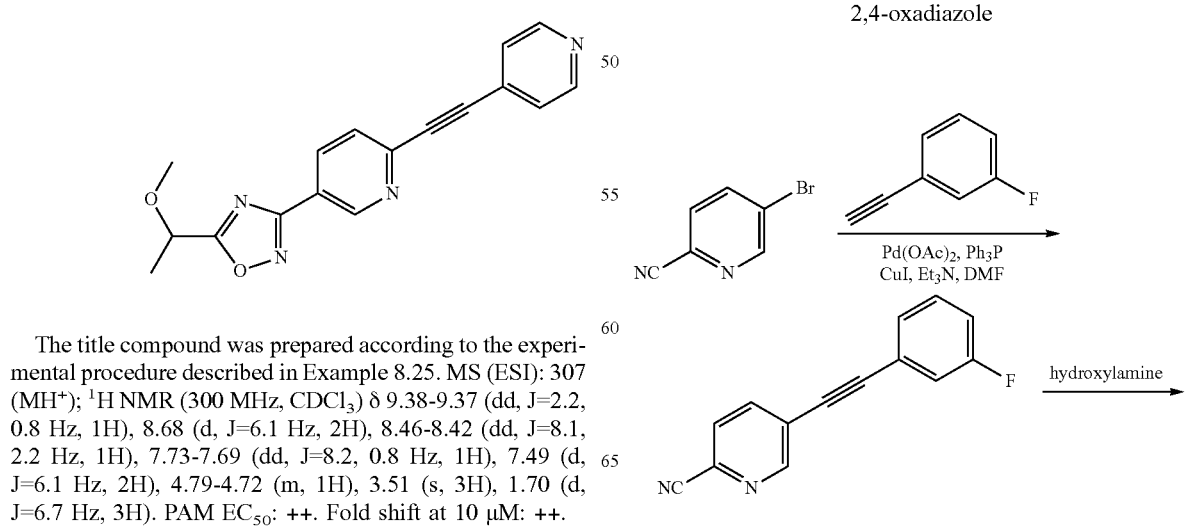

157

-continued

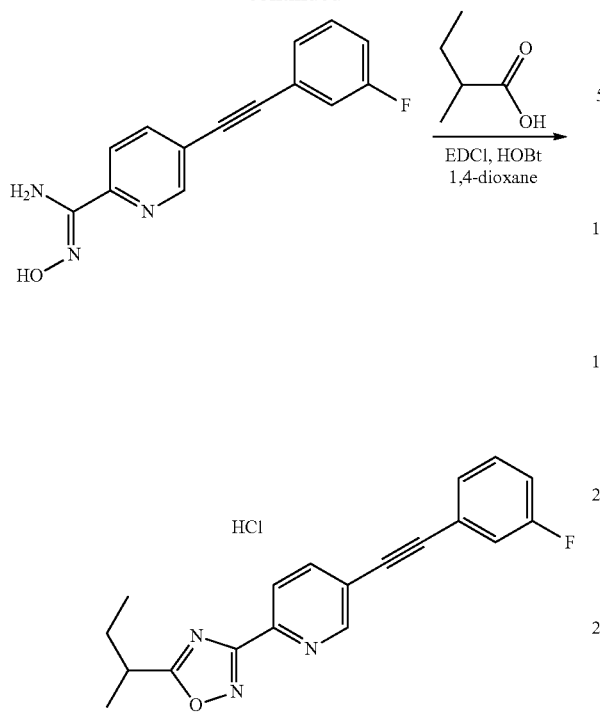

Example 16.1a

Synthesis of 5-((3fluorophenyl)ethynyl)picolinonitrile

The title compound was prepared according to the experimental procedure described in Example 8.1a. MS (ESI): 223 (MH⁺).

Example 16.1b

Synthesis of 5-((3-fluorophenyl)ethynyl)-N'-hydroxypicolinimidamide

The title compound was prepared according to the experimental procedure described in Example 8.1b. MS (ESI): 256 (MH⁺).

Example 16.1c

Synthesis of the HCl salt of 5-(sec-butyl)-3-(5-((3-fluorophenyl)ethynyl)pyridin-2-yl)-1,2,4-oxadiazole The title compound was prepared according to the experimental procedure described in Example 8.25. MS (ESI): 322 (MH⁺); $^1$H NMR (300 MHz, CDCl$_3$) δ 8.94-8.93 (dd, J=2.1, 0.8 Hz, 1H), 8.18-8.14 (dd, J=8.2, 0.8 Hz, 1H), 7.99-7.95 (dd, J=8.2, 2.1 Hz, 1H), 7.39-7.36 (m, 2H), 7.31-7.29 (m, 1H), 7.13-7.10 (m, 1H), 3.20-3.15 (m, 1H), 2.00-1.79 (m, 1H), 1.86-1.77 (m, 1H), 1.48 (d, J=7.1 Hz, 3H), 1.02-0.96 (t, J=7.4 Hz, 3H). PAM EC$_{50}$: ++++. Fold shift at 10 μM: ++.

158

Example 16.2

Synthesis of the HCl salt of Compound 95: 5-cyclopentyl-3-(5-((3-fluorophenyl)ethynyl)pyridin-2-yl)-1,2,4-oxadiazole

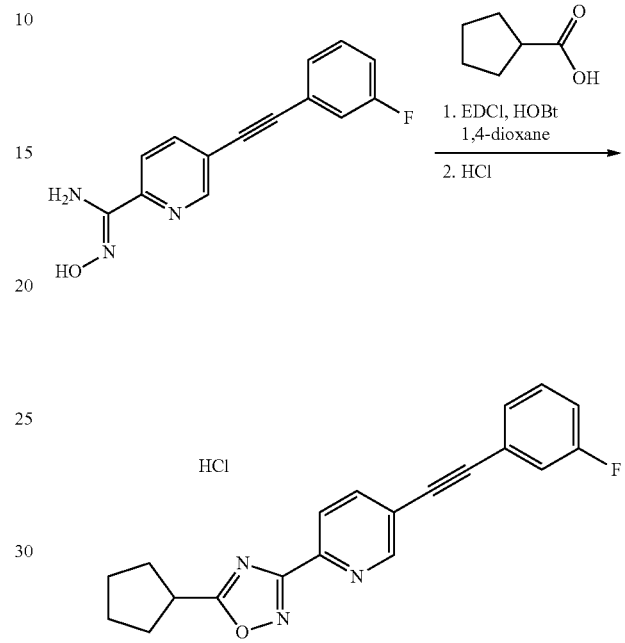

The title compound was prepared according to the experimental procedure described in Example 8.25. MS (ESI): 334 (MH⁺); $^1$H NMR (300 MHz, CDCl$_3$) δ 8.94-8.92 (dd, J=2.0, 0.8 Hz, 1H), 8.17-8.13 (dd, J=8.1, 2.1 Hz, 1H), 7.99-7.95 (dd, J=8.1, 2.1 Hz, 1H), 7.39-7.37 (m, 2H), 7.30-7.26 (m, 1H), 7.16-7.08 (m, 1H), 3.49-3.43 (m, 1H), 2.28-2.17 (m, 2H), 2.13-2.01 (m, 2H), 1.96-1.83 (m, 2H), 1.81-1.71 (m, 2H). PAM EC$_{50}$: ++++. Fold shift at 10 μM: +++.

Example 16.3

Synthesis of the HCl salt of Compound 96: 3-(5-((3-fluorophenyl)ethynyl)pyridin-2-yl)-5-(1-methoxyethyl)-1,2,4-oxadiazole

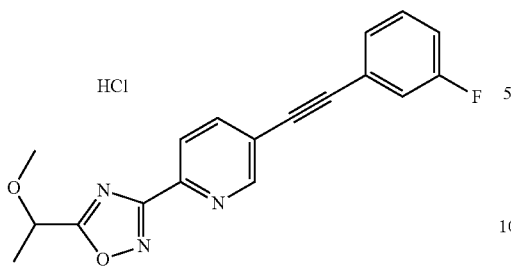

The title compound was prepared according to the experimental procedure described in Example 8.25. MS (ESI): 324 (MH+); 1H NMR (300 MHz, CD3OD) δ 8.93 (s, 1H), 8.33-8.26 (m, 2H), 7.49-7.45 (m, 2H), 7.40-7.36 (m, 1H), 7.26-7.20 (m, 1H), 4.87-4.83 (m, 1H), 3.48 (s, 3H), 1.66 (d, J=6.6 Hz, 3H). PAM EC50: ++++. Fold shift at 10 μM: +.

Example 16.4

Synthesis of the HCl salt of Compound 97: 3-(5-((3-fluorophenyl)ethynyl)pyridin-2-yl)-5-(1-methoxypropyl)-1,2,4-oxadiazole

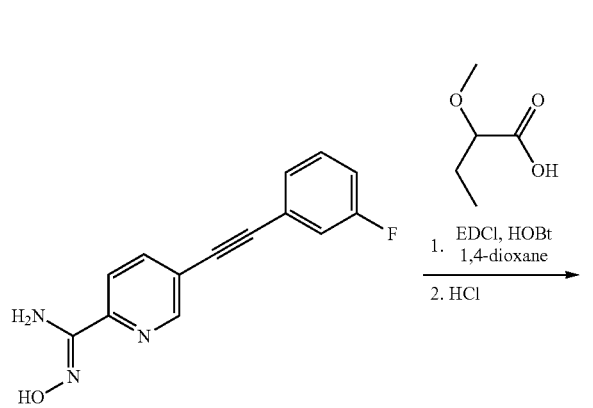

The title compound was prepared according to the experimental procedure described in Example 8.25. MS (ESI): 338 (MH+); 1H NMR (300 MHz, CD3OD) δ 8.92 (s, 1H), 8.33-8.25 (m, 2H), 7.49-7.45 (m, 2H), 7.40-7.36 (m, 1H), 7.26-7.20 (m, 1H), 4.69-4.64 (t, J=6.5 Hz, 1H), 3.48 (s, 3H), 2.08-1.99 (m, 2H), 1.06-1.01 (t, J=7.4 Hz, 3H). PAM EC50: ++++. Fold shift at 10 μM: ++.

Example 16.5

Synthesis of the HCl salt of Compound 98: 3-(5-((3-fluorophenyl)ethynyl)pyridin-2-yl)-5-(1-methoxypropyl)-1,2,4-oxadiazole

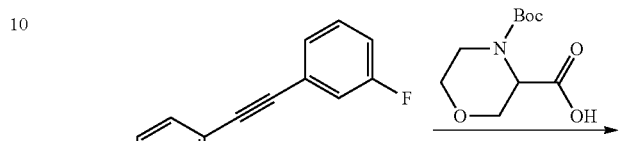

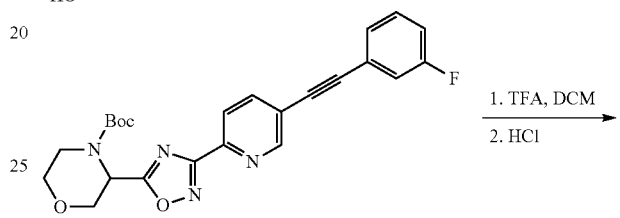

Example 16.5a

Synthesis of tert-butyl 3-(3-(5-((3-fluorophenyl)ethynyl)pyridin-2-yl)-1,2,4-oxadiazol-5-yl)morpholine-4-carboxylate The title compound was prepared according to the experimental procedure described in Example 8.25. MS (ESI): 451 (MH+).

Example 16.5b

Synthesis of the HCl salt of 3-(5-((3-fluorophenyl)ethynyl)pyridin-2-yl)-5-(1-methoxypropyl)-1,2,4-oxadiazole The title compound was prepared according to the experimental procedure described in Example 8.29b. MS (ESI): 351 (MH+); 1H NMR (300 MHz, CD3OD) δ 8.93-8.91 (dd, J=2.0, 0.8 Hz, 1H), 8.29-8.26 (m, 1H), 8.23-8.18 (m, 1H), 7.49-7.43 (m, 2H), 7.40-7.35 (m, 1H), 7.26-7.20 (m, 1H), 5.26-5.21 (m, 1H), 4.53-4.47 (m, 1H), 4.19-4.09 (m, 2H), 3.99-3.91 (m, 1H), 3.69-3.63 (m, 1H), 3.54-3.46 (m, 1H). PAM EC50: +++. Fold shift at 10 μM: ++.

Example 16.6

Synthesis of Compound 99: tert-butyl 2-(3-(5-((3-fluorophenyl)ethynyl)pyridin-2-yl)-1,2,4-oxadiazol-5-yl)azetidine-1-carboxylate

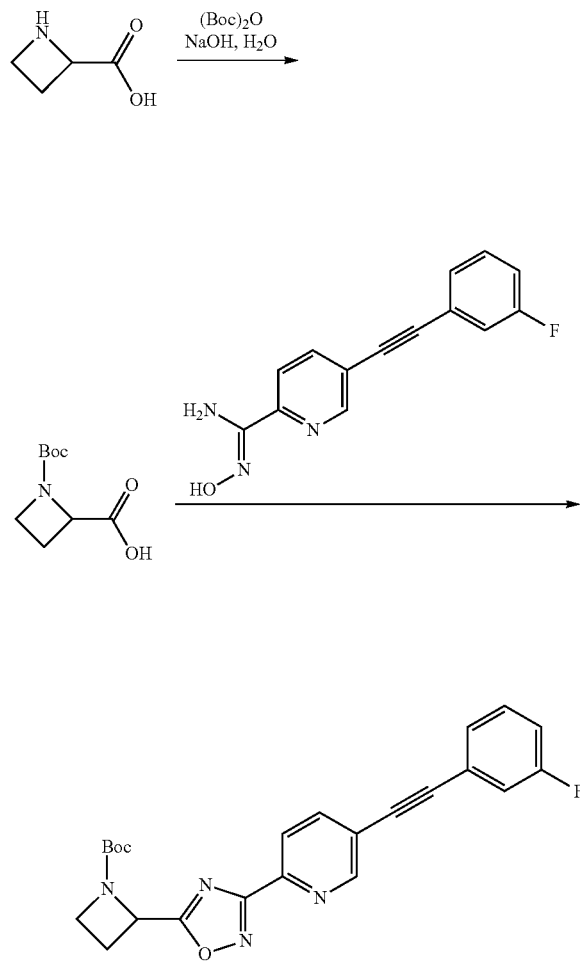

Example 16.6a

Synthesis of 1-(tert-butoxycarbonyl)azetidine-2-carboxylic acid

A solution of azetidine-2-carboxylic acid (2.0 g, 19.8 mmol, 1 equiv), (Boc)$_2$O (8.6 g, 39.6 mmol, 2 equiv) and NaOH (1.6 g, 39.6 mmol, 2 equiv) in water was stirred at rt overnight. The mixture was then adjusted to pH 2 with 0.1 N HCl and extracted with EtOAc (3×100 mL). The combined organic layers were washed with brine and dried over anhydrous sodium sulfate, then concentrated under reduced pressure to give the crude product, which was directly used for the next step without further purification.

Example 16.6b

Synthesis of tert-butyl 2-(3-(5-((3-fluorophenyl)ethynyl) pyridin-2-yl)-1,2,4-oxadiazol-5-yl)azetidine-1-carboxylate The title compound was prepared according to the experimental procedure described in Example 8.25. MS (ESI): 421 (MH$^+$); $^1$H NMR (300 MHz, CDCl$_3$) δ 8.95-8.93 (dd, J=2.1, 0.8 Hz, 1H), 8.19-8.16 (dd, J=8.1, 0.9 Hz, 1H), 8.00-7.96 (dd, J=8.1, 2.1 Hz, 1H), 7.40-7.36 (m, 2H), 7.31-7.30 (m, 1H), 7.16-7.09 (m, 1H), 5.53-5.47 (m, 1H), 4.25-4.18 (m, 1H), 4.13-4.07 (m, 1H), 2.78-2.72 (m, 1H), 2.70-2.61 (m, 1H), 1.39 (s, 9H). PAM EC$_{50}$: +.

Example 16.7

Synthesis of the HCl salt of Compound 100: 5-(azetidin-2-yl)-3-(5-((3-fluorophenyl)ethynyl)pyridin-2-yl)-1,2,4-oxadiazole

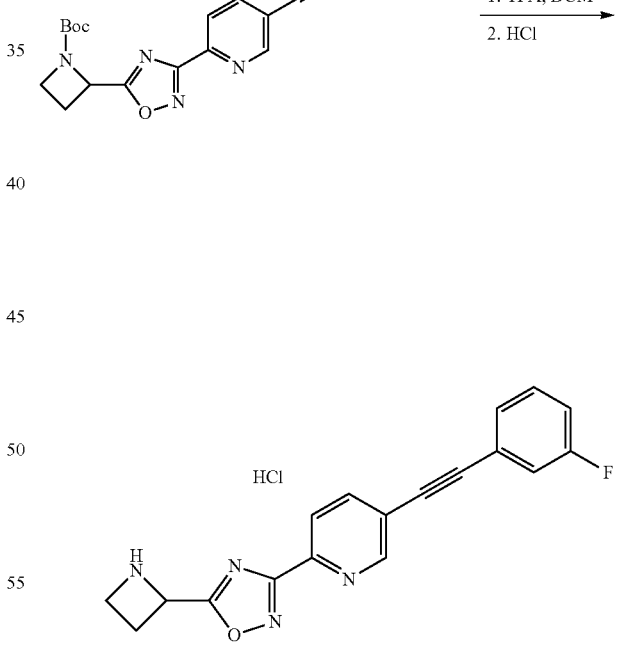

The title compound was prepared according to the experimental procedure described in Example 8.29b. MS (ESI): 321 (MH$^+$); $^1$H NMR (300 MHz, CD$_3$OD) δ 8.93-8.91 (dd, J=2.0, 0.8 Hz, 1H), 8.31-8.19 (m, 2H), 7.49-7.43 (m, 2H), 7.40-7.35 (m, 1H), 7.26-7.19 (m, 1H), 6.03-5.97 (t, J=8.3 Hz, 1H), 4.37-4.21 (m, 2H), 3.17-3.09 (m, 2H).

Example 16.8

Synthesis of the HCl salt of Compound 101: 3-(5-((3-fluorophenyl)ethynyl)pyridin-2-yl)-5-(1-methyl-azetidin-2-yl)-1,2,4-oxadiazole

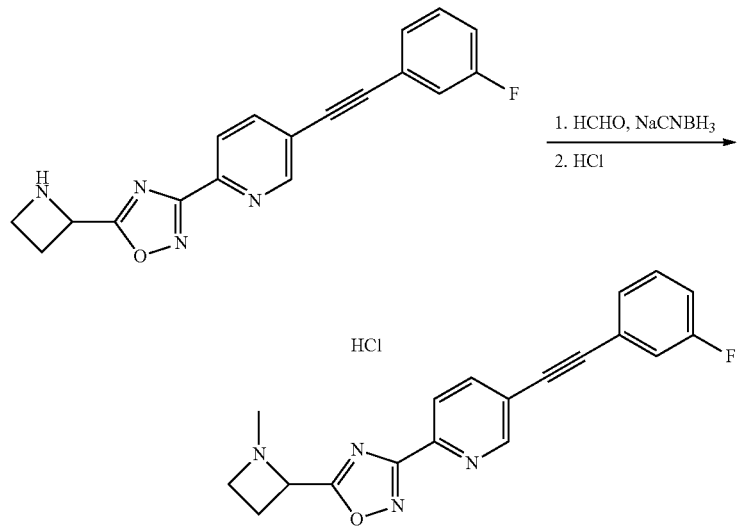

To a solution of 6'-bromo-1'H-spiro[piperidine-2,2'-pyrrolo[2,1-b]quinazolin]-9' (3'H)-one (0.1 g, 0.3 mmol, 1 equiv), aqueous formaldehyde (47.4 mg, 0.6 mmol, 2 equiv) and HOAc (2 mL) in methanol (5.0 mL) was added NaBH$_3$CN (1.89 mg, 0.03 mmol, 0.1 equiv) in portions at room temperature. After stirring for a few minutes, the reaction mixture was quenched with water (20 mL) and extracted with ethyl acetate (3×20 mL). The combined organic layers were dried over Na$_2$SO$_4$ and concentrated under reduced pressure to give 90 mg of the desired product, which was purified by silica gel chromatography. MS (ESI): 335 (MH$^+$); $^1$H NMR (300 MHz, CD$_3$OD) δ 8.92 (s, 1H), 8.31-8.27 (m, 1H), 8.23-8.19 (m, 1H), 7.49-7.43 (m, 2H), 7.40-7.36 (m, 1H), 7.26-7.20 (m, 1H), 6.00-5.94 (t, J=9.0 Hz, 1H), 4.38-4.28 (m, 2H), 3.19-2.99 (m, 5H). PAM EC$_{50}$: +++. Fold shift at 10 μM: +++.

Example 16.9

Synthesis of the HCl salt of Compound 102: 1-(3-(5-((3-fluorophenyl)ethynyl)pyridin-2-yl)-1,2,4-oxadiazol-5-yl)-N-methylmethanamine

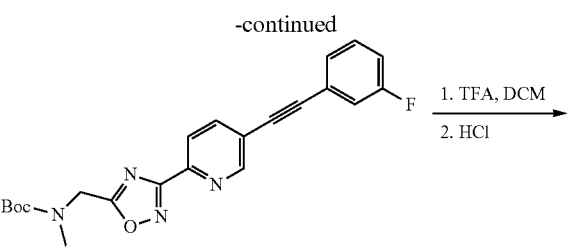

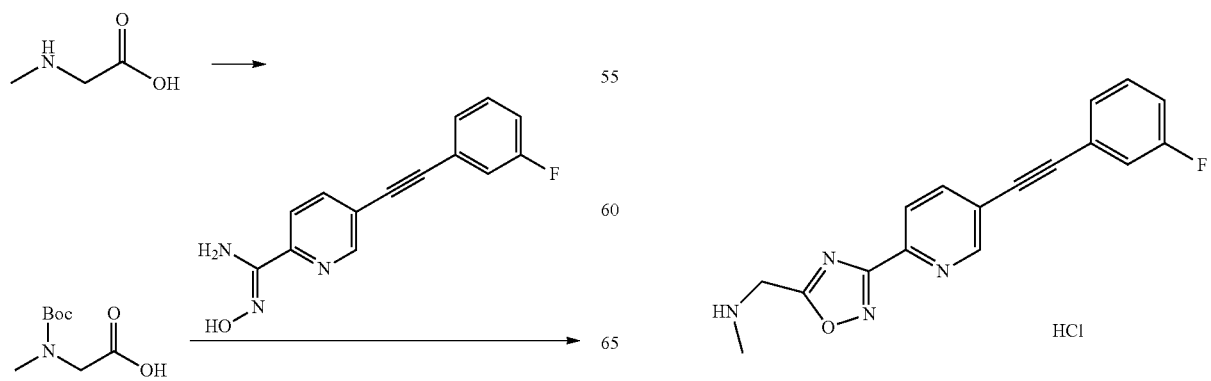

Example 16.9a

Synthesis of 2-(tert-butoxycarbonyl(methyl)amino)acetic acid

The title compound was prepared according to the experimental procedure described in Example 16.6a. MS (ESI): 190 (MH$^+$).

Example 16.9b

Synthesis of tert-butyl (3-(5-((3-fluorophenyl)ethynyl) pyridin-2-yl)-1,2,4-oxadiazol-5-yl)methyl (methyl)carbamate The title compound was prepared according to the experimental procedure described in Example 8.25. MS (ESI): 409 (MH$^+$).

Example 16.9c

Synthesis of the HCl salt of 1-(3-(5-((3-fluorophenyl)ethynyl)pyridine-2-yl)-1,2,4-oxadiazol-5-yl)-N-methylmethanamine The title compound was prepared according to the experimental procedure described in Example 8.29b. MS (ESI): 309 (MH$^+$); $^1$H NMR (300 MHz, CD$_3$OD) δ 8.96 (s, 1H), 8.35-8.26 (m, 2H), 7.51-7.43 (m, 2H), 7.39-7.36 (m, 1H), 7.26-7.19 (m, 1H), 4.80 (s, 2H), 2.99 (s, 3H). PAM EC$_{50}$: +.

Example 16.10

Synthesis of the HCl salt of Compound 103: 1-(3-(5-((3-fluorophenyl)ethynyl)pyridin-2-yl)-1,2,4-oxadiazol-5-yl)-N,N-dimethylmethanamine

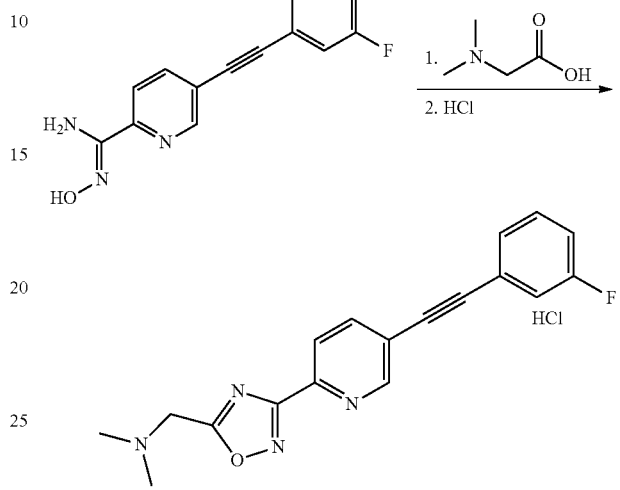

The title compound was prepared according to the experimental procedure described in Example 8.25. MS (ESI): 323 (MH$^+$); $^1$H NMR (300 MHz, CD$_3$OD) δ 8.93 (s, 1H), 8.32-8.29 (m, 1H), 8.25-8.21 (m, 1H), 7.49-7.43 (m, 2H), 7.40-7.35 (m, 1H), 7.25-7.19 (m, 1H), 5.00 (s, 2H), 3.19 (s, 6H). PAM EC$_{50}$: +++. Fold shift at 10 μM: +++.

Example 16.11

Synthesis of the HCl salt of Compound 104: 1-(3-(5-((3-fluorophenyl)ethynyl)pyridin-2-yl)-1,2,4-oxadiazol-5-yl)-N,N-dimethylethanamine

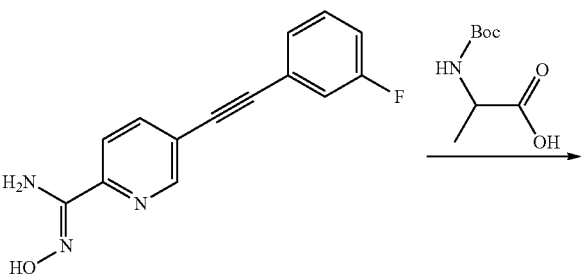

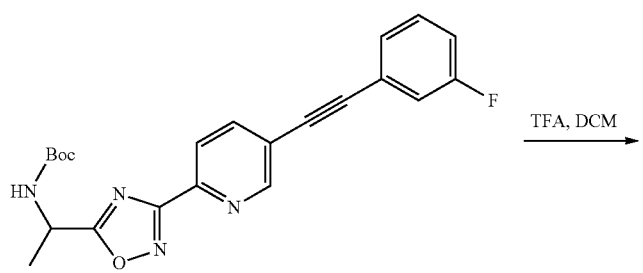

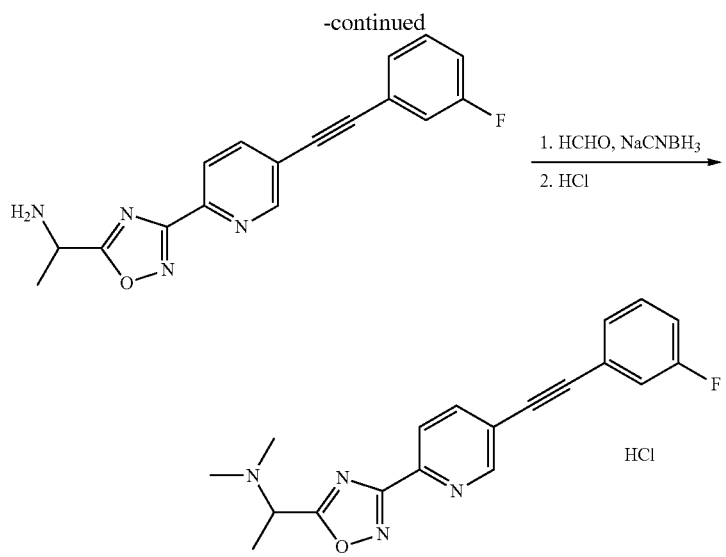

Example 16.11a

Synthesis of tert-butyl 1-(3-(5-((3-fluorophenyl)ethynyl) pyridin-2-yl)-1,2,4-oxadiazol-5-yl)ethylcarbamate The title compound was prepared according to the experimental procedure described in Example 8.25. MS (ESI): 409 (MH+).

Example 16.11b

Synthesis of 1-(3-(5-((3-fluorophenyl)ethynyl)pyridin-2-yl)-1,2,4-oxadiazol-5-yl)ethanamine The title compound was prepared according to the experimental procedure described in Example 8.29b. MS (ESI): 309 (MH+).

Example 16.11c

Synthesis of the HCl salt of 1-(3-(5-((3-fluorophenyl)ethynyl)pyridin-2-yl)-1,2,4-oxadiazol-5-yl)-N,N-dimethylethanamine The title compound was prepared according to the experimental procedure described in Example 16.8. MS (ESI): 337 (MH+); $^1$H NMR (300 MHz, D$_2$O) δ 8.94 (s, 1H), 8.33-8.27 (m, 2H), 7.54-7.47 (m, 3H), 7.36-7.34 (m, 1H), 5.28-5.21 (m, 1H), 3.08 (s, 6H), 1.93 (d, J=6.9 Hz, 3H). PAM EC$_{50}$: ++. Fold shift at 10 μM: +++.

Example 16.12

Synthesis of the HCl salt of Compound 105: (R)-1-(3-(5-((3-fluorophenyl)ethynyl)pyridin-2-yl)-1,2,4-oxadiazol-5-yl)-N,N-dimethylethanamine

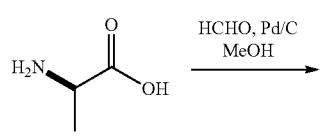

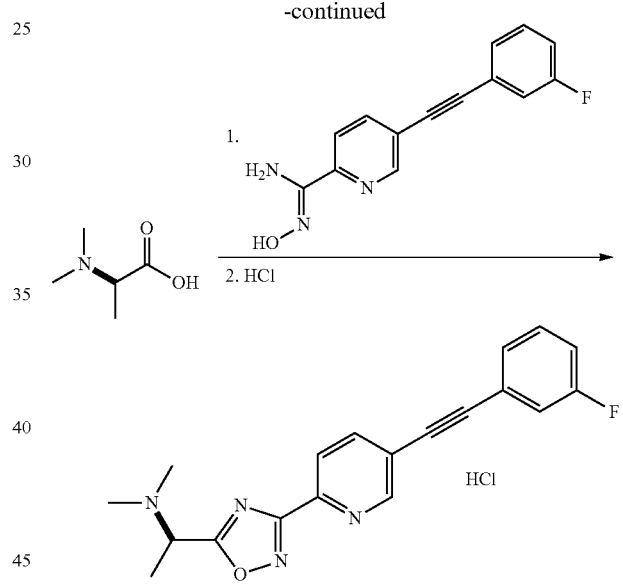

Example 16.12a

Synthesis of (R)-2-(dimethylamino)propanoic acid

A solution of (R)-2-aminopropanoic acid (5 g, 56.2 mmol, 1 equiv), excess formaldehyde solution and a catalytic amount of Pd/C in methanol (5.0 mL) was stirred at room temperature overnight. The reaction mixture was filtered and the filtrate was concentrated under reduced pressure to give the desired product, which was directly used for next step without further purification. MS (ESI): 118 (MH+).

Example 16.12b

Synthesis of (R)-1-(3-(5-((3-fluorophenyl)ethynyl) pyridine-2-yl)-1,2,4-oxadiazol-5-yl)-N,N-dimethylethanamine The title compound was prepared according to the experimental procedure described in Example 8.25. MS (ESI): 337

(MH+); 1H NMR (300 MHz, CD3OD) δ 8.92 (s, 1H), 8.30-8.28 (m, 1H), 8.23-8.19 (m, 1H), 7.51-7.43 (m, 2H), 7.40-7.35 (m, 1H), 7.26-7.19 (m, 1H), 5.31-5.24 (q, 1H), 3.10 (s, 6H), 1.93 (d, J=7.0 Hz, 3H). PAM EC50: +++. Fold shift at 10 μM: ++.

Example 16.13

Synthesis of the HCl salt of Compound 106: (S)-1-(3-(5-((3-fluorophenyl)ethynyl)pyridin-2-yl)-1,2,4-oxadiazol-5-yl)-N,N-dimethylethanamine

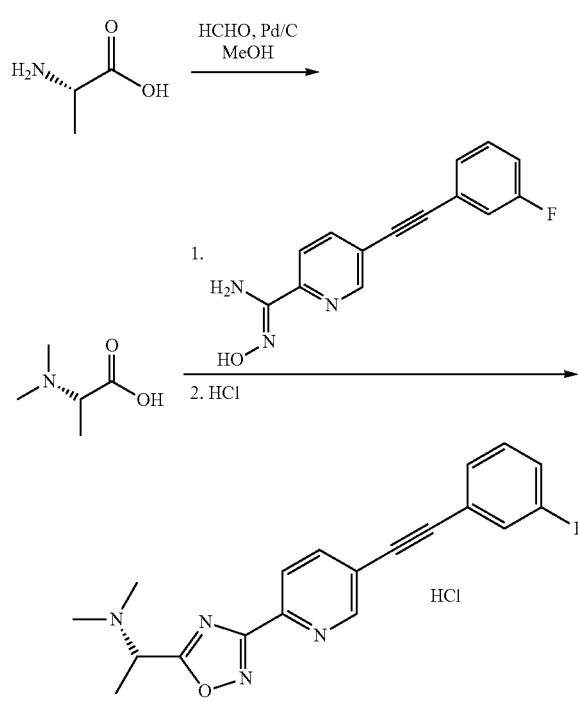

Example 16.13a

Synthesis of (S)-2-(dimethylamino)propanoic acid

The title compound was prepared according to the experimental procedure described in Example 16.12a. MS (ESI): 118 (MH+).

Example 16.13b

Synthesis of the HCl salt of (S)-1-(3-(5-((3-fluorophenyl)ethynyl)pyridine-2-yl)-1,2,4-oxadiazol-5-yl)-N,N-dimethylethanamine The title compound was prepared according to the experimental procedure described in Example 8.25. MS (ESI): 337 (MH+); 1H NMR (300 MHz, CD3OD) δ 8.93 (s, 1H), 8.32-8.30 (m, 1H), 8.25-8.22 (m, 1H), 7.48-7.43 (m, 2H), 7.40-7.35 (m, 1H), 7.26-7.20 (m, 1H), 5.32-5.25 (q, 1H), 3.10 (s, 6H), 1.93 (d, J=7.0 Hz, 3H). PAM EC50: ++++. Fold shift at 10 μM: +++.

Example 16.14

Synthesis of the HCl salt of Compound 107: 1-(3-(5-((3-fluorophenyl)ethynyl)pyridin-2-yl)-1,2,4-oxadiazol-5-yl)-N-methylethanamine

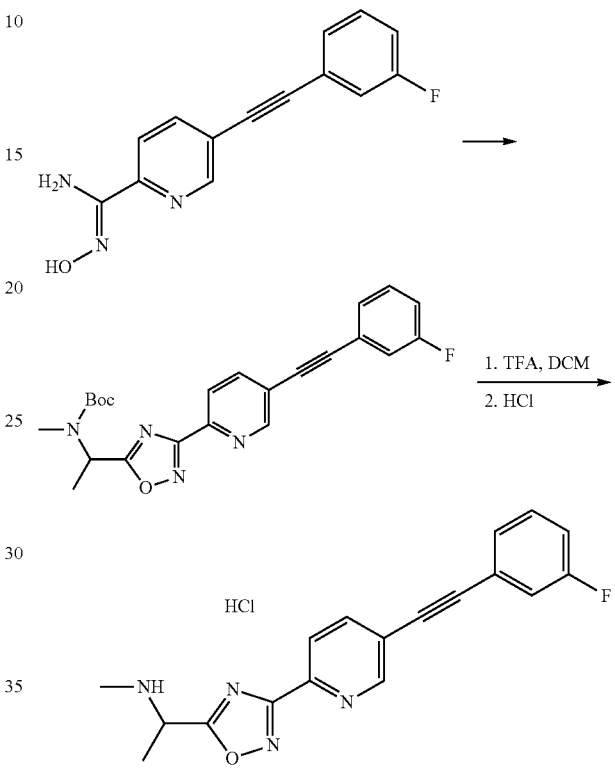

Example 16.14a

Synthesis of tert-butyl 1-(3-(5-((3-fluorophenyl)ethynyl)pyridin-2-yl)-1,2,4-oxadiazol-5-yl)ethyl(methyl)carbamate The title compound was prepared according to the experimental procedure described in Example 8.25. MS (ESI): 423 (MH+).

Example 16.14b

Synthesis of the HCl salt of 1-(3-(5-((3-fluorophenyl)ethynyl)pyridin-2-yl)-1,2,4-oxadiazol-5-yl)-N-methylethanamine The title compound was prepared according to the experimental procedure described in Example 8.29b. MS (ESI): 323 (MH+); 1H NMR (300 MHz, CD3OD) δ 8.93-8.92 (dd, J=1.9, 0.8 Hz, 1H), 8.31-8.21 (m, 2H), 7.50-7.43 (m, 2H), 7.40-7.36 (m, 1H), 7.26-7.19 (m, 1H), 5.10-5.03 (q, 1H), 2.93 (s, 3H), 1.87 (d, J=7.0 Hz, 3H). PAM EC50: +++. Fold shift at 10 μM: ++.

Example 16.15

Synthesis of the HCl salt of Compound 108: 3-(5-((3-fluorophenyl)ethynyl)pyridin-2-yl)-5-(1-(pyrrolidin-1-yl)ethyl)-1,2,4-oxadiazole

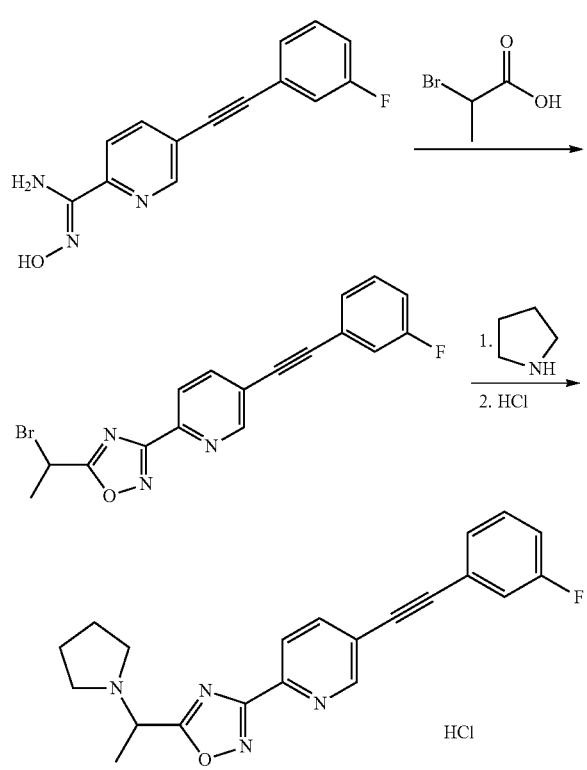

Example 16.15a

Synthesis of 5-(1-bromoethyl)-3-(5-((3-fluorophenyl) ethynyl)pyridin-2-yl)-1,2,4-oxadiazole The title compound was prepared according to the experimental procedure described in Example 8.25. MS (ESI): 372, 374 (MH+).

Example 16.15b

Synthesis of the HCl salt of 3-(5-((3-fluorophenyl) ethynyl)pyridin-2-yl)-5-(1-(pyrrolidin-1-yl)ethyl)-1,2,4-oxadiazole A solution of 5-(1-bromoethyl)-3-(5-((3-fluorophenyl) ethynyl)pyridin-2-yl)-1,2,4-oxadiazole (150 mg, 0.4 mmol, 1 equiv) and excess pyrrolidine in ethanol (5.0 mL) was stirred at 75° C. overnight. After cooling to rt, the reaction mixture was diluted with water (20 mL) and extracted with ethyl acetate (3×20 mL). The combined organic layers were dried over $Na_2SO_4$ and concentrated under reduced pressure to give 95.5 mg of the desired product, which was purified by silica gel chromatography. MS (ESI): 363 (MH+); $^1$H NMR (300 MHz, $CD_3OD$) δ 8.92 (s, 1H), 8.30-8.27 (m, 1H), 8.22-8.16 (m, 1H), 7.51-7.43 (m, 2H), 7.40-7.36 (m, 1H), 7.26-7.19 (m, 1H), 5.30-5.23 (q, 1H), 3.76-3.55 (m, 4H), 2.18 (br s, 4H), 1.93 (d, J=7.0 Hz, 3H). PAM $EC_{50}$: ++++. Fold shift at 10 μM: +++.

Example 16.16

Synthesis of the HCl salt of Compound 109: N-(1-(3-(5-((3-fluorophenyl)ethynyl)pyridin-2-yl)-1,2,4-oxadiazol-5-yl)ethyl)cyclopropanamine

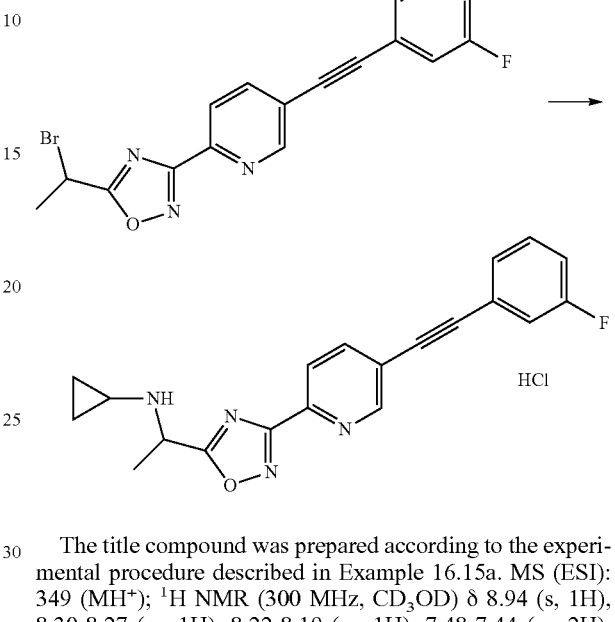

The title compound was prepared according to the experimental procedure described in Example 16.15a. MS (ESI): 349 (MH+); $^1$H NMR (300 MHz, $CD_3OD$) δ 8.94 (s, 1H), 8.30-8.27 (m, 1H), 8.22-8.19 (m, 1H), 7.48-7.44 (m, 2H), 7.39-7.35 (m, 1H), 7.23-7.20 (m, 1H), 5.25-5.22 (m, 1H), 3.02-2.99 (m, 1H), 1.91 (d, J=10.2 Hz, 3H), 1.03-0.92 (m, 4H). PAM $EC_{50}$: ++++.

Example 16.17

Synthesis of the HCl salt of Compound 110: N-(1-(3-(5-((3-fluorophenyl)ethynyl)pyridin-2-yl)-1,2,4-oxadiazol-5-yl)ethyl)propan-2-amine

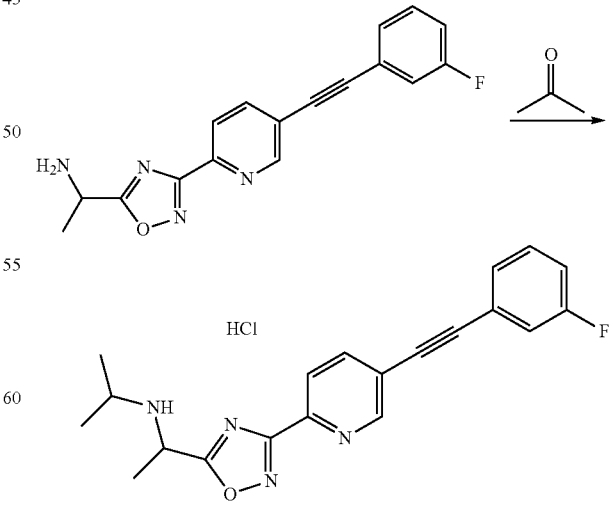

The title compound was prepared according to the experimental procedure described in Example 16.8a. MS (ESI):

351 (MH⁺); ¹H NMR (300 MHz, CD₃OD) δ 8.92 (s, 1H), 8.28-8.19 (m, 2H), 7.49-7.34 (m, 3H), 7.24-7.18 (m, 1H), 5.24-5.22 (m, 1H), 3.73-3.67 (m, 1H), 1.85 (d, J=6.4 Hz, 3H), 1.44 (m, 6H). PAM EC₅₀: +++. Fold shift at 10 μM: ++.

Example 16.18

Synthesis of the HCl salt of Compound 111: N,N-diethyl-1-(3-(5-((3-fluorophenyl)ethynyl)pyridin-2-yl)-1,2,4-oxadiazol-5-yl)ethanamine

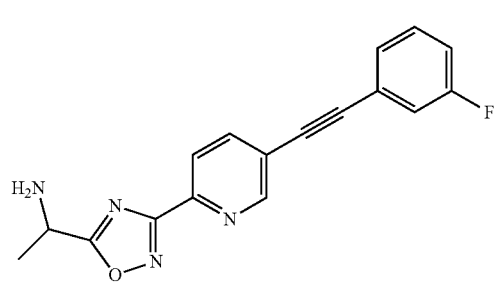

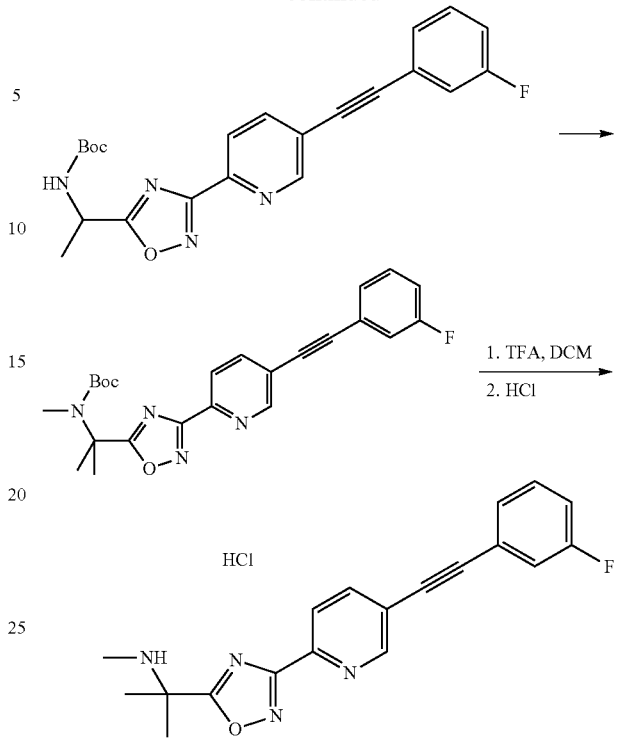

Example 16.19a

Synthesis of tert-butyl 1-(3-(5-((3-fluorophenyl)ethynyl) pyridin-2-yl)-1,2,4-oxadiazol-5-yl)ethylcarbamate The title compound was prepared according to the experimental procedure described in Example 8.25. MS (ESI): 409 (MH⁺).

The title compound was prepared according to the experimental procedure described in Example 16.8a. MS (ESI): 365 (MH⁺); ¹H NMR (300 MHz, CD₃OD) δ 8.93 (s, 1H), 8.30-8.28 (m, 1H), 8.24-8.20 (m, 1H), 7.49-7.45 (m, 2H), 7.40-7.36 (m, 1H), 7.26-7.20 (m, 1H), 5.45-5.38 (m, 1H), 3.50-3.48 (m, 4H), 1.93 (d, J=7.0 Hz, 3H), 1.49-1.44 (t, J=7.3 Hz, 6H). PAM EC₅₀: ++++. Fold shift at 10 μM: ++.

Example 16.19

Synthesis of the HCl salt of Compound 112: 2-(3-(5-((3-fluorophenyl)ethynyl)pyridin-2-yl)-1,2,4-oxadiazol-5-yl)-N-methylpropan-2-amine Example 16.19b Synthesis of tert-butyl 2-(3-(5-((3-fluorophenyl)ethynyl) pyridin-2-yl)-1,2,4-oxadiazol-5-yl)propan-2-yl(methyl)carbamate The title compound was prepared according to the experimental procedure described in Example 8.32a. MS (ESI): 437 (MH⁺).

Example 16.19c

Synthesis of the HCl salt of 2-(3-(5-((3-fluorophenyl)ethynyl)pyridin-2-yl)-1,2,4-oxadiazol-5-yl)-N-methylpropan-2-amine

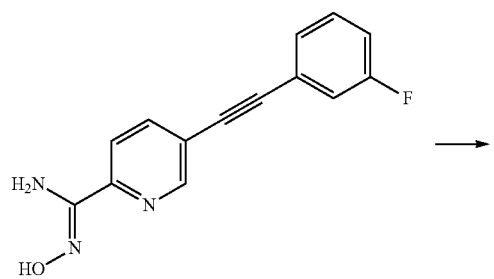

The title compound was prepared according to the experimental procedure described in Example 8.29b. MS (ESI): 337 (MH⁺); ¹H NMR (300 MHz, CD₃OD) δ 8.93-8.92 (m, 1H), 8.30-8.20 (m, 2H), 7.51-7.43 (m, 2H), 7.40-7.36 (m, 1H), 7.26-7.19 (m, 1H), 2.84 (s, 3H), 1.94 (s, 6H). PAM EC₅₀: ++++. Fold shift at 10 μM: ++.

Example 16.20

Synthesis of the HCl salt of Compound 113: 2-(3-(5-((3-fluorophenyl)ethynyl)pyridin-2-yl)-1,2,4-oxadiazol-5-yl)-N,N-dimethylpropan-2-amine

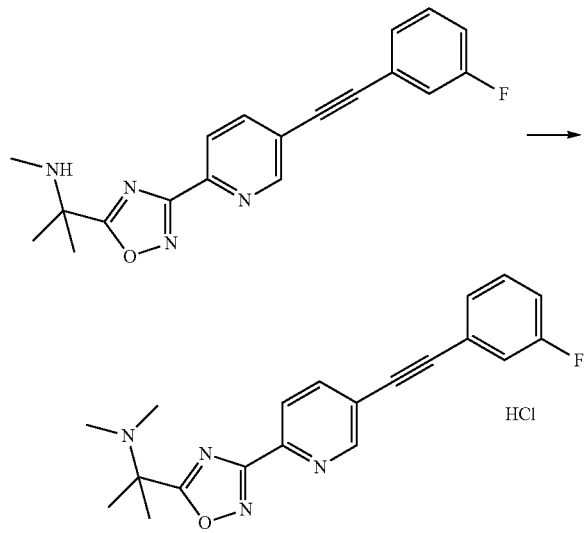

The title compound was prepared according to the experimental procedure described in Example 16.8a. MS (ESI): 351 (MH+); ¹H NMR (300 MHz, CD₃OD) δ 8.93 (d, J=1.0 Hz, 1H), 8.32-8.21 (m, 2H), 7.49-7.44 (m, 2H), 7.40-7.36 (m, 1H), 7.26-7.19 (m, 1H), 3.03 (s, 6H), 2.01 (s, 6H). PAM EC$_{50}$: ++++. Fold shift at 10 μM: ++.

Example 16.21

Synthesis of the HCl salt of Compound 114: 1-(3-(5-((3-fluorophenyl)ethynyl)pyridin-2-yl)-1,2,4-oxadiazol-5-yl)propan-1-amine

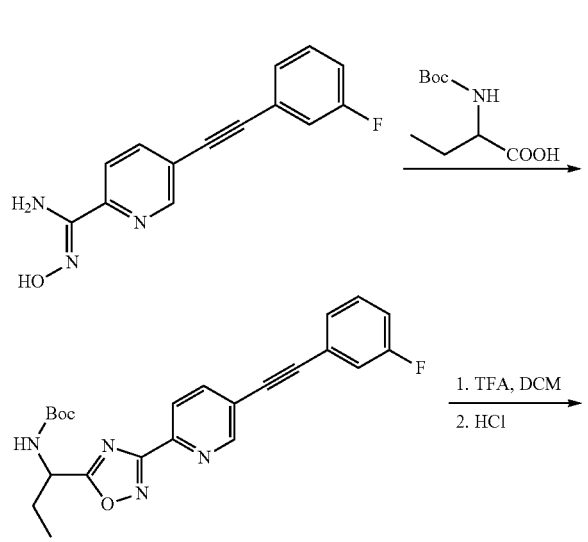

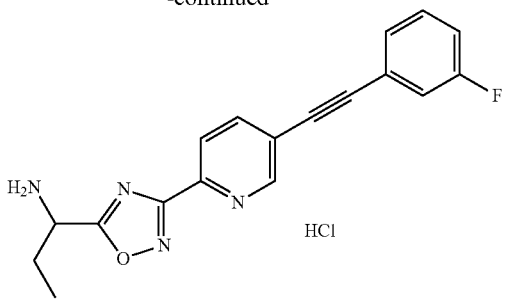

Example 16.21a

Synthesis of tert-butyl 1-(3-(5-((3-fluorophenyl)ethynyl)pyridin-2-yl)-1,2,4-oxadiazol-5-yl)propyl-carbamate The title compound was prepared according to the experimental procedure described in Example 8.25. MS (ESI): 423 (MH+).

Example 16.21b

Synthesis of the HCl salt of 1-(3-(5-((3-fluorophenyl)ethynyl)pyridin-2-yl)-1,2,4-oxadiazol-5-yl)propan-1-amine The title compound was prepared according to experimental procedure described in Example 8.29b. MS (ESI): 323 (MH+); ¹H NMR (300 MHz, CD₃OD) δ 8.91 (d, J=1.1 Hz, 1H), 8.24-8.20 (m, 2H), 7.49-7.43 (m, 2H), 7.39-7.35 (m, 1H), 7.26-7.19 (m, 1H), 4.96-4.91 (t, J=6.8 Hz, 1H), 2.26-2.18 (m, 2H), 1.17-1.11 (t, J=7.5 Hz, 3H). PAM EC$_{50}$: ++. Fold shift at 10 μM: ++.

Example 16.22

Synthesis of the HCl salt of Compound 115: 1-(3-(5-((3-fluorophenyl)ethynyl)pyridin-2-yl)-1,2,4-oxadiazol-5-yl)-N-methylpropan-1-amine

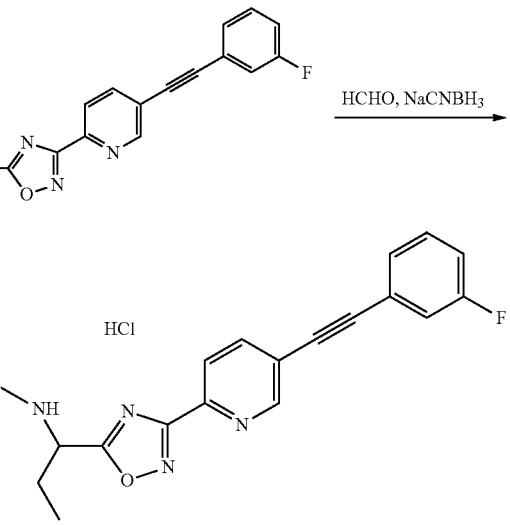

The title compound was prepared according to the experimental procedure described in Example 16.8a. MS (ESI): 337 (MH⁺); ¹H NMR (300 MHz, CD₃OD) δ 8.93 (s, 1H), 8.31-8.28 (m, 1H), 8.24-8.20 (m, 1H), 7.49-7.45 (m, 2H), 7.39-7.36 (m, 1H), 7.26-7.20 (m, 1H), 4.99-4.93 (m, 1H), 2.90 (s, 3H), 2.35-2.21 (m, 2H), 1.10-1.15 (t, J=7.4 Hz, 3H). PAM EC$_{50}$: +++. Fold shift at 10 µM: +++.

Example 16.23

Synthesis of the HCl salt of Compound 116: 1-(3-(5-((3-fluorophenyl)ethynyl)pyridin-2-yl)-1,2,4-oxadiazol-5-yl)-N,N-dimethylpropan-1-amine

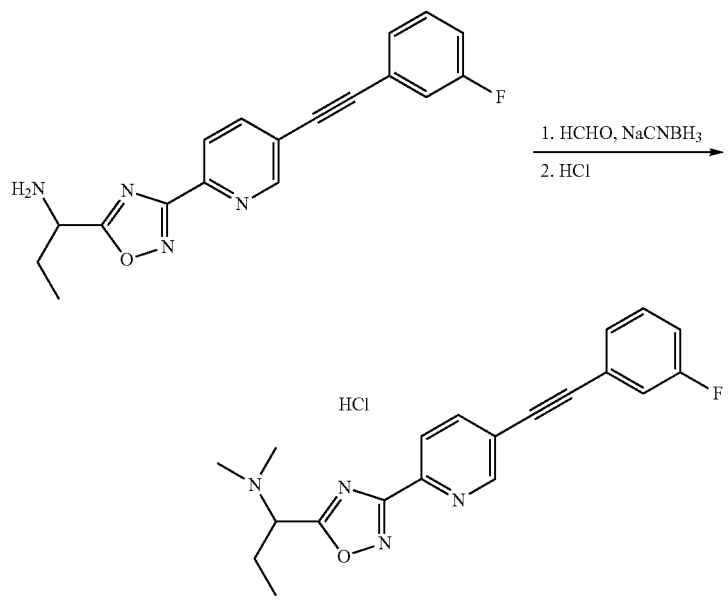

The title compound was prepared according to the experimental procedure described in Example 16.8a. MS (ESI): 351 (MH⁺); ¹H NMR (300 MHz, CD₃OD) δ 8.93 (d, J=1.2 Hz, 1H), 8.32-8.29 (m, 1H), 8.25-8.21 (m, 1H), 7.50-7.45 (m, 2H), 7.40-7.35 (m, 1H), 7.23-7.21 (m, 1H), 5.15-5.10 (t, J=7.4 Hz, 1H), 3.09 (s, 6H), 2.39-2.33 (m, 2H), 1.09-1.03 (t, J=7.4 Hz, 3H). PAM EC$_{50}$: ++++. Fold shift at 10 µM: ++.

Example 16.24

Synthesis of the HCl salt of Compound 117: N-(1-(3-(5-((3-fluorophenyl)ethynyl)pyridin-2-yl)-1,2,4-oxadiazol-5-yl)propyl)cyclopropanamine

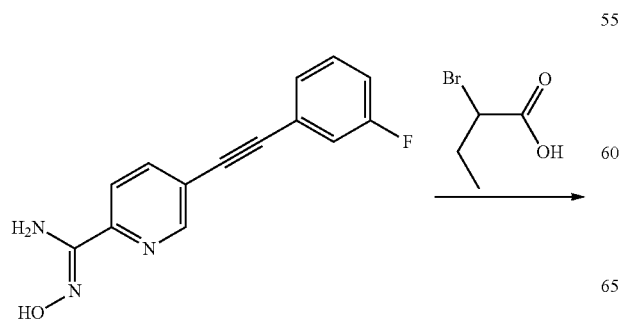

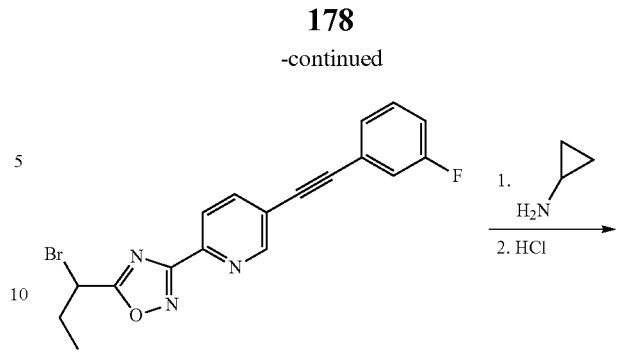

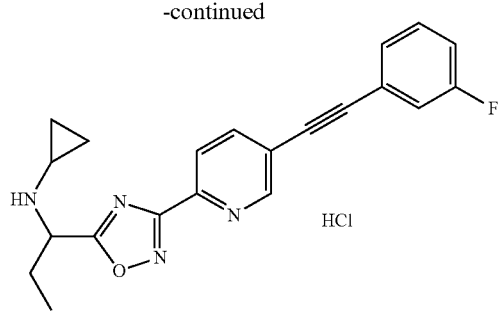

Example 16.24a

Synthesis of 5-(1-bromopropyl)-3-(5-((3-fluorophenyl)ethynyl)pyridin-2-yl)-1,2,4-oxadiazole The title compound was prepared according to the experimental procedure described in Example 8.25. MS (ESI): 386, 388 (MH⁺).

Example 16.24b

Synthesis of the HCl salt of N-(1-(3-(5-((3-fluorophenyl)ethynyl)pyridin-2-yl)-1,2,4-oxadiazol-5-yl)propyl)cyclopropanamine The title compound was prepared according to the experimental procedure described in Example 16.15a. MS (ESI): 363 (MH+); $^1$H NMR (300 MHz, CD$_3$OD) δ 8.94 (s, 1H), 8.32-8.28 (m, 1H), 8.25-8.22 (m, 1H), 7.52-7.44 (m, 2H), 7.40-7.36 (m, 1H), 7.26-7.19 (m, 1H), 5.16-5.11 (m, 1H), 2.99-2.91 (m, 1H), 2.43-2.22 (m, 2H), 1.08-1.04 (m, 3H), 1.01-0.89 (m, 4H). PAM EC$_{50}$: ++++. Fold shift at 10 μM: +++.

Example 16.25

Synthesis of the HCl salt of Compound 118: 1-(3-(5-((3-fluorophenyl)ethynyl)pyridin-2-yl)-1,2,4-oxadiazol-5-yl)-N,N-dimethylcyclopropanamine

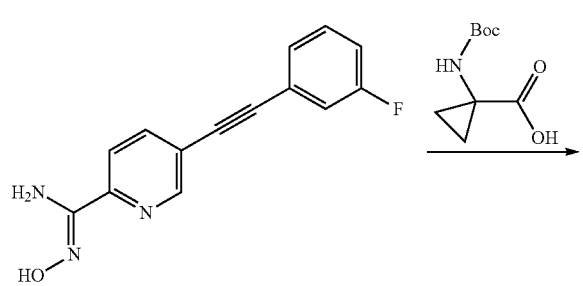

Example 16.25a

Synthesis of tert-butyl 1-(3-(5-((3-fluorophenyl)ethynyl)pyridin-2-yl)-1,2,4-oxadiazol-5-yl)cyclopropylcarbamate The title compound was prepared according to the experimental procedure described in Example 8.25. MS (ESI): 421 (MH+).

Example 16.25b

Synthesis of 1-(3-(5-((3-fluorophenyl)ethynyl)pyridin-2-yl)-1,2,4-oxadiazol-5-yl)cyclopropanamine The title compound was prepared according to the experimental procedure described in Example 8.29b. MS (ESI): 321 (MH+).

Example 16.25c

Synthesis of the HCl salt of 1-(3-(5-((3-fluorophenyl)ethynyl)pyridin-2-yl)-1,2,4-oxadiazol-5-yl)-N,N-dimethylcyclopropanamine The title compound was prepared according to the experimental procedure described in Example 16.8a. MS (ESI): 349 (MH+); $^1$H NMR (300 MHz, CD$_3$OD) δ 8.91 (d, J=1.2 Hz, 1H), 8.30-8.27 (m, 1H), 8.22-8.18 (m, 1H), 7.51-7.45 (m, 2H), 7.40-7.35 (m, 1H), 7.26-7.19 (m, 1H), 3.36 (s, 6H), 2.03 (s, 4H). PAM EC$_{50}$: ++++. Fold shift at 10 μM: ++.

Example 16.26

Synthesis of the HCl salt of Compound 119: 3-(5-((3-fluorophenyl)ethynyl)pyridin-2-yl)-5-(pyrrolidin-2-yl)-1,2,4-oxadiazole

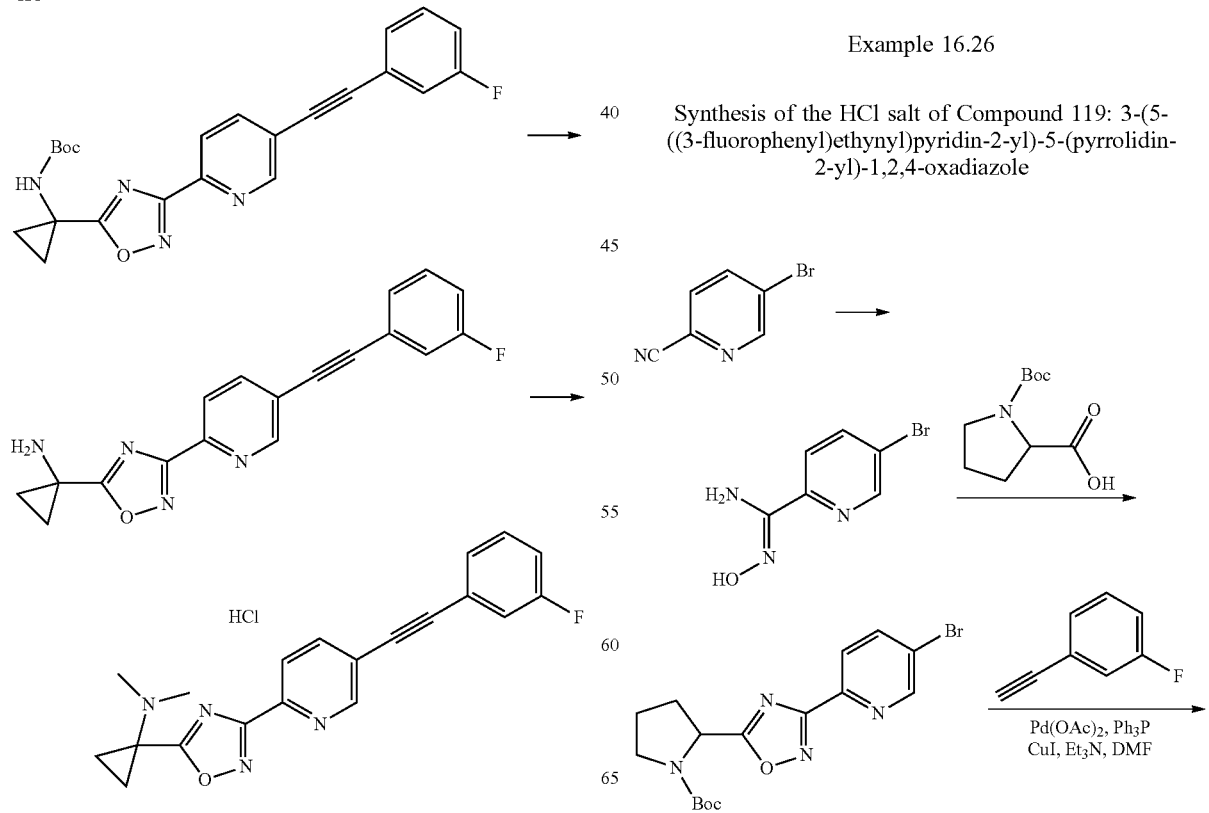

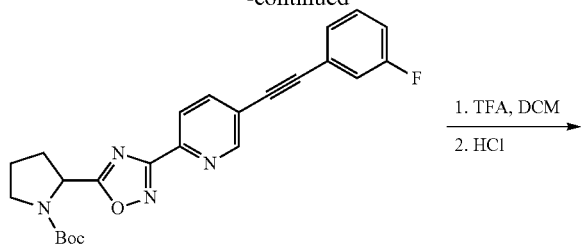

Example 16.26a

Synthesis of 5-bromo-N'-hydroxypicolinimidamide

The title compound was prepared according to the experimental procedure described in Example 8.1b. MS (ESI): 216, 218 (MH+).

Example 16.26b

Synthesis of tert-butyl 2-(3-(5-bromopyridin-2-yl)-1,2,4-oxadiazol-5-yl)pyrrolidine-1-carboxylate The title compound was prepared according to the experimental procedure described in Example 8.25. MS (ESI): 395, 397 (MH+).

Example 16.26c

Synthesis of tert-butyl 2-(3-(5-((3-fluorophenyl)ethynyl) pyridin-2-yl)-1,2,4-oxadiazol-5-yl)pyrrolidine-1-carboxylate The title compound was prepared according to the experimental procedure described in Example 8.1a. MS (ESI): 435 (MH+).

Example 16.26d

Synthesis of the HCl salt of 3-(5-((3-fluorophenyl)ethynyl)pyridin-2-yl)-5-(pyrrolidin-2-yl)-1,2,4-oxadiazole The title compound was prepared according to the experimental procedure described in Example 8.29b. MS (ESI): 335 (MH+); $^1$H NMR (300 MHz, CD$_3$OD) δ 8.92 (s, 1H), 8.29-8.22 (m, 2H), 7.49-7.45 (m, 2H), 7.40-7.25 (m, 1H), 7.36-7.20 (m, 1H), 5.29-5.24 (t, J=7.7 Hz, 1H), 3.66-3.55 (m, 2H), 2.73-2.68 (m, 1H), 2.52-2.45 (m, 1H), 2.36-2.27 (m, 2H). PAM EC$_{50}$: +.

Example 16.27

Synthesis of the HCl salt of Compound 120: (R)-3-(5-((3-fluorophenyl)ethynyl)pyridin-2-yl)-5-(pyrrolidin-2-yl)-1,2,4-oxadiazole The title compound was prepared according to the experimental procedure described in Example 16.26. MS (ESI): 335 (MH+); $^1$H NMR (300 MHz, CD$_3$OD) δ 8.91 (d, J=2.0 Hz, 1H), 8.29-8.18 (m, 2H), 7.49-7.44 (m, 2H), 7.40-7.35 (m, 1H), 7.23-7.20 (m, 1H), 5.29-5.24 (t, J=7.7 Hz, 1H), 3.65-3.55 (m, 2H), 2.73-2.68 (m, 1H), 2.52-2.45 (m, 1H), 2.34-2.26 (m, 2H). PAM EC$_{50}$: ++. Fold shift at 10 μM: +++.

Example 16.28

Synthesis of the HCl salt of Compound 121: (S)-3-(5-((3-fluorophenyl)ethynyl)pyridin-2-yl)-5-(pyrrolidin-2-yl)-1,2,4-oxadiazole

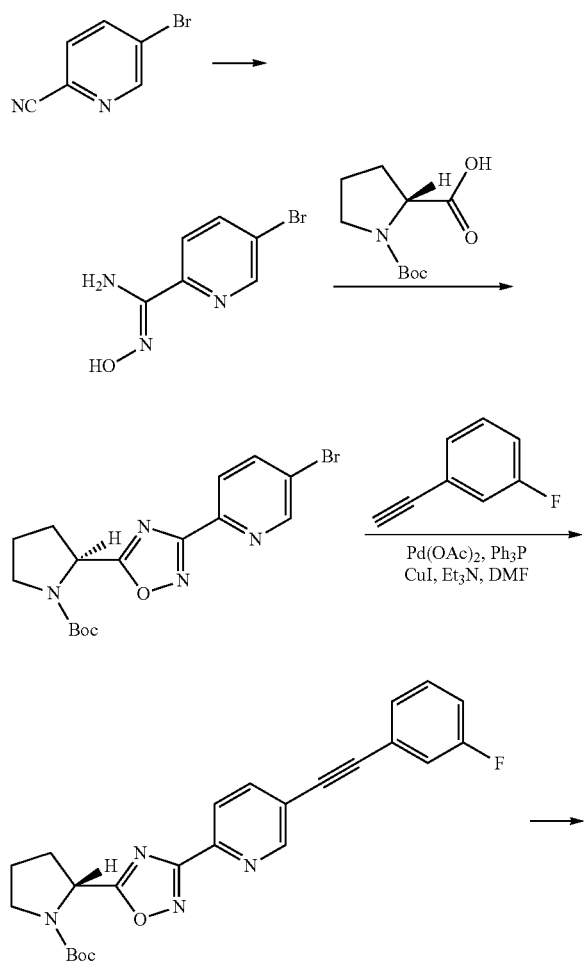

The title compound was prepared according to the experimental procedure described in Example 16.26. MS (ESI): 335 (MH+); ¹H NMR (300 MHz, CD₃OD) δ 8.91 (s, 1H), 8.29-8.18 (m, 2H), 7.48-7.43 (m, 2H), 7.39-7.35 (m, 1H), 7.26-7.19 (m, 1H), 5.30-5.24 (t, J=7.7 Hz, 1H), 3.67-3.56 (m, 2H), 2.73-2.68 (m, 1H), 2.50-2.45 (m, 1H), 2.34-2.27 (m, 2H). PAM EC₅₀: +.

Example 16.29

Synthesis of the HCl salt of Compound 122: 3-(5-((3-fluorophenyl)ethynyl)pyridin-2-yl)-5-(2-methylpyrrolidin-2-yl)-1,2,4-oxadiazole

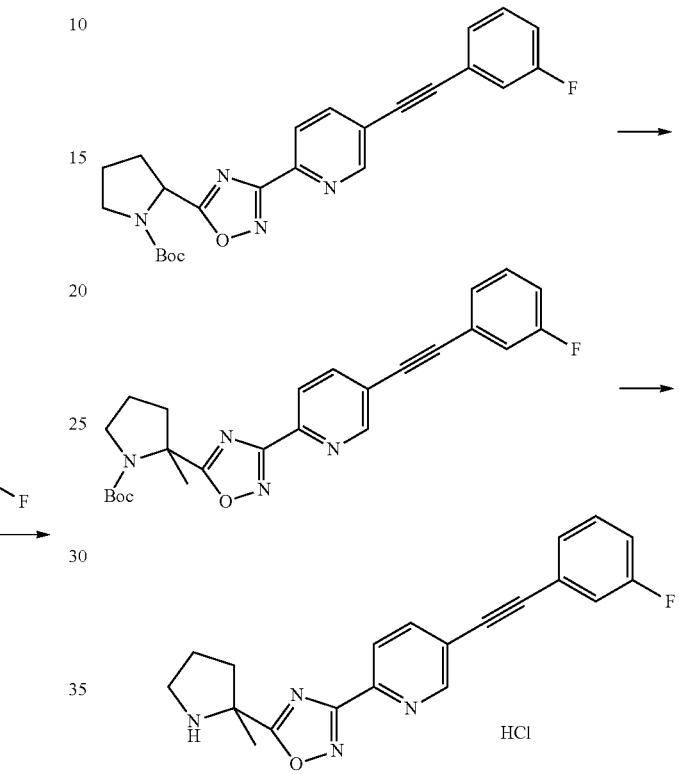

The title compound was prepared according to the experimental procedure described in Example 8.32. MS (ESI): 349 (MH+); ¹H NMR (300 MHz, CD₃OD) δ 8.90 (s, 1H), 8.28-8.19 (m, 2H), 7.48-7.43 (m, 2H), 7.36 (d, J=7.9 Hz, 1H), 7.25-7.19 (m, 1H), 3.72-3.63 (m, 2H), 2.76-2.71 (m, 1H), 2.46-2.29 (m, 3H), 2.01 (s, 3H). PAM EC₅₀: ++. Fold shift at 10 μM: +++.

Example 16.30

Synthesis of the HCl salt of Compound 123: 3-(5-((3-fluorophenyl)ethynyl)pyridin-2-yl)-5-(1-(3,3,3-trifluoropropyl)pyrrolidin-2-yl)-1,2,4-oxadiazole

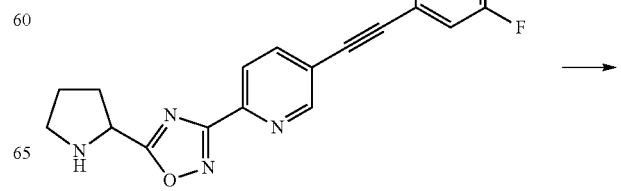

-continued

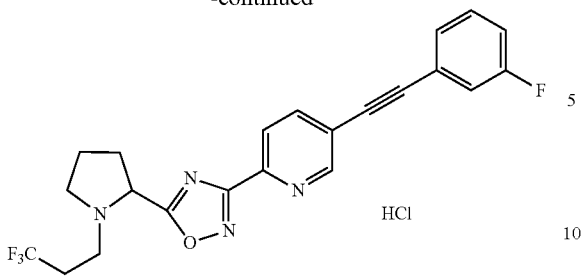

The title compound was prepared according to the experimental procedure described in Example 16.8a. MS (ESI): 335 (MH⁺); ¹H NMR (300 MHz, CD₃OD) δ 8.92 (s, 1H), 8.30-8.19 (m, 2H), 7.49-7.43 (m, 2H), 7.40-7.35 (m, 1H), 7.26-7.20 (m, 1H), 5.33-5.27 (t, J=8.1 Hz, 1H), 4.03-3.94 (m, 2H), 3.73-3.63 (m, 1H), 3.60-3.51 (m, 1H), 2.98-2.82 (m, 3H), 2.60-2.53 (m, 1H), 2.45-2.33 (m, 2H). PAM EC$_{50}$: ++++. Fold shift at 10 μM: +.

Example 16.31

Synthesis of the HCl salt of Compound 124: 3-(5-((3-fluorophenyl)ethynyl)pyridin-2-yl)-5-(1-(prop-2-yn-1-yl)pyrrolidin-2-yl)-1,2,4-oxadiazole

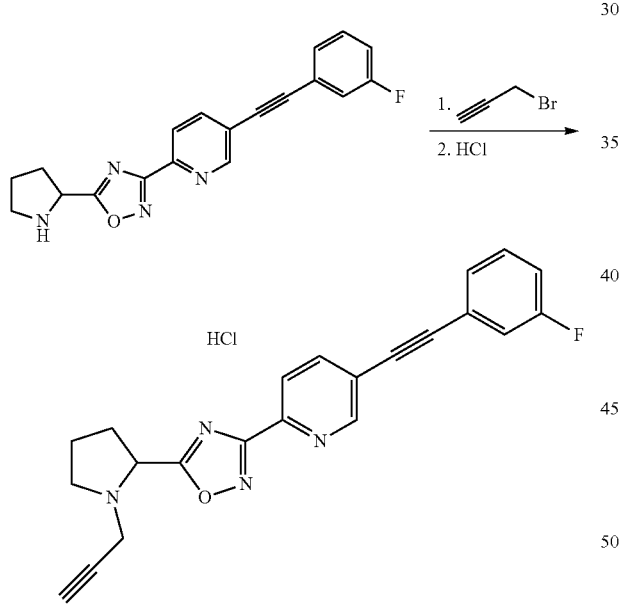

To a solution of 3-(5-((3-fluorophenyl)ethynyl)pyridin-2-yl)-5-(pyrrolidin-2-yl)-1,2,4-oxadiazole (70 mg, 0.21 mmol, 1 equiv) and K₂CO₃ (116 mg, 0.82 mmol, 4 equiv) in acetone (20 mL) was added 3-bromoprop-1-yne (49.6 mg, 0.42 mmol, 2 equiv). The reaction was kept at rt for 1 h, then quenched with water and extracted with ethyl acetate (3×20 mL). The combined organic layers were dried over Na₂SO₄ and concentrated under reduced pressure to give 72.5 mg of the desired product, which was purified by silica gel chromatography. MS (ESI): 373 (MH⁺); ¹H NMR (300 MHz, CD₃OD) δ 8.92 (s, 1H), 8.31-8.21 (m, 2H), 7.51-7.44 (m, 2H), 7.38-7.35 (m, 1H), 7.25-7.19 (m, 1H), 5.38-5.32 (m, 1H), 4.61-4.44 (m, 2H), 4.00-3.98 (m, 1H), 3.73-3.67 (m, 1H), 3.43 (s, 1H), 2.95-2.86 (m, 1H), 2.67-2.60 (m, 1H), 2.40-2.38 (m, 2H). PAM EC$_{50}$: ++++. Fold shift at 10 μM: +.

Example 16.32

Synthesis of the HCl salt of Compound 125: 2-(2-(3-(5-((3-fluorophenyl)ethynyl)pyridin-2-yl)-1,2,4-oxadiazol-5-yl)pyrrolidin-1-yl)acetonitrile

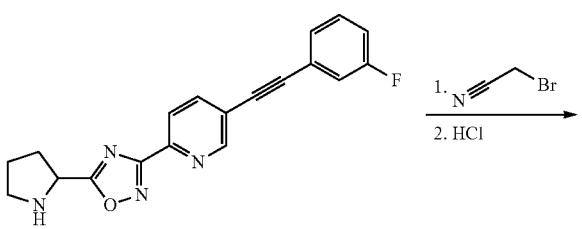

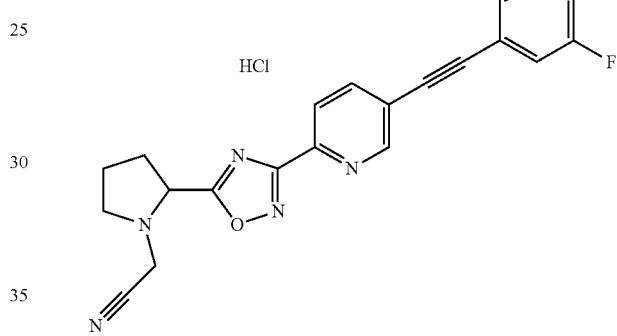

The title compound was prepared according to the experimental procedure described in Example 16.31. MS (ESI): 374 (MH⁺); ¹H NMR (300 MHz, CD₃OD) δ 8.95 (s, 1H), 8.37-8.30 (m, 2H), 7.49-7.45 (m, 2H), 7.39-7.36 (m, 1H), 7.26-7.20 (m, 1H), 4.52-4.47 (m, 1H), 4.17 (s, 2H), 3.47-3.43 (m, 1H), 3.10-3.01 (m, 1H), 2.62-2.55 (m, 1H), 2.43-2.36 (m, 1H), 2.19-2.12 (m, 2H). PAM EC$_{50}$: +++. Fold shift at 10 μM: +++.

Example 16.33

Synthesis of the HCl salt of Compound 126: 5-(1-cyclobutylpyrrolidin-2-yl)-3-(5-((3-fluorophenyl)ethynyl)pyridin-2-yl)-1,2,4-oxadiazole

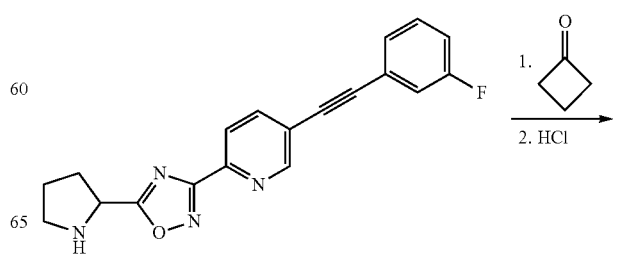

-continued

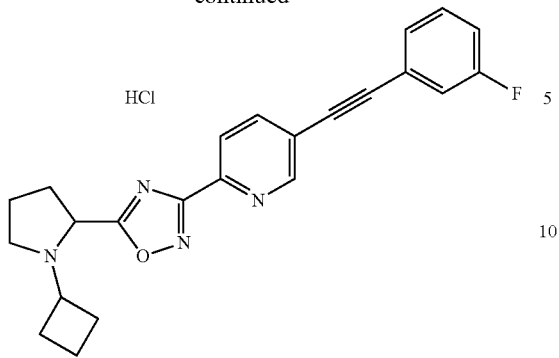

The title compound was prepared according to the experimental procedure described in Example 16.8a. MS (ESI): 389 (MH⁺); ¹H NMR (300 MHz, CD₃OD) δ 8.92 (s, 1H), 8.29-8.19 (m, 2H), 7.48-7.43 (m, 2H), 7.38-7.35 (m, 1H), 7.25-7.19 (m, 1H), 5.20 (br s, 1H), 4.10 (br s, 1H), 3.80 (br s, 1H), 3.46 (br s, 1H), 2.79-2.74 (m, 1H), 2.67-2.60 (m, 1H), 2.37-2.21 (m, 6H), 1.94-1.85 (m, 2H). PAM EC₅₀: +++. Fold shift at 10 μM: ++.

Example 16.34

Synthesis of the HCl salt of Compound 127: (S)-3-(5-((3-fluorophenyl)ethynyl)pyridin-2-yl)-5-(4-methylenepyrrolidin-2-yl)-1,2,4-oxadiazole The title compound was prepared according to the experimental procedure described in Example 8.25 and Example 8.29b. MS (ESI): 347 (MH⁺); ¹H NMR (300 MHz, CD₃OD) δ 8.92-8.90 (dd, J=2.0, 0.8 Hz, 1H), 8.29-8.25 (m, 1H), 8.22-8.18 (m, 1H), 7.51-7.42 (m, 2H) 7.40-7.38 (m, 1H), 7.26-7.19 (m, 1H), 5.48-5.42 (t, J=8.1, Hz, 1H), 5.41-5.36 (m, 2H), 4.33-4.15 (m, 2H), 3.47-3.38 (m, 1H), 3.24-3.13 (m, 1H). PAM EC₅₀: ++. Fold shift at 10 μM: +++.

Example 16.35

Synthesis of Compound 128: (4R)-tert-butyl 2-(3-(5-((3-fluorophenyl)ethynyl)pyridin-2-yl)-1,2,4-oxadiazol-5-yl)-4-hydroxypyrrolidine-1-carboxylate

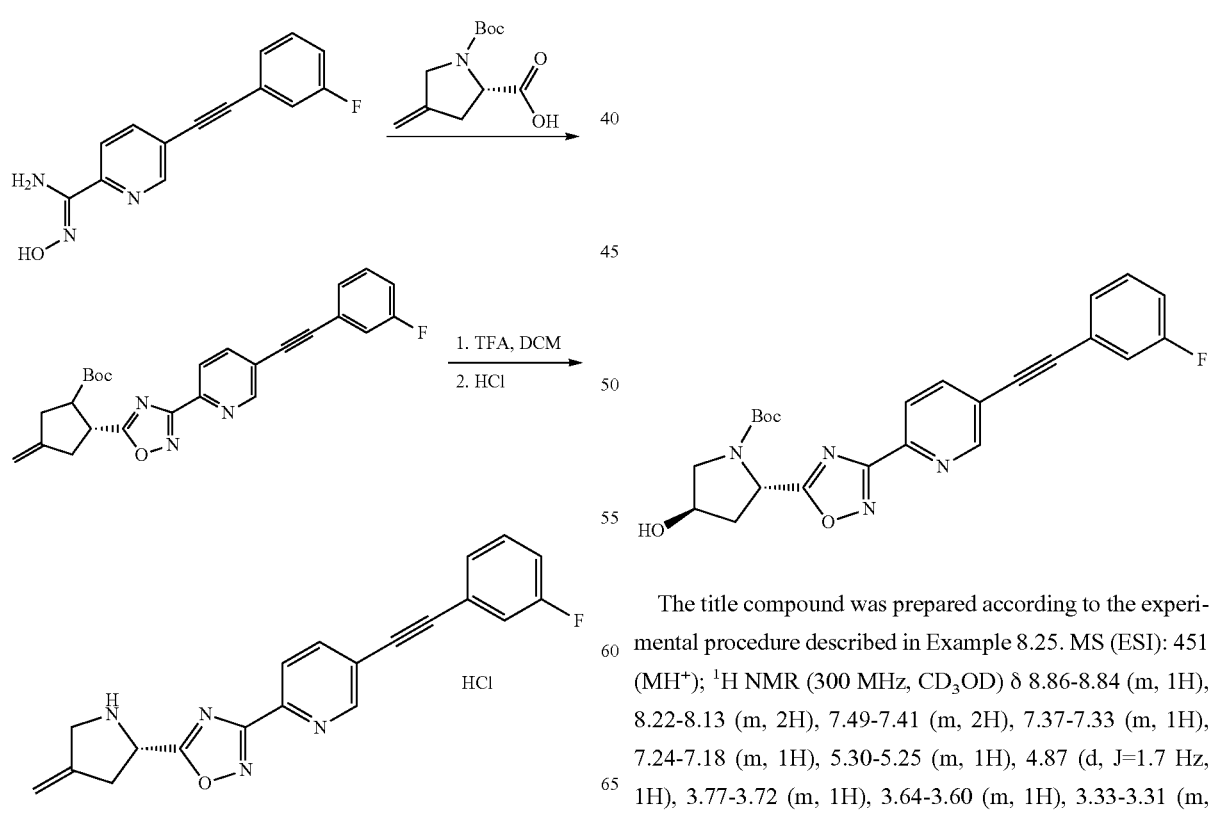

The title compound was prepared according to the experimental procedure described in Example 8.25. MS (ESI): 451 (MH⁺); ¹H NMR (300 MHz, CD₃OD) δ 8.86-8.84 (m, 1H), 8.22-8.13 (m, 2H), 7.49-7.41 (m, 2H), 7.37-7.33 (m, 1H), 7.24-7.18 (m, 1H), 5.30-5.25 (m, 1H), 4.87 (d, J=1.7 Hz, 1H), 3.77-3.72 (m, 1H), 3.64-3.60 (m, 1H), 3.33-3.31 (m, 1H), 2.50-2.29 (m, 1H), 1.47 (s, 9H).

Example 16.36

Synthesis of the HCl salt of Compound 129: (3R,5S)-5-(3-(5-((3-fluorophenyl)ethynyl)pyridin-2-yl)-1,2,4-oxadiazol-5-yl)pyrrolidin-3-ol

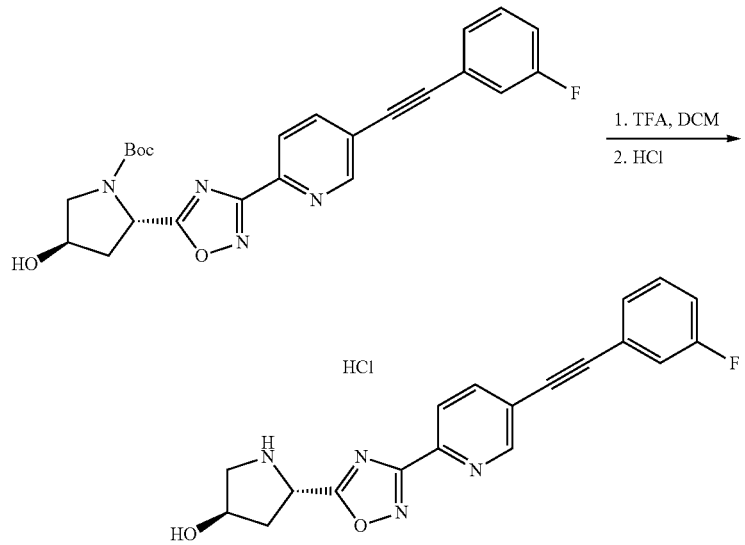

The title compound was prepared according to the experimental procedure described in Example 8.29b. MS (ESI): 351 (MH+); 1H NMR (300 MHz, CD3OD) δ 8.92-8.90 (dd, J=1.9, 0.8 Hz, 1H), 8.28-8.25 (m, 1H), 8.22-8.18 (m, 1H), 7.51-7.43 (m, 2H) 7.40-7.35 (m, 1H), 7.26-7.19 (m, 1H), 5.46-5.40 (m, 1H), 4.78-4.75 (m, 1H), 3.75-3.65 (m, 1H), 3.56-3.46 (m, 1H), 2.76-2.69 (m, 1H), 2.65-2.55 (m, 1H). PAM EC50: +.

Example 16.37

Synthesis of the HCl salt of Compound 130: (3R,5S)-5-(3-(5-((3-fluorophenyl)ethynyl)pyridin-2-yl)-1,2,4-oxadiazol-5-yl)-1-methylpyrrolidin-3-ol

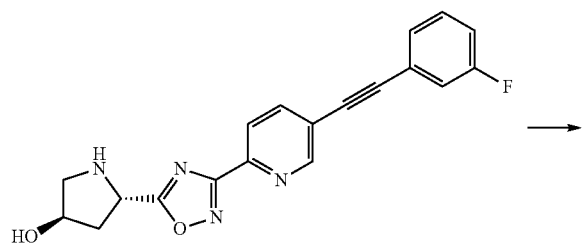

-continued

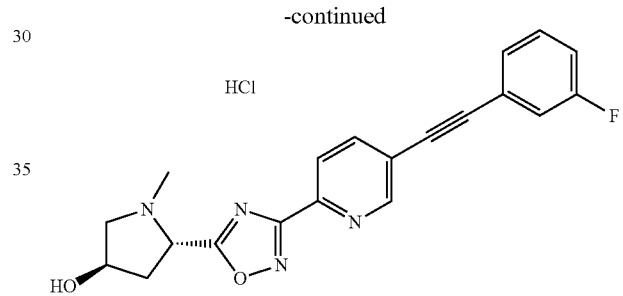

The title compound was prepared according to the experimental procedure described in Example 16.8a. MS (ESI): 365 (MH+); 1H NMR (300 MHz, CD3OD) δ 8.91 (d, J=1.2 Hz, 1H), 8.29-8.18 (m, 2H), 7.51-7.43 (m, 2H), 7.38-7.35 (m, 1H), 7.25-7.21 (m, 1H), 5.46-5.40 (m, 1H), 4.75 (s, 1H), 4.05 (d, J=8.7 Hz, 1H), 3.43 (d, J=11.7 Hz, 1H), 3.32 (s, 3H), 2.81-2.71 (m, 2H). PAM EC50: +++. Fold shift at 10 μM: +++.

Example 16.38

Synthesis of the HCl salt of Compound 131: (3R,5R)-5-(3-(5-((3-fluorophenyl)ethynyl)pyridin-2-yl)-1,2,4-oxadiazol-5-yl)pyrrolidin-3-ol

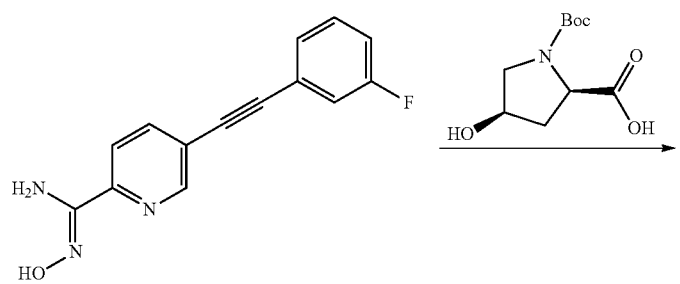

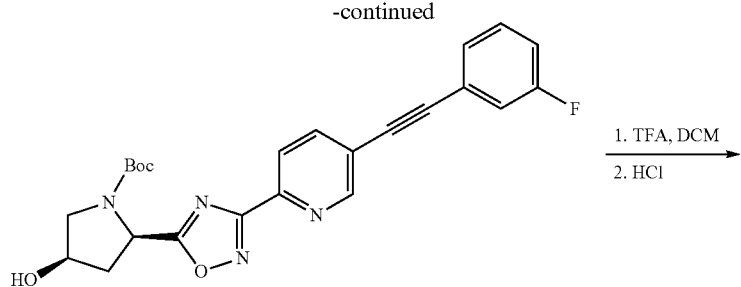

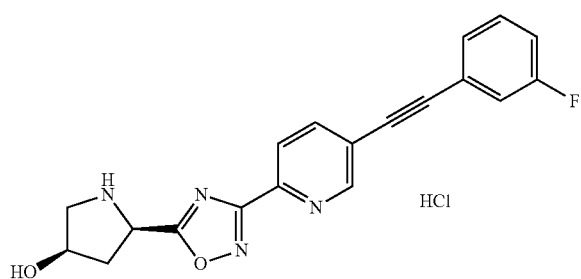

The title compound was prepared according to the experimental procedure described in Example 8.25 and Example 8.29b. MS (ESI): 351 (MH+); $^1$H NMR (300 MHz, CD$_3$OD) δ 8.91-8.90 (dd, J=1.9, 0.8 Hz, 1H), 8.29-8.26 (m, 1H), 8.22-8.18 (m, 1H), 7.49-7.43 (m, 2H), 7.40-7.35 (m, 1H), 7.26-7.19 (m, 1H), 5.40-5.35 (m, 1H), 4.73-4.70 (m, 1H), 3.53 (d, J=2.6 Hz, 2H), 2.87-2.79 (m, 1H), 2.71-2.69 (m, 1H).

Example 16.39

Synthesis of the HCl salt of Compound 132: (3R,5R)-5-(3-(5-((3-fluorophenyl)ethynyl)pyridin-2-yl)-1,2,4-oxadiazol-5-yl)-1-methylpyrrolidin-3-ol

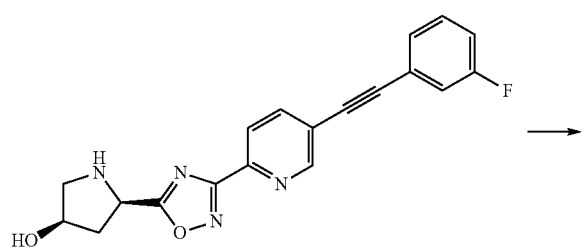

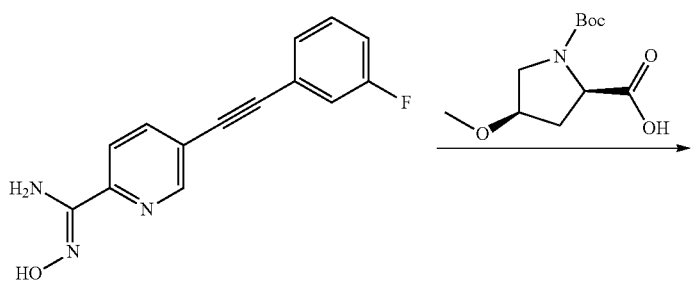

The title compound was prepared according to the experimental procedure described in Example 16.8a. MS (ESI): 365 (MH+); $^1$H NMR (300 MHz, CD$_3$OD) δ 8.92 (s, 1H), 8.30-8.19 (m, 2H), 7.52-7.43 (m, 2H), 7.40-7.35 (m, 1H), 7.26-7.19 (m, 1H), 5.17-5.13 (m, 1H), 4.73-4.69 (m, 1H), 3.77-3.72 (d, J=11.2 Hz, 1H), 3.50-3.44 (dd, J=11.6, 1.7 Hz, 1H), 3.25 (s, 3H), 3.10-3.02 (m, 1H), 2.70-2.63 (m, 1H). PAM EC$_{50}$: ++.

Example 16.40

Synthesis of the HCl salt of Compound 133: 3-(5-((3-fluorophenyl)ethynyl)pyridin-2-yl)-5-((2R,4R)-4-methoxypyrrolidin-2-yl)-1,2,4-oxadiazole

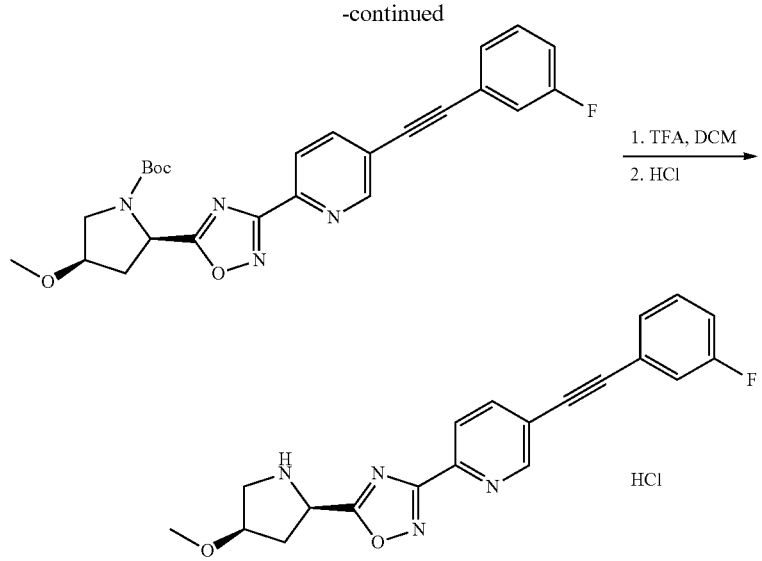

The title compound was prepared according to the experimental procedure described in Example 8.25 and Example 8.29b. MS (ESI): 365 (MH+); $^1$H NMR (300 MHz, CD$_3$OD) δ 8.91 (s, 1H), 8.28-8.19 (m, 2H), 7.49-7.43 (m, 2H), 7.39-7.36 (m, 1H), 7.26-7.20 (m, 1H), 5.40-5.35 (t, J=7.5 Hz, 1H), 4.36-4.33 (m, 1H), 3.74-3.70 (m, 1H), 3.56-3.50 (m, 1H), 3.34-3.33 (s, 3H), 2.85-2.81 (m, 2H). PAM EC$_{50}$: +++. Fold shift at 10 μM: ++.

Example 17.1

Synthesis of Compound 134: 5-(sec-butyl)-3-(5-(pyridin-2-ylethynyl)pyridin-2-yl)-1,2,4-oxadiazole

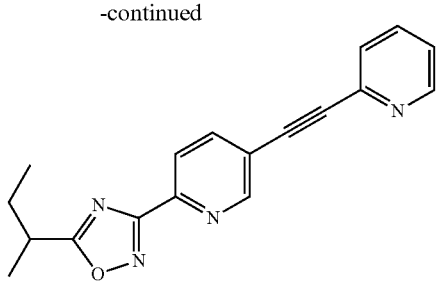

Example 17.1a

Synthesis of 5-(pyridin-2-ylethynyl)picolinonitrile

The title compound was prepared according to the experimental procedure described in Example 8.1a. MS (ESI): 206 (MH+).

Example 17.1b

Synthesis of N'-hydroxy-5-(pyridin-2-ylethynyl)picolinimidamide

The title compound was prepared according to the experimental procedure described in Example 8.1b. MS (ESI): 239 (MH+).

Example 17.1c

Synthesis of 5-(sec-butyl)-3-(5-(pyridin-2-ylethynyl)pyridin-2-yl)-1,2,4-oxadiazole The title compound was prepared according to the experimental procedure described in Example 8.25. MS (ESI): 305 (MH+); $^1$H NMR (300 MHz, CD$_3$OD) δ 8.93 (s, 1H), 8.63-8.61 (m, 1H), 8.23-8.22 (m, 2H), 7.97-7.91 (td, J=7.7, 1.7 Hz, 1H), 7.75 (d, J=7.8 Hz, 1H), 7.52-7.47 (m, 1H), 3.27-3.20 (m, 1H), 2.00-1.81 (m, 2H), 1.47 (d, J=7.0 Hz, 3H), 1.03-1.00 (t, J=7.4 Hz, 3H). PAM EC$_{50}$: +++. Fold shift at 10 μM: ++.

Example 17.2

Synthesis of Compound 135: 5-(1-methoxyethyl)-3-(5-(pyridin-2-ylethynyl)pyridin-2-yl)-1,2,4-oxadiazole

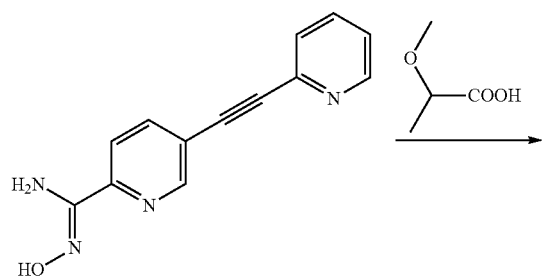

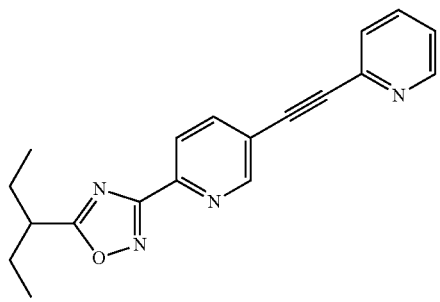

The title compound was prepared according to the experimental procedure described in Example 8.25. MS (ESI): 307 (MH+); $^1$H NMR (300 MHz, CDCl$_3$) δ 8.67 (s, 1H), 8.68-8.67 (dd, J=4.8, 0.6 Hz, 1H), 8.20-8.17 (m, 1H), 8.06-8.03 (m, 1H), 7.78-7.72 (m, 1H), 7.60 (d, J=7.8 Hz, 1H), 7.35-7.30 (m, 1H), 4.81-4.74 (m, 1H), 3.48 (s, 3H), 1.70 (d, J=6.6 Hz, 3H).

Example 17.3

Synthesis of Compound 136: 5-(pentan-3-yl)-3-(5-(pyridin-2-ylethynyl)pyridin-2-yl)-1,2,4-oxadiazole

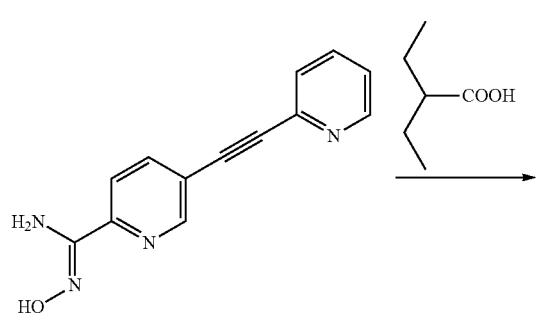

The title compound was prepared according to the experimental procedure described in Example 8.25. MS (ESI): 319 (MH+); $^1$H NMR (300 MHz, CD$_3$OD) δ 8.94-8.93 (m, 1H), 8.62 (d, J=4.3 Hz, 1H), 8.26-8.23 (m, 2H), 7.96-7.91 (td, J=8.7 Hz, 1.7 Hz, 1H), 7.75 (d, J=7.8 Hz 1H), 7.52-7.47 (m, 1H), 3.09-3.05 (t, J=7.2 Hz, 1H), 1.95-1.85 (m, 4H), 0.98-0.85 (t, J=7.5 Hz, 6H). PAM EC$_{50}$: ++++. Fold shift at 10 μM: ++.

Example 17.4

Synthesis of Compound 137: 5-cyclopentyl-3-(5-(pyridin-2-ylethynyl)pyridin-2-yl)-1,2,4-oxadiazole

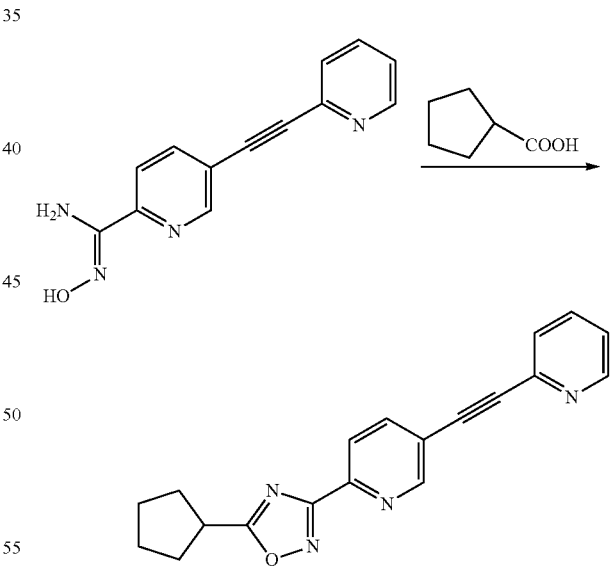

The title compound was prepared according to the experimental procedure described in Example 8.25. MS (ESI): 317 (MH+); $^1$H NMR (300 MHz, CD$_3$OD) δ 8.93 (s, 1H), 8.62 (d, J=4.2 Hz, 1H), 8.22 (s, 2H), 7.96-7.91 (t, J=7.6 Hz, 1H), 7.75 (d, J=7.8 Hz, 1H), 7.52-7.47 (m, 1H), 3.56-3.51 (m, 1H), 2.27-2.19 (m, 2H), 2.08-2.01 (m, 2H), 1.92-1.78 (m, 4H). PAM EC$_{50}$: +++. Fold shift at 10 μM: ++.

Example 17.5

Synthesis of Compound 138: 5-(1-methoxypropyl)-3-(5-(pyridin-2-ylethynyl)pyridin-2-yl)-1,2,4-oxadiazole

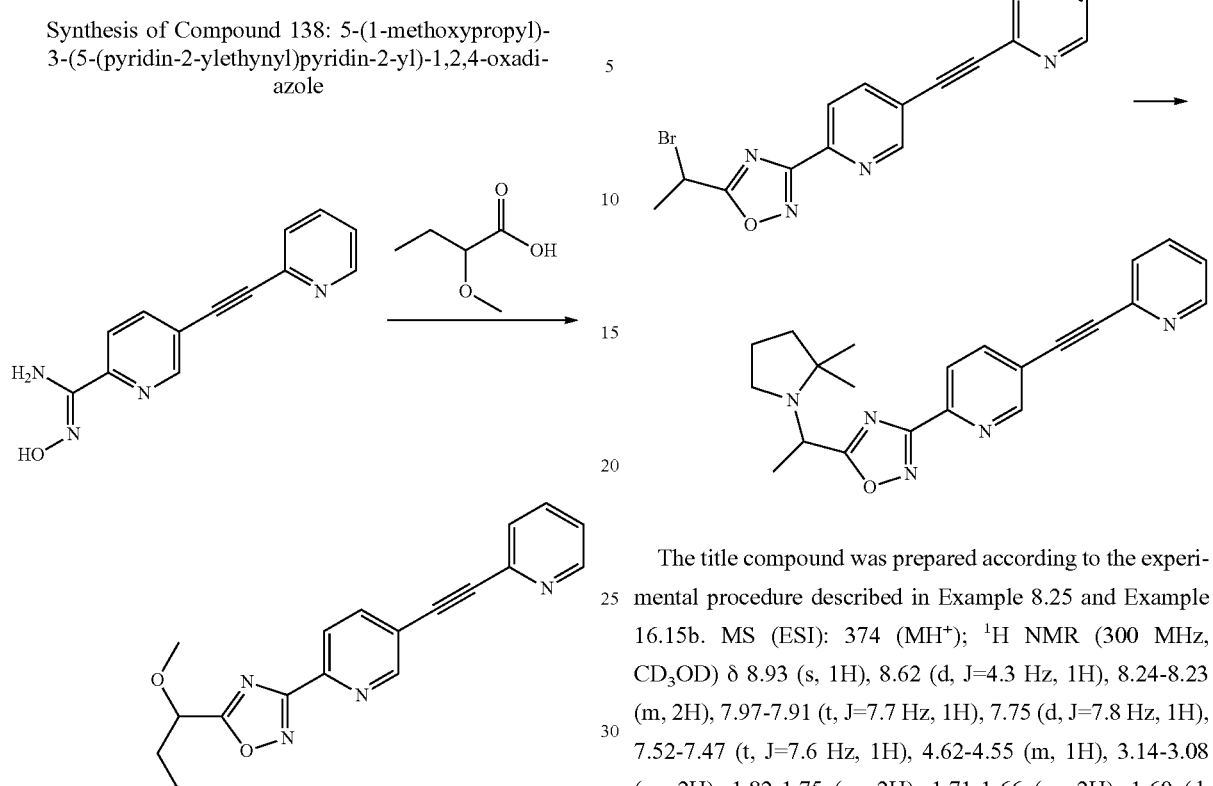

The title compound was prepared according to the experimental procedure described in Example 8.25. MS (ESI): 321 (MH⁺); $^1$H NMR (300 MHz, DMSO-d6) δ 8.99 (d, J=1.3 Hz, 1H), 8.65 (d, J=4.3 Hz, 1H), 8.28-8.25 (m, 1H), 8.19-8.16 (m, 1H), 7.94-7.88 (td, J=8.7 Hz, 1.7 Hz, 1H), 7.74 (d, J=8.1 Hz, 1H), 7.50-7.46 (m, 1H), 4.74-4.70 (t, J=6.4 Hz, 1H), 3.38 (s, 3H), 1.96-1.89 (m, 2H), 0.96-0.91 (t, J=7.4 Hz, 3H). PAM EC$_{50}$: ++.

Example 17.6

Synthesis of Compound 139: 5-(1-(2,2-dimethylpyrrolidin-1-yl)ethyl)-3-(5-(pyridin-2-ylethynyl)pyridin-2-yl)-1,2,4-oxadiazole The title compound was prepared according to the experimental procedure described in Example 8.25 and Example 16.15b. MS (ESI): 374 (MH⁺); $^1$H NMR (300 MHz, CD$_3$OD) δ 8.93 (s, 1H), 8.62 (d, J=4.3 Hz, 1H), 8.24-8.23 (m, 2H), 7.97-7.91 (t, J=7.7 Hz, 1H), 7.75 (d, J=7.8 Hz, 1H), 7.52-7.47 (t, J=7.6 Hz, 1H), 4.62-4.55 (m, 1H), 3.14-3.08 (m, 2H), 1.82-1.75 (m, 2H), 1.71-1.66 (m, 2H), 1.60 (d, J=7.0 Hz, 3H), 1.20 (s, 3H), 0.93 (s, 3H). PAM EC$_{50}$: +++. Fold shift at 10 μM: +++.

Example 17.7

Synthesis of Compound 140: N-(1-(3-(5-(pyridin-2-ylethynyl)pyridin-2-yl)-1,2,4-oxadiazol-5-yl)ethyl)propan-2-amine

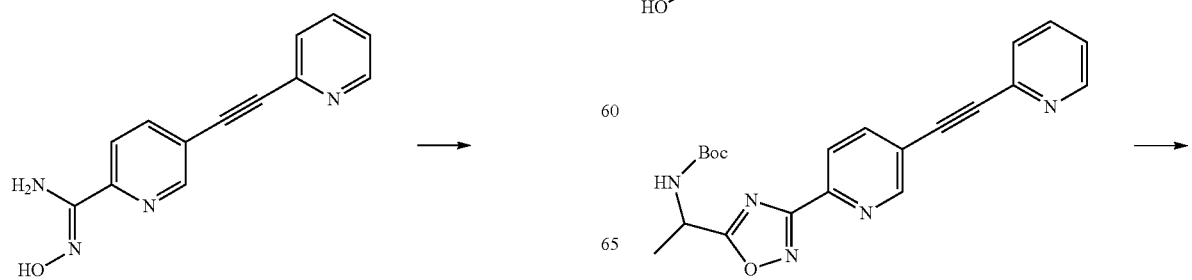

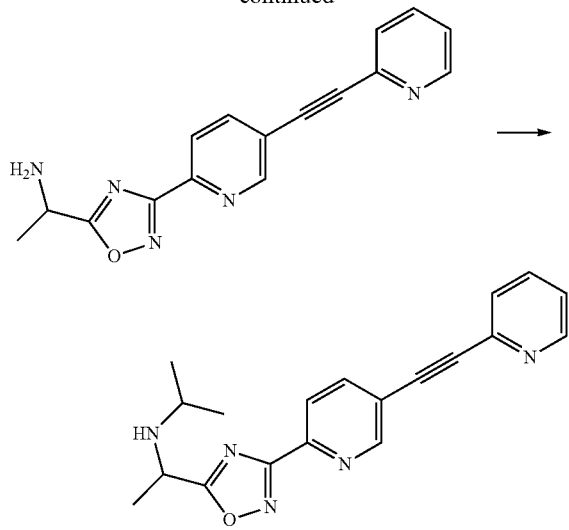

The title compound was prepared according to the experimental procedure described in Example 8.25, Example 8.29b and Example 16.8. MS (ESI): 334 (MH$^+$); $^1$H NMR (300 MHz, CD$_3$OD) δ 8.94 (s, 1H), 8.62 (d, J=4.7 Hz, 1H), 8.27-8.23 (m, 2H), 7.96-7.90 (t, J=7.7 Hz, 1H), 7.75 (d, J=7.8 Hz, 1H), 7.51-7.47 (t, J=7.6 Hz, 1H), 4.52-4.36 (m, 1H), 2.87-2.79 (m, 1H), 1.59 (d, J=6.9 Hz, 3H), 1.13-1.08 (m, 6H). PAM EC$_{50}$: ++.

Example 17.8

Synthesis of Compound 141: 2-methyl-N-(1-(3-(5-(pyridin-2-ylethynyl)pyridin-2-yl)-1,2,4-oxadiazol-5-yl)ethyl)propan-2-amine The title compound was prepared according to the experimental procedure described in Example 8.33b. MS (ESI): 348 (MH$^+$); $^1$H NMR (300 MHz, CD$_3$OD) δ 8.94 (s, 1H), 8.62 (d, J=4.3 Hz, 1H), 8.27-8.23 (m, 2H), 7.97-7.91 (t, J=7.7 Hz, 1H), 7.75 (d, J=7.8 Hz, 1H), 7.52-7.47 (t, J=7.6 Hz, 1H), 4.49-4.42 (m, 1H), 1.56 (d, J=6.9 Hz, 3H), 1.10 (s, 9H).

Example 17.9

Synthesis of Compound 142: 3-(5-(pyridin-2-ylethynyl)pyridin-2-yl)-5-(1-(pyrrolidin-1-yl)ethyl)-1,2,4-oxadiazole

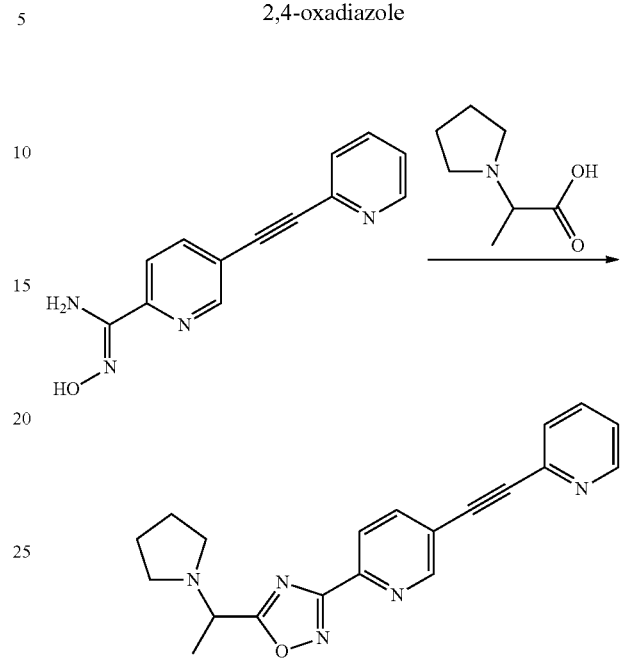

The title compound was prepared according to the experimental procedure Example 8.25. MS (ESI): 348 (MH$^+$); $^1$H NMR (300 MHz, CD$_3$OD) δ 8.93 (d, J=1.5 Hz, 1H), 8.61 (d, J=4.5 Hz, 1H), 8.27-8.23 (m, 2H), 7.96-7.90 (td, J=7.7, 1.7 Hz, 1H), 7.75 (d, J=7.8 Hz, 1H), 7.51-7.47 (m, 1H), 4.27-4.20 (m, 1H), 2.80-2.68 (m, 4H), 1.85-1.81 (m, 4H), 1.65 (d, J=6.9 Hz, 3H). PAM EC$_{50}$: +++. Fold shift at 10 μM: +++.

Example 17.10

Synthesis of Compound 143: N,N-dimethyl-1-(3-(5-(pyridin-2-ylethynyl)pyridin-2-yl)-1,2,4-oxadiazol-5-yl)ethanamine

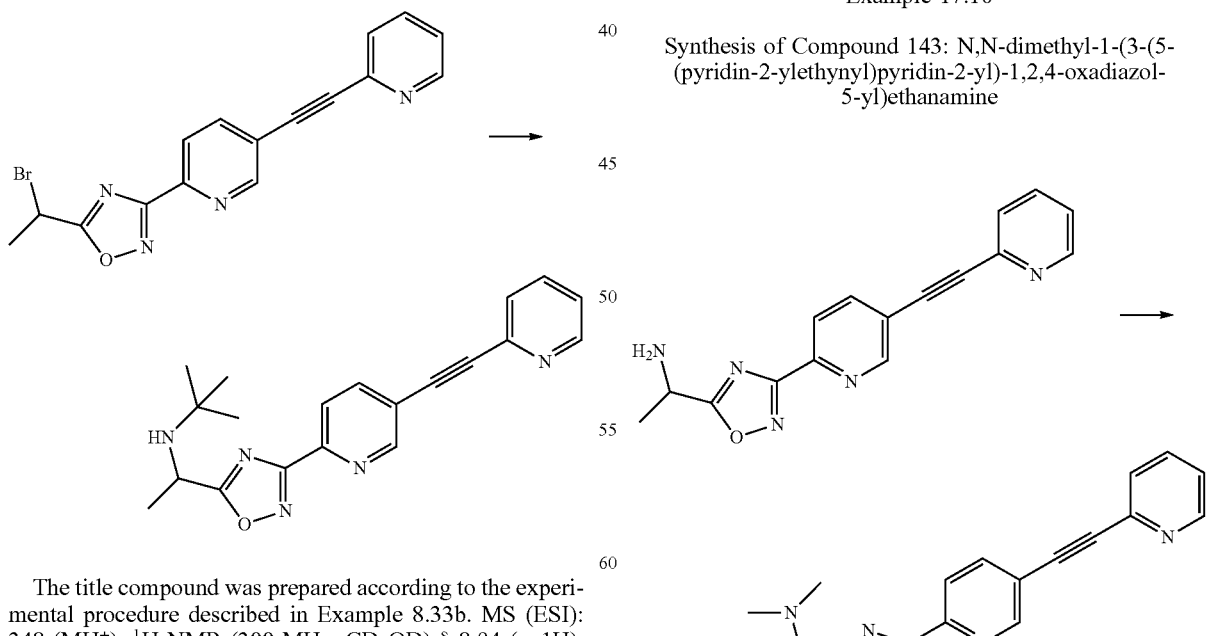

The title compound was prepared according to the experimental procedure described in Example 16.8. MS (ESI): 320 (MH+); 1H NMR (300 MHz, CD3OD) δ 8.94 (d, J=1.8 Hz, 1H), 8.62 (d, J=4.8 Hz, 1H), 8.26-8.24 (m, 2H), 7.94-7.91 (m, 1H), 7.75 (d, J=7.8 Hz, 1H), 7.52-7.47 (m, 1H), 4.29-4.26 (m, 1H), 2.38 (s, 6H), 1.61 (d, J=7.2 Hz, 3H). PAM EC50: ++. Fold shift at 10 μM: +++.

Example 17.11

Synthesis of Compound 144: N-methyl-2-(3-(5-(pyridin-2-ylethynyl)pyridin-2-yl)-1,2,4-oxadiazol-5-yl)propan-2-amine

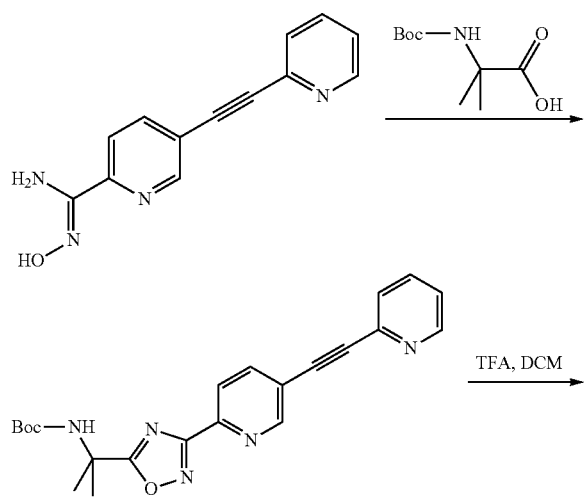

Example 17.11a

Synthesis of tert-butyl 2-(3-(5-(pyridin-2-ylethynyl) pyridin-2-yl)-1,2,4-oxadiazol-5-yl)propan-2-ylcarbamate The title compound was prepared according to the experimental procedure described in Example 8.25. MS (ESI): 406 (MH+).

Example 17.11b

Synthesis of 2-(3-(5-(pyridin-2-ylethynyl)pyridin-2-yl)-1,2,4-oxadiazol-5-yl)propan-2-amine The title compound was prepared according to the experimental procedure described in Example 8.29b. MS (ESI): 306 (MH+).

Example 17.11c

Synthesis of N-methyl-2-(3-(5-(pyridin-2-ylethynyl) pyridin-2-yl)-1,2,4-oxadiazol-5-yl)propan-2-amine A solution of 2-(3-(5-(pyridin-2-ylethynyl)pyridin-2-yl)-1,2,4-oxadiazol-5-yl)propan-2-amine (110 mg, 0.36), catalytic CH3COOH, and NaCNBH3 (0.5 g, 10 mmol) in methanol was stirred at room temperature. The aqueous formaldehyde solution was added in dropwise. The reaction was monitored by TLC during addition of formaldehyde. Then the suspension was diluted with water (30 mL) and extracted with EtOAc (3×30 mL). The combined organic layers were concentrated and 2.5 mg of the desired product was obtained by column chromatography purification. MS (ESI): 320 (MH+); 1H NMR (300 MHz, CD3OD) δ 8.94-8.93 (dd, J=1.7, 0.9 Hz, 1H), 8.62 (d, J=4.9 Hz, 1H), 8.28-8.24 (m, 2H), 7.96-7.91 (td, J=7.7, 1.7 Hz, 1H), 7.75 (d, J=7.8 Hz, 1H), 7.52-7.47 (m, 1H), 2.30 (s, 3H), 1.65 (s, 6H). PAM EC50: +.

Example 17.12

Synthesis of Compound 145: N,N-dimethyl-2-(3-(5-(pyridin-2-ylethynyl)pyridin-2-yl)-1,2,4-oxadiazol-5-yl)propan-2-amine

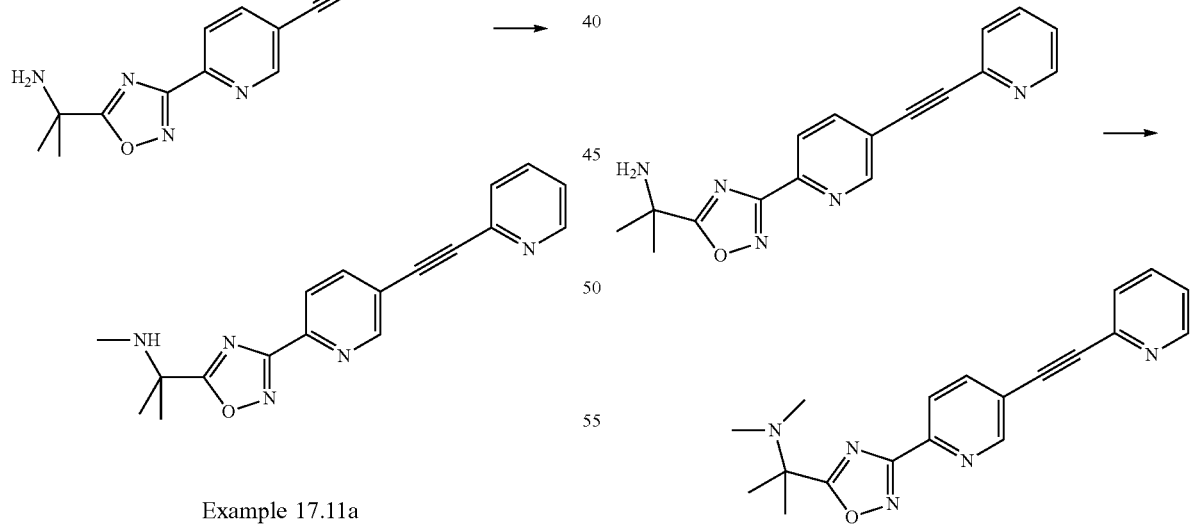

The title compound was prepared according to the experimental procedure described in Example 16.8. MS (ESI): 334 (MH+); 1H NMR (300 MHz, CD3OD) δ 8.94 (s, 1H), 8.62 (d, J=4.5 Hz, 1H), 8.28-8.21 (m, 2H), 7.96-7.90 (td, J=7.7, 1.7 Hz, 1H), 7.75 (d, J=7.8 Hz, 1H), 7.51-7.47 (m, 1H), 2.35 (s, 6H), 1.69 (s, 6H). PAM EC50: +++. Fold shift at 10 μM: +++.

Example 17.13

Synthesis of Compound 146: ethyl (1-(3-(5-(pyridin-2-ylethynyl)pyridin-2-yl)-1,2,4-oxadiazol-5-yl)propyl)carbamate

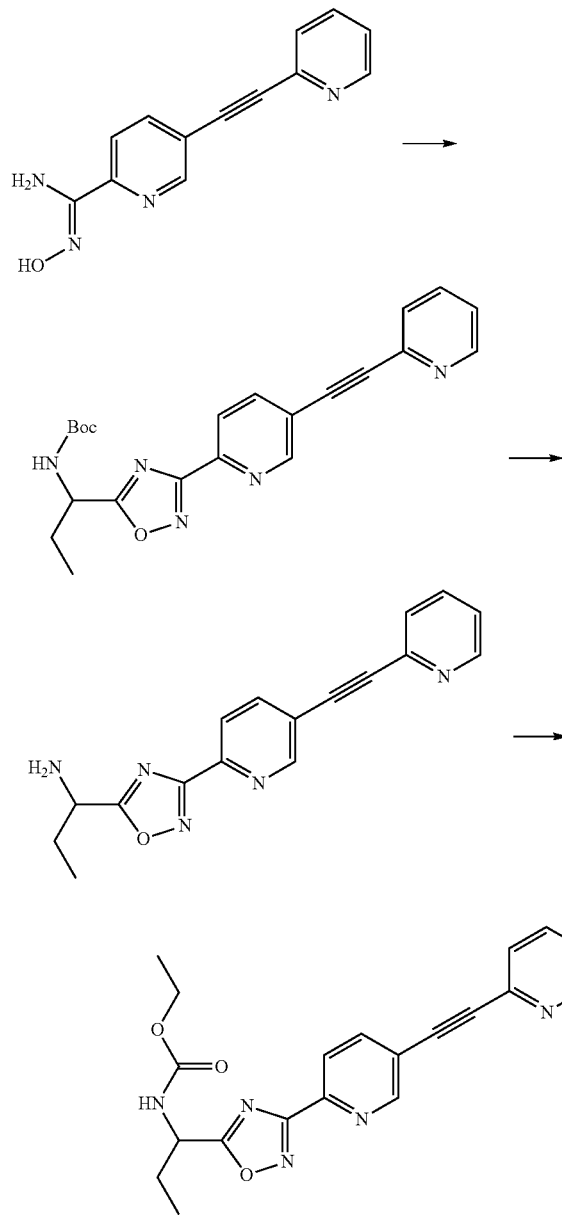

Example 17.13a

Synthesis of tert-butyl 1-(3-(5-(pyridin-2-ylethynyl)pyridin-2-yl)-1,2,4-oxadiazol-5-yl)propylcarbamate The title compound was prepared according to the experimental procedure described in Example 8.25. MS (ESI): 406 (MH$^+$).

Example 17.13b

Synthesis of 1-(3-(5-(pyridin-2-ylethynyl)pyridin-2-yl)-1,2,4-oxadiazol-5-yl)propan-1-amine The title compound was prepared according to the experimental procedure described in Example 8.29b. MS (ESI): 306 (MH$^+$).

Example 17.13c

Synthesis of ethyl 1-(3-(5-(pyridin-2-ylethynyl)pyridin-2-yl)-1,2,4-oxadiazol-5-yl)propylcarbamate To a solution of 1-(3-(5-(pyridin-2-ylethynyl)pyridin-2-yl)-1,2,4-oxadiazol-5-yl)propan-1-amine (120 mg, 0.393 mmol) and Et$_3$N (1 mL) in DCM (5 mL) was added ethyl chloroformate (150 mg, 1.4 mmol) dropwise at 0° C. After stirring for 3 h, the reaction mixture was diluted with water (30 mL) and extracted with EtOAc (3×50 mL). The solution was concentrated and purified by column chromatography to give 7.5 mg of the desired product. MS (ESI): 378 (MH$^+$); $^1$H NMR (300 MHz, CDCl$_3$) δ 9.01 (s, 1H), 8.68 (d, J=4.0 Hz, 1H), 8.17 (d, J=8.1 Hz, 1H), 8.04 (d, J=8.1 Hz, 1H), 7.79-7.73 (t, J=7.7 Hz, 1H), 7.61 (d, J=7.8 Hz, 1H), 7.35-7.31 (m, 1H), 5.42-5.40 (m, 1H), 5.19-5.17 (m, 1H), 4.20-4.13 (m, 2H), 2.13-1.94 (m, 1H), 1.30-1.25 (m, 3H), 1.06-1.01 (t, J=7.4 Hz, 3H). PAM EC$_{50}$: ++.

Example 17.14

Synthesis of Compound 147: N-methyl-1-(3-(5-(pyridin-2-ylethynyl)pyridin-2-yl)-1,2,4-oxadiazol-5-yl)propan-1-amine

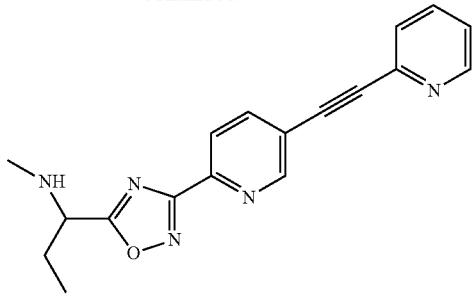

Example 17.14a

Synthesis of 5-(1-bromopropyl)-3-(5-(pyridin-2-ylethynyl)pyridin-2-yl)-1,2,4-oxadiazole The title compound was prepared according to the experimental procedure described in Example 8.25. MS (ESI): 369, 371 (MH$^+$).

Example 17.14b

Synthesis of N-methyl-1-(3-(5-(pyridin-2-ylethynyl)pyridin-2-yl)-1,2,4-oxadiazol-5-yl)propan-1-amine The title compound was prepared according to the experimental procedure described in Example 8.33b. MS (ESI): 320 (MH$^+$); $^1$H NMR (300 MHz, CD$_3$OD) δ 8.95 (s, 1H), 8.62 (d, J=4.7 Hz, 1H), 8.29-8.22 (m, 2H), 7.94-7.91 (td, J=7.8, 1.6 Hz, 1H), 7.75 (d, J=7.6 Hz, 1H), 7.52-7.48 (dd, J=7.6, 4.9 Hz, 1H), 4.05-4.00 (m, 1H), 2.40 (s 3H), 2.23-2.18 (m, 2H), 1.01-0.96 (t, J=7.4 Hz, 3H).

Example 17.15

Synthesis of Compound 148: N,N-dimethyl-1-(3-(5-(pyridin-2-ylethynyl)pyridin-2-yl)-1,2,4-oxadiazol-5-yl)propan-1-amine

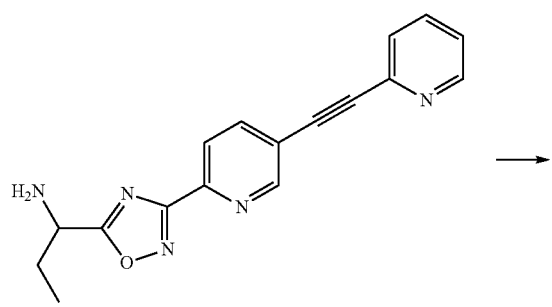

The title compound was prepared according to the experimental procedure described in Example 16.8. MS (ESI): 334 (MH$^+$); $^1$H NMR (300 MHz, CD$_3$OD) δ 9.01 (s, 1H), 8.67 (d, J=4.8 Hz, 1H), 8.19 (d, J=8.1 Hz, 1H), 8.06-8.03 (dd, J=8.1, 2.0 Hz, 1H), 7.78-7.53 (m, 1H), 7.50-7.45 (m, 1H), 7.35-7.30 (m, 1H), 3.96-3.91 (m, 1H), 2.36 (s, 6H), 2.12-1.98 (m, 2H), 1.01-0.96 (t, J=7.4 Hz, 3H). PAM EC$_{50}$: +++. Fold shift at 10 μM: +++.

Example 17.16

Synthesis of Compound 149: N-(1-(3-(5-(pyridin-2-ylethynyl)pyridin-2-yl)-1,2,4-oxadiazol-5-yl)propyl)cyclopropanamine

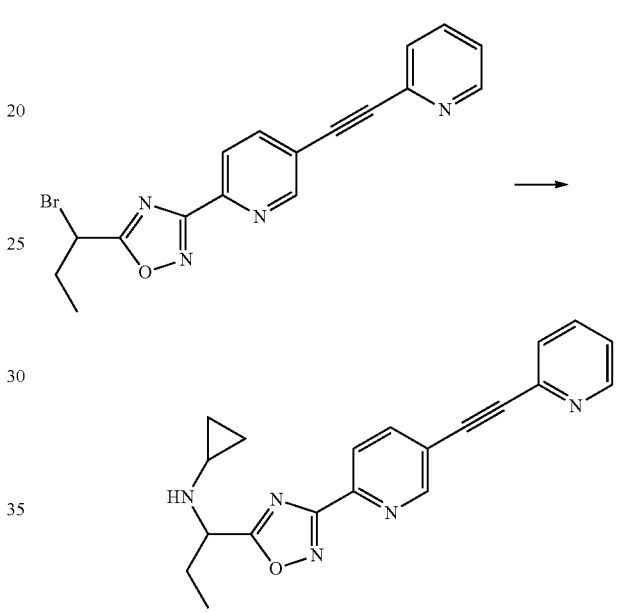

The title compound was prepared according to the experimental procedure described in Example 8.33b. MS (ESI): 346 (MH$^+$); $^1$H NMR (300 MHz, CD$_3$OD) δ 8.95 (s, 1H), 8.62 (d, J=5.5 Hz, 1H), 8.26-8.24 (m, 2H), 7.94-7.91 (m, 1H), 7.75 (d, J=7.8 Hz, 1H), 7.51-7.48 (m, 1H), 4.59 (s 1H), 2.17-2.11 (m, 1H), 2.02-1.92 (m, 2H), 1.27-1.22 (t, J=7.1 Hz, 4H), 0.46-0.39 (m, 3H). PAM EC$_{50}$: +.

Example 17.17

Synthesis of Compound 150: 5-(1-methylazetidin-2-yl)-3-(5-(pyridin-2-ylethynyl)pyridin-2-yl)-1,2,4-oxadiazole

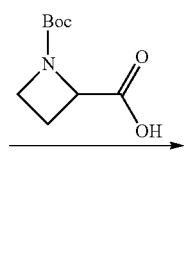

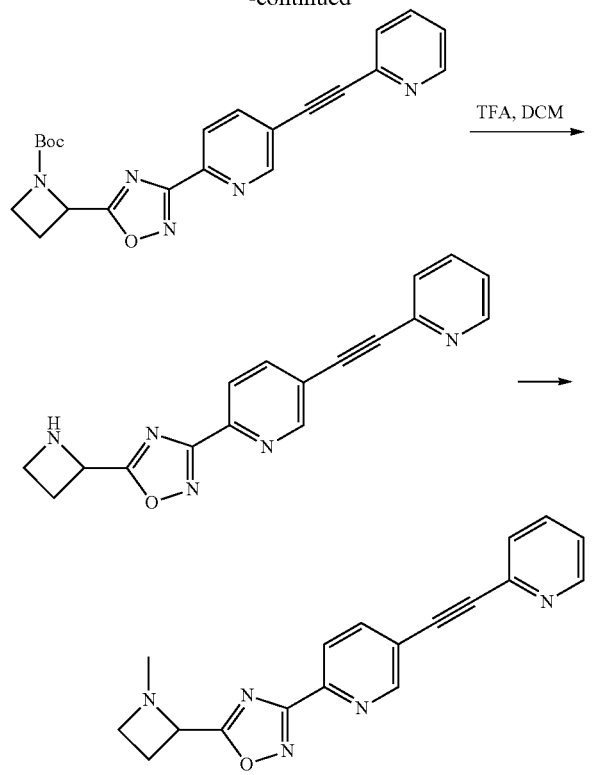

Example 17.17a

Synthesis of tert-butyl 2-(3-(5-(pyridin-2-ylethynyl)pyridin-2-yl)-1,2,4-oxadiazol-5-yl)azetidine-1-carboxylate The title compound was prepared according to the experimental procedure described in Example 8.25. MS (ESI): 404 (MH$^+$).

Example 17.17b

Synthesis of 5-(azetidin-2-yl)-3-(5-(pyridin-2-ylethynyl)pyridin-2-yl)-1,2,4-oxadiazole The title compound was prepared according to the experimental procedure described in Example 8.29b. MS (ESI): 304 (MH$^+$).

Example 17.17c

Synthesis of 5-(1-methylazetidin-2-yl)-3-(5-(pyridin-2-ylethynyl)pyridin-2-yl)-1,2,4-oxadiazole The title compound was prepared according to the experimental procedure described in Example 16.8. MS (ESI): 318 (MH$^+$); $^1$H NMR (300 MHz, CDCl$_3$) δ 9.00 (s, 1H), 8.68 (d, J=4.4 Hz, 1H), 8.20 (d, J=8.0 Hz, 1H), 8.06-8.03 (dd, J=8.1, 2.0 Hz, 1H), 7.78-7.72 (t, J=7.7 Hz, 1H), 7.60 (d, J=7.8 Hz, 1H), 7.35-7.31 (t, J=4.9 Hz, 1H), 4.41-4.36 (t, J=8.1 Hz, 1H), 3.62-3.59 (m, 1H), 3.13-3.08 (m, 1H), 2.75-2.68 (m, 1H), 2.47-2.45 (m, 4H). PAM EC$_{50}$: +.

Example 17.18

Synthesis of Compound 151: 3-(5-(pyridin-2-ylethynyl)pyridin-2-yl)-5-(pyrrolidin-2-yl)-1,2,4-oxadiazole

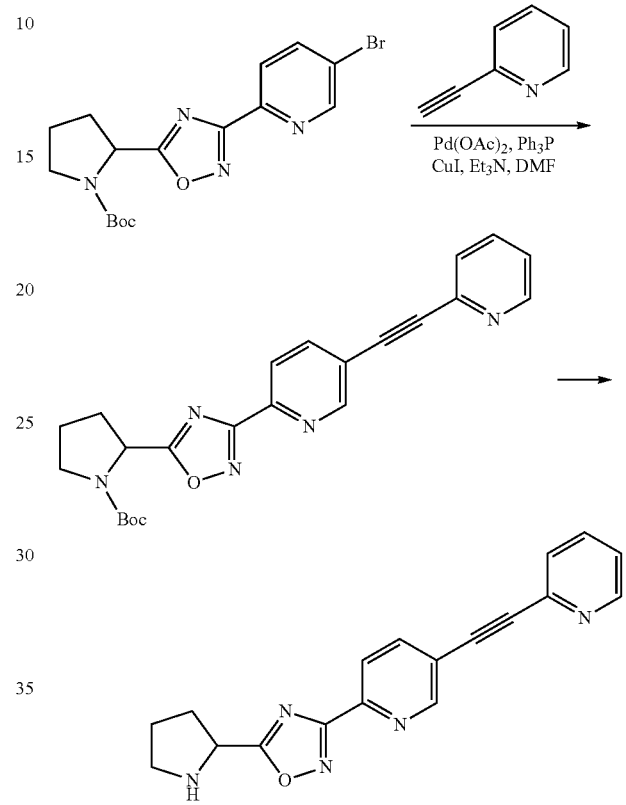

Example 17.18a

Synthesis of tert-butyl 2-(3-(5-(pyridin-2-ylethynyl)pyridin-2-yl)-1,2,4-oxadiazol-5-yl)pyrrolidine-1-carboxylate The title compound was prepared according to the experimental described in Example 8.1a. MS (ESI): 418 (MH$^+$).

Example 17.18b

Synthesis of 3-(5-(pyridin-2-ylethynyl)pyridin-2-yl)-5-(pyrrolidin-2-yl)-1,2,4-oxadiazole The title compound was prepared according to the experimental procedure described in Example 8.29b. MS (ESI): 318 (MH$^+$); $^1$H NMR (300 MHz, CD$_3$OD) δ 9.07 (d, J=1.8 Hz, 1H), 8.91-8.88 (dd, J=5.7, 0.9 Hz, 1H), 8.61-8.55 (td, J=8.0, 1.6 Hz, 1H), 8.42-8.34 (m, 2H), 8.26 (d, J=8.0 Hz, 1H), 8.06-8.01 (m, 1H), 5.32-5.26 (t, J=7.7 Hz, 1H), 3.66-3.56 (m, 2H), 2.88-2.67 (m, 1H), 2.60-2.45 (m, 1H), 2.41-2.23 (m, 2H). PAM EC$_{50}$: +. Fold shift at 10 μM: +.

209

Example 17.19

Synthesis of Compound 152: 5-(5,5-dimethylpyrrolidin-2-yl)-3-(5-(pyridin-2-ylethynyl)pyridin-2-yl)-1,2,4-oxadiazole

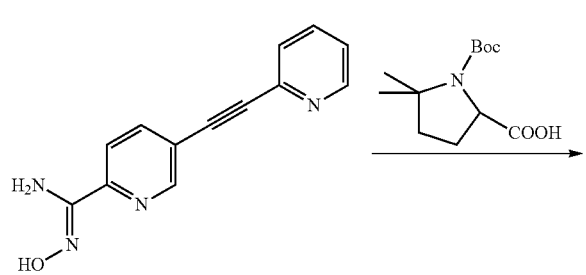

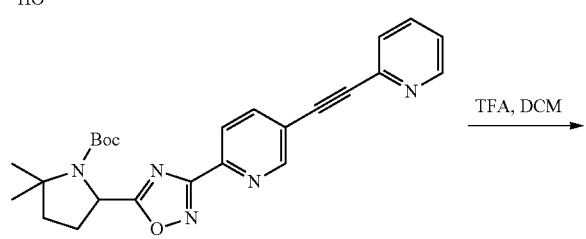

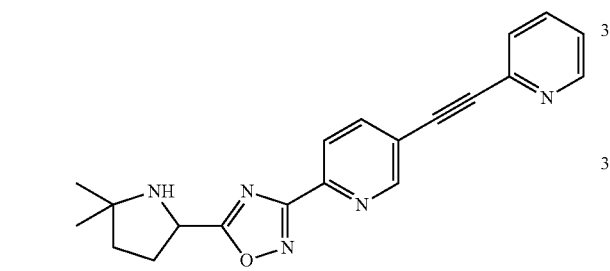

Example 17.19a

Synthesis of tert-butyl 2,2-dimethyl-5-(3-(5-(pyridin-2-ylethynyl)pyridin-2-yl)-1,2,4-oxadiazol-5-yl)pyrrolidine-1-carboxylate The title compound was prepared according to the experimental procedure described in Example 8.25. MS (ESI): 446 (MH+).

Example 17.19b

Synthesis of 5-(5,5-dimethylpyrrolidin-2-yl)-3-(5-(pyridin-2-ylethynyl)pyridin-2-yl)-1,2,4-oxadiazole The title compound was prepared according to the experimental procedure described in Example 8.29b. MS (ESI): 346 (MH+); $^1$H NMR (300 MHz, CD$_3$OD) δ 8.93 (s, 1H), 8.62 (d, J=3.8 Hz, 1H), 8.24 (s, 2H), 7.96-7.91 (m 1H), 7.77-7.74 (d, J=8.1 Hz, 1H), 7.52-7.47 (m, 1H), 4.87-4.70 (m, 1H), 2.54-2.34 (m, 2H), 1.90-1.75 (m, 2H), 1.29 (d, J=3.1 Hz, 6H).

210

Example 17.20

Synthesis of Compound 153: 3-(5-(pyridin-2-ylethynyl)pyridin-2-yl)-5-(1,5,5-trimethylpyrrolidin-2-yl)-1,2,4-oxadiazole

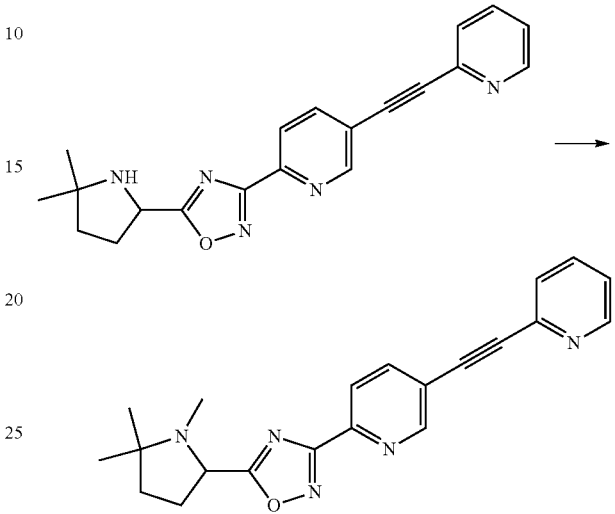

The title compound was prepared according to the experimental procedure described in Example 16.8. MS (ESI): 360 (MH+); $^1$H NMR (300 MHz, CDCl$_3$) δ 9.00 (s, 1H), 8.68 (d, J=4.2 Hz, 1H), 8.18 (d, J=8.1 Hz, 1H), 8.05-8.02 (dd, J=8.1, 1.8 Hz, 1H), 7.78-7.73 (m, 1H), 7.60 (d, J=7.7 Hz, 1H), 7.34-7.28 (m, 1H), 4.11-4.07 (m, 1H), 2.31 (s, 3H), 2.27-2.14 (m, 2H), 2.04-1.94 (m, 1H), 1.81-1.74 (m, 1H), 1.25 (s, 3H), 1.01 (s, 3H). PAM EC$_{50}$: +++.

Example 17.21

Synthesis of Compound 154: (R)-5-(4,4-difluoro-1-methylpyrrolidin-2-yl)-3-(5-(pyridin-2-ylethynyl)pyridin-2-yl)-1,2,4-oxadiazole

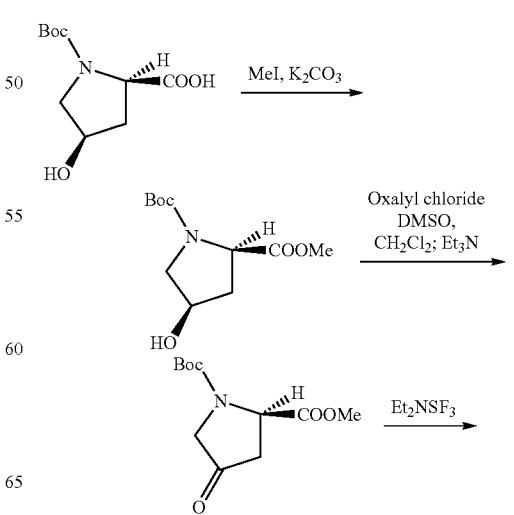

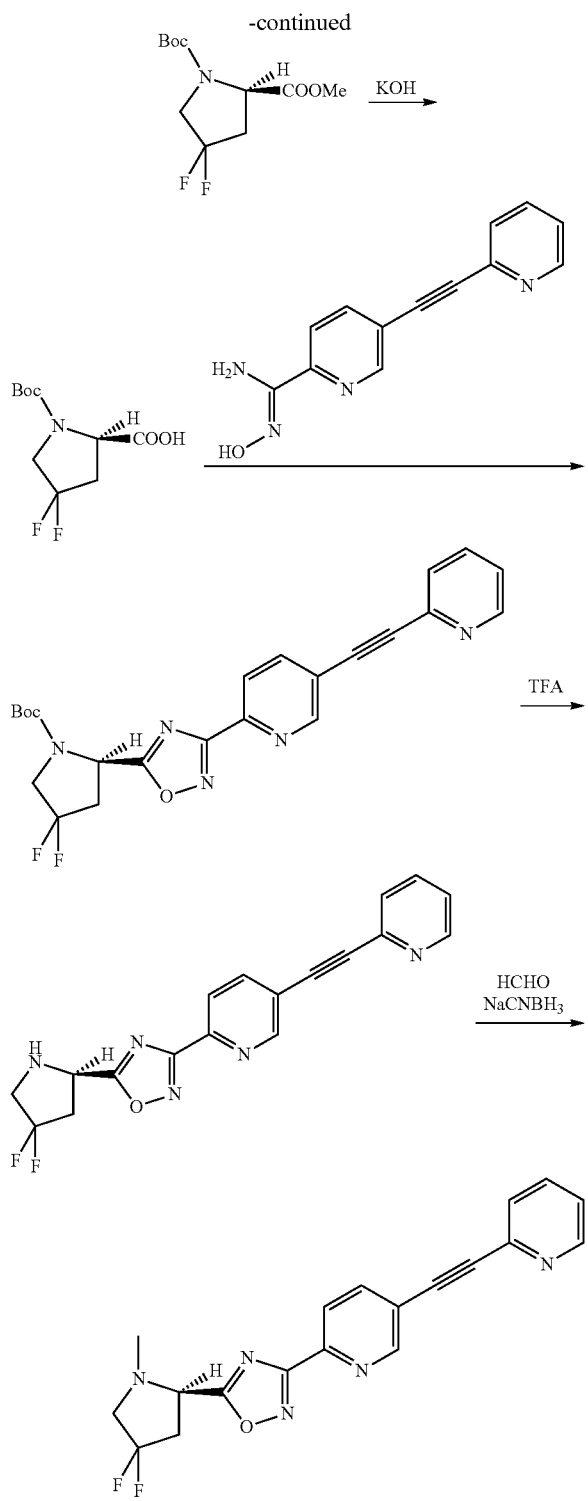

Example 17.21a

Synthesis of (2R,4R)-1-tert-butyl-2-methyl-4-hydroxypyrrolidine-1,2-dicarboxylate A solution of (2R,4R)-1-(tert-butoxycarbonyl)-4-hydroxypyrrolidine-2-carboxylic acid (10.0 g, 43.3 mmol), methyl iodide (9.2 g, 65.0 mmol), and potassium carbonate (12.0 g, 86.6 mmol) in DMF (120 mL) was stirred at room temperature overnight. The mixture was then diluted with H$_2$O (500 mL) and extracted with EtOAc (4×500 mL), the combined organic layers were washed with brine and dried over Na$_2$SO$_4$. After filtration, the solution was concentrated to give the desired product, which was directly used for the next step without further purification. MS (ESI): 246 (MH$^+$).

Example 17.21b

Synthesis of (R)-1-tert-butyl 2-methyl 4-oxopyrrolidine-1,2-dicarboxylate

A stirred solution of oxalyl chloride (1.9 g, 15.0 mmol) in dichloromethane (20 mL) under N$_2$ at −78° C. was treated with DMSO (13.3 mL, 18.8 mmol) in dichloromethane (20 mL) dropwise over 15 min. The mixture was stirred at −78° C. for 20 min, then (2R,4R)-1-tert-butyl-2-methyl 4-hydroxypyrrolidine-1,2-dicarboxylate (3.0 g, 12.5 mmol) dissolved in dichloromethane (15 mL) was added over 20 min. The reaction mixture was stirred at −60° C. for 40 min, then triethylamine (5 mL, 35.0 mmol) diluted with dichloromethane (10 mL) was added dropwise over 10 min. The mixture was gradually warmed to room temperature over 30 min. Then the reaction was quenched with aqueous ammonium chloride and extracted with dichloromethane (3×200 mL). The combined organic layers were washed with brine, dried over Na$_2$SO$_4$, concentrated and purified by column chromatography to give 2.1 g of the desired product. MS (ESI): 244 (MH$^+$).

Example 17.21c

Synthesis of (R)-1-tert-butyl 2-methyl 4,4-difluoropyrrolidine-1,2-dicarboxylate To a solution of (R)-1-tert-butyl 2-methyl 4-oxopyrrolidine-1,2-dicarboxylate (1.0 g, 4.1 mmol) in dichloromethane (20 mL) was added diethylaminosulfur trifluoride (2.0 g, 12.3 mmol) at −78° C. over 20 min. The reaction mixture was stirred at −78° C. for 1 h and warmed to room temperature for 1 h. Then the reaction was quenched with aqueous sodium carbonate and extracted with dichloromethane (3×100 mL). The combined organic layers were washed with brine, dried over Na$_2$SO$_4$, concentrated, and purified by column chromatography to give 780 mg of the desired product. MS (ESI): 266 (MH$^+$).

Example 17.21d

Synthesis of (R)-1-(tert-butoxycarbonyl)-4,4-difluoropyrrolidine-2-carboxylic acid To a solution of (R)-1-tert-butyl 2-methyl 4,4-difluoropyrrolidine-1,2-dicarboxylate (0.9 g, 3.4 mmol) in methanol (20 mL) was added potassium hydroxide (0.29 g, 5.1 mmol) dissolved in water (20 mL). The reaction mixture was stirred at room temperature for 1 h. After removing the methanol, the solution was adjusted to pH 3 with diluted HCl and extracted with dichloromethane (4×50 mL). The organic phase was washed with brine, dried over Na$_2$SO$_4$, and concentrated to give the desired product. MS (ESI): 252 (MH$^+$).

Example 17.21e

Synthesis of (R)-tert-butyl 4,4-difluoro-2-(3-(5-(pyridin-2-ylethynyl)pyridin-2-yl)-1,2,4-oxadiazol-5-yl)pyrrolidine-1-carboxylate The title compound was prepared according to the experimental procedure described in Example 8.25. MS (ESI): 454 (MH+).

Example 17.21f

Synthesis of (R)-tert-butyl 4,4-difluoro-2-(3-(5-(pyridin-2-ylethynyl)pyridin-2-yl)-1,2,4-oxadiazol-5-yl)pyrrolidine-1-carboxylate The title compound was prepared according to the experimental procedure described in Example 8.29b. MS (ESI): 354 (MH+).

Example 17.21g

Synthesis of (R)-5-(4,4-difluoro-1-methylpyrrolidin-2-yl)-3-(5-(pyridin-2-ylethynyl)pyridin-2-yl)-1,2,4-oxadiazole The title compound was prepared according to the experimental procedure described in Example 16.8. MS (ESI): 368 (MH+); $^1$H NMR (300 MHz, CDCl$_3$) δ 9.00 (s, 1H), 8.68 (d, J=4.3 Hz, 1H), 8.20-8.17 (m, 1H), 8.07-8.04 (m, 1H), 7.76-7.73 (m, 1H), 7.62-7.59 (m, 1H), 7.35-7.31 (m, 1H), 4.20-4.14 (t, J=8.1 Hz, 1H), 2.96-2.78 (m, 4H), 2.48 (s, 3H). mGluR5 PAM EC$_{50}$: +. Fold shift at 10 μM: ++.

Example 17.22

Synthesis of Compound 155: (S)-5-(4,4-difluoro-1-methylpyrrolidin-2-yl)-3-(5-(pyridin-2-ylethynyl)pyridin-2-yl)-1,2,4-oxadiazole

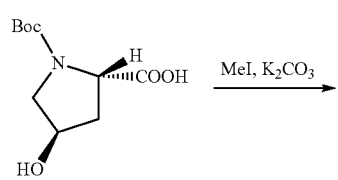
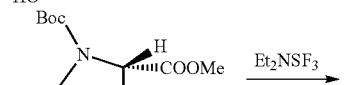
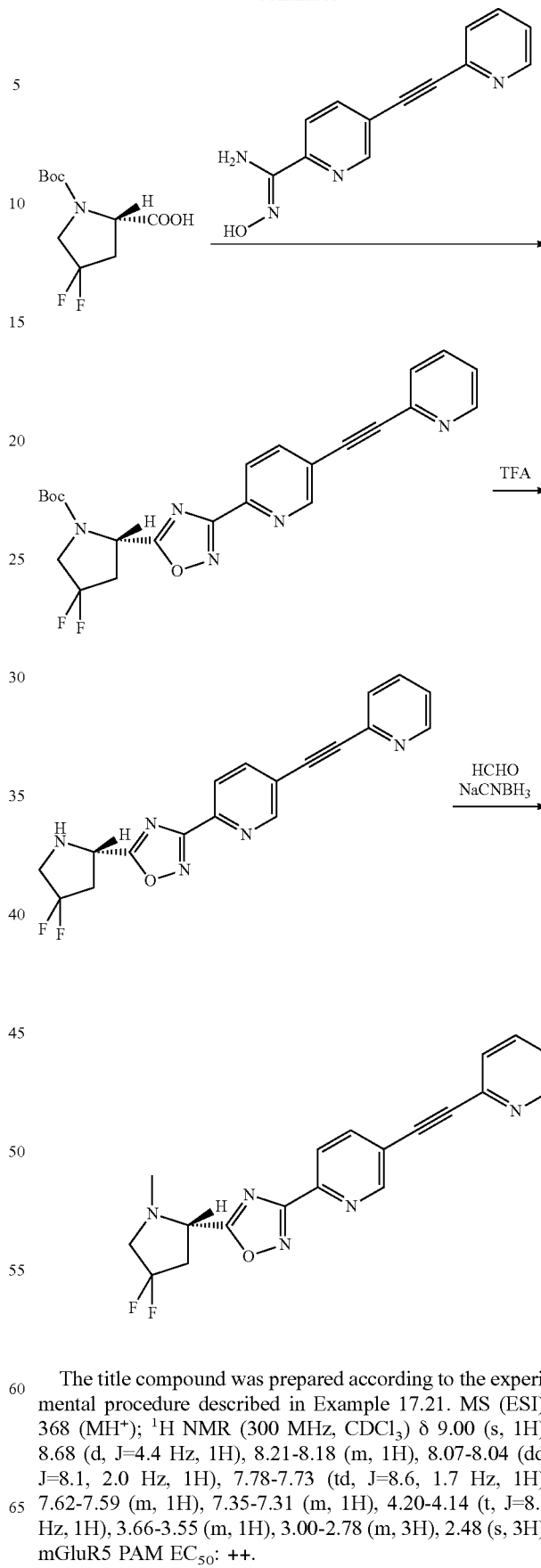

The title compound was prepared according to the experimental procedure described in Example 17.21. MS (ESI): 368 (MH+); $^1$H NMR (300 MHz, CDCl$_3$) δ 9.00 (s, 1H), 8.68 (d, J=4.4 Hz, 1H), 8.21-8.18 (m, 1H), 8.07-8.04 (dd, J=8.1, 2.0 Hz, 1H), 7.78-7.73 (td, J=8.6, 1.7 Hz, 1H), 7.62-7.59 (m, 1H), 7.35-7.31 (m, 1H), 4.20-4.14 (t, J=8.1 Hz, 1H), 3.66-3.55 (m, 1H), 3.00-2.78 (m, 3H), 2.48 (s, 3H). mGluR5 PAM EC$_{50}$: ++.

Example 17.23

Synthesis of Compound 156: 5-((2R,4S)-4-fluoro-1-methylpyrrolidin-2-yl)-3-(5-(pyridin-2-ylethynyl)pyridin-2-yl)-1,2,4-oxadiazole

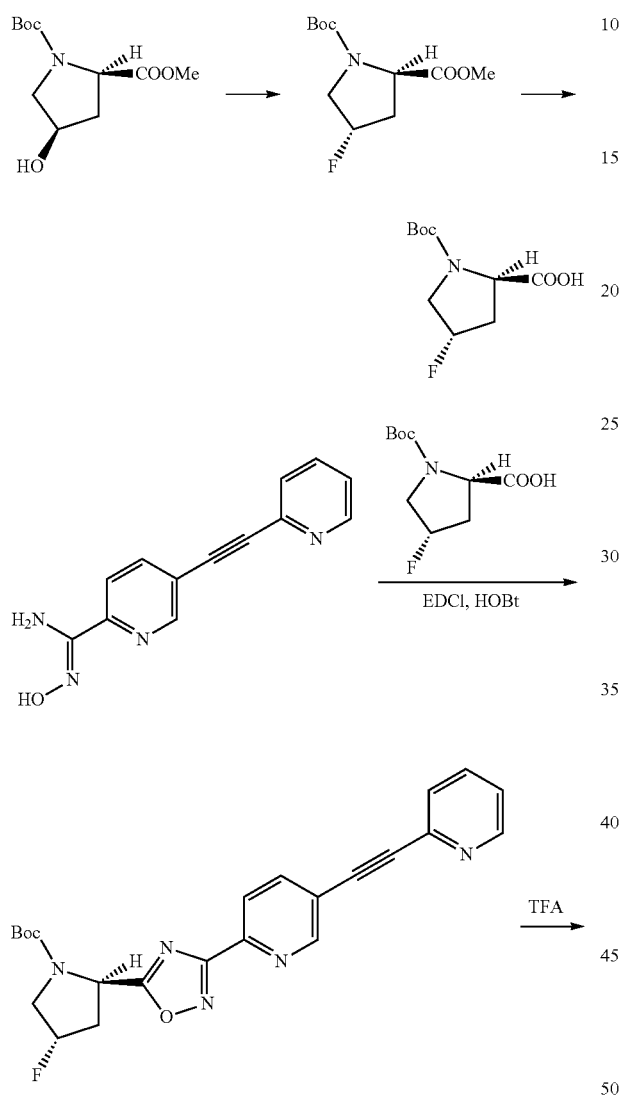

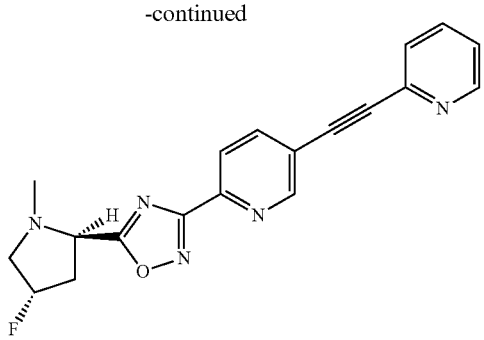

Example 17.23a

Synthesis of (2R,4S)-1-tert-butyl 2-methyl 4-fluoropyrrolidine-1,2-dicarboxylate To a solution of (2R,4R)-1-tert-butyl 2-methyl-4-hydroxypyrrolidine-1,2-dicarboxylate (1.0 g, 4.1 mmol) in dichloromethane (20 mL) was added diethylaminosulfur trifluoride (2.0 g, 12.3 mmol) at −78° C. over 20 min. The reaction mixture was stirred at −78° C. for 1 h and then warmed to room temperature for 1 h. Then the reaction was quenched with aqueous sodium carbonate and extracted with dichloromethane (3×100 mL). The combined organic layers were washed with brine, dried over $Na_2SO_4$, concentrated, and purified by column chromatography to give 670 mg of the desired product. MS (ESI): 248 (MH$^+$).

Example 17.23b

Synthesis of 5-((2R,4S)-4-fluoro-1-methylpyrrolidin-2-yl)-3-(5-(pyridin-2-ylethynyl)pyridin-2-yl)-1,2,4-oxadiazole The title compound was prepared according to the experimental procedure described in Example 17.21. MS (ESI): 350 (MH$^+$); $^1$H NMR (300 MHz, CDCl$_3$) δ 9.00 (d, J=1.3 Hz, 1H), 8.68 (d, J=4.7 Hz, 1H), 8.19-8.17 (m, 1H), 8.06-8.03 (m, 1H), 7.78-7.72 (td, J=8.6, 1.6 Hz, 1H), 7.60 (d, J=7.8 Hz, 1H), 7.35-7.31 (m, 1H), 5.46-5.27 (m, 1H), 4.30-4.25 (t, J=8.4 Hz, 1H), 3.72-3.57 (m, 1H), 2.94-2.80 (m, 1H), 2.66-2.53 (m, 5H). mGluR5 PAM EC$_{50}$: +.

Example 17.24

Synthesis of Compound 157: 5-((2S,4S)-4-methoxypyrrolidin-2-yl)-3-(5-(pyridin-2-ylethynyl)pyridin-2-yl)-1,2,4-oxadiazole

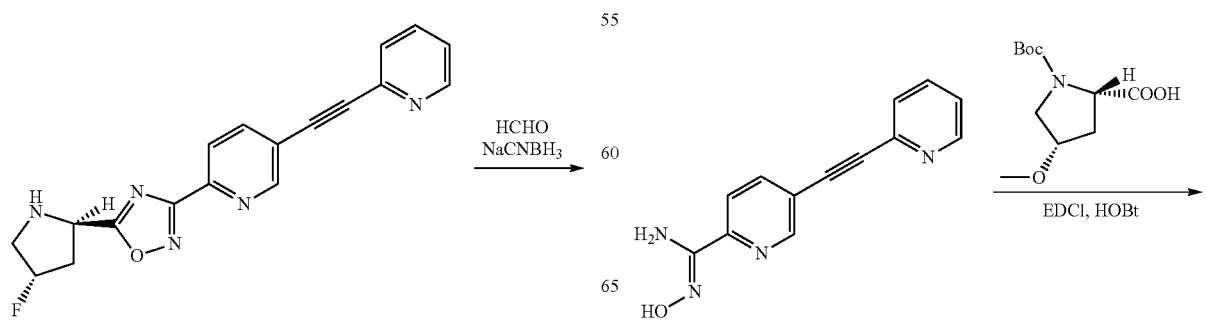

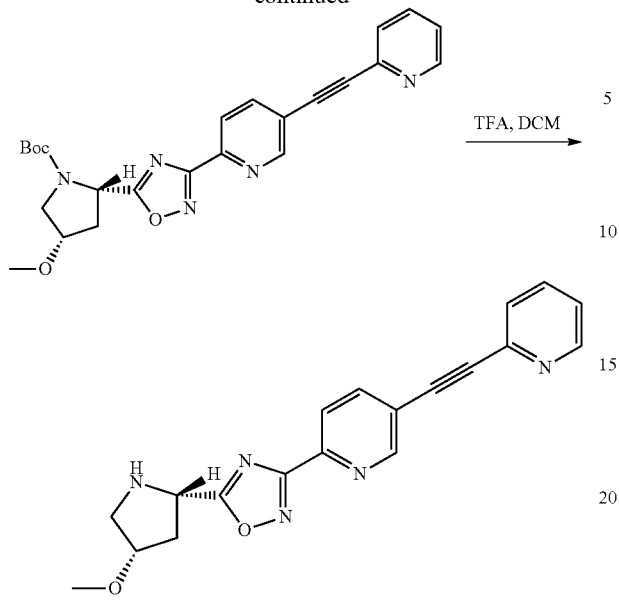

Example 17.24a

Synthesis of (2S,4S)-tert-butyl 4-methoxy-2-(3-(5-(pyridin-2-ylethynyl)pyridin-2-yl)-1,2,4-oxadiazol-5-yl)pyrrolidine-1-carboxylate The title compound was prepared according to the experimental procedure described in Example 8.25. MS (ESI): 448 (MH⁺).

Example 17.24b

Synthesis of 5-((2S,4S)-4-methoxypyrrolidin-2-yl)-3-(5-(pyridin-2-ylethynyl)pyridin-2-yl)-1,2,4-oxadiazole The title compound was prepared according to the experimental procedure described in Example 8.29b. MS (ESI): 348 (MH⁺); $^1$H NMR (300 MHz, CD$_3$OD) δ 8.93 (s, 1H), 8.61 (d, J=4.2 Hz, 1H), 8.28-8.23 (m, 2H), 7.96-7.90 (m 1H), 7.76-7.74 (m, 1H), 7.51-7.47 (m, 1H), 4.64-4.60 (m, 1H), 4.11-4.07 (m, 1H), 3.27 (s, 3H), 3.24-3.18 (m, 1H), 3.14-3.09 (m, 1H), 2.59-2.49 (m, 1H), 2.43-2.36 (m, 1H).

Example 17.25

Synthesis of Compound 169: 5-((2R,4R)-4-fluoro-1-methylpyrrolidin-2-yl)-3-(5-(pyridin-2-ylethynyl)pyridin-2-yl)-1,2,4-oxadiazole

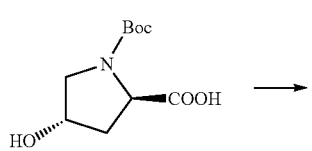

The title compound was prepared according to the experimental procedure described in Example 17.23. MS (ESI): 350 (MH⁺); $^1$H NMR (300 MHz, CD$_3$OD) δ 8.94 (s, 1H), 8.62 (d, J=7.6 Hz, 1H), 8.29-8.22 (m, 2H), 7.96-7.91 (m, 1H), 7.75 (d, J=7.8 Hz, 1H), 7.51-7.47 (m, 1H), 5.38-5.17 (m, 1H), 3.94-3.88 (t, J=8.3 Hz, 1H), 3.47-3.37 (m, 1H), 2.85-2.73 (m, 1H), 2.67-2.46 (m, 5H). mGluR5 PAM EC$_{50}$: +.

Example 17.26

Synthesis of Compound 171: 5-(2-azabicyclo[3.1.0]hexan-1-yl)-3-(5-(pyridin-2-ylethynyl)pyridin-2-yl)-1,2,4-oxadiazole

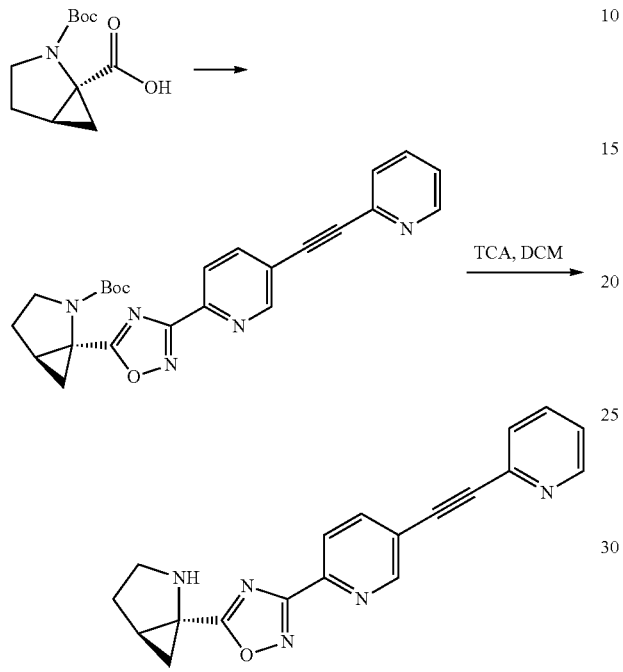

The title compound was prepared according to the experimental procedure described in Example 8.25 and Example 8.29b. MS (ESI): 330 (MH+); ¹H NMR (300 MHz, CDCl₃) δ 8.99 (s, 1H), 8.67 (d, J=4.5 Hz, 1H), 8.17 (d, J=8.1 Hz, 1H), 8.04-8.01 (dd, J=8.1, 1.9 Hz, 1H), 7.78-7.72 (m, 1H), 7.60 (d, J=7.7 Hz, 1H), 7.35-7.32 (m, 1H), 3.39-3.33 (m, 1H), 2.93-2.84 (m, 1H), 2.35-2.28 (m, 1H), 2.26-2.15 (m, 1H), 2.06-2.00 (m, 1H), 1.89-1.79 (m, 1H), 1.56-1.53 (m, 1H).

Example 17.27

Synthesis of Compound 172: 5-((1S,5R)-2-methyl-2-azabicyclo[3.1.0]hexan-1-yl)-3-(5-(pyridin-2-ylethynyl)pyridin-2-yl)-1,2,4-oxadiazole

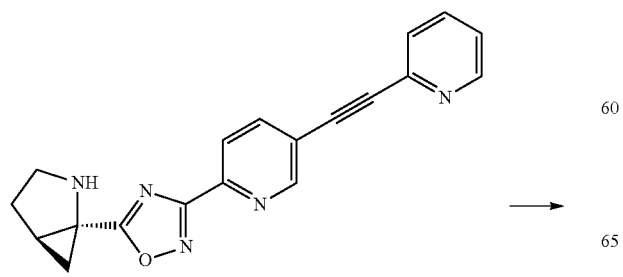

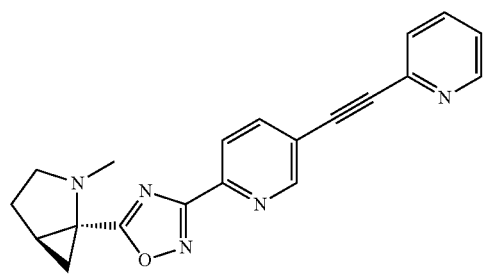

The title compound was prepared according to the experimental procedure described in Example 16.8. MS (ESI): 348 (MH+); ¹H NMR (300 MHz, CDCl₃) δ 8.99 (d, J=1.2 Hz, 1H), 8.68 (d, J=4.7 Hz, 1H), 8.21 (d, J=8.1 Hz, 1H), 8.05-8.01 (dd, J=8.1, 2.0 Hz, 1H), 7.78-7.72 (m, 1H), 7.60 (d, J=7.8 Hz, 1H), 7.35-7.30 (m, 1H), 3.32-3.27 (m, 1H), 2.55 (s, 3H), 2.27-2.18 (m, 4H), 2.07-2.00 (m, 2H). mGluR5 PAM EC₅₀: +.

Example 17.28

Synthesis of diastereoisomers Compound 173 and Compound 174 5-(1-azabicyclo[2.2.1]heptan-2-yl)-3-(5-(pyridin-2-ylethynyl)pyridin-2-yl)-1,2,4-oxadiazole

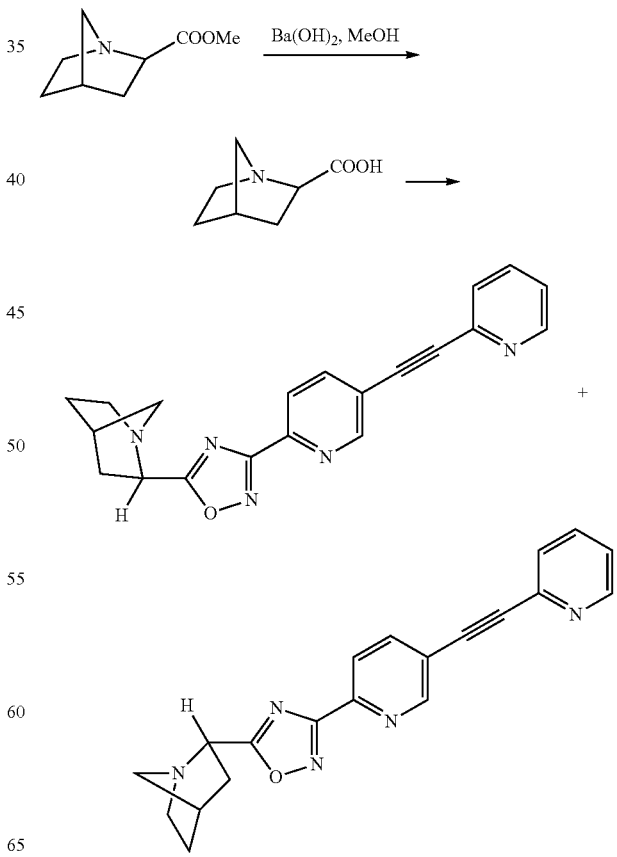

Example 17.28a

Synthesis of 1-azabicyclo[2.2.1]heptane-2-carboxylic acid

A solution of methyl 1-azabicyclo[2.2.1]heptane-2-carboxylate (a cis and trans mixture) (200 mg, 1.28 mmol) and aqueous 1N Ba(OH)$_2$ (10 mL) in methanol (10 mL) was stirred at room temperature overnight. Then the solvent was removed and the residue was diluted with 20 mL of water. The resulting suspension was filtered and the filtrate was concentrated to give the crude product, which was directly used for the next step without further purification. MS (ESI): 142 (MH$^+$).

Example 17.28b

Synthesis of diastereoisomeric Compound 173 and Compound 174 5-(1-azabicyclo[2.2.1]heptan-2-yl)-3-(5-(pyridin-2-ylethynyl)pyridin-2-yl)-1,2,4-oxadiazole The title compounds were prepared according to the experimental procedure described in Example 8.25.

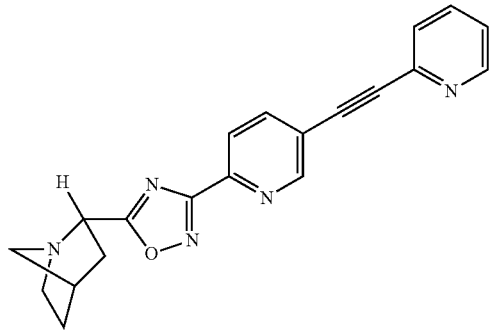 [SMILES: C(#Cc1ccccn1)c1ccc(-c2noc(C3CC4CCN3C4)n2)nc1]

Compound 173: the trans isomeric 5-(1-azabicyclo[2.2.1]heptan-2-yl)-3-(5-(pyridin-2-ylethynyl)pyridin-2-yl)-1,2,4-oxadiazole: MS (ESI): 344 (MH$^+$); $^1$H NMR (300 MHz, CDCl$_3$) δ 9.01 (s, 1H), 8.68 (d, J=4.3 Hz, 1H), 8.20 (d, J=8.1 Hz, 1H), 8.07-8.03 (dd, J=8.0, 1.6 Hz, 1H), 7.78-7.73 (m, 1H), 7.61 (d, J=7.7 Hz, 1H), 7.35-7.28 (m, 1H), 4.43-4.39 (m, 1H), 2.83-2.76 (m, 3H), 2.65 (d, J=9.3 Hz 1H), 2.51-2.47 (m, 1H), 2.20-2.13 (m, 1H), 1.96-1.90 (m, 1H), 1.71-1.62 (m, 1H), 1.32-1.27 (m, 1H).

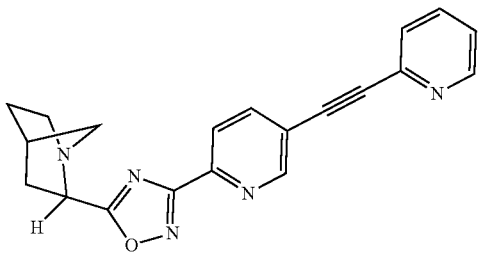 [SMILES: C(#Cc1ccccn1)c1ccc(-c2noc(C3CC4CCN3C4)n2)nc1]

Compound 174: The cis isomeric 5-(1-azabicyclo[2.2.1]heptan-2-yl)-3-(5-(pyridin-2-ylethynyl)pyridin-2-yl)-1,2,4-oxadiazole MS (ESI): 344 (MH$^+$); $^1$H NMR (300 MHz, CDCl$_3$) δ 8.99 (s, 1H), 8.68 (d, J=4.7 Hz, 1H), 8.18 (d, J=8.1 Hz, 1H), 8.05-8.01 (dd, J=8.1, 1.9 Hz, 1H), 7.78-7.72 (m, 1H), 7.60 (d, J=7.8 Hz, 1H), 7.34-7.28 (m, 1H), 4.02-3.98 (m, 1H), 3.10-2.90 (m, 1H), 2.78-2.72 (m, 3H), 2.44 (d, J=9.6 Hz, 1H), 2.26-2.23 (m, 1H), 1.82-1.62 (m, 2H), 1.31-1.27 (m, 1H). mGluR5 PAM EC$_{50}$: ++. Fold shift at 10 µM: +++.

Example 17.29

Synthesis of Compound 170:5-(hexahydro-1H-pyrrolizin-7a-yl)-3-(5-(pyridin-2-ylethynyl)pyridin-2-yl)-1,2,4oxadiazole

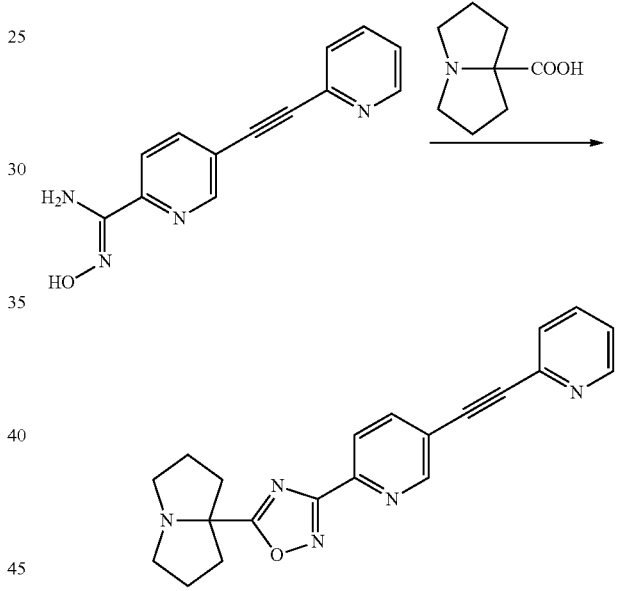

A solution of N'-hydroxy-5(pyridin-2-ylethynyl)picolnimidamide (0.3 g, 1.26 mmol, 1 equiv), hexahydro-1H-pyrrolizine-7a-carboxylic acid (0.29 g, 1.89 mmol, 1.5 equiv), EDCI (0.48 g, 2.52 mmol, 2.0 equiv) and HOBT (0.34 g, 2.52 mmol, 2.0 equiv) in DMF (20 mL) was stirred at 70° C. overnight. After cooling to room temperature, the reaction mixture was quenched with water and extracted with ethyl acetate (3×20 mL). The combined organic layers were dried over Na$_2$SO$_4$, filtered and concentrated. The residue was purified by silica gel chromatography to give the desired product (15.2 mg). MS (ESI+): m/z 358 (M+H$^+$); $^1$H NMR (300 MHz, CDCl$_3$): δ 8.99 (s, 1H), 8.68-8.67 (d, J=4.34 Hz, 1H), 8.20-8.18 (m, 1H), 8.04-8.01 (m, 1H), 7.78-7.24 (td, J=1.65 Hz, 7.71=Hz, 1H), 7.62-7.59 (m, 1H), 7.35-7.30 (m, 1H), 3.35-3.28 (m, 2H), 2.81-2.73 (m, 2H). 2.66-2.55 (m, 2H), 2.06-2.00 (m, 6H). PAM EC$_{50}$: +++.

Example 18.1

Synthesis of the HCl salt of Compound 158: 5-(sec-butyl)-3-(5-(pyridin-4-ylethynyl)pyridin-2-yl)-1,2,4-oxadiazole

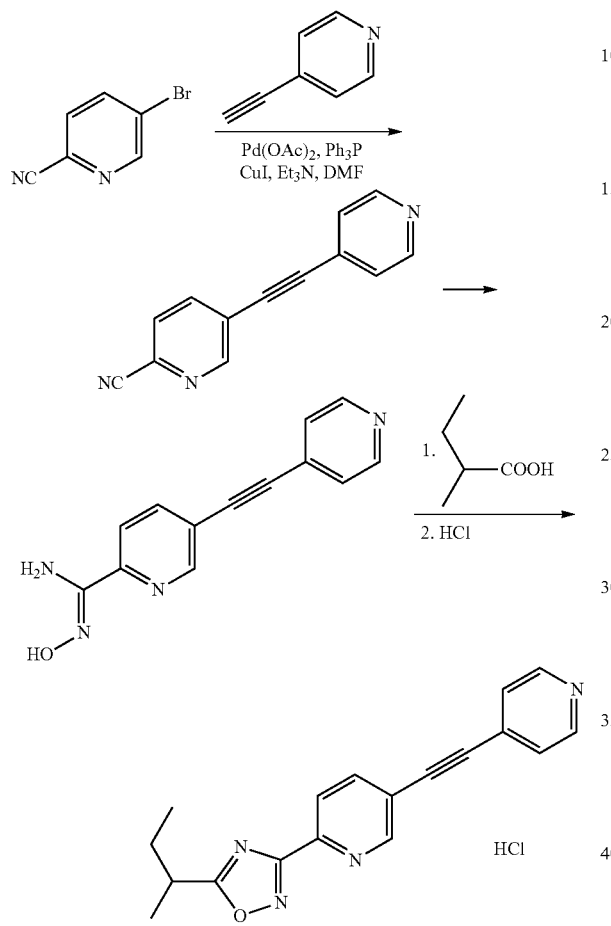

Example 18.1a

Synthesis of 5-(pyridin-4-ylethynyl)picolinonitrile

The title compound was prepared according to the experimental procedure described in Example 8.1a. MS (ESI): 206 (MH$^+$).

Example 18.1b

Synthesis of N-hydroxy-5-(pyridin-4-ylethynyl)picolinimidamide

The title compound was prepared according to the experimental procedure described in Example 8.1b. MS (ESI): 239 (MH$^+$).

Example 18.1c

Synthesis of the HCl salt of 5-(sec-butyl)-3-(5-(pyridin-4-ylethynyl)pyridin-2-yl)-1,2,4-oxadiazole The title compound was prepared according to the experimental procedure described in Example 8.25. MS (ESI): 305 (MH$^+$); $^1$H NMR (300 MHz, CDCl$_3$) δ 8.96-8.95 (dd, J=2.0, 0.8 Hz, 1H), 8.67 (d, J=6.0 Hz, 2H), 8.20-8.17 (dd, J=8.2, 0.8 Hz, 1H), 8.02-7.98 (dd, J=8.1, 2.1 Hz, 1H), 7.44 (d, J=6.1 Hz, 2H), 3.23-3.16 (m, 1H), 2.03-1.93 (m, 1H), 1.86-1.77 (m, 1H), 1.48 (d, J=7.0 Hz, 3H), 1.01-0.96 (t, J=7.4 Hz, 3H). PAM EC$_{50}$: ++++. Fold shift at 10 μM: ++.

Example 18.2

Synthesis of Compound 159: 5-(1-methoxyethyl)-3-(5-(pyridin-4-ylethynyl)pyridin-2-yl)-1,2,4-oxadiazole

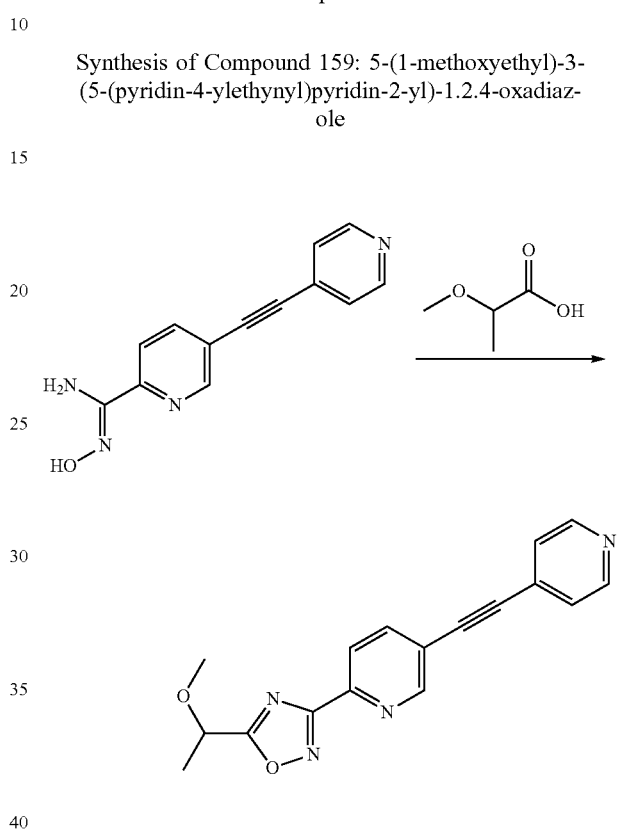

The title compound was prepared according to the experimental procedure described in Example 8.25. MS (ESI): 307 (MH$^+$); $^1$H NMR (300 MHz, CD$_3$OD) δ 9.03 (s, 1H), 8.93 (d, J=6.8 Hz, 2H), 8.33 (d, J=1.1 Hz, 2H), 8.29 (d, J=6.8 Hz, 2H), 4.85-4.83 (m, 1H), 3.49 (s, 3H), 1.67 (d, J=6.7 Hz, 3H). PAM EC$_{50}$: ++. Fold shift at 10 μM: +.

Example 18.3

Synthesis of Compound 160: 5-(pentan-3-yl)-3-(5-(pyridin-4-ylethynyl)pyridin-2-yl)-1,2,4-oxadiazole

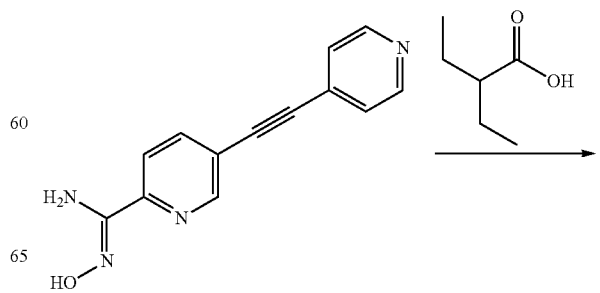

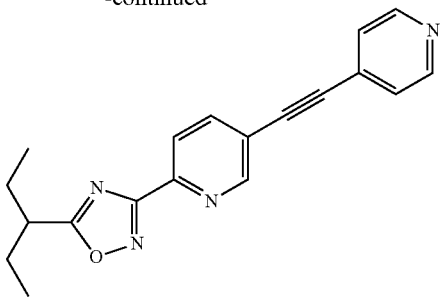

The title compound was prepared according to the experimental procedure described in Example 8.25. MS (ESI): 319 MH+); ¹H NMR (300 MHz, CDCl₃) δ 8.95-8.93 (m, 3H), 8.34 (s, 2H), 8.28 (d, J=6.5 Hz, 2H), 3.11-3.06 (m, 1H), 1.96-1.86 (m, 4H), 0.98-0.93 (t, J=7.4 Hz, 6H). PAM EC₅₀: +++. Fold shift at 10 μM: +.

Example 18.4

Synthesis of the HCl salt of Compound 161: 5-(1-methoxypropyl)-3-(5-(pyridin-4-ylethynyl)pyridin-2-yl)-1,2,4-oxadiazole

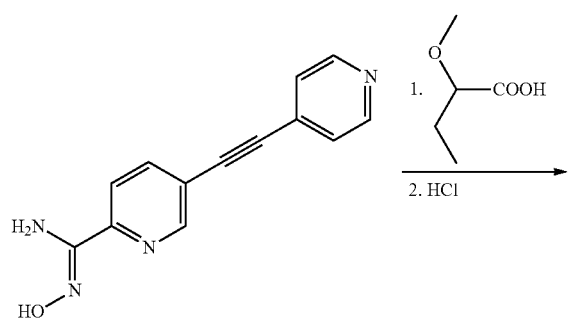

The title compound was prepared according to the experimental procedure described in Example 8.25. MS (ESI): 321 MH+); ¹H NMR (300 MHz, CD₃OD) δ 9.04 (s, 1H), 8.95-8.93 (dd, J=5.7, 0.9 Hz, 2H), 8.34 (d, J=1.7 Hz, 2H), 8.31-8.28 (dd, J=5.7, 1.2 Hz, 2H), 4.69-4.64 (t, J=6.5 Hz, 1H), 3.48 (s, 3H), 2.07-1.99 (m, 2H), 1.06-1.01 (t, J=7.4 Hz, 3H). PAM EC₅₀: +++. Fold shift at 10 μM: ++.

Example 18.5

Synthesis of the HCl salt of Compound 162: 3-(5-(pyridin-4-ylethynyl)pyridin-2-yl)-5-(pyrrolidin-2-yl)-1,2,4-oxadiazole

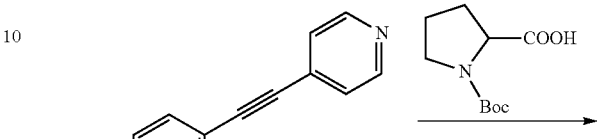
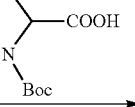
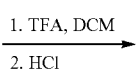
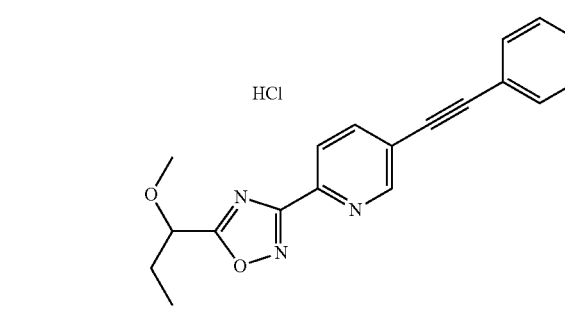

The title compound was prepared according to the experimental procedure described in Example 8.25 and Example 8.29b. MS (ESI): 318 (MH+); ¹H NMR (300 MHz, CD₃OD) δ 9.07 (s, 1H), 8.95 (d, J=6.7 Hz, 2H), 8.37 (s, 2H), 8.30-8.28 (m, 2H), 5.31-5.26 (t, J=7.7 Hz, 1H), 3.69-3.49 (m, 2H), 2.75-2.66 (m, 1H), 2.53-2.46 (m, 1H), 2.36-2.27 (m, 2H).

Example 18.6

Synthesis of the HCl salt of Compound 163: N-methyl-1-(3-(5-(pyridin-4-ylethynyl)pyridin-2-yl)-1,2,4-oxadiazol-5-yl)ethanamine

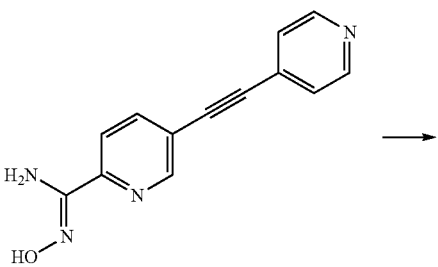

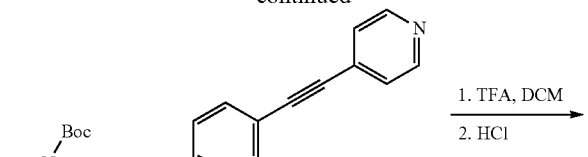

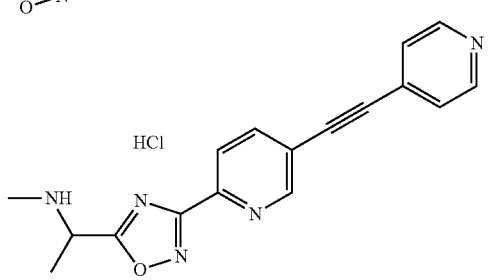

The title compound was prepared according to the experimental procedure described in Example 8.25 and Example 8.29b. MS (ESI): 306 (MH+); 1H NMR (300 MHz, CD3OD) δ 9.07 (s, 1H), 8.97-8.94 (m, 2H), 8.41 (s, 2H), 8.37-8.28 (m, 2H), 5.11-5.04 (m, 1H), 2.95 (s, 3H), 1.87 (d, J=6.9 Hz, 3H).

Example 19.1

Synthesis of the HCl salt of Compound 164: 3-(5-(pyridin-3-ylethynyl)pyridin-2-yl)-5-(pyrrolidin-2-yl)-1,2,4-oxadiazole The title compound was prepared according to the experimental procedure described in Example 8.1a and Example 8.29b. MS (ESI): 318(MH+); 1H NMR (300 MHz, CD3OD) δ 9.24 (s, 1H), 9.02 (s, 1H), 8.93 (d, J=5.7 Hz, 1H), 8.87 (d, J=7.8 Hz, 1H), 8.34 (s, 2H), 8.23-8.18 (m, 1H), 5.31-5.01 (t, J=7.7 Hz, 1H), 3.69-3.53 (m, 2H), 2.78-2.66 (m, 1H), 2.54-2.42 (m, 1H), 2.36-2.25 (m, 2H).

Example 20.1

Synthesis of the HCl salt of Compound 165: 3-(5-(phenylethynyl)pyridin-2-yl)-5-(pyrrolidin-2-yl)-1,2,4-oxadiazole

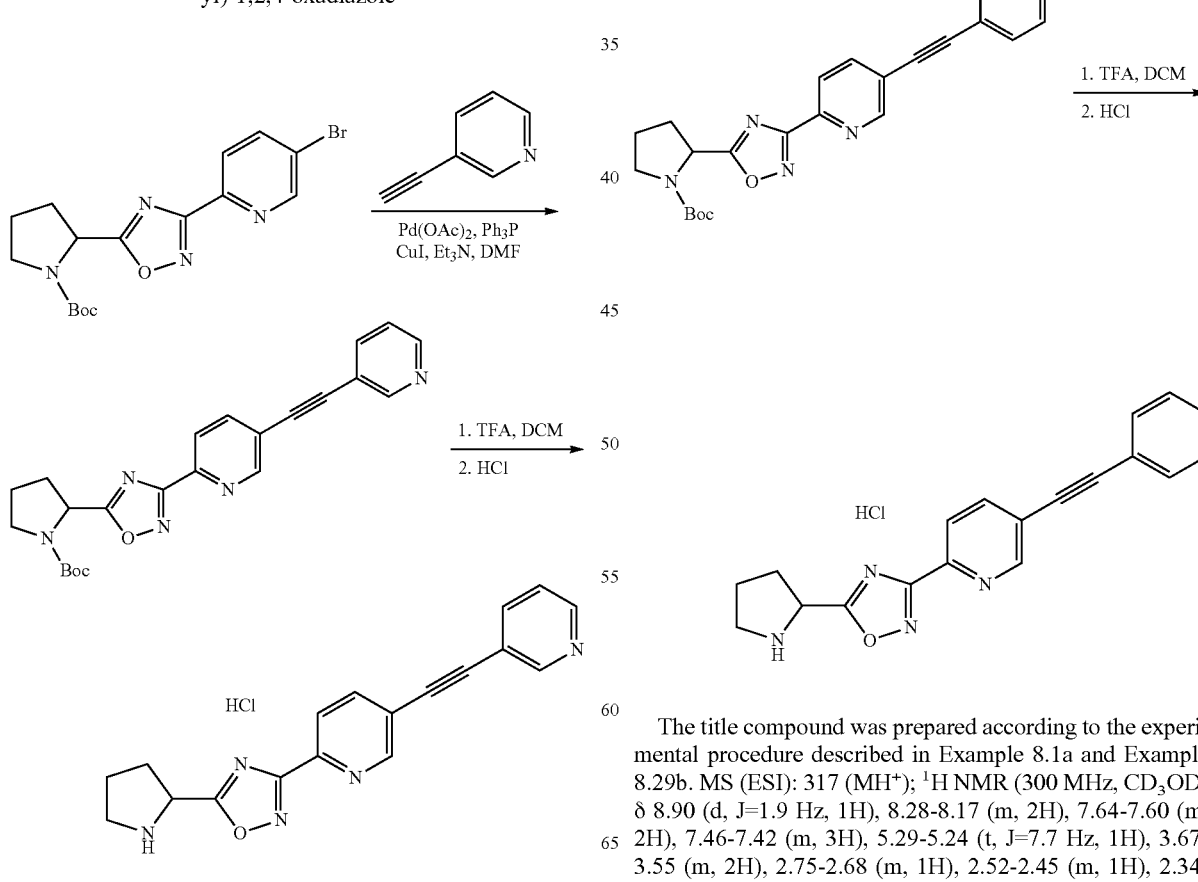

The title compound was prepared according to the experimental procedure described in Example 8.1a and Example 8.29b. MS (ESI): 317 (MH+); 1H NMR (300 MHz, CD3OD) δ 8.90 (d, J=1.9 Hz, 1H), 8.28-8.17 (m, 2H), 7.64-7.60 (m, 2H), 7.46-7.42 (m, 3H), 5.29-5.24 (t, J=7.7 Hz, 1H), 3.67-3.55 (m, 2H), 2.75-2.68 (m, 1H), 2.52-2.45 (m, 1H), 2.34-2.27 (m, 2H). PAM EC50: +.

Example 21.1

Synthesis of Compound 166: 3-(5-((3-chlorophenyl)ethynyl)pyridin-2-yl)-5-(pyrrolidin-2-yl)-1,2,4-oxadiazole

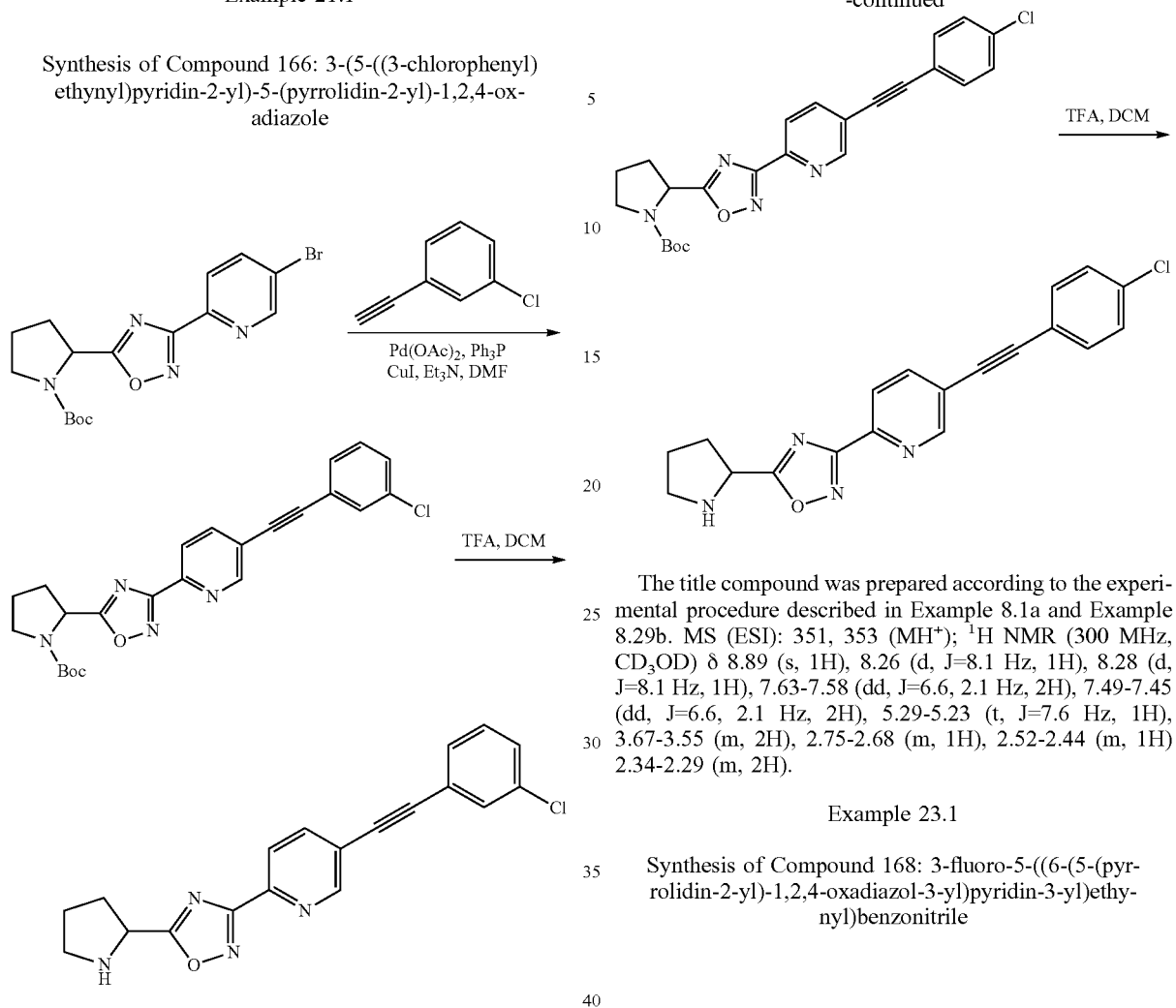

The title compound was prepared according to the experimental procedure described in Example 8.1a and Example 8.29b. MS (ESI): 351, 353 (MH+); $^1$H NMR (300 MHz, CD$_3$OD) δ 8.92 (s, 1H), 8.29-8.19 (m, 2H), 7.65 (s, 1H), 7.56 (d, J=7.1 Hz, 1H), 7.50-7.41 (m, 2H), 5.27 (t, J=7.6 Hz, 1H), 3.67-3.54 (m, 2H), 2.75-2.68 (m, 1H) 2.52-2.45 (m, 1H), 2.34-2.27 (m, 2H). PAM EC$_{50}$: +.

Example 22.1

Synthesis of Compound 167: 3-(5-(phenylethynyl)pyridin-2-yl)-5-(pyrrolidin-2-yl)-1,2,4-oxadiazole

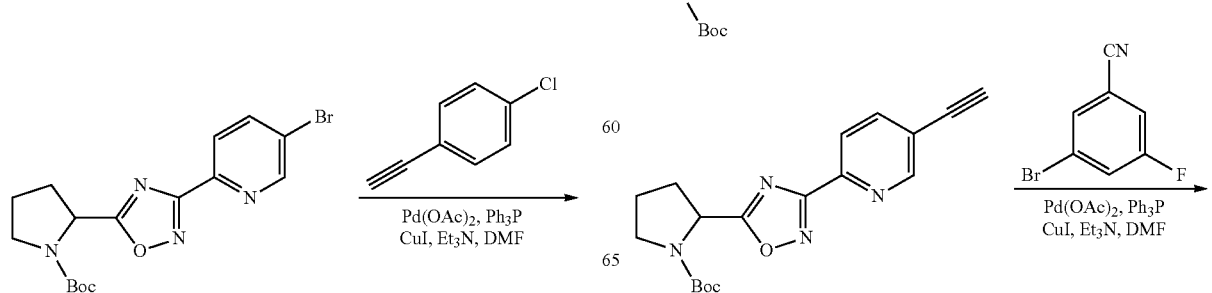

The title compound was prepared according to the experimental procedure described in Example 8.1a and Example 8.29b. MS (ESI): 351, 353 (MH+); $^1$H NMR (300 MHz, CD$_3$OD) δ 8.89 (s, 1H), 8.26 (d, J=8.1 Hz, 1H), 8.28 (d, J=8.1 Hz, 1H), 7.63-7.58 (dd, J=6.6, 2.1 Hz, 2H), 7.49-7.45 (dd, J=6.6, 2.1 Hz, 2H), 5.29-5.23 (t, J=7.6 Hz, 1H), 3.67-3.55 (m, 2H), 2.75-2.68 (m, 1H), 2.52-2.44 (m, 1H) 2.34-2.29 (m, 2H).

Example 23.1

Synthesis of Compound 168: 3-fluoro-5-((6-(5-(pyrrolidin-2-yl)-1,2,4-oxadiazol-3-yl)pyridin-3-yl)ethynyl)benzonitrile

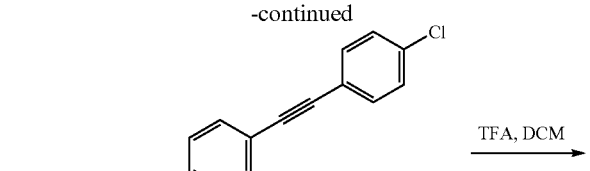

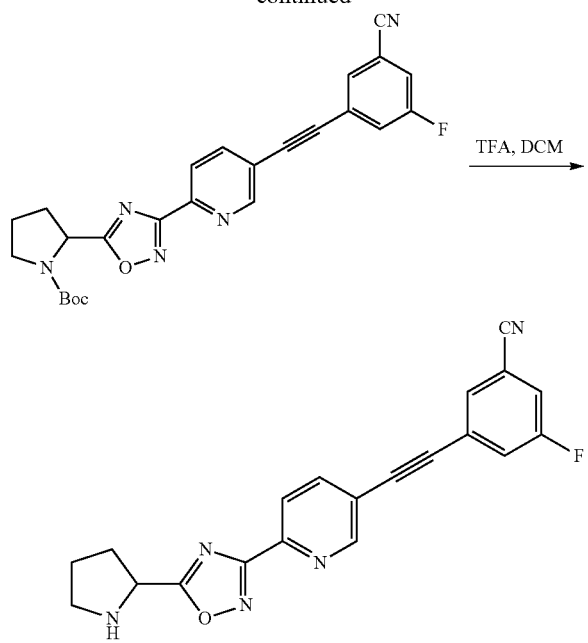

Example 23.1a

Synthesis of tert-butyl-2-(3-(5-(((trimethylsilyl)ethynyl)pyridin-2-yl)-1,2,4-oxadiazol-5-yl)pyrrolidine-1-carboxylate A solution of tert-butyl-2-(3-(5-bromopyridin-2-yl)-1,2,4-oxadiazol-5-yl) pyrrolidine-1-carboxylate (560 mg, 1.42 mmol), ethynyltrimethylsilane (345 mg, 3.54 mmol), Pd(OAc)$_2$ (64 mg, 0.28 mmol), PPh$_3$ (297 mg, 1.14 mmol), CuI (27 mg, 0.14 mmol), and Et$_3$N (1 mL) in DMF (50 mL) was stirred in a sealed tube at 70° C. for 3.5 h. After cooling to room temperature, the reaction mixture was diluted with H$_2$O and extracted with EtOAc (3×100 mL). The combined organic layers were washed with brine and dried over anhydrous sodium sulfate. After filtration and concentration, the crude product was purified by silica gel chromatography to produce 170 mg of the desired product. MS (ESI): 413 (MH$^+$).

Example 23.1b

Synthesis of tert-butyl-2-(3-(5-ethynylpyridin-2-yl)-1,2,4-oxadiazol-5-yl)pyrrolidine-1-carboxylate A solution of tert-butyl-2-(3-(5-(((trimethylsilyl)ethynyl)pyridin-2-yl)-1,2,4-oxadiazol-5-yl)pyrrolidine-1-carboxylate (170 mg, 0.41 mmol) and aqueous 1N KOH (10 mL) in methanol was stirred at room temperature for 5 min. Then the reaction mixture was diluted with water and extracted with EtOAc (3×100 mL). The combined organic layers were washed with brine and dried over anhydrous sodium sulfate. After filtration and concentration, the crude product was purified by silica gel chromatography to produce 116 mg of the desired product. MS (ESI): 341 (MH$^+$).

Example 23.1c

Synthesis of tert-butyl 2-(3-(5-((3-cyano-5-fluorophenyl)ethynyl)pyridin-2-yl)-1,2,4-oxadiazol-5-yl)pyrrolidine-1-carboxylate The title compound was prepared according to the experimental procedure described in Example 8.1a. MS (ESI): 460 (MH$^+$).

Example 23.1d

Synthesis of 3-fluoro-5-((6-(5-(pyrrolidin-2-yl)-1,2,4-oxadiazol-3-yl)pyridin-3-yl)ethynyl)benzonitrile The title compound was prepared according to the experimental procedure described in Example 8.29b. MS (ESI): 360 (MH$^+$); $^1$H NMR (300 MHz, CD$_3$OD) δ 8.92 (br s, 1H), 8.36 (br s, 1H), 8.27-8.24 (d, J=8.0, 1H), 7.87 (s, 1H), 7.77-7.67 (m, 2H), 5.30-5.25 (t, J=7.4 Hz, 1H), 3.67-3.55 (m, 2H), 2.76-2.68 (m, 1H) 2.53-2.45 (m, 1H), 2.36-2.29 (m, 2H).

It will be understood that the invention has been described by way of example only and modifications may be made whilst remaining within the scope and the spirit of the invention.

The invention claimed is:
1. A compound of formula (I) or a pharmaceutically acceptable salt thereof:

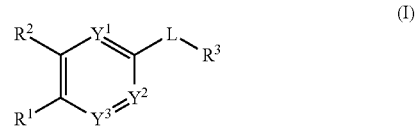

wherein
Y$^1$, Y$^2$, and Y$^3$ are each independently CR$^4$ or N;

R$^1$ is

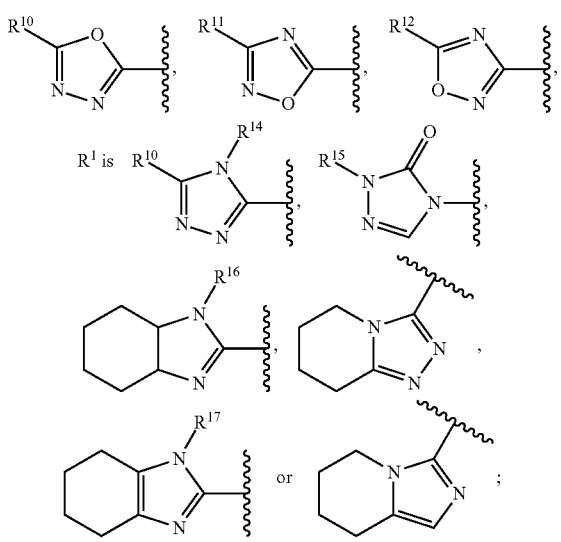

each R$^2$ and R$^4$ is independently hydrogen, halogen, alkyl, heteroalkyl, cycloalkyl, heterocycloalkyl, aryl, aralkyl, heteroaralkyl, or heteroaryl;

$R^3$ is alkyl, heteroalkyl, heterocycloalkyl, cycloalkyl, aryl, heteroaryl, aralkyl or heteroaralkyl, wherein said heteroaryl is monocyclic;

L is —C≡C—,

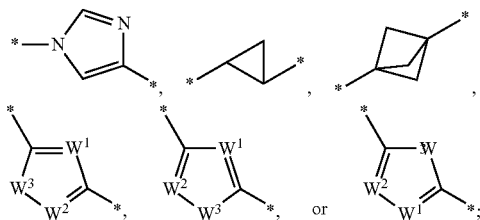

$W^1$ and $W^2$ are each independently N or CH;
$W^3$ is O, S or $NR^5$,
$R^5$ and $R^6$ are each independently hydrogen or alkyl;
$R^{10}$, $R^{11}$, $R^{12}$, and $R^{13}$ are each independently hydrogen, alkyl, cycloalkyl, heteroaryl, heteroalkyl, aralkyl or 3 to 8-membered heterocyclyl; and $R^{14}$, $R^{15}$, $R^{16}$ and $R^{17}$ are each independently hydrogen, alkyl; or $R^{13}$ and $R^{14}$ together with the atoms to which they are attached are linked to form a heterocyclyl ring, wherein at least one of $Y^1$, $Y^2$, and $Y^3$ is nitrogen.

2. The compound of claim 1, wherein $R^2$ and $R^4$ are hydrogen.

3. The compound of claim 1, wherein $R^3$ is aryl or monocyclic heteroaryl.

4. A compound of formula (II) or a pharmaceutically acceptable salt thereof:

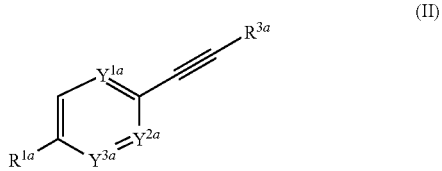

(II)

wherein
$Y^{1a}$, $Y^{2a}$, and $Y^{3a}$ are each independently $CR^{4a}$ or N;
$R^{1a}$ is

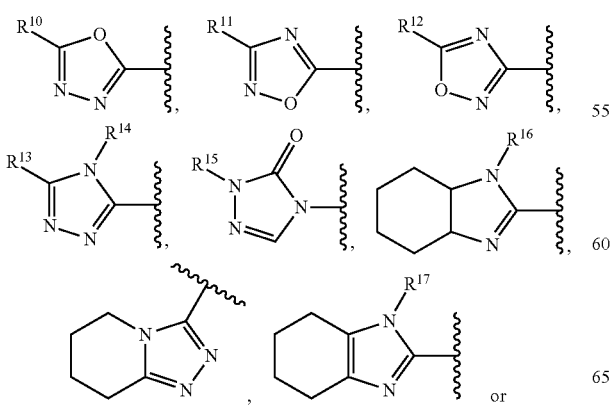

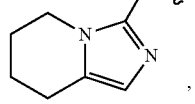

$R^{3a}$ is alkyl, heteroalkyl, cycloalkyl, heterocycloalkyl, aryl, heteroaryl, aralkyl or Heteroaralkyl, wherein said heteroaryl is monocyclic; and
$R^{4a}$ is hydrogen, alkyl, heteroalkyl, cycloalkyl, heterocycloalkyl, aryl, aralkyl, heteroaralkyl, or heteroaryl;
$R^{10}$, $R^{11}$, $R^{12}$, and $R^{13}$ are each independently hydrogen, alkyl, cycloalkyl, heteroaryl, heteroalkyl, aralkyl or 3 to 8-membered heterocyclyl; and
$R^{14}$, $R^{15}$, $R^{16}$ and $R^{17}$ are each independently hydrogen, alkyl; or $R^{13}$ and $R^{14}$ together with the atoms to which they are attached are linked to form a heterocyclyl ring.

5. The compound of claim 4, wherein at least one of $Y^{1a}$, $Y^{2a}$, and $Y^{3a}$ is nitrogen.

6. The compound of claim 4, wherein $Y^{1a}$, $Y^{2a}$, and $Y^{3a}$ are $CR^{4a}$.

7. The compound of claim 4, wherein $R^{4a}$ is hydrogen.

8. The compound of claim 4, wherein $R^{3a}$ is aryl or monocyclic heteroaryl.

9. The compound of claim 8, wherein $R^{3a}$ is

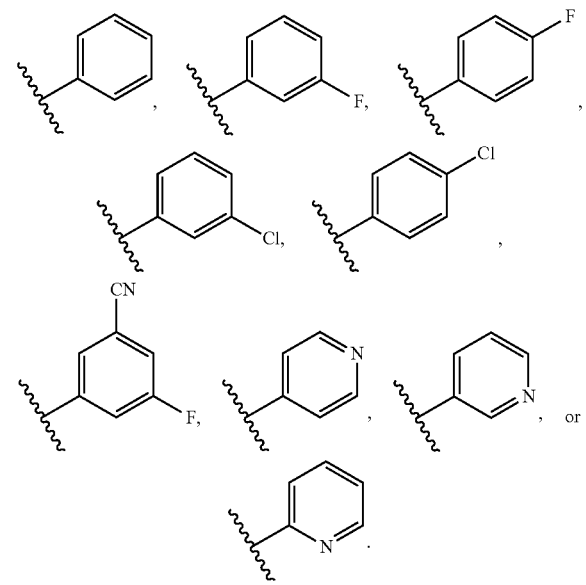

10. The compound of claim 4, where $R^{1a}$ is

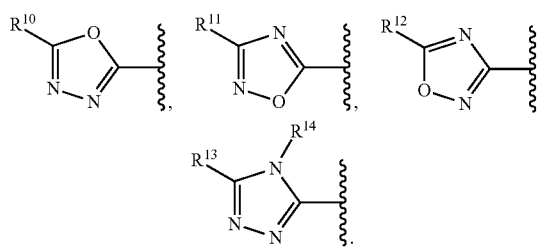

11. The compound of claim 4, wherein the compound of formula II is a compound of formula IIa:

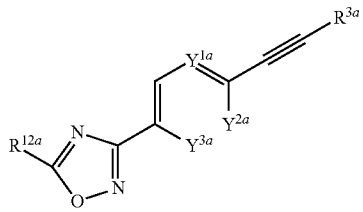

(IIa)

wherein

Y$^{1a}$, Y$^{2a}$, and Y$^{3a}$ are each independently CR$^{4a}$ or N;

R$^{3a}$ is alkyl, heteroalkyl, cycloalkyl, heterocycloalkyl, cycloalkyl, aryl, heteroaryl, aralkyl or heteroaralkyl, wherein said heteroaryl is monocyclic;

R$^{4a}$ is hydrogen, alkyl, heteroalkyl, cycloalkyl, heterocycloalkyl, aryl, aralkyl, heteroaralkyl, or heteroaryl; and R$^{12a}$ is alkyl, heterocyclic, heteroaryl, cycloalkYl, acyl, alkoxycarbonyl, heteroarylalkyl, heterocyclicalkyl or aralky.

12. The compound of claim 11, wherein, R$^{12a}$ is hydrogen, methyl, ethyl, n-propyl, isopropyl, t-butyl, isobutyl, sec-butyl, cyclopropyl, cyclobutyl, cyclopentyl, cyclohexyl, benzyl, methylamine, ethylmethylamine, methylaminomethyl, dimethylaminomethyl, ethoxymethyl, methoxyethyl, acyl, ethoxycarbonyl,

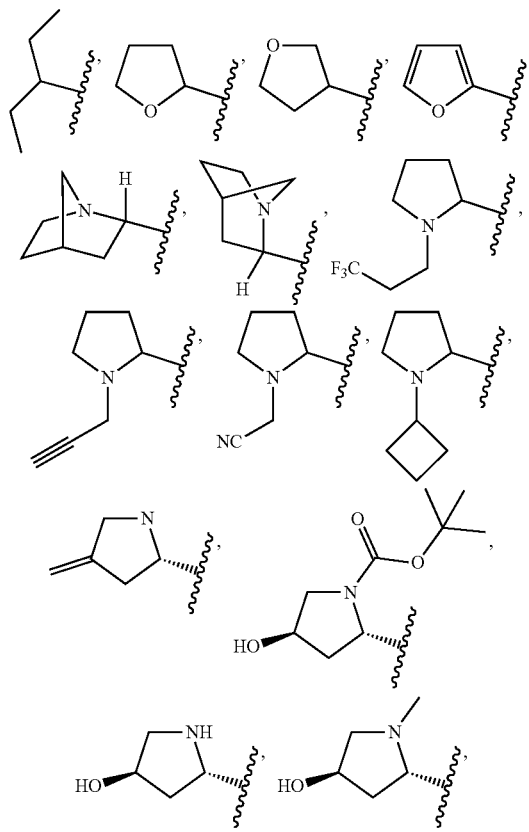

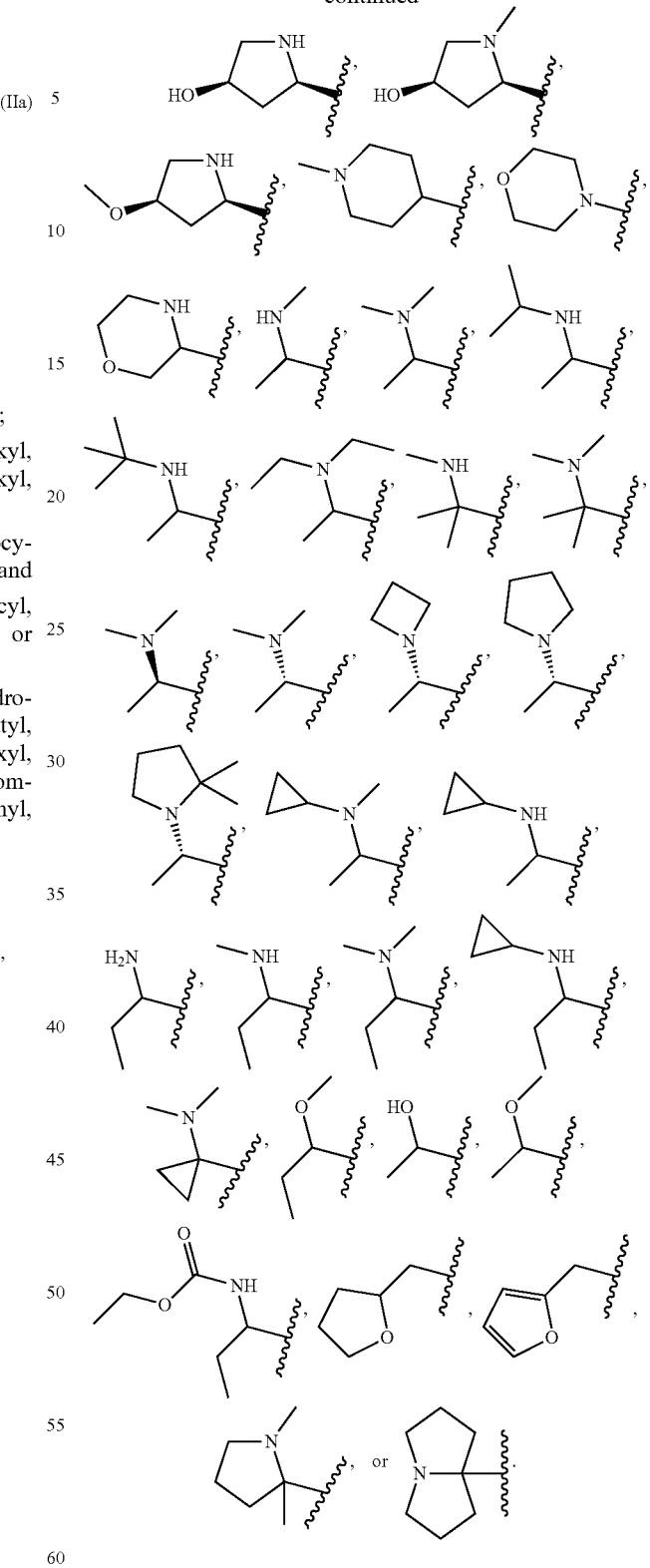

13. A pharmaceutical composition comprising a therapeutically effective amount of a compound according to claim 1 or claim 4 and a pharmaceutically acceptable carrier.

14. A compound, selected from the group consisting of:
2-cyclopentyl-5-(4-((3-fluorophenyl)ethynyl)phenyl)-1,3,4-oxadiazole;

2-(sec-butyl)-5-(4-((3-fluorophenyl)ethynyl)phenyl)-1,3,4-oxadiazole;
2-(pentan-3-yl)5-(4-(pyridine-4-ylethynyl)phenyl)-1,3,4-oxadiazole;
2-(4-((3-fluorophenyl)ethynyl)phenyl)-5-(pentan-3-yl)-1,3,4-oxadiazole;
2-(4-(phenylethynyl)phenyl)-3a,4,5,6,7,7a-hexahydro-1H-benzo[d]imidazole;
3-(4-((4-fluorophenyl)ethynyl)phenyl)-1,5,6,7,8,8a-hexahydrolinidazo[1,5-a-]pyridine;
2-(4-(phenylethynyl)phenyl)-3a, 4,5,6,7,7a-hexahydro-1H-benzo [d] imidazole;
3(4((4-fluorophenyl)ethynl)phenyl)-5,6,7,8-tetrahydronnidazo[1,5-a]pyridine;
3 -cyclopentyl-5-4-((3-fluorophenyl)ethynyl)phenyl)-4H-1,2,4-triazole;
2-(4-methyl-5-(pyrrolidin-1-yl)ethyl)-4H-1,2,4-triazol-3-yl)-5-(pyridi-n-2-ylethynyl)pyridine;
3-(4-((4-fluorophenyl)ethynyl)phenyl)-5,6,7,8-tetrahydro-[1,2,4]triazolo[-4,3-a]pyridine;
1-(sec-butyl)-4-(4-(pyridin-4-ylethynyl)phenyl)-1H-1,2,4-triazol-5(4H)-one;
3-(tert-butyl)-5-(4-((3-fluorophenyl)ethynyl)phenyl)-1,2,4-oxadiazole;
3-cyclopentyl-5-(4-((3-fluorophenyl)ethynyl)phenyl)-1,2,4-oxadiazole;
3-(sec-butyl)-5-(4-((3-fluorophenyl)ethynyl)phenyl)-1,2,4-oxadiazole;
3-(4-((3-fluorophenyl)ethynyl)phenyl)-1,2,4-oxadiazole;
3-(4-((3-fluorophenyl)ethynyl)phenyl)-1,2,4-oxadiazole;
5-ethyl-3-(4-((3-fluorophenyl)ethynyl)phenyl)-1,2,4-oxadiazole;
3-(4-((3-fluorophenyl)ethynyl)phenyl)-5-propyl-1,2,4-oxadiazole;
3-(4-((3-fluorophenyl)ethynyl)phenyl)-5-isopropyl-1,2,4-oxadiazole;
5-cyclopropyl-3-(4-((3-fluorophenyl)ethynyl)phenyl)-1,2,4-oxadiazole;
3-(4-((3-fluorophenyl)ethynyl)phenyl)-5-isobutyl-1,2,4-oxadiazole;
5-(tert-butyl)-3-(4-((3-fluorophenyl)ethynyl)phenyl)-1,2,4-oxadiazole;
5-cyclobutyl-3-(4-((3-fluorophenyl)ethynyl)phenyl)-1,2,4-oxadiazole;
5-5-(sec-butyl)-3-(4-((3-fluorophenyl)ethynyl)phenyl)-1,2,4-oxadiazole;
(S)-5-(sec-butyl)-3-(4-((3-fluorophenyl)ethynyl)phenyl)-1,2,4-oxadiazole;
(R)-5-(sec-butyl)-3-(4-((3-fluorophenyl)ethynyl)phenyl)-1,2,4-oxadiazole;
5-cyclopentyl-3-(4-((3-fluorophenyl)ethynyl)phenyl)-1,2,4-oxadiazole;
5-cyclohexyl-3-(4-((3-fluorophenyl)ethynyl)phenyl)-1,2,4-oxadiazole;
3-(4-((3-fluorophenyl)ethynyl)phenyl)-5-(pentan-3-yl)-1,2,4-oxadiazole;
5-benzyl-3-(4-((3-fluorophenyl)ethynyl)phenyl)-1,2,4-oxadiazole;
5-benzyl-3-(4-((3-fluorophenyl)ethynyl)phenyl)-1,2,4-oxadiazole;
3-(4-((3-fluorophenyl)ethynyl)phenyl)-5-((tetrahydrofuran-2-yl)methyl)-1,-2,4-oxadiazole;
3-(4-((3-fluorophenyl)ethynyl)phenyl)-5-(furan-2-ylmethyl)-1,2,4-oxadiazole;
3-(4-((3-fluorophenyl)ethynyl)phenyl)-5-(tetrahydrofuran-2-yl)-1,2,4-oxadiazole;
3-(4-((3-fluorophenyl)ethynyl)phenyl)-5-(2-methoxyethyl)-1,2,4-oxadiazole;
3-(4-((3-fluorophenyl)ethynyl)phenyl)-5-(tetrahydro-2H-pyran-4-yl)-1,2,4-oxadiazole;
3-(4-((3-fluorophenyl)ethynyl)phenyl)-5-(furan-2-yl)-1,2,4-oxadiazole;
3-(4-((3-fluorophenyl)ethynyl)phenyl)-5-(tetrahydrofuran-3-yl)-1,2,4-oxadiazole;
3-(4-((3-fluorophenyl)ethynyl)phenyl)-5-(1-methoxypropyl)-1,2,4-oxadiazole;
3-(4-((3-fluorophenyl)ethynyl)phenyl)-5-(1-methylpiperidin-4-yl)-1,2,4-oxadiazole;
3-(4-((3-fluorophenyl)ethynyl)phenyl)-5-(1-methylpyrrolidin-2-yl)-1,2,4-oxadiazole;
3-(4-((3-fluorophenyl)ethynyl)phenyl)-5-(1-methylpyrrolidin-2-yl)-1,2,4-oxadiazole;
5-(1-ethylpyrrolidin-2-yl)-3-(4-((3-fluorophenyl)ethynyl)phenyl)-1,2,4-oxadiazole;
3-(4-((3-fluorophenyl)ethynyl)phenyl)-5-(1-isopropylpyrrolidin-2-yl)-1,2,-4-oxadiazole;
5-(1-cyclobutylpyrrolidin-2-yl)-3-(4-((3-fluorophenyl)ethynyl)phenyl)-1,2-,4-oxadiazole
5-(1,2-dimethylpyrrolidin-2-yl)-3-(5-((3-fluorophenyl)ethynyl)pyridin-2-y-l)-1,2,4-oxadiazole;
5-(1-(azetidin-1-yl)ethyl)-3-(4-((3-fluorophenyl)ethynyl)phenyl)-1,2,4-oxadiazole;
3-(4-((3-fluorophenyl)ethynyl)phenyl)-5-(1-(pyrrolidin-1-yl)ethyl)-1,2,4-oxadiazole;
N-(1-(3-(4-((3-fluorophenyl)ethynyl)phenyl)-1,2,4-oxadiazol-5-yl)ethyl)-N -methylcyclopropanamine;
ethyl 3--(4-((3-fluorophenyl)ethynyl)phenyl)-1,2,4-oxadiazole-5-carboxylate;
1-(3-(4-((3-fluorophenyl)ethynyl)phenyl)-1,2,4-oxadiazol-5-yl)ethanone;
1-(3-(4-((3-fluorophenyl)ethynyl)phenyl)-1,2,4-oxadiazol-5-yl)ethanol;
3-(4-((3-fluorophenyl)ethynyl)phenyl)-5-(1-methoxyethyl)-1,2,4-oxadiazole;
3-(4-((3-fluorophenyl)ethynyl)phenyl)5-(pyrrolidin-1-yl)-1,2,4-oxadiazole;
4-3-(4-((3-fluorophenyl)ethynyl)phenyl)-1,2,4-oxadiazol-5-yl)morpholine;
N-ethyl-3-(4-((3-fluorophenyl)ethynyl)phenyl)-N-methyl-1,2,4-oxadiazol-5-amine;
3-(4-((3-fluorophenyl)ethynyl)phenyl)-N-methyl-1,2,4-oxadiazol-5-amine;
3-(4-((4-fluorophenyl)ethynyl)phenyl)-5-isopropyl-1,2,4-oxadiazole;
5-(sec-butyl)-3-(4-((4-fluorophenyl)ethynyl)phenyl)-1,2,4-oxadiazole;
5-cyclopentyl-3-(4-((4-fluorophenyl)ethynyl)phenyl)-1,2,4-oxadiazole;
5-(tert-butyl)-3-(4-((4-fluorophenyl)ethynyl)phenyl)-1,2,4-oxadiazole;
5-(tert-butyl)-3-(4-((4-fluorophenyl)ethynyl)phenyl)-1,2,4-oxadiazole;
5-(1-methoxyethyl)-3-(4-(pyridin-2-ylethynyl)phenyl)-1,2,4-oxadiazole;
5-(1-methoxypropyl)-3-(4-(pyridin-2-ylethynyl)phenyl)-1,2,4-oxadiazole;
5-(1-methylpyrrolidin-2-yl)-3-(4-(pyridin-2-ylethynyl)phenyl)-1,2,4-oxadiazole;
5-(sec-butyl)-3-(4-(pyridin-4-ylethynyl)phenyl)-1,2,4-oxadiazole;
(S)-5-(sec-butyl)-3-(4-(pyridin-4-ylethynyl)phenyl)-1,2,4-oxadiazole;

(R)-5-(sec-butyl)-3-(4-(pyridin-4-ylethynyl)phenyl)-1,2,4-oxadiazole;
5-(1-methoxyethyl)-3-(4-(pyridin-4-ylethynyl)phenyl)-1,2,4-oxadiazole;
5-(pentan-3-yl)-3-(4-(pyridin-4-ylethynyl)phenyl)-1,2,4-oxadiazole;
5-(1-methoxypropyl)-3-(4-(pyridin-4-ylethynyl)phenyl)-1,2,4-oxadiazole;
3-(4-(pyridin-4-ylethynyl)phenyl)-5-(pyrrolidin-2-yl)-1,2,4-oxadiazole;
5-(1-methylpyrrolidin-2-yl)-3-(4-(pyridin-4-ylethynyl)phenyl)-1,2,4-oxadiazole;
N-methyl-1-(3-(4-(pyridin-4-ylethynyl)phenyl)-1,2,4-oxadiazol-5-yl)ethanamine;
N,N-dimethyl-1-(3-(4-(pyridin-4-ylethynyl)phenyl)-1,2,4-oxadiazol-5-yl)ethanamine;
5-(sec-butyl)-3-(4-(pyridin-3-ylethynyl)phenyl)-1,2,4-oxadiazole;
5-(sec-butyl)-3-(6-((3-fluorophenyl)ethynyl)pyridin-3-yl)-1,2,4-oxadiazole;
5-cyclopentyl-3-(6-((3-fluorophenyl)ethynyl)pyridin-3-yl)-1,2,4-oxadiazole;
3-(6-((3-fluorophenyl)ethynyl)pyridin-3-yl)-5-(1-methoxyethyl)-1,2,4-oxadiazole;
3-(6-((3-fluorophenyl)ethynyl)pyridin-3-yl)-5-(1-methoxypropyl)-1,2,4-oxadiazole;
5-(sec-butyl)-3-(6-(pyridin-2-ylethynyl)pyridin-3-yl)-1,2,4-oxadiazole;
5-(pentan-3-yl)-3-(6-(pyridin-2-ylethynyl)pyridin-3-yl)-1,2,4-oxadiazole;
5-(1-methoxyethyl)-3-(6-(pyridin-2-ylethynyl)pyridin-3-yl)-1,2,4-oxadiazole;
5-(1-methoxypropyl)-3-(6-(pyridin-2-ylethynyl)pyridin-3-yl)-1,2,4-oxadiazole;
5-(sec-butyl)-3-(6-(pyridin-4-ylethynyl)pyridin-3-yl)-1,2,4-oxadiazole;
5-(pentan-3-yl)-3-(6-(pyridin-4-ylethynyl)pyridin-3-yl)-1,2,4-oxadiazole;
5-(1-methoxyethyl)-3-(6-(pyridin-4-ylethynyl)pyridin-3-yl)-1,2,4-oxadiazole;
5-(pentan-3-yl)-3-(6-(pyridin-4-ylethynyl)pyridin-3-yl)-1,2,4-oxadiazole;
5-(sec-butyl)-3-(5-((3-fluorophenyl)ethynyl)pyridin-2-yl)-1,2,4-oxadiazole;
5-cyclopentyl-3-(5-((3-fluorophenyl)ethynyl)pyridin-2-yl)-1,2,4-oxadiazole;
3-(5-((3-fluorophenyl)ethynyl)pyridin-2-yl)-5-(1-methoxyethyl)-1,2,4-oxadiazole;
3-(5-((3-fluorophenyl)ethynyl)pyridin-2-yl)-5-(1-methoxypropyl)-1,2,4-oxadiazole;
3-(5-((3-fluorophenyl)ethynyl)pyridin-2-yl)-5-(1-methoxypropyl)-1,2,4-oxadiazole;
tert-butyl 2-(3-(5-((3-fluorophenyl)ethynyl)pyridin-2-yl)-1,2,4-oxadiazol-5-yl)azeti-dine-1-carboxylate;
5-(azetidin-2-yl)-3-(5-((3-fluorophenyl)ethynyl)pyridin-2-yl)-1,2,4-oxadiazole;
3-(5-((3-fluorophenyl)ethynyl)pyridin-2-yl)-5-(1-methylazetidin-2-yl)-1,2,4-oxadiazole;
1-(3-(5-((3-fluorophenyl)ethynyl)pyridin-2-yl)-1,2,4-oxadiazol-5-yl)-N-methylmethanamine;
1-(3-(5-((3-fluorophenyl)ethynyl)pyridin-2-yl)-1,2,4-oxadiazol-5-yl)-N,N-dimethylmethanamine;
1-(3-(5-((3-fluorophenyl)ethynyl)pyridin-2-yl)-1,2,4-oxadiazol-5-yl)-N,N-dimethylethanamine;
(R)-1-(3-(5-((3-fluorophenyl)ethynyl)pyridin-2-yl)-1,2,4-oxadiazol-5-yl)-N,N-dimethylethanamine;
(S)-1-(3-(5-((3-fluorophenyl)ethynyl)pyridin-2-yl)-1,2,4-oxadiazol-5-yl)-N,N-dimethylethanamine;
1-(3-(5-(3-fluorophenyl)ethynyl)pyridin-2-yl)-1,2,4-oxadiazol-5-yl)-N-methylethanamine;
3-(5-((3-fluorophenyl)ethynyl)pyridin-2-yl)-5-(1-(pyrrolidin-1-yl)ethyl)-1,2,4-oxadiazole
N-(1-(3-(5-((3-fluorophenyl)ethynyl)pyridin-2-yl)-1,2,4-oxadiazol-5-yl)ethyl)cyclopropanamine;
N-(1-(3-(5-((3-fluorophenyl)ethynyl)pyridin-2-yl)-1,2,4-oxadiazol-5-yl)ethyl)propan-2-amine;
N,N-diethyl-1-(3-(5-((3-fluorophenyl)ethynyl)pyridin-2-yl)-1,2,4-oxadiazo-1-5-yl)ethanamine;
2-(3-(5-((3-fluorophenyl)ethynyl)pyridin-2-yl)-1,2,4-oxadiazol-5-yl)-N-methylpropan-2-amine;
2-(3-(5-((3-fluorophenyl)ethynyl)pyridin-2-yl)-1,2,4-oxadiazol-5-yl)-N,N-dimethylpropan-2-amine;
1-(3-(5-((3-fluorophenyl)ethynyl)pyridin-2-yl)-1,2,4-oxadiazol-5-yl)propan-1-amine;
1-(3-(5-((3-fluorophenyl)ethynyl)pyridin-2-yl)-1,2,4-oxadiazol-5-yl)-N-methylpropan-1-amine;
1-(3-(5-((3-fluorophenyl)ethynyl)pyridin-2-yl)-1,2,4-oxadiazol-5-yl)-N,N-dimethylpropan-1-amine;
N-(1-(3-(5-((3-fluorophenyl)ethynyl)pyridin-2-yl)-1,2,4-oxadiazol-5-yl)propyl) cyclopropanamine;
1-(3-(5-((3-fluorophenyl)ethynyl)pyridin-2-yl)-1,2,4-oxadiazol-5-yl)-N,N-dimethylcyclopropanamine;
3-(5-((3-fluorophenyl)ethynyl)pyridin-2-yl)-5-(pyrrolidin-2-yl)-1,2,4-oxadiazole;
(R)-3-(5-((3-fluorophenyl)ethynyl)pyridin-2-yl)-5-(pyrrolidin-2-yl)-1,2,4-oxadiazole;
(S)-3-(5-((3-fluorophenyl)ethynyl)pyridin-2-yl)-5-(pyrrolidin-2-yl)-1,2,4-oxadiazole;
3-(5-((3-fluorophenyl)ethynyl)pyridin-2-yl)-5-(2-methylpyrrolidin-2-yl)-1,2,4-oxadiazole;
3-(5-((3-fluorophenyl)ethynyl)pyridin-2-yl)-5-(3,3,3-trifluoropropyl)p-yrrolidin-2-yl) -1,2,4-oxadiazole;
3-(5-((3-fluorophenyl)ethynyl)pyridin-2-yl)-5-(1-(prop-2-yn-1-yl)pyrrolidin-2-yl)-1,2,4-oxadiazole;
2-(2-(3-(5-((3-fluorophenyl)ethynyl)pyridin-2-yl)-1,2,4-oxadiazol-5-yl)pyrrolidin-1-yl)acetonitrile;
5-(1-cyclobutylpyrrolidin-2-yl)-3-(5-((3-fluorophenyl)ethynyl)pyridin-2-y-l)-1,2,4-oxadiazole;
(S)-3-(5-((3-fluorophenyl)ethynyl)pyridin-2-yl)-5-(4-methylenepyrrolidin-2-yl)-1,2,4-oxadiazole;
(4R)-tert-butyl 2-(3-(5-((3-fluorophenyl)ethynyl)pyridin-2-yl)-1,2,4-oxadiazol-5-yl)-4-hydroxypyrrolidine-1-carboxylate;
(3R,5S)-5-(3-(5-((3-fluorophenyl)ethynyl)pyridin-2-yl)-1,2,4-oxadiazol-5-yl)pyrrolidin-3-ol;
(3R,5S)-5-(3-(5-((3-fluorophenyl)ethynyl)pyridin-2-yl)-1,2,4-oxadiazol-5-yl)-1-methylpyrrolidin-3-ol;
(3R,5R)-5-(3-(5-((3-fluorophenyl)ethynyl)pyridin-2-yl)-1,2,4-oxadiazol-5-yl)pyrrolidin-3-ol;
(3R,5R)-5-(3-(5-((3-fluorophenyl)ethynyl)pyridin-2-yl)-1,2,4-oxadiazol-5-yl)-1-methylpyrrolidin-3-ol;
3-(5-((3-fluorophenyl)ethynyl)pyridin-2-yl)-5-((2R,4R)-4-methoxypyrrolidi-n-2-yl)-1,2,4-oxadiazole;
5-(sec-butyl)-3-(5-(pyridin-2-ylethynyl)pyridin-2-yl)-1,2,4-oxadiazole;
5-(1-methoxyethyl)-3-(5-(pyridin-2-ylethynyl)pyridin-2-yl)-1,2,4-oxadiazole;
5-(pentan-3-yl)-3-(5-(pyridin-2-ylethynyl)pyridin-2-yl)-1,2,4-oxadiazole;
5-cyclopentyl-3-(5-(pyridin-2-ylethynyl)pyridin-2-yl)-1,2,4-oxadiazole;
5-(1-methoxypropyl)-3-(5-(pyridin-2-ylethynyl)pyridin-2-yl)-1,2,4-oxadiazole;

5-(1-(2,2-dimethylpyrrolidin-1-yl)ethyl)-3-(5-(pyridin-2-ylethynyl)pyridin-2-yl)-1,2,4-oxadiazole;
N-(1-(3-(5-(pyridin-2-ylethynyl)pyridin-2-yl)-1,2,4-oxadiazol-5-yl)ethyl)-propan-2-amine;
2-methyl-N-(1-(3-(5-(pyridin-2-ylethynyl)pyridin-2-yl)-1,2,4-oxadiazol-5-yl)ethyl)propan-2-amine;
3-(5-(pyridin-2-ylethynyl)pyridin-2-yl)-5-(1-(pyrrolidin-1-yl)ethyl)-1,2,-4-oxadiazole;
N,N-dimethyl-1-(3-(5-(pyridin-2-ylethynyl)pyridin-2-yl)-1,2,4-oxadiazol-5-yl)ethanamine;
N-methyl-2-(3-(5-(pyridin-2-ylethynyl)pyridin-2-yl)-1,2,4-oxadiazol-5-yl)-propan-2-amine;
N,N-dimethyl-2-(3-(5-(pyridin-2-ylethynyl)pyridin-2-yl)-1,2,4-oxadiazol-5-yl)propan-2-amine;
ethyl(1-(3-(5-(pyridin-2-ylethynyl)pyridin-2-yl)-1,2,4-oxadiazol-5-yl)propyl)carbamate;
N-methyl-1-(3-(5-(pyridin-2-ylethynyl)pyridin-2-yl)-1,2,4-oxadiazol-5-yl)-propan-1-amine;
N,N-dimethyl-1-(3-(5-(pyridin-2-ylethynyl)pyridin-2-yl)-1,2,4-oxadiazol-5-yl)propan-1-amine;
N-(1-(3-(5-(pyridin-2-ylethynyl)pyridin-2-yl)-1,2,4-oxadiazol-5-yl)propyl) cyclopropanamine;
5-(1-methylazetidin-2-yl)-3-(5-(pyridin-2-ylethynyl)pyridin-2-yl)-1,2,4-oxadiazole;
3-(5-(pyridin-2-ylethynyl)pyridin-2-yl)-5-(pyrrolidin-2-yl)-1,2,4-oxadiazole;
5-(5,5-dimethylpyrrolidin-2-yl)-3-(5-(pyridin-2-ylethynyl)pyridin-2-yl)-1-,2,4-oxadiazole;
3-(5-(pyridin-2-ylethynyl)pyridin-2-yl)-5-(1,5,5-trimethylpyrrolidin-2-yl-)-1,2,4-oxadiazole;
(R)-5-(4,4-difluoro-1-methylpyrrolidin-2-yl)-3-(5-(pyridin-2-ylethynyl)py-ridin-2-yl)-1,2,4-oxadiazole;
(S)-5-(4,4-difluoro-1-methylpyrrolidin-2-yl)-3-(5-(pyridin-2-ylethynyl)py-ridin-2-yl)-1,2,4-oxadiazole;
5-((2R,4S)-4-fluoro-1-methylpyrrolidin-2-yl)-3-(5-(pyridin-2-ylethynyl)py-ridin-2-yl)-1,2,4-oxadiazole;
5-((2S,4S)-4-methoxypyrrolidin-2-yl)-3-(5-(pyridin-2-ylethynyl)pyridin-2-yl)-1,2,4-oxadiazole;
5-(sec-butyl)-3-(5-(pyridin-4-ylethynyl)pyridin-2-yl)-1,2,4-oxadiazole;
5-(1methoxyethyl)-3-(5-(pyridin-4-ylethynyl)pyridin-2-yl)-1.2.4-oxadiazole;
5-(pentan-3-yl)-3-(5-(pyridin-4-ylethynyl)pyridin-2-yl)-1,2,4-oxadiazole;
5-(1-methoxypropyl)-3-(5-(pyridin-4-ylethynyl)pyridin-2-yl)-1,2,4-oxadiazole;
3-(5-(pyridin-4-ylethynyl)pyridin-2-yl)-5-(pyrrolidin-2-yl)-1,2,4-oxadiazole
N-methyl-1-(3-(5-(pyridin-4-ylethynyl)pyridin-2-yl)-1,2,4-oxadiazol-5-yl)-ethanamine;
3-(5-(pyridin-3-ylethynyl)pyridin-2-yl)-5-(pyrrolidin-2-yl)-1,2,4-oxadiazole;
3-(5-(phenylethynyl)pyridin-2-yl)-5-(pyrrolidin-2-yl)-1,2,4-oxadiazole;
3-(5((3-chlorophenyl)ethynyl)pyridin-2-yl)-5-(pyrrolidin-2-yl)-1,2,4-oxadiazole;
3-(5-(phenylethynyl)pyridin-2-yl)-5-(pyrrolidin-2-yl)-1,2,4-oxadiazole;
3-fluoro-5-((6-(5-(pyrrolidin-2-yl)-1,2,4-oxadiazol-3-yl)pyridin-3-yl)ethynyl)benzonitrile;
5-((2R,4R)-4-fluoro-1-methylpyrrolidin-2-yl)-3-(5-(pyridin-2-ylethynyl)pyridin-2-yl)-1,2,4-oxadiazole;
5-(2-azabicyclo[3.1.0]hexan-1-yl)-3-(5-(pyridin-2-ylethynyl)pyridin-2-yl)-1,2,4-oxadiazole;
5-((1S,5R)-2-methyl-2-azabicyclo[3,1.0]hexan-1-yl)-3-(5-(pyridin-2-ylethynyl)pyridin-2-yl) -1,2,4-oxadiazole;
5-(1-azabicyclo[2.2.1]heptan-2-yl)-3-(5-(pyridin-2-ylethynyl)pyridin-2-yl-)-1,2,4-oxadiazole;
5-(1-azabicyclo[2.2.1]heptan-2-yl)-3-(5-(pyridin-2-ylethynyl)pyridin-2-yl-)-1,2,4-oxadiazole;
and
5-(hexahydro-1H-pyrrolizin-7a-yl)-3-(5-(pyridin-2-ylethynyl)pyridin-2-yl) -1,2,4-oxadiazole,
or a pharmaceutically acceptable salt thereof.

* * * * *